US009187557B2

(12) United States Patent
Nakamura et al.

(10) Patent No.: US 9,187,557 B2
(45) Date of Patent: Nov. 17, 2015

(54) GENES AND POLYPEPTIDES RELATING TO BREAST CANCERS

(71) Applicant: ONCOTHERAPY SCIENCE, INC., Kanagawa (JP)

(72) Inventors: Yusuke Nakamura, Tokyo (JP); Toyomasa Katagiri, Tokyo (JP); Shuichi Nakatsuru, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 14/162,487

(22) Filed: Jan. 23, 2014

(65) Prior Publication Data
US 2014/0228238 A1    Aug. 14, 2014

Related U.S. Application Data

(62) Division of application No. 12/377,024, filed as application No. PCT/JP2007/065992 on Aug. 10, 2007, now Pat. No. 8,673,548.

(60) Provisional application No. 60/837,428, filed on Aug. 10, 2006, provisional application No. 60/840,250, filed on Aug. 25, 2006, provisional application No. 60/915,022, filed on Apr. 30, 2007.

(51) Int. Cl.
| G01N 33/50 | (2006.01) |
| C07K 14/47 | (2006.01) |
| G01N 33/574 | (2006.01) |
| C07K 16/18 | (2006.01) |
| C12Q 1/48 | (2006.01) |
| A61K 31/7088 | (2006.01) |

(52) U.S. Cl.
CPC .............. *C07K 16/18* (2013.01); *A61K 31/7088* (2013.01); *C07K 14/47* (2013.01); *C07K 14/4748* (2013.01); *C12Q 1/485* (2013.01); *G01N 33/5011* (2013.01); *G01N 33/5035* (2013.01); *G01N 33/57415* (2013.01); *C12N 2310/14* (2013.01); *G01N 2333/9121* (2013.01); *G01N 2510/00* (2013.01)

(58) Field of Classification Search
None
See application file for complete search history.

(56) References Cited

U.S. PATENT DOCUMENTS

| 6,656,698 | B1 | 12/2003 | Meyers et al. |
| 7,531,300 | B2 | 5/2009 | Nakamura et al. |
| 2003/0099974 | A1 | 5/2003 | Lillie et al. |
| 2003/0105000 | A1 | 6/2003 | Pero et al. |
| 2003/0219748 | A1 | 11/2003 | Sun et al. |
| 2005/0064402 | A1 | 3/2005 | Goldsworthy et al. |
| 2009/0163524 | A1 | 6/2009 | Johnson et al. |
| 2009/0175844 | A1 | 7/2009 | Nakamura et al. |
| 2009/0208514 | A1 | 8/2009 | Nakamura et al. |
| 2009/0286856 | A1 | 11/2009 | Nakamura et al. |
| 2011/0263566 | A1 | 10/2011 | Matsuo et al. |
| 2012/0014996 | A1 | 1/2012 | Nakamura et al. |

FOREIGN PATENT DOCUMENTS

| EP | 1074617 A2 | 2/2001 |
| EP | 1661986 A1 | 5/2006 |
| WO | 01/75067 A2 | 10/2001 |
| WO | 02/29104 A2 | 4/2002 |
| WO | 02/059260 A2 | 8/2002 |
| WO | 02/059271 A2 | 8/2002 |
| WO | 03/043568 A2 | 5/2003 |
| WO | 03/064599 A2 | 8/2003 |
| WO | 03/070889 A2 | 8/2003 |
| WO | 2004/016225 A2 | 2/2004 |
| WO | 2004/031410 A2 | 4/2004 |
| WO | 2005/028676 A2 | 3/2005 |
| WO | 2006/085684 A2 | 8/2006 |
| WO | 2006/110593 A2 | 10/2006 |
| WO | 2007/013575 A2 | 2/2007 |
| WO | 2007/013671 A2 | 2/2007 |

OTHER PUBLICATIONS

Curigliano, G., et al., "Breast cancer vaccines: a clinical reality or fairy tale?" *Annals of Oncology*, vol. 17(5), pp. 750-762 (May 2006, Epub Nov. 17, 2005).

Mathelin, C., et al., "Circulating proteinic biomarkers and breast cancer," *Gynecol. Obstet. Fertil.*, vol. 34(7-8), pp. 638-646 (Jul.-Aug. 2006, Epub Jul. 28, 2006).

Peng, X. et al., "Prohibitin is a Novel Target Gene of Vitamin D Involved in It's Antiproliferative Action in Breast Cancer Cells," *Cancer Res.*, vol. 66(14), pp. 7361-7369 (Jul. 15, 2006).

Abe, Y., et al., "Cloning and Expression of a Novel MAPKK-like Protein Kinase, Lymphokine-activated Killer T-cell-originated Protein Kinase, Specifically Expressed in the Testis and Activited Lymphoid Cells," *J. Biol. Chem.*, vol. 275(28), pp. 21525-21531 (Jul. 14, 2000).

Gaudet, S., et al., "Characterization of PDZ-binding kinase, a mitotic kinase," *Proc. Natl. Acad. Sci. USA.*, vol. 97(10), pp. 5167-5172 (May 9, 2000).

Matsumoto, S., et al., "Characterization of a MAPKK-like protein kinase TOPK," *Biochem. Biophys. Res. Commun.*, vol. 325(3), pp. 997-1004 (Dec. 17, 2004).

(Continued)

*Primary Examiner* — Peter J Reddig
(74) *Attorney, Agent, or Firm* — Kilpatrick Townsend & Stockton LLP

(57) ABSTRACT

The present application provides novel human genes A7322, whose expression is markedly elevated in breast cancer. The present application also provides human genes F3374 whose expression is markedly elevated in breast cancer. These genes and polypeptides encoded thereby can be used, for example, in the diagnosis of breast cancer, and as target molecules for developing drugs against breast cancer. The invention features methods of screening for modulators of the kinase activity of PBK/TOPK. The invention further provides methods of screening for agents to prevent or treat cancer, such as breast cancer.

1 Claim, 25 Drawing Sheets

(56) References Cited

OTHER PUBLICATIONS

Park, J-H., et al., "PDZ-Binding Kinase/T-LAK Cell-Originated Protein Kinase, a Putative Cancer/Testis Antigen with an Oncogenic Activity in Breast Cancer," *Cancer Res.*, vol. 66(18), pp. 9186-9195 (Sep. 15, 2006).

Park, J-H., et al., "PBK/TOPK (PDZ-binding kinase/T-LAK cell-originated protein kinase) as a novel molecular target for breast cancer therapy," *Proceedings of the 66th Annual Meeting of the Japanse Center Association*, p. 78, Abstract No. EW17-4 (Aug. 25, 2007).

Watanabe, T., et al., "Identification and characterization of a novel gene CXADRL1 whose expression is frequently up-regulated in differentiated-type of gastric cancer," *Proceedings of the 61st Annual Meeting of the Japanese Cancer Association*, p. 77, Abstract No. 2027 (Aug. 25, 2002).

Zhao, S., et al., "PDZ-binding kinase participates in spermatogenesis," *Int. J. Biochem. Cell. Biol.*, vol. 33(6), pp. 631-636 (Jun. 2001).

U.S. Appl. No. 11/913,147, which is a U.S. National Phase (371) of PCT/JP2006/314946, filed Jul. 21, 2006, 237 pgs.

U.S. Appl. No. 13/238,273, filed Sep. 21, 2011, 120 pages.

U.S. Appl. No. 13/246,639, filed Sep. 27, 2011, 164 pages.

U.S. Appl. No. 13/061,123, filed May 19, 2011, 103 pages.

Katagiri, T., "Novel targeting therapeutic strategy for treatment of estrogen-dependent breast cancer," *Proceedings of the 70th Annual Meeting of the Japanese Cancer Association*, p. 276, Abstract #S17-3 (Sep. 5, 2011).

Fujibuchi, et al., "Expression and phosphorylation of TOPK during spermatogenesis," *Dev Growth Differ.*, vol. 47(9), pp. 637-644 (Dec. 2005).

Keydar, et al., "Establishment and Characterization of a Cell Line of Human Breast Carcinoma Origin," *Eur J Cancer*, vol. 15(5), pp. 659-670 (May 1979).

Nandi, et al., "Protein expression of PDZ-binding kinase is up-regulated in hematologic malignancies and strongly down-regulated during terminal differentiation of HL-60 leukemic cells," *Blood Cells Mol Dis.*, vol. 32(1), pp. 240-245 (Jan. 2004-Feb. 2004).

Simons, et al., "PBK/TOPK is a Novel Mitototic Kinase Which is Upregulated in Burkitt's Lymphoma and Other Highly Proliferative Malignant Cells," *Blood Cells Mol Dis.*, vol. 27(5), pp. 825-829 (Sep. 2001-Oct. 2001).

Yang, et al., "Crystal structure of an activated Akt/Protein Kinase B ternary complex with GSK3-peptide and AMP-PNP," *Nat Struct Biol.*, vol. 9(12), pp. 940-944 (Dec. 2002).

Yuryev, et al., "Novel Raf kinase protein-protein interactions found by an exhaustive yeast two-hybrid analysis," *Genomics*, vol. 81(2), pp. 112-125 (Feb. 2003).

Zykova, et al., "Lymphokine-Activated Killer T-Cell-Originated Protein Kinase Phosphorylation of Histone H2AX Prevents Arsenite-Induced Apoptosis in RPMI7951 Melanoma Cells," *Clin Cancer Res.*, vol. 12(23), pp. 6884-6893 (Dec. 1, 2006).

U.S. Appl. No. 13/536,327, 204 pages, filed Jun. 28, 2012.

Badache, et al., "The ErbB2 Sginaling Network as a Target for Breast Cancer Therapy," *J Mammary Gland Biol Neoplasia*, vol. 11(1), pp. 13-25 (Jan. 2006).

Beresford, et al., "Measuring proliferation in breast cancer: Practicalities and applications," *Breast Cancer Res.*, vol. 8(6):216, 11 pages (2006).

Desrivieres, et al. "The Biological Functions of the Versatile Transcription Factors STAT3 and STAT5 and New Strategies for their Targeted Inhibition," *J Mammary Gland Biol Neoplasia*, vol. 11(1), pp. 75-87 (Jan. 2006).

Faltus, et al., "Silencing of the *HER2/neu* Gene by siRNA Inhibits Proliferation and Induces Apoptosis in *HER/neu*-Overexpressing Breast Cancer Cells," *Neoplasia*, vol. 6(6), pp. 785-795 (Nov. 2004-Dec. 2004).

Kim, et al., "Activation of an estrogen/estrogen receptor signaling by BIG3 through its inhibitory effect on nuclear transport of PHB2/REA in breast cancer," *Cancer Sci.*, vol. 100(8), pp. 1468-1478 (Epub May 6, 2009, Aug. 2009).

Zhao, et al., NCBI GenBank Accession No. AF237709.1, 2 pages, retrieved from http://www.ncbi.nlm.nih.gov/nuccore/AF237709.1 (downloaded Aug. 30, 2012).

Van, et al., "Histone H3 phosphorylation is required for the initiation, but not maintenance, of mammalian chromosome condensation," *J Cell Sci.*, vol. 111(Pt. 23), pp. 3497-3506 (Dec. 1998).

Rudikoff et al., "Single amino acid substitution altering antigen-binding specificity", *PNAS USA*; 1982, vol. 79, pp. 1979-1983.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", *J. of Cell Bio.*, 1990, vol. 111, pp. 2129-2138.

Skolnick et al., "From genes to protein structure and function; novel applications of computational approaches in the genomic era", *Tibtech*, 2000, vol. 18, pp. 34-39.

Ibragimova et al., "Stability of the β-Sheet of the WW Domain: A Molecular Dynamics Simulation Study", *Biophysical Journal*, 1999, vol. 77, pp. 2191-2198.

Rapoport et al., "A novel mitotic kinase is upregulated in Burkitt's lymphoma cells and other neoplastic cell lines", *Blood*, 2000, vol. 96, No. 11, pt. 1: 699a.

U.S. Appl. No. 14/353,261, filed Apr. 21, 2014, 94 pages.

Fig.1
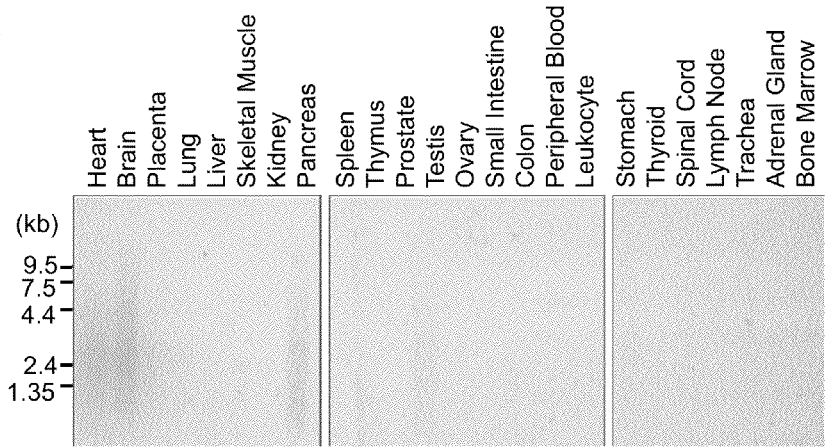
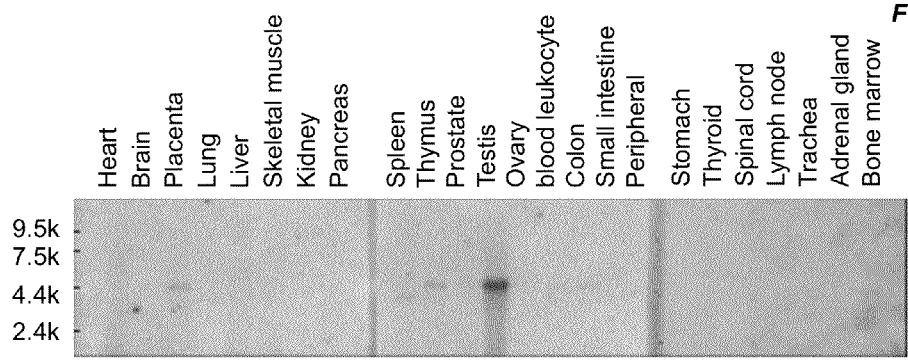
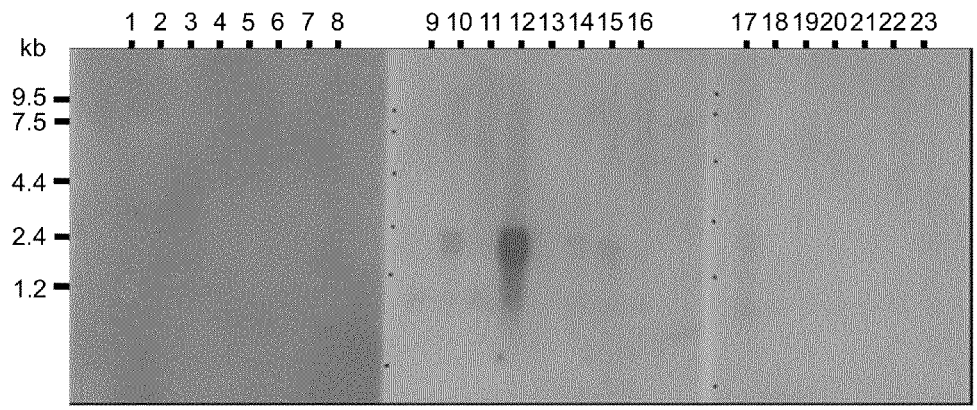

Fig.1
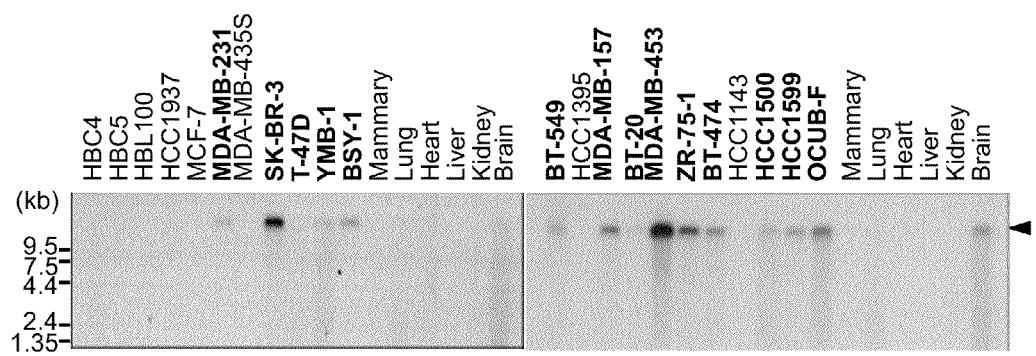
*A7322*
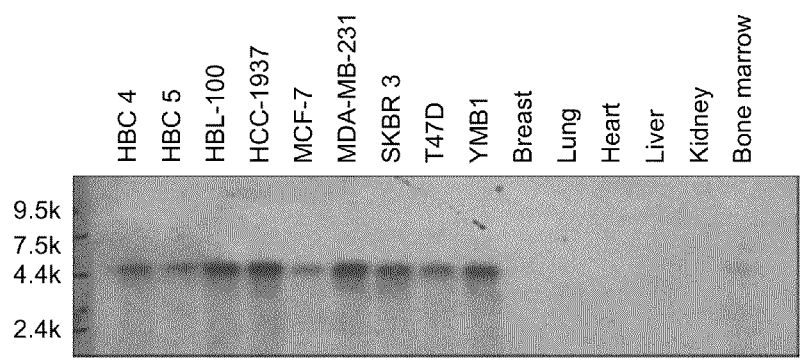
*F3374*
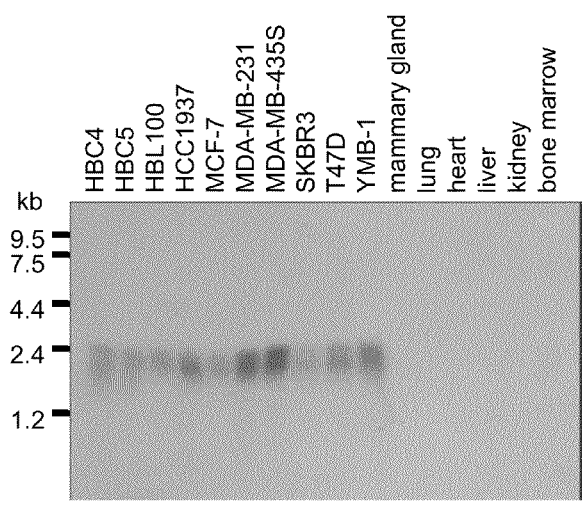
*PBK/TOPK*

Fig.1
E
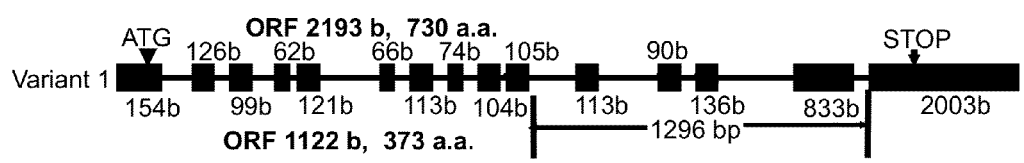
F
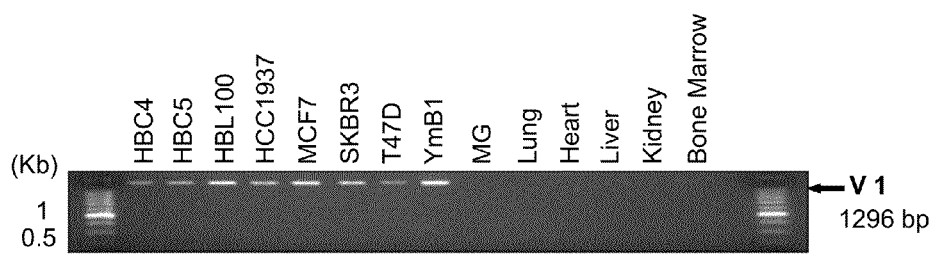
G
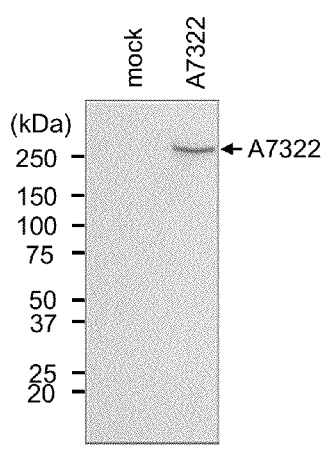
IB: FLAG

Fig.3
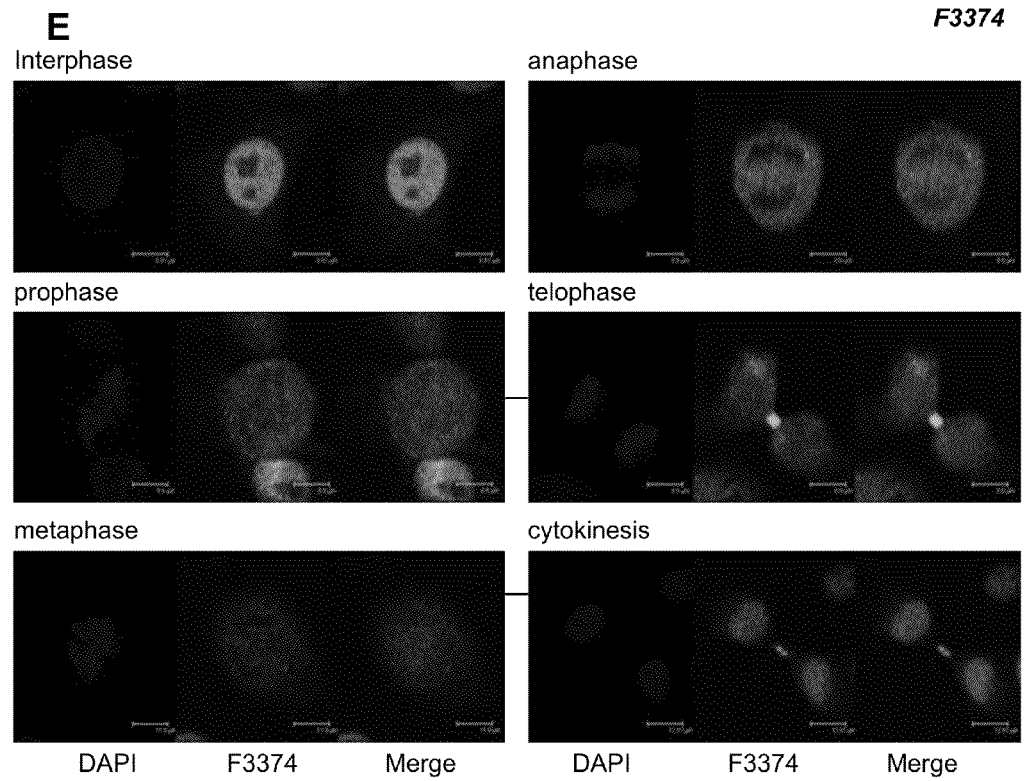
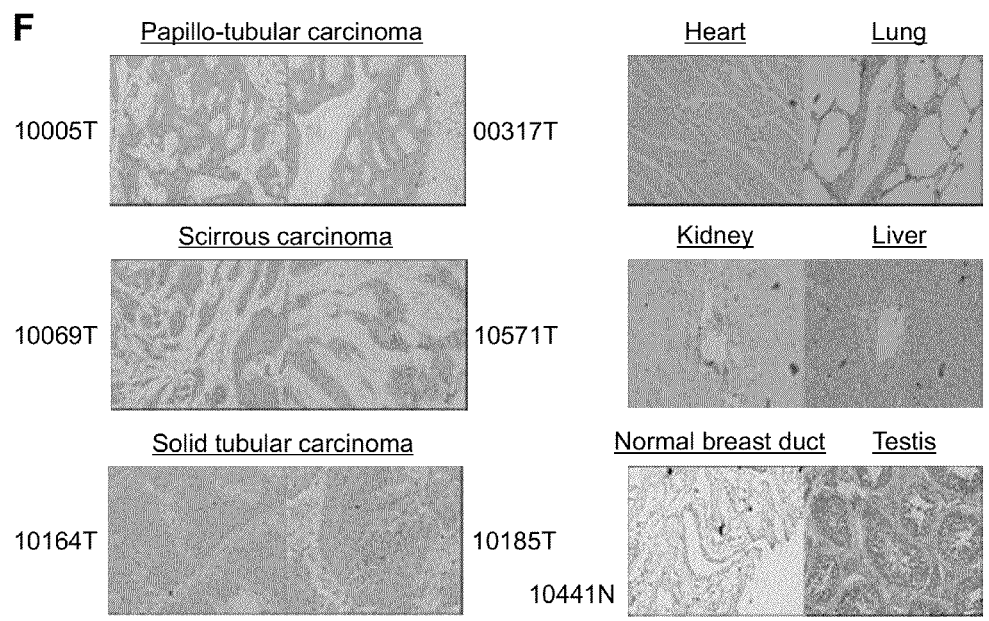

Fig.9
A                                                                 *A7322*
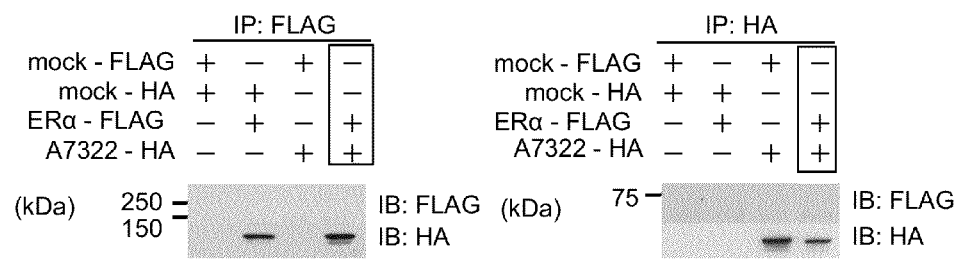
B
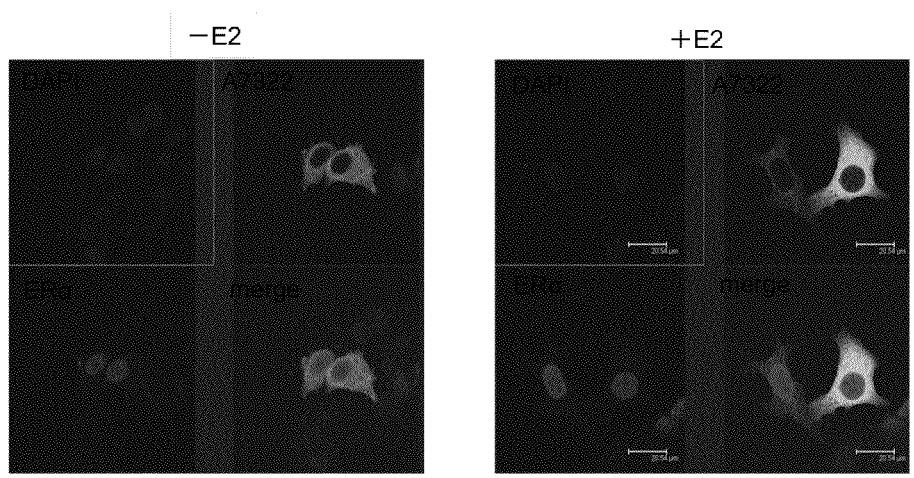
C
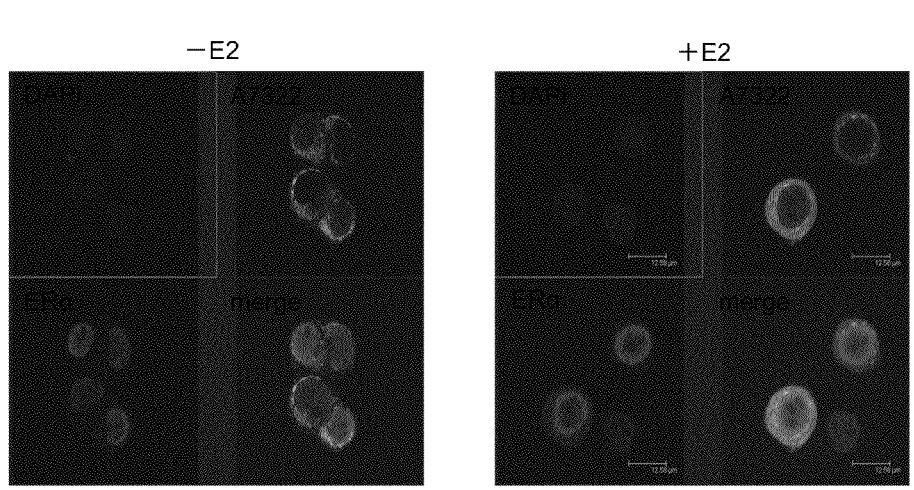

GENES AND POLYPEPTIDES RELATING TO BREAST CANCERS

This application is a divisional application of U.S. application Ser. No. 12/377,024, filed Feb. 10, 2009, issued as U.S. Pat. No. 8,673,548, which is a U.S. National Stage Application of PCT/JP2007/065992, filed Aug. 10, 2007, which claims the benefit of U.S. Provisional Application Ser. No. 60/837,428, filed Aug. 10, 2006, U.S. Provisional Application Ser. No. 60/840,250, filed Aug. 25, 2006 and U.S. Provisional Application Ser. No. 60/915,022, filed Apr. 30, 2007, the contents of which are hereby incorporated by reference in their entirety.

REFERENCE TO SEQUENCE LISTING

The Sequence Listing written in file "87331-896787-018610US-SEQLIST.txt" created Jan. 21, 2014, and containing 136,050 bytes, machine format IBM-PC, MS-Windows operating system, is hereby incorporated by reference in its entirety for all purposes.

FIELD OF THE INVENTION

The present invention relates to the field of biological science, more specifically to the field of cancer research. In particular, the present invention relates to cancer related genes, A7322, F3374 and PBK/TOPK, involved in the proliferation mechanism of breast cancer, as well as polypeptides encoded by the genes. The genes and polypeptides of the present invention can be used, for example, in the prognosis and diagnosis of breast cancer, and as target molecules for developing drugs against breast cancer.

BACKGROUND OF THE INVENTION

Breast cancer, a genetically heterogeneous disease, is the most common malignancy in women. An estimation of approximately 800,000 new cases worldwide was reported each year (Parkin D M, et al., (1999). CA Cancer J Clin 49: 33-64). Mastectomy is still currently the first option for the medical treatment. Despite surgical removal of the primary tumors, relapse at local or distant sites may occur due to micrometastasis undetectable at the time of diagnosis (Saphner T, et al., (1996). J Clin Oncol, 14, 2738-46). Cytotoxic agents are usually administered as adjuvant therapy after surgery, aiming to kill those residual or pre-malignant cells. Treatment with conventional chemotherapeutic agents is often empirical and is mostly based on histological tumor parameters. In the absence of specific mechanistic understanding, target-directed drugs, are therefore becoming the bedrock treatment for breast cancer. Tamoxifen and aromatase inhibitors, two representatives of its kind, have proven to elicit efficacious responses when used as adjuvant or chemoprevention in patients with metastasized breast cancer (Fisher B, et al., (1998). J Natl Cancer Inst, 90, 1371-88; Cuzick J (2002). Lancet 360, 817-824). However, the drawback is that only patients' expressing estrogen receptors are sensitive to these drugs. Moreover, concerns have recently been raised regarding their side effects, for example endometrial cancer resulting from long term tamoxifen treatment and bone fractures resulting from aromatase therapy in the postmenopausal women (Coleman R E (2004). Oncology. 18 (5 Suppl 3), 16-20).

In spite of recent progress in diagnostic and therapeutic strategies, prognosis of patients with advanced cancers remains very poor. Although molecular studies have revealed the involvement of alterations in tumor suppressor genes and/or oncogenes in carcinogenesis, the precise mechanisms still remain to be elucidated.

cDNA microarray technologies have enabled the construction of comprehensive profiles of gene expression in normal and malignant cells, and the comparison of gene expression in malignant and corresponding normal cells (Okabe et al., Cancer Res 61:2129-37 (2001); Kitahara et al., Cancer Res 61:3544-9 (2001); Lin et al., Oncogene 21:4120-8 (2002); Hasegawa et al., Cancer Res 62:7012-7 (2002)). This approach facilitates the understanding of the complex nature of cancer cells, and helps to elucidate the mechanism of carcinogenesis. Identification of genes that are deregulated in tumors can lead to more precise and accurate diagnosis of individual cancers, and to the development of novel therapeutic targets (Bienz and Clevers, Cell 103:311-20 (2000)). To disclose mechanisms underlying tumors from a genome-wide point of view, and discover target molecules for diagnosis and development of novel therapeutic drugs, the present inventors analyzed the expression profiles of tumor cells using a cDNA microarray of 23,040 genes (Okabe et al., Cancer Res 61:2129-37 (2001); Kitahara et al., Cancer Res 61:3544-9 (2001); Lin et al., Oncogene 21:4120-8 (2002); Hasegawa et al., Cancer Res 62:7012-7 (2002)).

Studies designed to reveal mechanisms of carcinogenesis have already facilitated the identification of molecular targets for anti-tumor agents. For example, inhibitors of farnesyltransferase (FTIs), which were originally developed to inhibit the growth-signaling pathway related to Ras and whose activation depends on post-translational farnesylation, have been shown to be effective in treating Ras-dependent tumors in animal models (Sun J, et al., Oncogene. 1998; 16:1467-73). Clinical trials on humans, using a combination of anti-cancer drugs and the anti-HER2 monoclonal antibody, trastuzumab, to antagonize the proto-oncogene receptor HER2/neu, have achieved improved clinical responses and overall survival of breast cancer patients (Molina M A, et al., Cancer Res. 2001; 61:4744-9). A tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (O'Dwyer M E & Druker B J, Curr Opin Oncol. 2000; 12:594-7). Therefore, gene products commonly up-regulated in cancerous cells may serve as potential targets for developing novel anti-cancer agents.

For example, a new approach of cancer therapy using gene-specific siRNA was attempted in clinical trials (Bumcrot D et al., Nat Chem Biol 2006 December, 2(12): 711-9). RNAi seems to have already earned a place among the major technology platforms (Putral L N et al., Drug News Perspect 2006 July-August, 19(6): 317-24; Frantz S, Nat Rev Drug Discov 2006 July, 5(7): 528-9; Dykxhoorn D M et al., Gene Ther 2006 March, 13(6): 541-52). Nevertheless, there are several challenges that need to be faced before RNAi can be applied in clinical use. These challenges include poor stability of RNA in vivo (Hall A H et al., Nucleic Acids Res 2004 Nov. 15, 32(20): 5991-6000, Print 2004; Amarzguioui M et al., Nucleic Acids Res 2003 Jan. 15, 31(2): 589-95), toxicity as an agent (Frantz S, Nat Rev Drug Discov 2006 July, 5(7): 528-9), mode of delivery, the precise sequence of the siRNA or shRNA used, and cell type specificity. It is well-known fact that there are possible toxicities related to silencing of partially homologous genes or induction of universal gene suppression by activating the interferon response (Judge A D et al., Nat Biotechnol 2005 April, 23(4): 457-62, Epub 2005

Mar. 20; Jackson A L & Linsley P S, Trends Genet. 2004 November, 20(11): 521-4). Therefore, double-stranded molecules targeting cancer-specific genes devoid of adverse side-effects, are needed for the development of anticancer drugs.

Alternatively, it has been demonstrated that CD8+ cytotoxic T lymphocytes (CTLs) recognize epitope peptides derived from tumor-associated antigens (TAAs) presented on the MHC Class 1 molecule, and lyse tumor cells. Since the discovery of the MAGE family as the first example of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994)). Some of the discovered TAAs are now in the stage of clinical development as targets of immunotherapy. TAAs discovered to date include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Natl Acad Sci USA 94: 1914-8 (1997)). On the other hand, gene products which had been demonstrated to be specifically over-expressed in tumor cells, have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and the like.

In spite of significant progress in basic and clinical research concerning TAAs (Rosenberg et al., Nature Med 4: 321-7 (1998); Mukherji et al., Proc Natl Acad Sci USA 92: 8078-82 (1995); Hu et al., Cancer Res 56: 2479-83 (1996)), only a limited number of candidate TAAs for the treatment of adenocarcinomas, including breast cancer, are currently available. TAAs abundantly expressed in cancer cells, and at the same time whose expression is restricted to cancer cells, would be promising candidates as immunotherapeutic targets. Further, identification of new TAAs inducing potent and specific anti-tumor immune responses is expected to encourage clinical use of peptide vaccination strategies in various types of cancer (Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994); Shichijo et al., J Exp Med 187: 277-88 (1998); Chen et al., Proc Natl Acad Sci USA 94: 1914-8 (1997); Harris, J Natl Cancer Inst 88: 1442-55 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., Int J Cancer 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., Cancer Res 60: 3550-8 (2000); Nishizaka et al., Cancer Res 60: 4830-7 (2000); Tamura et al., Jpn J Cancer Res 92: 762-7 (2001)). However, both of HLA-A24 and HLA-A0201 are popular HLA alleles in Japanese, as well as Caucasian populations (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Histocompatibility Workshop and Conference Oxford University Press, Oxford, 1065 (1992); Williams et al., Tissue Antigen 49: 129 (1997)). Thus, antigenic peptides of cancers presented by these HLAs may be especially useful for the treatment of cancers among Japanese and Caucasian populations. Further, it is known that the induction of low-affinity CTL in vitro usually results from the use of a peptide at a high concentration, generating a high level of specific peptide/MHC complexes on antigen presenting cells (APCs), which will effectively activate these CTL (Alexander-Miller et al., Proc Natl Acad Sci USA 93: 4102-7 (1996)).

To determine the mechanism of breast carcinogenesis and identify novel diagnostic markers and/or drug targets for the treatment of these tumors, the present inventors analyzed the expression profiles of genes in breast carcinogenesis using a genome-wide cDNA microarray containing 27,648 genes. From a pharmacological point of view, suppressing oncogenic signals is easier in practice than activating tumor-suppressive effects. Thus, the present inventors searched for genes that were up-regulated during breast carcinogenesis.

Since cytotoxic drugs often cause severe adverse reactions, thoughtful selection of novel target molecules on the basis of well-characterized mechanisms of action will facilitate development of effective anti-cancer drugs with minimum risk of side effects. Toward this goal, the inventors previously performed expression profile analysis of 81 breast cancers (Nishidate T et al., Int J Oncol 2004, 25: 797-819) and 29 normal human tissues (Saito-Hisaminato A et al., DNA Res 2002, 9: 35-45; WO05/028676) and found dozens of genes that were highly and universally up-regulated in breast cancer cells.

PBK (PDZ-binding kinase)/TOPK (T-LAK cell-originated protein kinase) gene is one of these genes which was found to be significantly over-expressed in the great majority of breast cancer cases examined (the PBK/TOPK gene is dubbed "A7870" in WO05/028676). Further, the present inventors demonstrated that a small-interfering RNA (siRNA) designed to reduce the expression of the PBK/TOPK gene has a growth-inhibitory effect on breast cancer cells expressing the gene.

PBK/TOPK is a member of the Ser/Thr kinase family and was first identified as a Dlg1-interacting protein by yeast two-hybrid screening and characterized as a mitotic kinase with PDZ-binding motif at the C-terminus (Gaudet S et al., Proc Natl Acad Sci USA 2000, 97: 5167-72). PBK/TOPK was also indicated by another group as a MAPKK-like protein kinase that phosphorylates p38 protein (Abe Y et al., J Biol Chem 2000, 275: 21525-31). In addition, the possible interaction between Raf and PBK/TOPK was shown by yeast two-hybrid screening analysis (Yuryev A et al., Genomics 2003, 81: 112-25). These two findings implied that PBK/TOPK might involve the MAPK pathway.

Post-translational modifications at the N-terminal portion of histone H3, including acetylation, methylation, and phosphorylation were described previously (Martin C & Zhang Y, Nat Rev Mol Cell Biol 2005, 6: 838-49; Nowak S J et al., Trends Genet. 2004, 214-20; Prigent C & Dimitrov S, J Cell Sci 2003, 116: 3677-85). Among them, phosphorylation of histone H3 at Ser10 is known to be involved in the initiation of mammalian chromosome condensation, an essential event in cell mitosis (Prigent C & Dimitrov S, J Cell Sci 2003, 116: 3677-85; Van Hooser A et al., J Cell Sci 1998, 111: 3497-506). According to the "ready production label" model, Ser10 phosphorylation of histone H3 reaches the maximum level in metaphase, as an indication that the chromosomes are ready to be separated, and then Ser10 is dephosphorylated accompanied by metaphase/anaphase transition (Hans F & Dimitrov S, Oncogene 2001, 20: 3021-7). Interestingly, previous reports indicated that okadaic acid ("OA") induced Ser10 phosphorylation of histone H3 through inhibition of protein phosphatases (PPs) (Murnion M E et al., J Biol Chem 2001, 276: 26656-65; Eyers P A et al., Curr Biol 2003, 13: 691-7). For example, Aurora-A is known to be deactivated by protein phosphatase 2A (PP2A), but to be reactivated by its autophosphorylation through binding with TPX2 (Targeting protein for *Xenopus* kinesin-like protein 2) protein that impair the activity of PP2A (Eyers P A et al., Curr Biol 2003, 13: 691-7).

Entry into mitosis in mammalian cells is triggered by activation of the CDK1-cyclin B1 kinase targeting a lot of substrates to induce subsequent mitotic processes (Nigg E A., Nat Rev Mol Cell Biol 2: 21-32 (2001)). Those substrates are also involved in the late stage of cell mitosis through a phosphorylation by CDK1-cyclin B1 complex; APC (anaphase-promoting complex) ubiqutin ligase that is activated to initiate mitotic exit (Kraft C et al., EMBO J. 22: 6598-609 (2003)) and conformational proteins that obtain a docking site with PLK1, such as INCENP (inner centromere protein, Goto H et al., Nat Cell Biol 8: 180-7 (2006)) and PRC1 (protein regulator of cytokinesis 1, Neef R et al., Nat Cell Biol 9: 436-44 (2007)) required for metaphase-anaphase transition and cytokinesis, respectively. Moreover, it implies a role of close cooperation between protein kinases and phosphatases to promote cell mitosis because recent works reported that the activity of Protein phosphatase 1 (PP1α has an inactive phosphorylation site (Thr320) targeted by CDK1-cyclin B1 kinase (Kwon Y G et al., Proc Natl Acad Sci USA 94: 2168-73 (1997)). Although it has been reported that PBK/TOPK can be phosphorylated at Thr9 by CDK1-cyclin B1, how activation of PBK/TOPK by CDK1-cyclin B1 complex mitotic cells and its function of in cell proliferation and cancer progression is still largely unknown.

SUMMARY OF THE INVENTION

Accordingly, it is an object of the present invention to provide novel proteins involved in the proliferation mechanism of breast cancer cells and the genes encoding such proteins, as well as methods for producing and using the same in the diagnosis and treatment of breast cancer.

Among the transcripts that were commonly up-regulated in breast cancers, human genes PBK/TOPK, A7322 and F3374 were identified, respectively. Furthermore, reduction of PBK/TOPK, A7322 and F3374 expression by transfection of their specific small interfering RNAs inhibited the growth of breast cancer cells. Many anticancer drugs, such as inhibitors of DNA and/or RNA synthesis, metabolic suppressors, and DNA intercalators, are not only toxic to cancer cells but also for normally growing cells. However, agents suppressing the expression of PBK/TOPK, A7322 or F3374 will not adversely affect other organs due to the fact that an expression of the gene in normal organs is restricted, for example, to the brain for A7322 or testis and thymus, placenta and bone marrow for F3374.

Thus, the present invention provides isolated nucleic acid molecules comprising PBK/TOPK, F3374 and A7322 (SEQ ID NO: 79) genes. The nucleic acid molecules are candidates as prognostic and diagnostic markers for cancer as well as promising potential targets for developing new strategies for diagnosis and effective therapeutic anti-cancer agents. Further, the present invention provides polypeptides encoded by these genes, as well as the production and the use of the same.

The present invention also provides a method of producing a protein by transfecting or transforming a host cell with a polynucleotide sequence encoding at least one of a PBK/TOPK, F3374 or A7322 protein, and expressing the polynucleotide sequence. In addition, the present invention provides vectors comprising a nucleotide sequence encoding at least one of a PBK/TOPK, F3374 or A7322 protein, and host cells harboring a polynucleotide encoding an A7322 protein. Such vectors and host cells may be used for producing the PBK/TOPK, F3374 and A7322 proteins.

An antibody or non-antibody binding protein that recognizes a PBK/TOPK, F3374 or A7322 protein is also provided by the present application. In part, an inhibitory polynucleotide, e.g., antisense DNA, ribozyme, and siRNA (small interfering RNA) of the PBK/TOPK, F3374 or A7322 gene is also provided.

The present invention further provides a method for diagnosis of breast cancer that includes the step of determining an expression level of a A7322 or F3374V1 gene in a biological sample of specimen and comparing the expression level of the A7322 or F3374V1 gene with that in normal sample, wherein a high expression level of the A7322 or F3374V1 gene in the sample is indicative of breast cancer.

Further, a method of screening for a compound useful in the treatment of breast cancer is provided. The method includes the step of contacting an A7322 or F3374V1 polypeptide with test compounds, and selecting test compounds that bind to the A7322 or F3374V1 polypeptide.

The present invention further provides a method of screening for a compound useful in the treatment of breast cancer, wherein the method includes the step of contacting an A7322 or F3374V1 polypeptide with a test compound, and selecting the test compound that suppresses the biological activity of the A7322 or F3374V1 polypeptide.

The present application also provides a pharmaceutical composition useful in the treatment of breast cancer. The pharmaceutical composition may be, for example, an anti-cancer agent. The pharmaceutical composition comprise at least a portion of the antisense S-oligonucleotides or siRNA of the A7322, F3374V1 or AURKB polynucleotide sequence shown and described in SEQ ID NO: 34, 35, 37, 38, 67 or 68 respectively.

The present invention further provides methods for treating breast cancer using the pharmaceutical compositions provided by the present invention.

In addition, the present invention provides a method for treating or preventing breast cancer comprising the step of administering an A7322 or F3374V1 polypeptide. Anti-tumor immunity is induced by the administration of such an A7322 or F3374V1 polypeptide. Thus, the present invention also provides a method for inducing anti-tumor immunity comprising the step of administering the A7322 or F3374V1 polypeptide, as well as pharmaceutical compositions for treating or preventing breast cancer comprising the A7322 or F3374V1 polypeptide.

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

The present invention is also based, at least in part, on the discovery of a novel mechanism of PBK/TOPK to phosphorylate histone H3 at Ser10 in vitro and in vivo. Since PBK/TOPK is a cancer/testis antigen and its kinase function is likely to be related to its oncogenic activity, the protein is also a promising molecular target for breast cancer therapy.

Specifically, the present invention provides a method of screening for an agent that induces apoptosis in breast cancer cells. The screening can also be conducted by contacting a PBK/TOPK polypeptide with a substrate phosphorylated by the PBK/TOPK polypeptide and an agent under a condition that allows phosphorylation of the substrate; detecting the phosphorylation level of the substrate; comparing the phosphorylation level of the substrate with the phosphorylation level of the substrate detected in the absence of the agent; and selecting the agent that reduced the phosphorylation level of the polypeptide. According to this method, histone or a fragment thereof that comprises at least its phosphorylation site, e.g., Ser10 of histone H3, can be used as the substrate.

Identified agents screened through the above mentioned methods induce apoptosis in breast cancer cells. Therefore, the screened agents serve as candidates for treating or preventing breast cancer. Thus, the present invention also provides methods of screening agents for treating or preventing breast cancer by preventing or inhibiting PBK/TOPK phosphorylation of Ser10 of H3.

The present invention further provides a method of screening for a compound useful in the treatment of breast cancer, wherein the method includes the step of contacting the PBK/TOPK with CDK1, CyclinB1 and a test compound, and selecting the compound that suppresses the phosphorylation level of the PBK/TOPK polypeptide.

The present invention also relates to methods for treatment and/or prevention of breast cancer comprising the step of administering an inhibitory polypeptide that contains MEGISNFKTPSKLSEKKK (SEQ ID NO: 98); or a polynucleotide encoding the same. Furthermore, the present invention relates to the use of polypeptides of the invention; or the use of nucleotides encoding the same, in manufacturing pharmaceutical formulations for the treatment and/or prevention of breast cancer.

The present invention further provides a method of screening for a compound useful in the treatment of breast cancer, wherein the method includes the step of contacting a test compound with a cell which expresses protein phosphatase 1 alpha (PP1α) and the PBK/TOP polypeptide, and selecting the test compound that suppresses the phosphorylation level of the PBK/TOPK polypeptide.

The present invention further provides a method of screening for a compound useful in the treatment of breast cancer, wherein the method includes the step of contacting the PBK/TOPK polypeptide with the p47 polypeptide, the p97 polypeptide and a test compound, and selecting the test compound that suppresses the binding between PBK/TOPK and p47 or the phosphorylation level of the p97 polypeptide.

The present invention further provides a method of screening for a compound useful in the treatment of breast cancer, wherein the method includes the step of contacting a test compound with a cell which expresses the PBK/TOP polypeptide, and selecting the test compound that alters the intercellular junction to the long intercellular bridges and/or increase the G2/M population of the cell.

(D) Lambda phosphatase experiment when expressed exogenously with F3374 deletion constructs (Δ-1, Δ-2 and Δ-3), respectively.

(E) Subcellular localization of endogenous PRC1 protein in breast cancer cells during cell cycle. HBC5 cells were immunocytochemically stained using affinity-purified anti-F3374 polyclonal antibody (red) and DAPI (blue) to discriminate nucleus (see the Materials and Methods). White arrows indicate localization of F3374 in midbody of telophase cells.

(F) Immunohistochemical staining results of breast cancer and normal breast tissue sections. Endogenous F3374 protein was stained by use of anti-F3374 antibody. The expression was hardly detected from normal breast tissues (10441N), but cancer cells were intensely stained in all of cancer tissues investigated including papillotubular (10005T and 00317T), scirrhous (10069T and 10571T) and solid-tubular (10164T and 10185T), carcinomas. Representative figures were from microscopic observation with original magnification, ×200. Representative images of immunohistochemical staining of F3374 in normal human tissue sections (heart, lung, kidney, liver and testis). Endogenous F3374 protein was stained by anti-F3374 antibody. Original magnification ×50.

Figure 4:
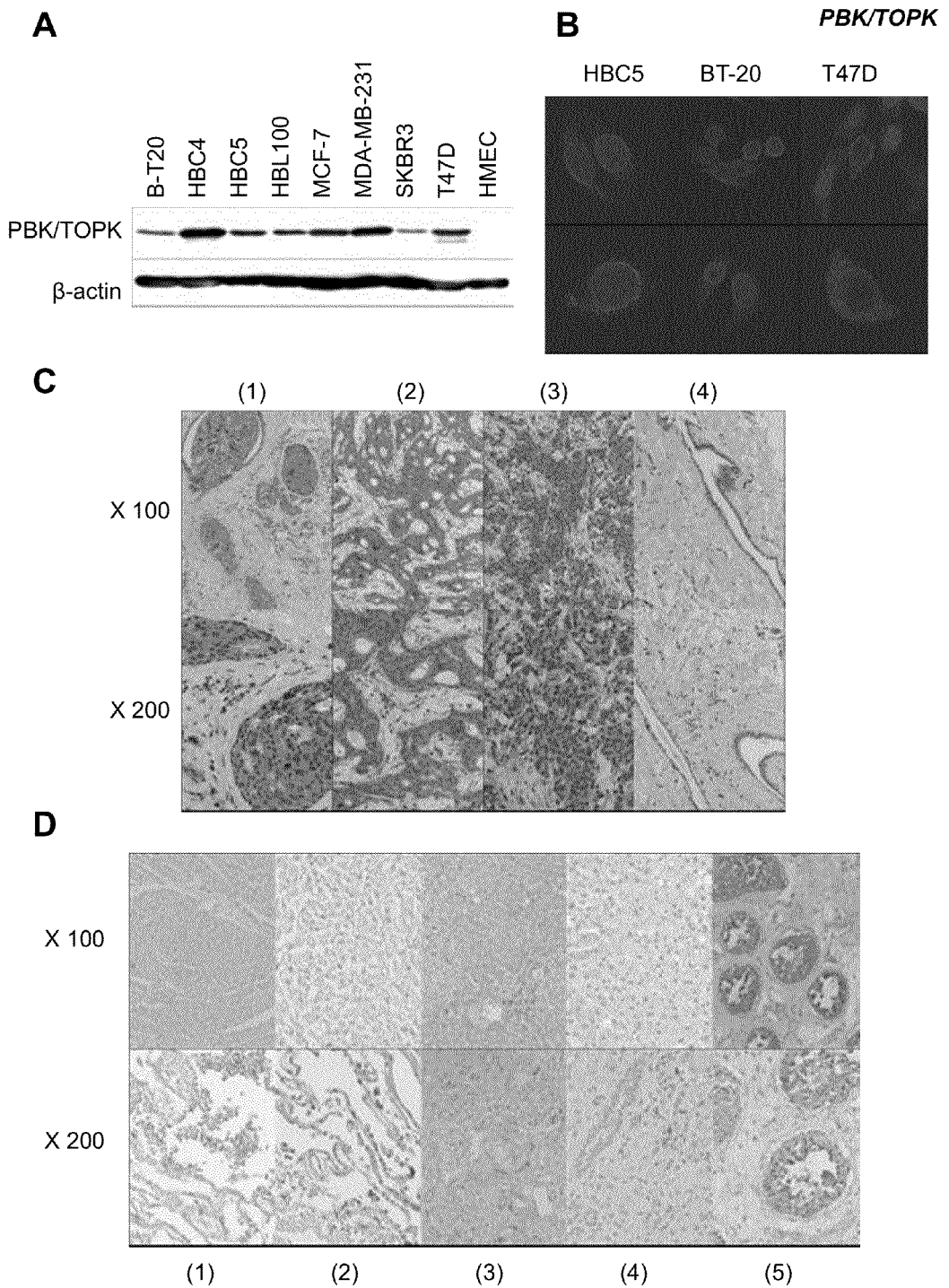

FIG. 4. Expression of PBK/TOPK Protein in Breast Cancer Cell-Lines and Tissue Sections.

(A) Expression of endogenous PBK/TOPK protein in breast cancer cell lines and HMEC by western blot analysis using anti-PBK/TOPK monoclonal antibody.

(B) Subcellular localization of endogenous PBK/TOPK protein in breast cancer cell lines, T47D, BT-20, and HBC5 immunocytochemically stained with anti-PBK/TOPK monoclonal antibody (red) and DAPI (blue) to discriminate nucleus. Endogenous PBK/TOPK protein was stained in the cytoplasm.

(C) Immunohistochemical staining of breast cancer (1-3) and normal breast (4) tissue sections. Endogenous PBK/TOPK protein was stained with anti-PBK/TOPK monoclonal antibody. The expression of the protein could be hardly detected in normal breast tissues (4), but the cytoplasm of cancer cells were intensely stained in all of the investigated cancer tissues including intraductal (1), papillo-tubular (2), and scirrhous carcinoma (3). The panels depict representative microphotographs with original magnification, left; ×100 and right; ×200.

Figure 1:
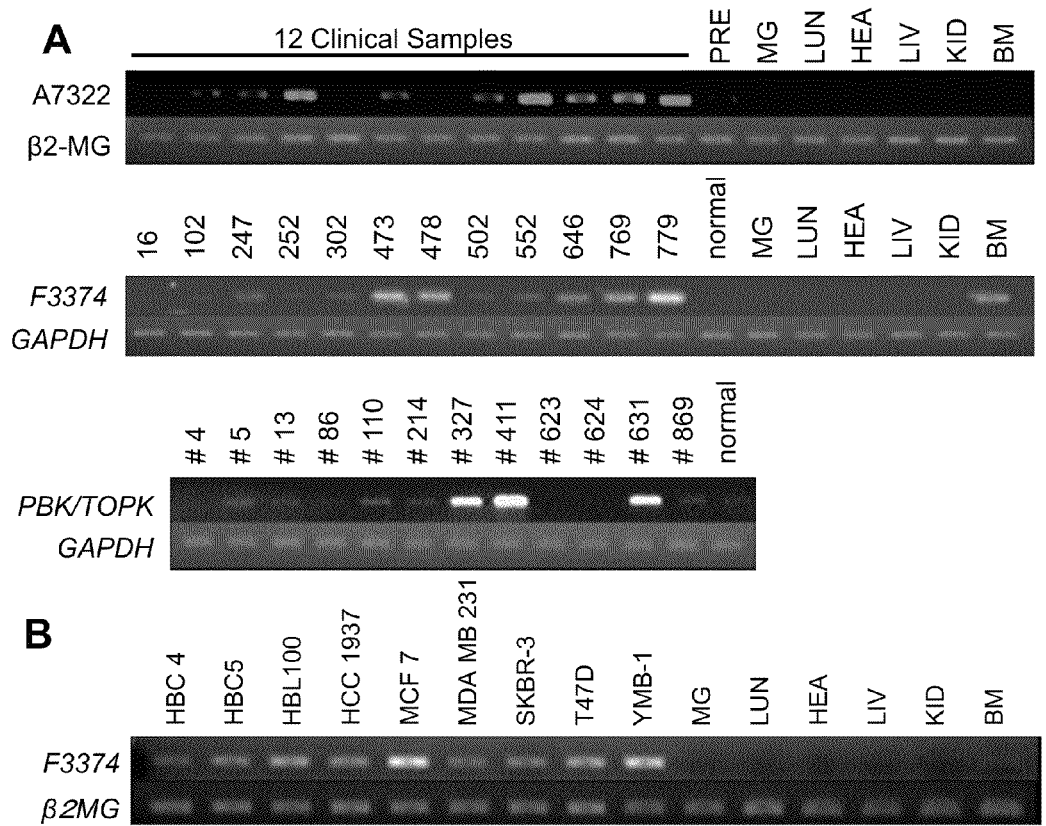
FIG. 1. Expression of A7322 and F3374 in Breast Cancer and Normal Tissues.
(A) Expression of A7322 in tumor cells from 12 breast cancer patients (3T, 31T, 149T, 175T, 431T, 453T, 491T, 554T, 571T, 709T, 772T and 781T), expression of F3374 in tumor cells from breast cancer cases (16, 102, 247, 252, 302, 473, 478, 502, 552, 646, 769 and 779) and expression of PBK/TOPK in tumor cells from breast cancer cases (#4, 5, 13, 86, 110, 214, 327, 411, 623, 624, 631 and 869) by semi-quantitative RT-PCR.
(B) Expression of F3374 in 9 breast cancer cell-lines (HBC4, HBC5, HBL100, HCC1937, MCF7, MDA-MB-231, SKBR3, T47D, YMB1) and normal human tissues (mammary gland, lung, heart, liver, kidney and brain) by semi-quantitative RT-PCR.
(C) Northern blot analysis of A7322, F3374 and PBK/TOPK with multiple human tissues. The MTN membranes included human normal tissues from 1; heart, 2; brain, 3; placenta, 4; lung, 5; liver, 6; skeletal muscle, 7; kidney, 8; pancreas, 9; spleen, 10; thymus, 11; prostate, 12; testis, 13; ovary, 14; small intestine, 15; colon, 16; peripheral blood leukocyte, 17; stomach, 18; thyroid, 19; spinal cord, 20; lymph node, 21; trachea, 22; adrenal gland, and 23; bone marrow.
(D) Northern blot analysis of A7322 with 22 breast cancer cell lines (HBC4, HBC5, HBL100, HCC1937, MCF7, MDA-MB-231, MDA-MB-435S, SKBR3, T47D, YMB1, BSY-1, BT-549, HCC1935, MDA-MB-157, BT-20, MDA-MB-453, ZR75-1, BT474, HCC1143, HCC1500, HCC1599, OCUB-F) and normal human tissues (mammary gland, lung, heart, liver, kidney and brain), of F3374 with breast cancer cell lines and normal human tissues including breast, lung, heart, liver, kidney and bone marrow, and of PBK/TOPK with breast cancer cell line (HBC4, HBC5, HBL100, HCC1937, NCF-7, MDA-MB-231MDA-MB-435S, SKBR3, T47D and YBB-1) and normal human tissue (mammary gland, lung, heart, liver, kidney and bone marrow).
(E) Genomic structure of F3374V1.
(F) Expression pattern of F3374V1 in breast cancer cell lines and normal tissue by semi-quantitative RT-PCR.
(G) Expression of exogenous A7322 protein in BT-549 cells by Western-blot analysis.

(D) Expression patterns of PBK/TOPK protein in normal human tissues. Tissues of heart (1), lung (2), liver (3), kidney (4) and testis (5) were examined using anti-PBK/TOPK monoclonal antibody. As the results, the expressed PBK/TOPK protein was hardly detected in the 4 vital organs (1-4) but highly stained in testis, exclusively at the outer layer of seminiferous tubules (5). These immunohistochemical staining results correlated well with the result of MTN (FIG. 1C). The panels depict representative microphotographs with original magnification, left; ×100 and right; ×200.

Figure 5:
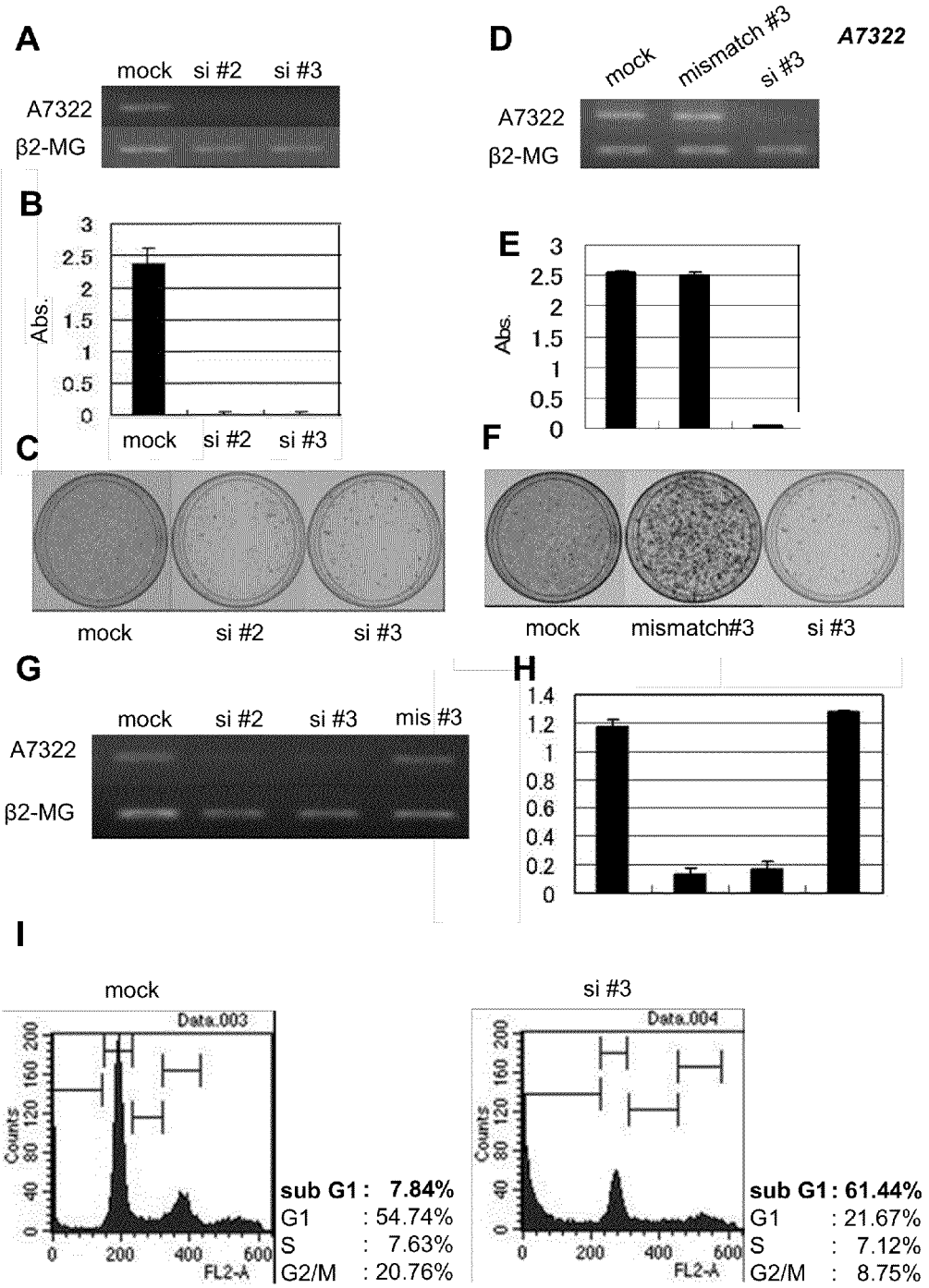

FIG. 5. Growth-Inhibitory Effects of Small-Interfering RNAs (siRNAs) Designed to Reduce Expression of A7322 in Breast Cancer Cells.

(A) Semi-quantitative RT-PCR showing suppression of endogenous expression of A7322 in breast cancer cell lines, BT-549 cells. β2MG was used as an internal control.

(B) MTT assay demonstrating a decrease in the numbers of colonies by knockdown of A7322 in BT-549 cells.

(C) Colony-formation assay demonstrating a decrease in the numbers of colonies by knockdown of A7322 in BT-549 cells.

(D) Semi-quantitative RT-PCR showing suppression of endogenous expression of A7322 in BT-549 cells. Knock-down effect of siRNAs-mismatch designed not to reduce expression of A7322.

(E) MTT assay demonstrating a decrease in the numbers of colonies by knockdown of A7322 in BT-549 cells.

(F) Colony-formation assay demonstrating a decrease in the numbers of colonies by knockdown of A7322 in BT-549 cells.

(G) Knock-down effect of siRNAs-mismatch designed not to reduce expression of A7322 in breast cancer cell lines, BT-474 cells by semi-quantitative RT-PCR.

(H) MTT assay demonstrating a decrease in the numbers of colonies by A7322-mismatched siRNAs (mis-#3; originally designed from si-#3) in BT-474 cells.

(I) FACS analysis showing the increased population of apoptotic cells (represented by sub-G1 percentage) by the suppression of endogenous expression of A7322 in BT-474 breast cancer cells. A total of 10,000 cells were equally counted from mock and si-#3 transfected BT-474 cells at 2 days after neomycin selection.

Figure 6:
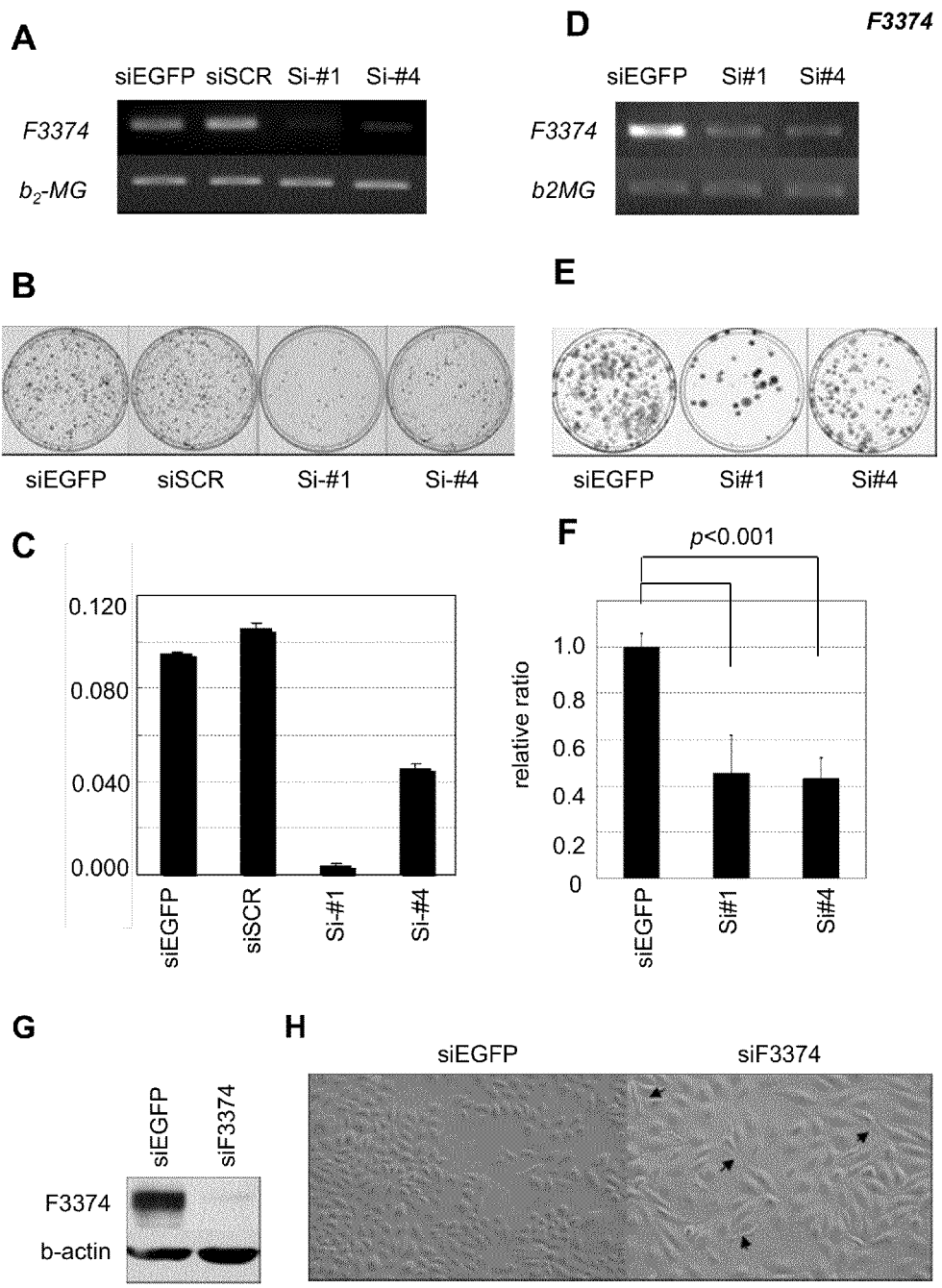

FIG. 6. Growth-Inhibitory Effects of Small-Interfering RNAs (siRNAs) Designed to Reduce Expression of F3374 in Breast Cancer Cells.

(A) Semi-quantitative RT-PCR showing suppression of endogenous expression of F3374 in breast cancer cell line, T47D cells. β2MG was used as an internal control.

(B) Colony-formation assay demonstrating a decrease in the numbers of colonies by knockdown of F3374 in BT-549 cells.

(C) MTT assay demonstrating a decrease in the numbers of colonies by knockdown of F3374 in T47D cells.

(D) Semi-quantitative RT-PCR showing suppression of endogenous expression of F3374 by F3374-specific siRNAs (si#1 and si#4) in breast cancer cell line, HBC4. β2MG served as a loading control.

(E) Colony-formation assay demonstrating a decrease in the number of colonies by knockdown of F3374 in HBC4 cells.

(F) MTT assay demonstrating a decrease in the number of colonies by knockdown of F3374 in HBC4 cells (si#1 and si#4; $p<0.001$, respectively; unpaired t test).

(G) Silencing of endogenous F3374 expression by siRNA was confirmed by western blot analysis. β-actin served as a loading control.

(H) Morphological changes of HBC4 cells transfected with siF3374 by microscopy. The siEGFP was used as a control siRNA. The arrows indicate two separating-cells (right panel).

Figure 7:
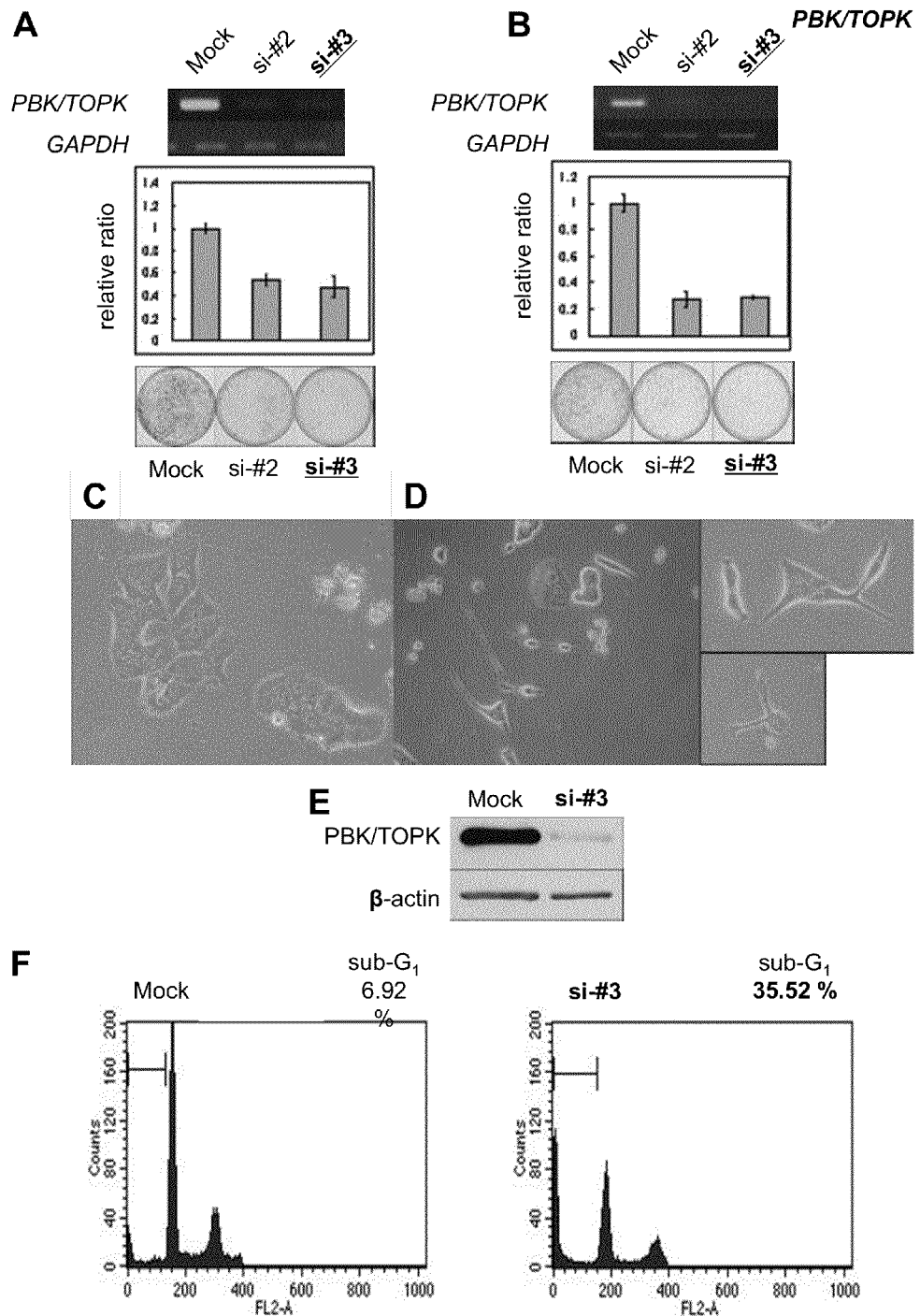

FIG. 7. Growth Inhibitory Effects of PBK/TOPK-siRNAs on Breast Cancer Cell-Lines.

(A)-(B) The results of semi-quantitative RT-PCR showed PBK/TOPK silencing 11 days after neomycin selection. GAPDH served as an internal control. MTT assays were performed to evaluate cell viability at day 11 and the standardized results are graphed taking the result of Mock as 1.0. Colony formation assays were carried out 3 weeks after selection (see 'Materials and Methods'). Two siRNA constructs (si-#2 and #3) showed knock-down effects against internal PBK/TOPK expression and inhibited cell growth in both cell-lines, T47D (A) and BT-20 (B). Mock was used as negative control.

(C)-(D) The phenotypic differences between Mock control (C) and si-#3-induced T47D cells (D) were investigated by microscopic observation, 2 weeks after neomycin selection. Irregular appearances were observed for PBK/TOPK-depleted cells; prolonged midbody, abolished and uncontrolled cytokinesis (D).

(E) shows the result of Western blotting confirming silencing of internal PBK/TOPK expression.

(F) depicts the result of FACS showing more population of apoptotic cells (represented by sub-G1 percentage) in si-#3-induced T47D cells rather than in Mock control transfected cells. In total, 10,000 cells were equally counted from Mock- and si-#3 transfected T47D cells.

Figure 8:
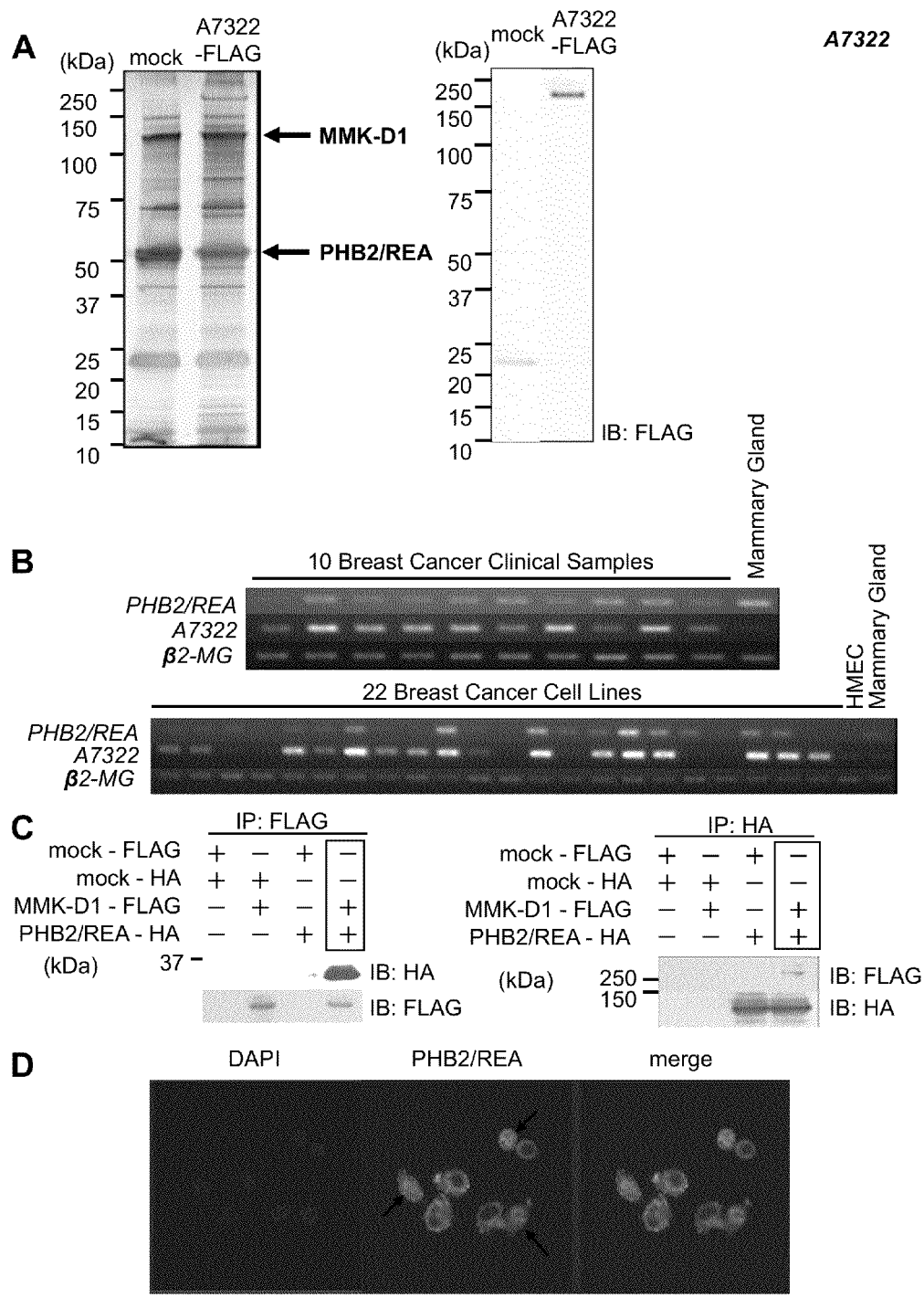

FIG. 8. Identification of PHB2/REA as an Interacting Protein of A7322.

(A) Silver staining of SDS-PAGE gels containing immunoprecipitated proteins. BT-549 cells were transfected with mock (mock lane) or FLAG-tagged A7322 (A7322-FLAG lane). Differential bands appeared in the A7322 lane were subjected to mass spectrometry analysis, and identified one of the bands shown near 33 kDa as PHB2/REA. Right panel shows Western blot analysis of immunoprecipitated samples. The expression of FLAG-tagged A7322 were detected by using anti-FLAG M2 monoclonal antibody.

(B) Semi-quantitative RT-PCR results for PHB2/REA and A7322 transcripts in breast cancer clinical samples (4T, 13T, 86T, 138T, 327T, 341T, 411T, 631T, 818T and 846T) and mammary gland. β2-MG served as an internal control. Semi-quantitative RT-PCR results for PHB2/REA and A7322 transcripts in breast cancer cell lines (HBC4, HBC5, HBL100, HCC1937, MCF-7, MDA-MB-231, MDA-MB-4355, SK-BR-3, T-47D, YMB-1, BSY-1, BT-549, HCC1935, MDA-MB-157, BT-20, MDA-MB-453, ZR-75-1, BT474, HCC1143, HCC1500, HCC1599, OCUB-F), HMEC and mammary gland. β2-MG served as an internal control.

(C) Interaction of A7322 and PHB2/REA protein. COS-7 cells were transfected with a combination of FLAG-tagged mock, FLAG-tagged A7322, HA-tagged mock and HA-tagged PHB2/REA, immunoprecipitated with anti-FLAG M2 agarose, and immunoblotted with anti-HA high affinity (3F10) rat monoclonal antibody. The 4th lane transfected with FLAG-tagged A7322 and HA-tagged PHB2/REA showed the direct binding of these two proteins. Right panel shows the confirmation of the interaction of A7322 and PHB2/REA protein by immunoprecipitate with anti-HA agarose conjugate and immunoblot with anti-FLAG M2 monoclonal antibody. The 4th lane transfected with FLAG-tagged A7322 and HA-tagged PHB2/REA showed the direct binding of these two proteins.

(D) Endogenous expression of PHB2/REA in breast cancer cells. Immunocytochemical staining were performed in SK-BR-3 breast cancer cells using anti-PHB2/REA polyclonal antibody (green) and DAPI (blue) to discriminate nucleus. Endogenous PHB2/REA showed the localization mainly in cytoplasm, though some cells also showed the localization in the nucleus (arrows).

FIG. 9. A7322 Shows No Direct Binding with ERα Protein.

(A) Confirmation of no interaction of A7322 and ERα protein. COS-7 cells were transfected with a combination of HA-tagged mock (mock-HA), HA-tagged A7322 (A7322-HA), FLAG-tagged mock (mock-FLAG) and FLAG-tagged ERα (ERα-FLAG), immunoprecipitated with anti-FLAG M2 agarose, and immunoblotted with anti-HA high affinity (3F10) rat monoclonal antibody. The 4th lane transfected with A7322-HA and ERα-FLAG showed no direct binding of these two proteins. Right panel shows the confirmation of the interaction of A7322 and ERα protein by immunoprecipitate with anti-HA agarose conjugate and immunoblot with anti-FLAG M2 monoclonal antibody. The 4th lane transfected with A7322-HA and ERα-FLAG showed no direct binding of these two proteins.

(B) Sub-cellular localization of A7322 and ERα under estradiol treatment. MCF-7 (ER+) cells were transfected with A7322-HA (green) and ERα-FLAG (red) for 24 hours and treated with DMSO (−E2; left panel) or 1 μM E2 (+E2; right panel) for another 24 hours. A7322 remained in cytoplasm under E2. Same experiments were performed using SK-BR-3 (ER−) cells. (C) showing no movement of A7322 under E2.

Figure 10:
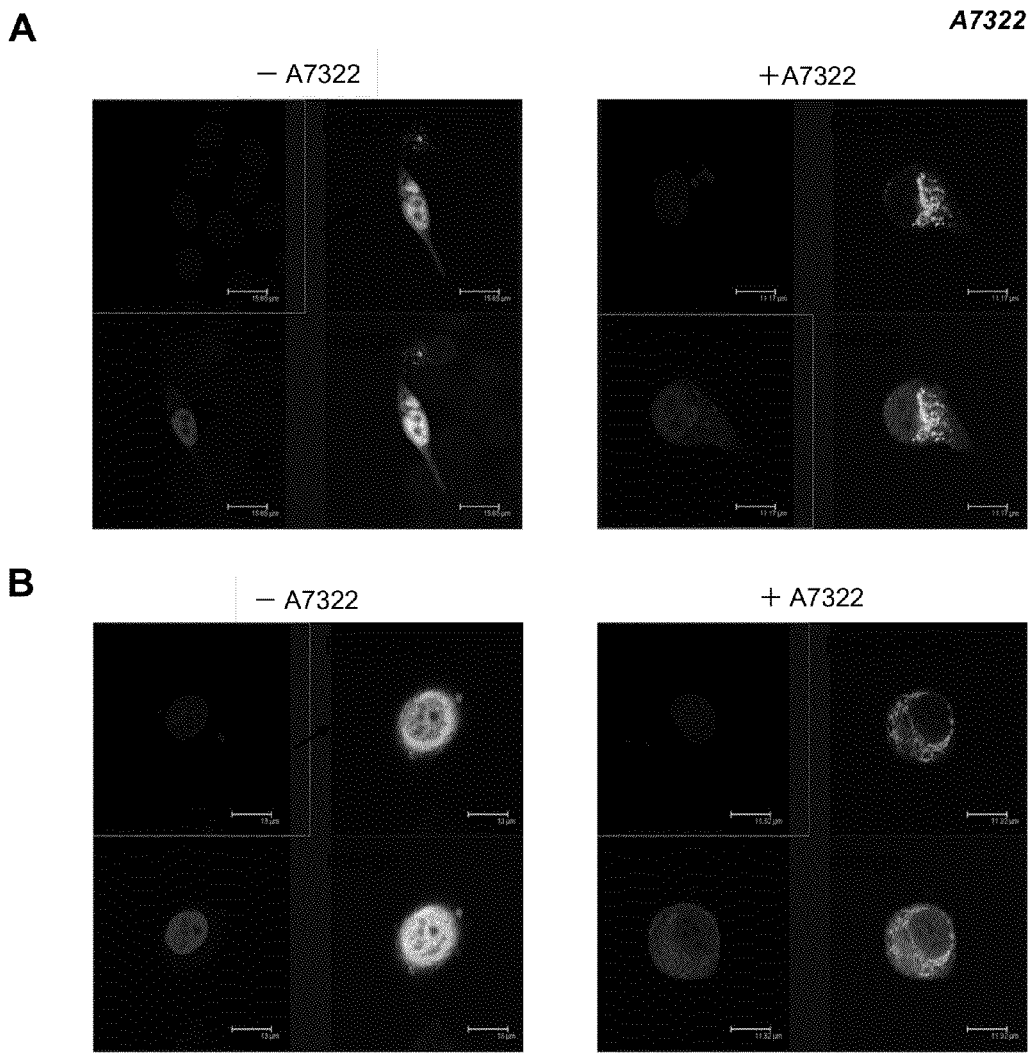
Figure 10:
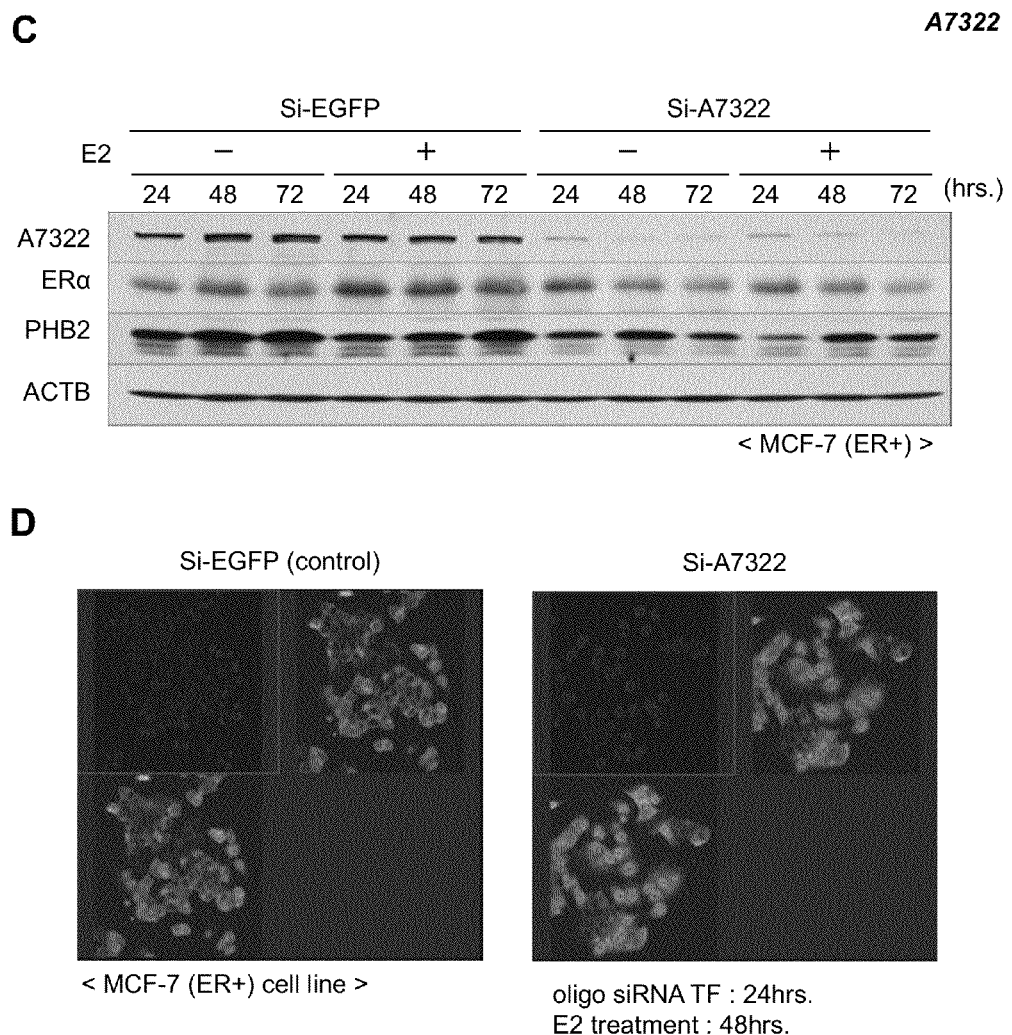

FIG. 10. Inhibition of the Nuclear Translocation of PHB2/REA by A7322.

(A) Sub-cellular localization of PHB2/REA in the presence of A7322. MCF-7 (ER+) cells were transfected with HA-tagged PHB2/REA (green), FLAG-tagged ERα (red), and FLAG-tagged mock (−A7322; left panel) or FLAG-tagged A7322 (red) (+A7322; right panel) for 24 hours and treated with 1 μM of E2 for another 24 hours. Arrow in the left panel shows the nuclear translocation of PHB2/REA in the absence of A7322, while PHB2/REA remained in cytoplasm by the presence of A7322 shown in the right panel.

(B) Same experiments were performed using SK-BR-3 (ER−) cells, showing the inhibition of the nuclear translocation of PHB2/REA by the presence of A7322.

(C) Knockdown expression of A732, ERα and PHB2 at the protein level using siRNA oligonucleotides. The si-EGFP was used as a control siRNA. ACTB served as a loading control for western blotting analysis.

(D) Sub-cellular localization of endogenous PHB2/REA in the absence of A7322. MCF-7 (ER+) cells were treated with si-A7322 or si-EGFP as a control. Twenty-four hours after treatment of siRNAs, cells were treated with E2 for 48 hours, and then were analyzed by immunocytochemical staining.

Figure 11:
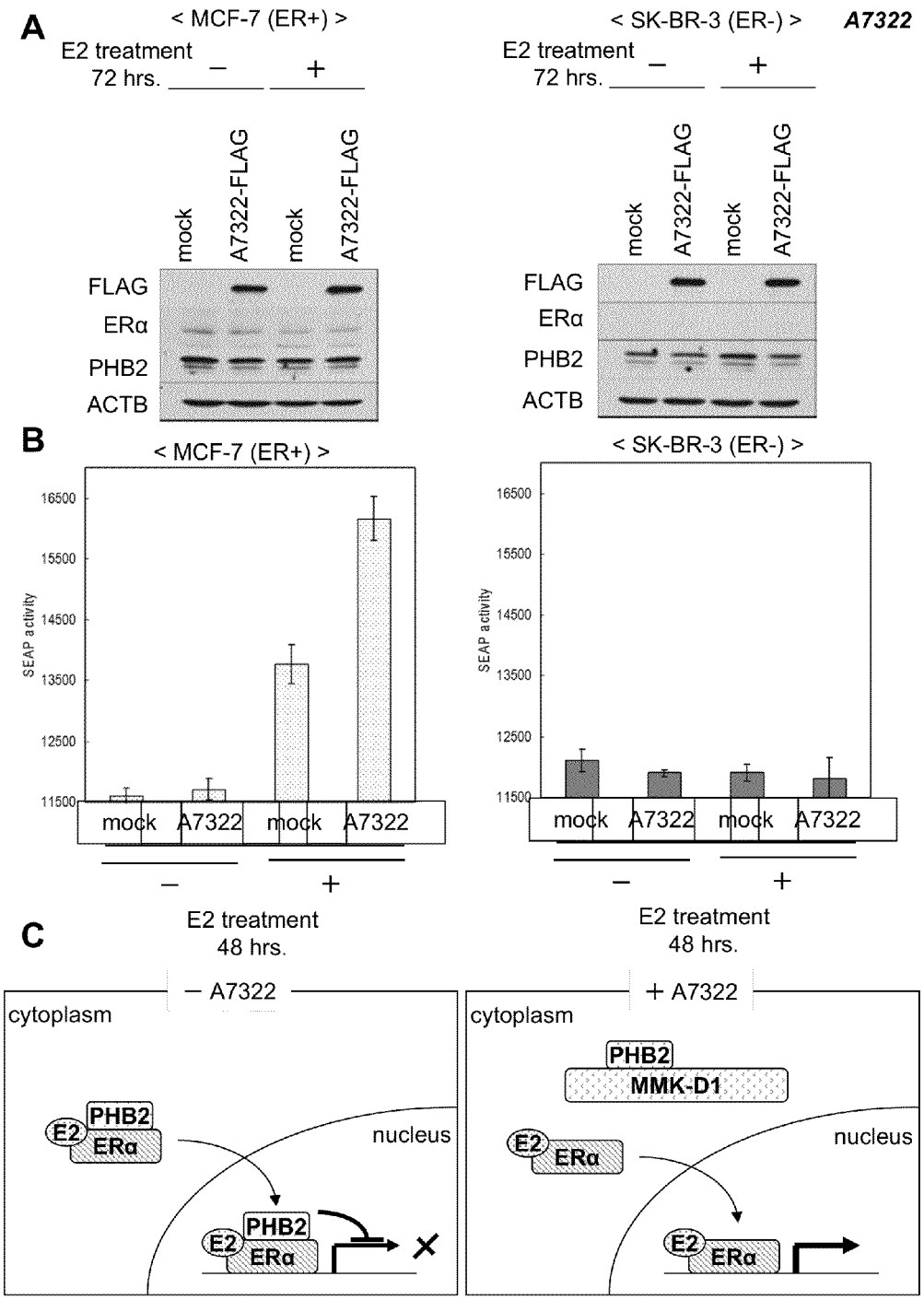

FIG. 11. Enhancement of ER Transcriptional Activity by Inhibition of Nuclear Translocation of Endogenous PHB2/REA.

(A) Expression of exogenous A7322 and endogenous PHB2/REA proteins in MCF-7 and SK-BR-3 cells.

(B) SEAP assay to determine the transcriptional activity of ERα. MCF-7 (ER+) or SK-BR-3 (ER−) cells were co-transfected the FLAG-tagged A7322 (FLAG-A7322) construct and an estrogen responsive reporter gene (pERE-TA-SEAP) construct or a mock control and a pERE-TA-SEAP reporter construct, respectively.

(C) shows Summary of the inhibition of nuclear translocation of PHB2/REA by A7322. In the absence of A7322 (− A7322), PHB2/REA translocates to the nucleus with ERα and repress the transcriptional activity of the estradiol-liganded ERα (left panel). On the other hand, in the presence of A7322 (+ A7322), PHB2/REA binds to A7322 in cytoplasm and inhibit the nuclear translocation of PHB2/REA, urge to enhance the transcriptional activity of ERα (right panel).

Figure 12:
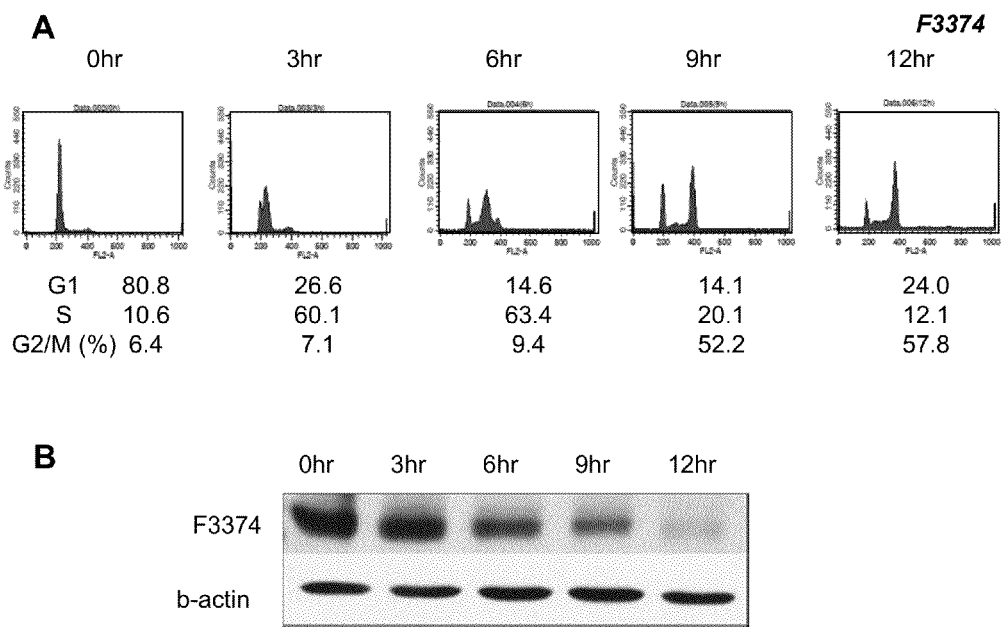

FIG. 12. Cell-Cycle Dependent Expression of F3374.

(A) FACS analysis showed population of T47D cells collected every three hours from 0 to 12 hours after synchronization.

(B) Western blot analysis of F3374 during mitosis in T47D cells. It is notable that expression of F3374 was the highest at 0 to 3 hours (G1/S phase) after the release from the cell-cycle arrest, and its phosphorylation became evident between 9-12 hours (G2/M phase) after the release from cell-cycle arrest.

Figure 13:
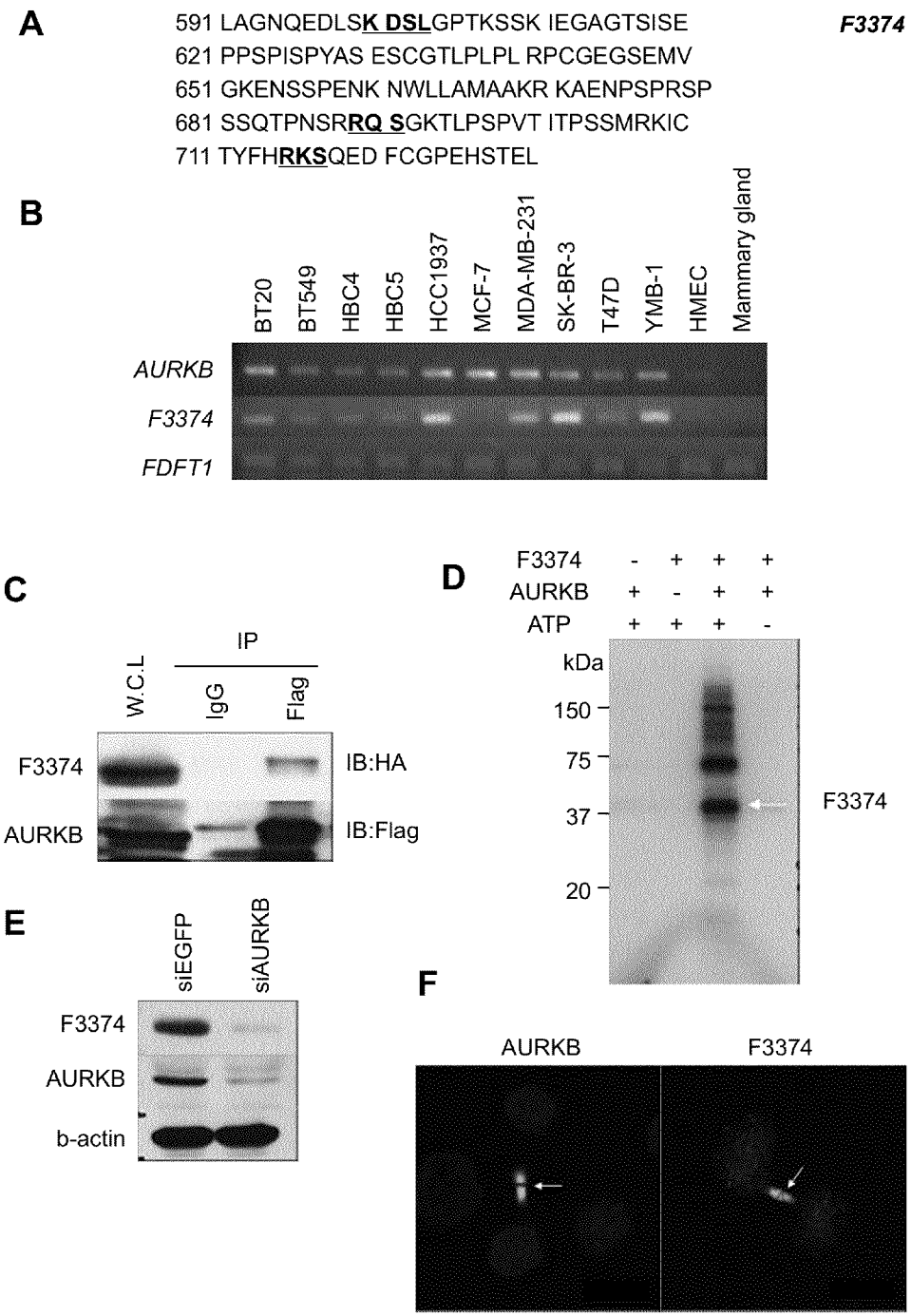

FIG. 13. F3374 Protein Expression was Regulated by AURKB.
- (A) The deduced amino-acid sequence of C-terminal F3374 protein (591-730 amino-acid) (SEQ ID NO:122). The three putative consensus phosphorylation sites for Aurora kinase ([R/K]X[T/S] and [R/K]X[T/S][I/LN]; were indicated by underlines.
- (B) Semi-quantitative RT-PCR experiments for F3374 and AURKB transcripts in 11 breast cancer cell-lines (BT-20, BT549, HBC4, HBC5, HCC1937, MCF-7, MDA-MB-231, SK-BR-3, T47D and YMB-1), human mammary epithelial cell-line (HMEC) and normal mammary gland. FDFT1 was used as a quantitative control.
- (C) Co-immunoprecipitation of F3374 and AURKB proteins. Cell lysates from HEK293T cells transfected with HA-tagged F3374 and Flag-tagged AURKB proteins were immunoprecipitated with either mouse anti-Flag or normal mouse IgG. Immunoprecipitates were immunoblotted using mouse anti-HA antibody. W.C.L indicates whole cell lysates.
- (D) In vitro kinase assay was performed with purified C-terminal recombinant protein of F3374 (36 kDa, including histidine-tag). F3374 recombinant protein was added to the reaction mixture including ARUKB (see text). Arrow indicates phosphorylated F3374.
- (E) Depletion of endogenous expression of AURKB with AURKB specific siRNA treatment led to reduce total amount and phosphorylation of F3374 protein. β-actin served as a quantity control of protein.
- (F) T47D cells were immunocytochemically stained using affinity-purified anti-F3374 and AURKB polyclonal antibodies (green) and DAPI (blue) to discriminate nucleus (see the Materials and Methods). The arrows indicate AURKB and F3374 proteins in cytokinesis in T47D cells, respectively.

Figure 14:
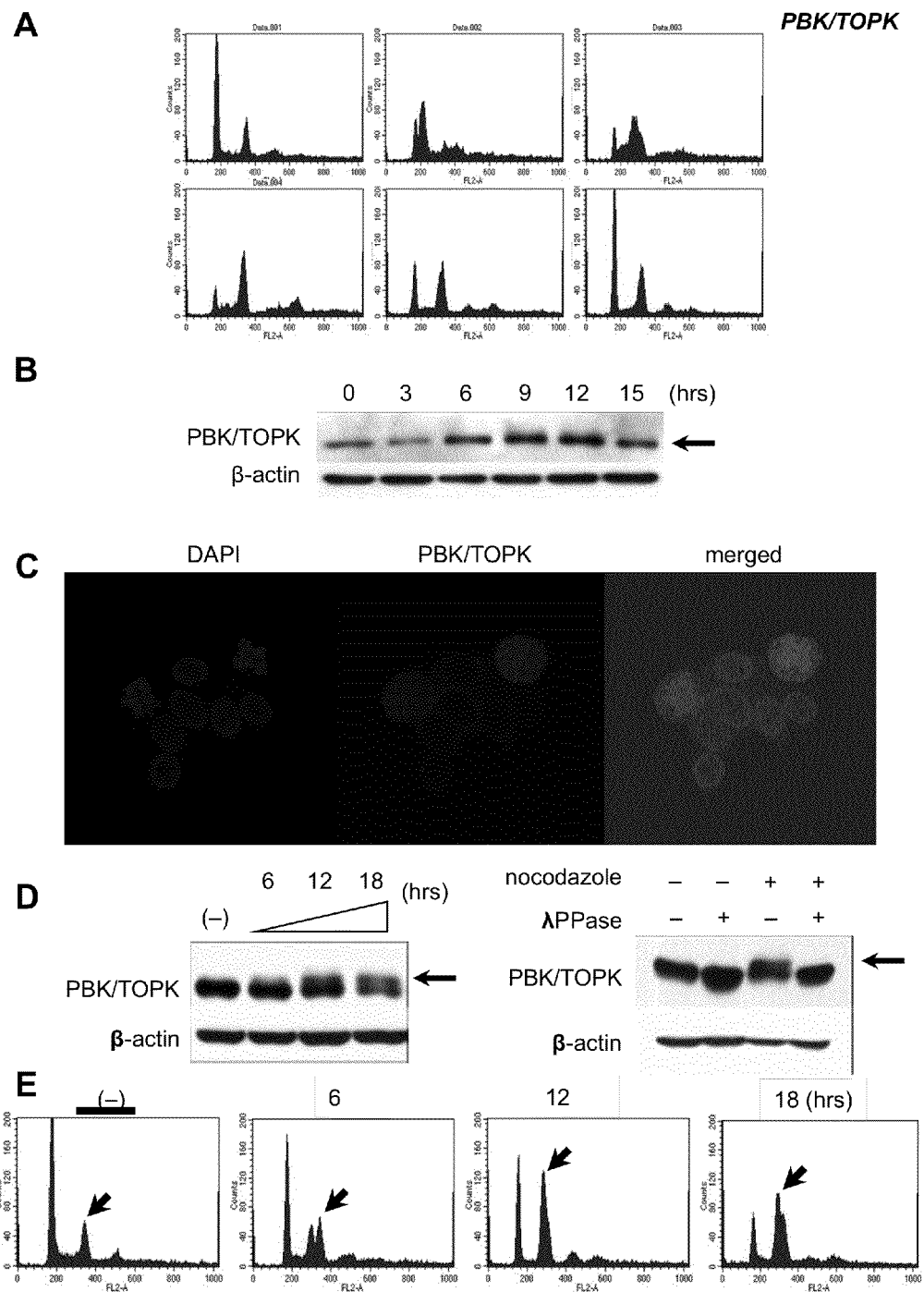

FIG. 14. Phosphorylation of PBK/TOPK Proteins During Mitosis.
- (A) depicts the result of FACS analysis showing a population of cells collected at every 3 h from 0 to 15 h after synchronization.
- (B) depicts the result of Western blotting examining PBK/TOPK expression. It is notable that PBK/TOPK is phosphorylated and up-regulated from 6 to 12 h after cell cycle releasing, which represents G2/M phase as shown in (A).
- (C) shows representative immunocytochemical staining 12 h after cell cycle releasing. Intense staining of endogenous PBK/TOPK was detected near condensed chromosome at prophase or metaphase (indicated by arrows).
- (D) depicts the result of phosphorylation of PBK/TOPK during mitosis. Treatment with 0.3 ug/mL of nocodazole for 6, 12 and 18 h showed time-dependent increased intensity of phosphorylated PBK/TOPK (left panel). The cell lysates were further incubated with/without 1 U of lambda phosphatase for 2 h at 30° C., revealing slowly migrated band indicated by arrows as being the phosphorylated PBK/TOPK protein (right panel).
- (E) depicts the result of FACS analysis showing that the proportion of the cells at G2/M phase (arrow) elevated from 6 to 18 h after treatment with nocodazole.

Figure 15:
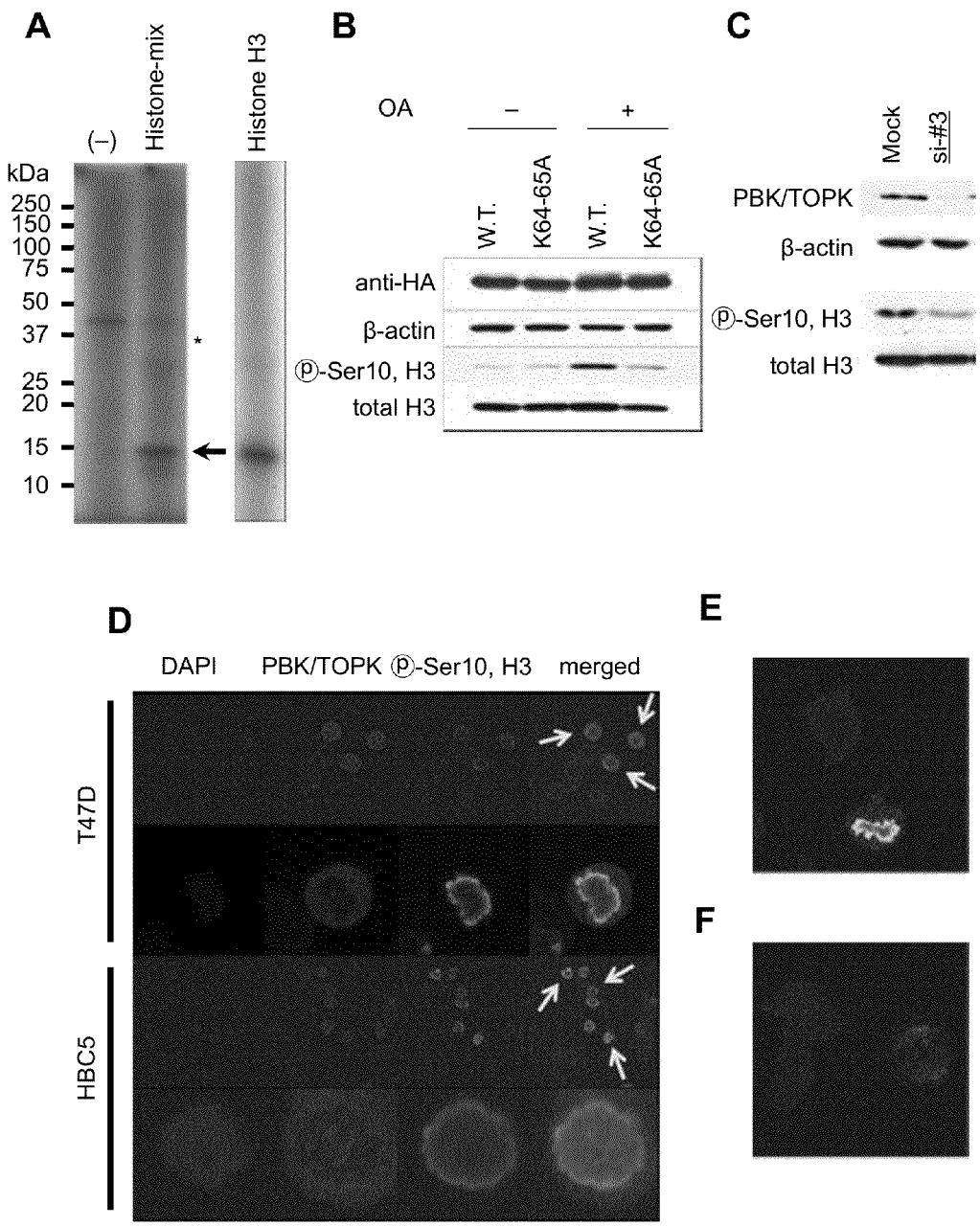

FIG. 15. PBK/TOPK Protein Phosphorylates Ser10-Histone H3 In Vitro and In Vivo.
- (A) depicts the result of in vitro kinase assay performed with purified recombinant protein of PBK/TOPK (40 kDa, including histidine-tag). In addition to PBK/TOPK, histone mixture or histone H3 was added as substrate. Phosphorylated histone H3 and autophosphorylation of PBK/TOPK is indicated by an arrow and asterisk (*), respectively.
- (B) T47D cells were transfected with wild-type and kinase-dead mutant (K64-65A), followed by treatment with 100 nM okadaic acid (OA) for 6 h. OA treatment resulted in phosphorylation of both PBK/TOPK proteins (arrow), but only the wild-type protein induced phosphorylation of H3 as detected by the phosphorylation of Ser10-specific antibody.
- (C) shows that internal expression of PBK/TOPK was silenced in T47D cells by siRNA (si-#3), after transfection and neomycin selection for 2 weeks. Consequently, PBK/TOPK-depletion was accompanied by reduced phosphorylation of histone H3 at Ser10. Beta-actin and total H3 were also examined as a loading control.
- (D) depicts the result of immunocytochemical staining analysis of PBK/TOPK and histone H3. The results showed that PBK/TOPK (red) merged with phosphorylated histone H3 at Ser10 (green) on condensed chromosome (blue) of mitotic cells (prophase) in breast cancer cell-lines, T47D and HBC5.
- (E) shows subcellular localization of PBK/TOPK and phosphorylated histone H3 at serine 10 in metaphase of T47D cells.
- (F) shows that PBK/TOPK expression and histone H3 phosphorylation diminished in anaphase cells (an open arrow). The block arrows indicate cells at interphase.

Figure 16:
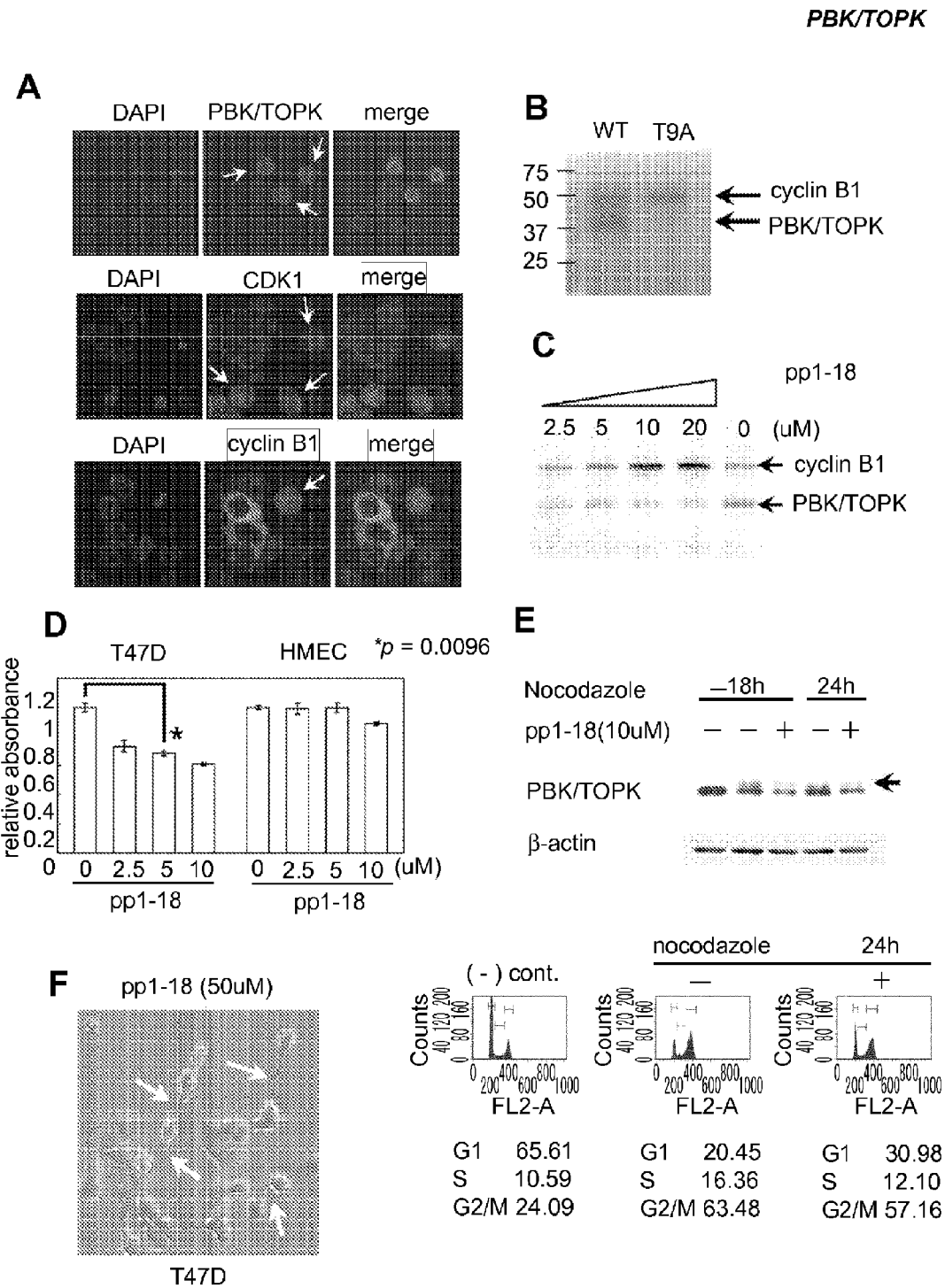

FIG. 16. Phosphorylation of PBK/TOPK Protein by CDK1-Cyclin B1 in Mitotic Cells.
- (A) Nuclear-translocation of endogenous PBK/TOPK, CDK1 and cyclin B1 in mitotic cells of breast cancer cell line, T47D cells. The arrows indicate nuclear-translocation of PBK/TOPK (upper panels), CDK1 (middle panels) and cyclin B1 (lower panels) in mitotic cells.
- (B) PBK/TOPK was directly phosphorylated by CDK1-cyclin B1 in vitro. The wildtype-PBK/TOPK (WT) recombinant protein was phosphorylated by CDK1-cyclin B1 recombinant protein, but alanine-substituted mutant at Thr9-PBK/TOPK (T9A) was not.
- (C) Inhibition of phosphorylation of PBK/TOPK at Thr 9 by CDK1-cyclin B1 by pp1-18 peptide. The efficacy of the peptide blocking the CDK1-cyclin B1-induced phosphoryaltion of TOPK was examined by in vitro kinase assay. The recombinant proteins of TOPK and CDK1-cyclin B1 were incubated with the addition of permeable peptide at the concentration of 0, 5, 10 and 20 μM, respectively. The phosphorylated proteins were observed after SDS-PAGE and autoradiography.
- (D) Treatment of pp1-18 peptide significantly suppressed cell growth of PBK/TOPK-expressing T47D dose-dependently (P=0.0096 Student's t-test). On the other hand, pp1-18 peptide did not affect the growth of PBK/TOPK-negative HMEC cells. The number of viable cells was measured by MTT assay.
- (E) The effect on cell cycle of T47D cells by treatment of pp1-18 peptide. T47D cells were treated with nocodazole (0.3 μg/mL) and subsequently, added with pp1-18 peptide (10 μM) for further 18 or 24 hours before harvest, and then did western blotting analysis using anti-PBK/TOPK antibody and FACS analysis.

(F) Morphological changes of T47D cells treated with 50 µM of pp1-18 peptide by microscopy. The arrows indicate the long intercellular bridge of cells treated with pp1-18 peptide during cytokinesis.

Figure 17:
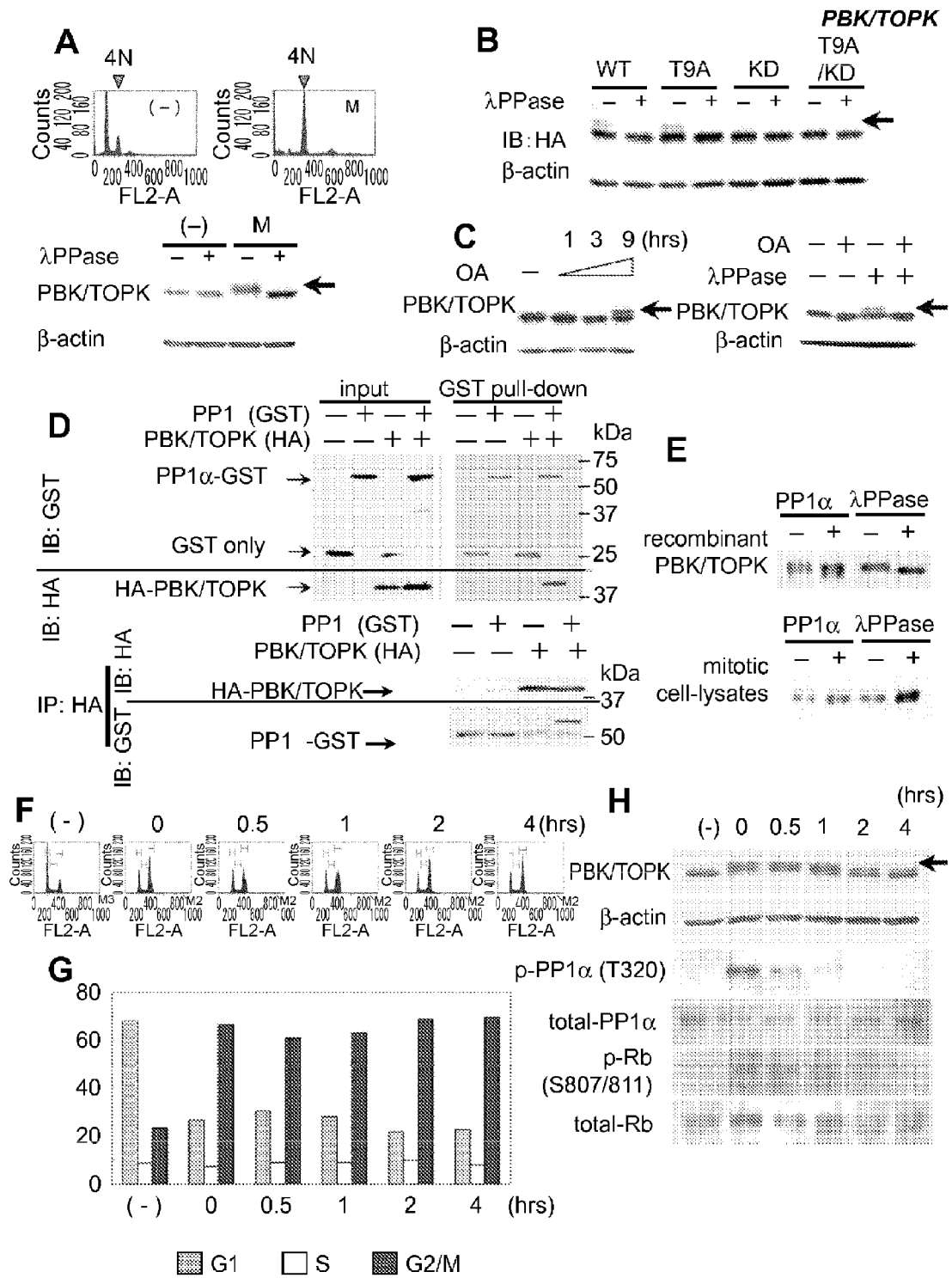

FIG. 17. Autophosphorylation of PBK/TOPK Protein or Phosphorylation of PBK/TOPK Regulated by PP1α in Mitotic Cells and Activation of PBK/TOPK Or Inactivation of PP1α by CDK1.

(A) PBK/TOPK was phosphorylated in mitotic cells. T47D cells were treated with nocodazole for 18 hours, and the performed FACS analysis and lambda phosphatase assay.

(B) Autophosphorylation of PBK/TOPK in mitotic cells. T47D cells were transfected with wild-type TOPK (WT), alanine-substituted mutant at Thr9 (T9A), kinase-dead (KD), and double mutant (T9A/KD), respectively, and performed western blotting analysis using anti-HA monoclonal antibody. WT and T9A were phosphorylated, but KD and T9A/KD were not.

(C) Phosphorylation of PBK/TOPK was induced by treatment of okadaic acid (OA). T47D cells were treated with 100 nM of okadaic acid (OA), and harvested cells at 1, 3 and 9 hours after treatment. The phosphorylated band appeared after 9 hours treatment with OA, and was verified by λPPase assay.

(D) Interaction of PBK/TOPK and PP1α. COS-7 cells were co-transfected with GST-fused PP1α (GST-PP1α and HA-tagged PBK/TOPK (HA-PBK/TOPK), and pull-dowed with equilibrated Glutathione Sepharose 4B beads or immunoprecipitated with anti-HA monoclonal antibody, and subsequently did western blotting analysis using anti-GST or HA monoclonal antibodies.

(E) TOPK was dephosphorylated in mitotic cells by treatment of PP1α as well as treatment or λPPase.

(F) T47D cells were treated with nocodazole for 16 hours, subsequently, incubated with 25 nM of CDK1 inhibitor from 0 to 4 hours before collection, and did FACS analysis.

(G) The population (%) of each cell cycle in various time points (0, 0.5, 1, 2 and 4 hours) after CDK1 inhibitor treatment was graphed.

(H) Equal amounts of total protein were immunoblotted with anti-TOPK monoclonal antibody, anti-phospho-PP1α (Thr320) polyclonal antibody, anti-total-PP1α polyclonal antibody, anti-phospho-Rb (Ser807/811) polyclonal, and anti-total-Rb monoclonal antibody, respectively.

Figure 18:
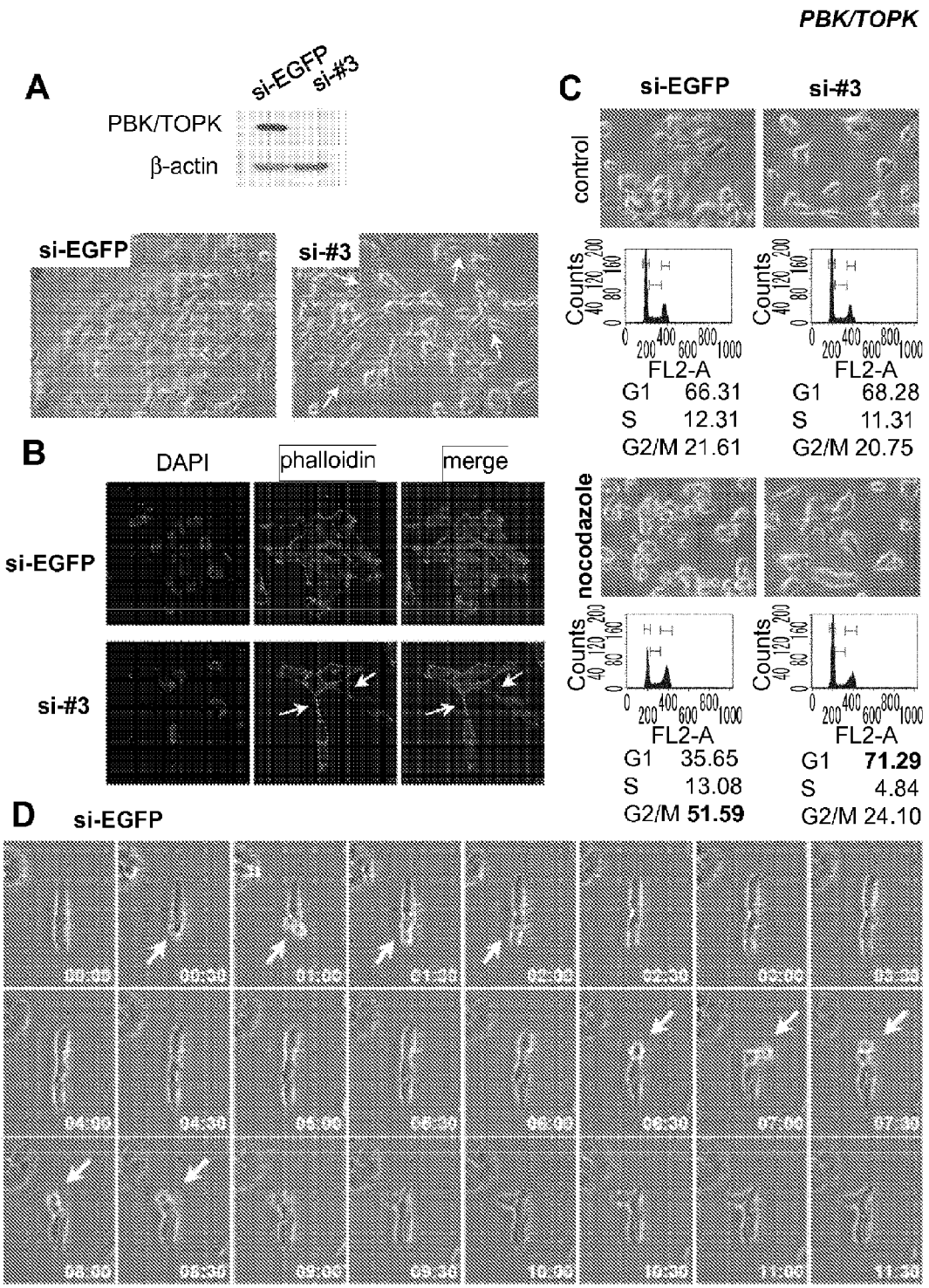
Figure 18:
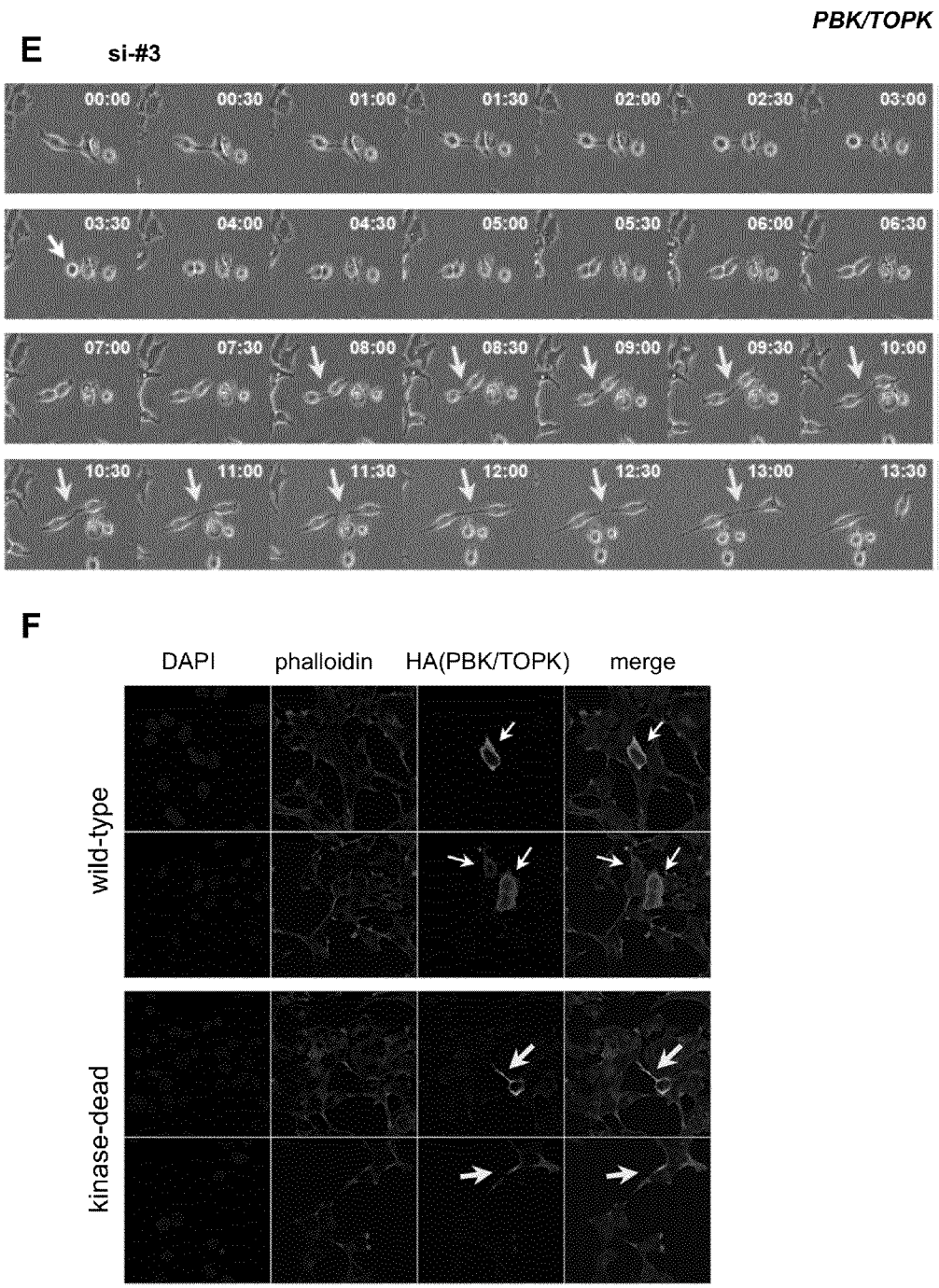

FIG. 18. PBK/TOPK-Depletion by siRNA Resulted in Mitotic Failure and G1 Arrest (A) Western blotting analysis for knockdown of PBK/TOPK expression at protein level by si-TOPK-#3. PBK/TOPK expression was drastically suppressed in si-TOPK-#3-treated T47D cells compared with in siEGFP-treated cells. β-actin was served as a control of western blotting analysis.

(B) Cellular morphology was observed by a phase contrast microscopy at 2 days after transfection with si-TOPK-#3 or siEGFP (upper panels). Cellular morphology was also investigated by immunocytochemical staining 2 days after transfection with si-TOPK-#3 or siEGFP (lower panels). To clarify a shape of cell, the actin structure was stained with Alexa Fluor 594 phalloidin, and nuclei were counter-stained with DAPI.

(C) T47D cells were transfected with si-TOPK-#3 or siEGFP. Two days after transfection, cells were treated with 0.3 µg/mL of nocodazole and incubated for additional 24 hours. Cellular morphology and cell cycle were investigated by a phase contrast microscopy and FACS analyses, respectively.

(D) T47D cells were transfected with si-EGFP as a control, and the duration of cell mitosis was measured by a Time-lapse microscopy.

(E) T47D cells were transfected with TOPK-#3 and the duration of cell mitosis was measured by a Time-lapse microscopy.

(F) T47D cells were transfected with wildtype (WT) or kinase-dead of HA-tagged TOPK-expression vectors, and subsequently were transfected with si-EGFP or si-TOPK-#3, respectively. Forty-eight hours after transfection of each siRNA, we did immunocytochemical staining. The exogenously expressed TOPK proteins were immunostained with anti-HA monoclonal antibody. The actin structure was stained with Alexa Fluor 594 phalloidin diluted, and nuclei were counter-stained with DAPI.

Figure 19:
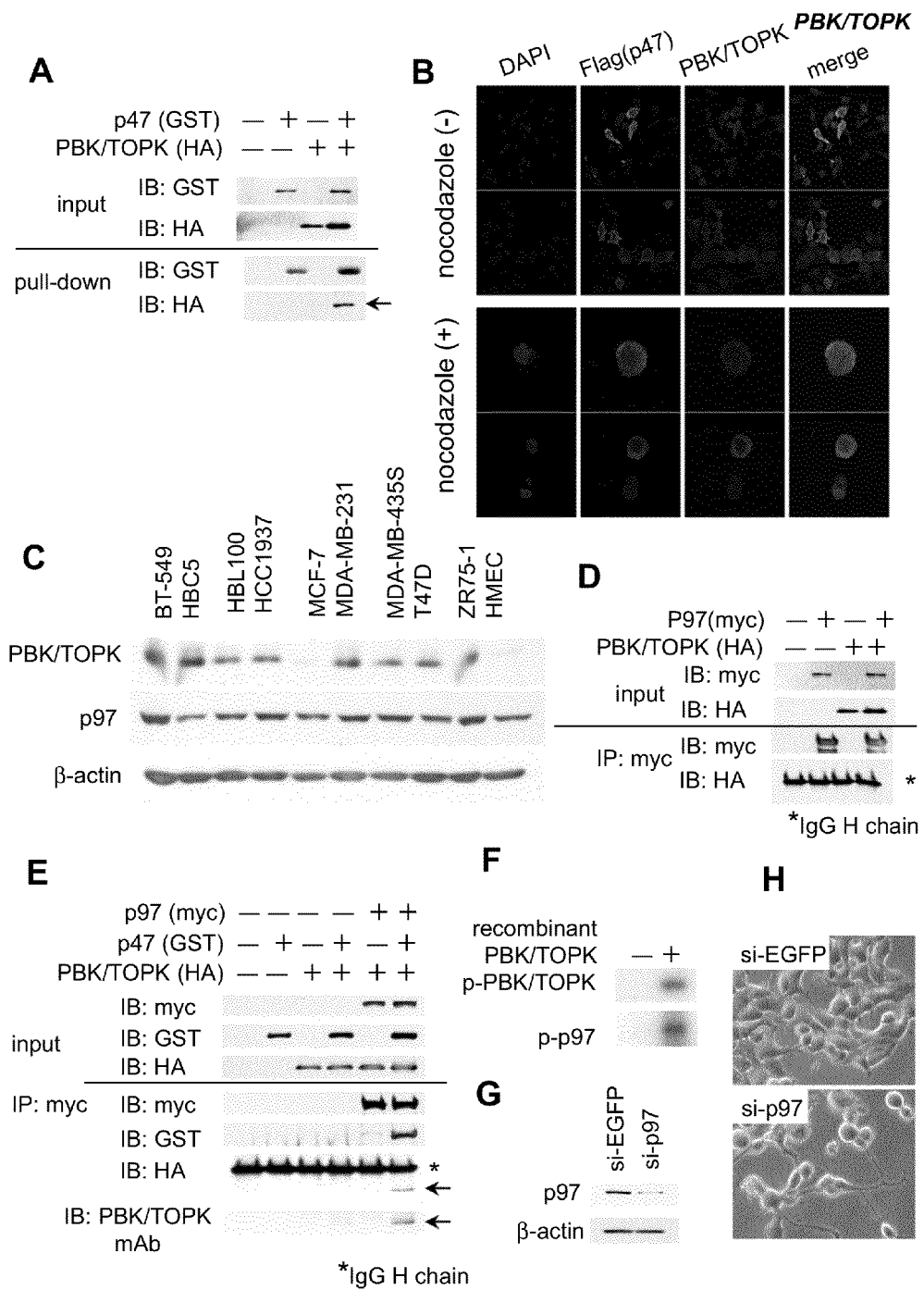

FIG. 19. PBK/TOPK Phosphorylates p97/VCP Protein In Vitro and In Vivo (A) Interaction of PBK/TOPK with p47 protein. COS-7 cells were transfected with HA-tagged PBK/TOPK (HA-PBK/TOPK) construct, and then were lysed with lysis buffer. Subsequently, cell lysates were mixed together with GST-tagged p47 (GST-p47) recombinant proteins, and then pull-downed with GST-beads. Immunoblotting of the precipitates using anti-HA antibodies indicated that GST-p47 was co-precipitated with HA-PBK/TOPK.

(B) The colocalization of the exogenously expressed P47 and endogenous PBK-TOPK in T47D cells with or without nocodazole treatment.

(C) Expression pattern of p97 and PBK/TOPK proteins in breast cancer cell lines. Equal amounts of total protein were prepared from breast cancer cell-lines (BT-549, HBC5, HCC1937, MCF-7, MDA-MB-231, MDA-MB-4355, T47D, and ZR75-1) and HBL100, and a human mammalian epithelial cell-line (HMEC). After SDS-PAGE and membrane transfer, the proteins were immunoblotted with anti-TOPK monoclonal antibody or anti-p97 polyclonal antibody. β-actin was served as a control of western blotting analysis.

(D) Interaction of PBK/TOPK and p97 protein by co-IP experiments. We co-transfected with HA-PBK/TOPK and myc-tagged p97 (myc-p97) constructs into COS7 cells, and then co-immunoprecipitated with HA-tag antibody. HA-PBK/TOPK did not directly interact with myc-p97.

(E) PBK/TOPK binds to p47/p97 complex via p47 protein as an adaptor. COS-7 cells were tri-transfected with GST-fused p47, myc-tagged p97, or HA-tagged TOPK constructs. The complex among those proteins were immunoprecipitaed using anti-GST antibody or anti-myc monoclonal antibody, and then western blotting with anti-HA or -myc monoclonal antibodies, respectively. After washing five times with lysis buffer and SDS-PAGE, those interactions between proteins were investigated as mentioned above.

(F) in vitro kinase assay for p97. The immuonoprecipitated p97 protein was incubated with recombinant TOPK protein for 30 minutes at 30° C.

(G) T47D cells were transfected with 100 µmol each of the siRNA duplexes of si-EGFP and si-p97. (H) Two days after transfection with the siRNAs, cellular morphology was observed by a phase contrast microscopy.

DETAILED DESCRIPTION OF THE PREFERRED EMBODIMENTS

Overview

In an effort to understand the carcinogenic mechanisms associated with cancer and identify potential targets for developing novel anti-cancer agents, large scale analyses of gene expression patterns in purified populations of breast cancer cells were performed using a cDNA microarray representing 27,648 genes. More particularly, to isolate novel molecular targets for treatments of breast cancer, using a combination of cDNA microarray and laser beam microdissection, precise genome-wide expression profiles of 81 breast tumors were examined.

Among the up-regulated genes, the present inventors focused on A7322 whose expressions were up-regulated in the majority of breast cancer specimens. Subsequent semi-quantitative RT-PCR and Northern blot confirmed that A7322 was up-regulated in clinical breast cancer specimens and breast cancer cell lines, but not expressed in normal organs except brain. Since the assembled cDNA sequence of A7322 in the NCBI database was shorter than an approximately 15 kb transcript from northern blot analysis, the present inventors performed exon-connection and 5' RACE experiments to obtain full-length of A7322 mRNA. Finally a cDNA sequence of 14,763 nucleotides (Genbank accession Number; AB252196), containing an open reading frame of 6,534 nucleotides (172-6702 of SEQ ID NO: 79) encoding a 2,177 amino-acid protein was obtained. The simple modular architecture research tool (SMART) program revealed that the predicted A7322 protein contained a Sec7 domain between codon 586 and 798 required for proper protein transport through the Golgi.

Furthermore, the present inventors identified PHB2/REA (GenBank Accession No. NM_007273) as an A7322-interacting protein. A7322 and PHB2/REA co-localize in the cytoplasm of breast cancer cells. A7322 functions in breast carcinogenesis by reactivation of ERα through inhibition of nuclear-translocation of the PHB2/REA protein.

Among the up-regulated genes, inventors also focused on identification of the full-length cDNA sequences of F3374V1 comprising 4,221 nucleotides (GenBank accession; NM_016448), with an open reading frame of 2,193 nucleotides that encodes a 730 amino-acid polypeptide. The F3374V1 gene has 15 exons. RT-PCR showed F3374V1 (1,296 bp) was dominantly overexpressed in breast cancer cells as compared with normal human tissues. Subsequent semi-quantitative RT-PCR and Northern blot analyses confirmed that F3374 was over-expressed in 10 of 12 breast cancer specimens and all tested breast cancer cell lines, compared with normal human tissues except testis, thymus, placenta and bone marrow. Immunohistochemical staining analysis using an anti-F3374 polyclonal antibody that detected the endogenous F3374 showed cell cycle-dependent localization in breast cancer cells.

Treatment of breast cancer cells with small interfering RNAs (siRNAs) effectively inhibited the expression of A7322 and F3374, and suppressed cell/tumor growth of breast cancer cell lines BT-549 and BT-474 for A7322, or cell lines T47D and HBC4 for F3374, showing that these genes play a key role in cell growth proliferation. These findings are consistent with the conclusion that overexpression of A7322 and F3374 is involved in breast tumorigenesis and provides promising strategies for specific treatment for breast cancer patients.

Furthermore, the present inventors found interaction of F3374 protein with and its phosphorylation by the mitotic kinase Aurora-B (AURKB). It was demonstrated that depletion of the mitotic kinase AURKB expression with siRNA in breast cancer cells reduced the phosphorylation of F3374 protein and decreased the stability of the F3374 protein.

Thus, genes A7322 and F3374, that were significantly over-expressed in breast cancer cells were isolated. It was confirmed by semi-quantitative RT-PCR and Northern blot analysis that the expression patterns of A7322 and F3374 were specifically overexpressed in breast cancer cells. It was reported previously that ESTs of both A7322 and F3374 were up-regulated in bladder cancers and non-small cell lung cancers. However, the relationship of these genes to breast cancer was previously unknown. Furthermore, the invention provides for the first time the full length nucleotide sequences of these genes.

The present inventors focused on the PBK/TOPK gene among the genes detected using cDNA microarray techniques to be over-expressed in breast cancers but not expressed in normal human tissues except testis and thymus Immunohistochemical analysis also supported the high level of endogenous PBK/TOPK expression as consistent with the results of Northern blot analysis. In addition, knock down of the endogenous PBK/TOPK expression via siRNA techniques resulted in growth suppression of breast cancer cell-lines (FIGS. 5A and B), demonstrating an oncogenic role of PBK/TOPK gene in breast cancer cells.

In addition to hitherto reported important roles of PBK/TOPK in testis, findings by the present inventors of its sub-cellular translocation during M-phase indicated its critical function at mitosis in cancer cells. Moreover, knockdown of PBK/TOPK expression with specific-siRNAs was demonstrated to cause dysfunction of cytokinesis and subsequently led to apoptosis of cancer cells (FIG. 5C to F). These results are consistent with the conclusion that PBK/TOPK plays an important role in cell division and cytokinesis. It is notable that microscopic and FACS observations for the siRNA effect of PBK/TOPK are quite similar with those of Annexin 11 which is required for cytokinesis completion; knockdown of Annexin 11 resulted in narrow cytoplasmic bridge and increased population of cells at sub-G1 (Tomas A et al., J Cell Biol 2004, 165: 813-22).

Since PBK/TOPK contains a kinase domain, the present inventors treated the cells with several kinds of stimuli including OA (okadaic acid), PMA (phorbol 12-myristate 13-acetate), β-estradiol, and nocodazole in order to investigate its relationship with estrogen receptor and cell mitotic signals, respectively (data not shown). Among these stimuli, OA, a specific inhibitor of serine/threonine protein phosphatase causing mitosis-like processes in interphase cells, chromosome condensation, and entry into mitosis in the Cdc2 independent manner (Ajiro K et al., J Biol Chem 1996, 271: 13197-201; Gowdy P M et al., J Cell Sci 1998, 111: 3401-10), was found to cause phosphorylation of PBK/TOPK.

In contrast to the prediction that PBK/TOPK is an upstream kinase of p38 (Abe Y et al., J Biol Chem 2000, 275: 21525-31) and p42/ERK2, which was up-regulated commonly in breast cancer cell-lines, in vitro kinase assays failed to show phosphorylation of these proteins (data not shown). Instead, as first reported in the present invention, high selective phosphorylation of histone H3 was observed with PBK/TOPK. Interestingly, phosphorylation at the N-terminus of histone H3 (Ser10) indicates that this phosphorylation step is an early mitotic event, accompanied with chromosome condensation after OA treatment (Ajiro K et al., J Biol Chem 1996, 271: 13197-201).

Further, since immunostaining experiments using breast cancer cells revealed subcellular localization of PBK/TOPK around the chromosome in the cells at mitosis, especially at pro- and metaphase (FIG. 8C), PBK/TOPK was examined to determine whether it phosphorylates histone H3 at serine 10 in vivo. A comparison of the wild-type and kinase-dead (K64-65A mutant: lysine 64 and 65 in SEQ ID NO: 92 change to alanine mutant) PBK/TOPK proteins with or without OA stimulation demonstrated that PBK/TOPK phosphorylated serine 10 of histone H3 (FIG. 9B), and endogenous PBK/TOPK protein merged well with phosphorylated histone H3 in mitotic cells (FIG. 9D).

Cell-cycle-dependent Ser10 phosphorylation of histone H3 correlates with PBK/TOPK expression level and localization, particularly in the early stage of mitosis (FIGS. 9D and E). Therefore, the PBK/TOPK-histone H3 pathway promotes mitotic events and thus enhances cancer cell proliferation, similarly to Pak1 whose significant role in breast cancer cells has been indicated (Li F et al., EMBO Rep 2002, 3: 767-73). However, morphological changes of the cells in which PBK/TOPK was knocked down by siRNA implied presence of other substrates involved in cytokinesis (FIG. 5).

The present invention is based in part on the discovery that PBK/TOPK is over-expressed in breast cancer and its kinase activity plays a significant role in mammary carcinogenesis including breast cancer cell growth. Furthermore, the fact that PBK/TOPK expression pattern as the cancer/testis antigen demonstrates PBK/TOPK to be a promising molecular target for breast cancer therapy through cancer vaccine-mediated immunotherapy and/or inhibition of PBK/TOPK-specific kinase function. Thus, the use of PBK/TOPK kinase activity as an index provides strategies to develop anti-cancer agents.

DEFINITIONS

The words "a", "an", and "the" as used herein mean "at least one" unless otherwise specifically indicated.

The gene(s) that differentially expressed in breast cancer ("BC") are collectively referred to herein as "BC gene(s)", "BC nucleic acid(s)" or "BC polynucleotide(s)" and the corresponding encoded polypeptides are referred to as "BC polypeptide(s)" or "BC protein(s)". BC gene is selected from the group consisting of A7332, F3374V1, PHB2/REA and PBK/TOPK genes.

Unless otherwise defined, all technical and scientific terms used herein have the same meaning as commonly understood by one of ordinary skill in the art to which this invention belongs. In case of conflict, the present specification, including definitions, will control.

Nucleotides, Polypeptides, Vectors and Host Cells

The present invention encompasses the human gene A7322, including a polynucleotide sequence as described in SEQ ID NO: 79, as well as degenerates and mutants thereof, to the extent that they encode an A7322 protein, including the amino acid sequence set forth in SEQ ID NO: 80 or its functional equivalent. Examples of polypeptides functionally equivalent to A7322 include, for example, homologous proteins of other organisms corresponding to the human A7322 protein, as well as mutants of human A7322 proteins.

The present invention also encompasses novel human gene F3374V1 including polynucleotide sequences described in SEQ ID NO: 81, as well as degenerates and mutants thereof, to the extent that they encode an F3374V1 protein, including the amino acid sequence set forth in SEQ ID NO: 82 or its functional equivalent. Examples of polypeptides functionally equivalent to F3374V1 include, for example, homologous proteins of other organisms corresponding to the human F3374V1 protein, as well as mutants of human F3374V1 protein. However, those mutants keep the phosphorylation region, e.g. 591aa to 730aa of F3374V1 but not restricted.

The nucleotide sequence of human PHB2/REA gene is shown in SEQ ID NO: 89 and also available as GenBank Accession No. NM_007273.3. The amino acid sequence encoding the human PHB2/REA gene is shown in SEQ ID NO: 90 and is also available as GenBank Accession No. NP_009204. In the present invention, the polypeptide encoded by the PHB2/REA gene is referred to as "PHB2/REA", and sometimes as "PHB2/REA polypeptide" or "PHB2/REA protein".

The nucleotide sequence of human AURKB gene is shown in SEQ ID NO: 87 and also available as GenBank Accession No. NM_004217. The amino acid sequence encoding the human AURKB gene is shown in SEQ ID NO: 88. In the present invention, the polypeptide encoded by the AURKB gene is referred to as "AURKB", and sometimes as "AURKB polypeptide" or "AURKB protein".

The nucleotide sequence of human PBK/TOPK gene is shown in SEQ ID NO: 91 and is also available as GenBank Accession No. AF237709. Herein, the phrase "PBK/TOPK gene" encompasses the human PBK/TOPK gene as well as those of other animals including non-human primate, mouse, rat, dog, cat, horse, and cow but are not limited thereto, and includes allelic mutants and genes found in other animals as corresponding to the PBK/TOPK gene. The amino acid sequence encoding the human PBK/TOPK gene is shown in SEQ ID NO: 92 and is also available as GenBank Accession No. AAF71521.1. In the present invention, the polypeptide encoded by the PBK/TOPK gene is referred to as "PBK/TOPK", and sometimes as "PBK/TOPK polypeptide" or "PBK/TOPK protein".

The nucleotide sequence of human CDK1 gene is shown in SEQ ID NO: 94 and is also available as GenBank Accession No. NM_001786. Herein, the phrase "CDK1 gene" encompasses the human CDK1 gene as well as those of other animals including non-human primate, mouse, rat, dog, cat, horse, and cow but are not limited thereto, and includes allelic mutants and genes found in other animals as corresponding to the CDK1 gene. The amino acid sequence encoding the human CDK1 gene is shown in SEQ ID NO: 95, the polypeptide encoded by the CDK1 gene is referred to as "CDK1", and sometimes as "CDK1 polypeptide" or "CDK1 protein".

The nucleotide sequence of human CyclinB1 gene is shown in SEQ ID NO: 96 and is also available as GenBank Accession No. NM_031966. Herein, the phrase "CyclinB gene" encompasses the human CyclinB1 gene as well as those of other animals including non-human primate, mouse, rat, dog, cat, horse, and cow but are not limited thereto, and includes allelic mutants and genes found in other animals as corresponding to the CyclinB1 gene. The amino acid sequence encoding the human CyclinB1 gene is shown in SEQ ID NO: 97. In the present invention, the polypeptide encoded by the CyclinB1 gene is referred to as "CyclinB1", and sometimes as "CyclinB1 polypeptide" or "CyclinB1 protein".

The nucleotide sequence of human Protein Phosohatase 1-alpha (PP1α gene is shown in SEQ ID NO: 115 and is also available as GenBank Accession No. NM_002708. Herein, the phrase "PP1α gene" encompasses the human PP1α gene as well as those of other animals including non-human primate, mouse, rat, dog, cat, horse, and cow but are not limited thereto, and includes allelic mutants and genes found in other animals as corresponding to the PP1α gene. The amino acid sequence encoding the human PP1α gene is shown in SEQ ID NO: 116. In the present invention, the polypeptide encoded by the PP1α gene is referred to as "PP1α", and sometimes as "PP1α polypeptide" or "PP1α protein".

The nucleotide sequence of human p47 gene is shown in SEQ ID NO: 117 and is also available as GenBank Accession No. NM_016143. Herein, the phrase "p47 gene" encompasses the human p47 gene as well as those of other animals including non-human primate, mouse, rat, dog, cat, horse, and cow but are not limited thereto, and includes allelic mutants and genes found in other animals as corresponding to the p47 gene. The amino acid sequence encoding the human p47 gene is shown in SEQ ID NO: 118. In the present invention, the polypeptide encoded by the p47 gene is referred to as "p47", and sometimes as "p47 polypeptide" or "p47 protein".

The nucleotide sequence of human p97 gene is shown in SEQ ID NO: 119 and is also available as GenBank Accession No. NM_007126. Herein, the phrase "p97 gene" encompasses the human p97 gene as well as those of other animals including non-human primate, mouse, rat, dog, cat, horse, and cow but are not limited thereto, and includes allelic mutants and genes found in other animals as corresponding to the p97 gene. The amino acid sequence encoding the human p97 gene is shown in SEQ ID NO: 120. In the present invention, the polypeptide encoded by the p97 gene is referred to as "p97", and sometimes as "p97 polypeptide" or "p97 protein"

Methods for preparing polypeptides functionally equivalent to a given protein are well known by a person skilled in the art and include known methods of introducing mutations into the protein. For example, one skilled in the art can prepare polypeptides functionally equivalent to the human BC proteins or AURKB by introducing an appropriate mutation in the amino acid sequence of either of these proteins by site-directed mutagenesis (Hashimoto-Gotoh et al., Gene 152:271-5 (1995); Zoller and Smith, Methods Enzymol 100: 468-500 (1983); Kramer et al., Nucleic Acids Res. 12:9441-9456 (1984); Kramer and Fritz, Methods Enzymol 154: 350-67 (1987); Kunkel, Proc Natl Acad Sci USA 82: 488-92 (1985); Kunkel, Methods Enzymol 204: 125-139 (1991)). Amino acid mutations can occur in nature, too. The polypeptide of the present invention includes those proteins having the amino acid sequences of the human BC proteins or AURKB in which one or more amino acids are mutated, provided resulting mutated polypeptides that are functionally equivalent to the human BC proteins or AURKB. The number of amino acids to be mutated in such a mutant is generally 10 amino acids or less, preferably 6 amino acids or less, and more preferably 3 amino acids or less.

The terms "polypeptide", "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

The terms "gene", "polynucleotides", "oligonucleotide", "nucleotides" and "nucleic acids" are used interchangeably herein unless otherwise specifically indicated and are similarly to the amino acids referred to by their commonly accepted single-letter codes. The terms apply to nucleic acid (nucleotide) polymers in which one or more nucleic acids are linked by ester bonding. The polynucleotide, oligonucleotide, nucleotides, or nucleic acids may be composed of DNA, RNA or a combination thereof.

As use herein, the term "double-stranded molecule" refers to a nucleic acid molecule that inhibits expression of a target gene including, for example, short interfering RNA (siRNA; e.g., double-stranded ribonucleic acid (dsRNA) or small hairpin RNA (shRNA)) and short interfering DNA/RNA (siD/RNA; e.g. double-stranded chimera of DNA and RNA (dsD/R-NA) or small hairpin chimera of DNA and RNA (shD/R-NA)).

In the present invention, the term "functionally equivalent" means that the subject polypeptide has the activity to promote cell proliferation like the BC proteins and to confer oncogenic activity to cancer cells. Assays for determining such activities are well known in the art. For example, whether the subject polypeptide has a cell proliferation activity or not can be judged by introducing the DNA encoding the subject polypeptide into a cell expressing the respective polypeptide, and detecting promotion of proliferation of the cells or increase in colony forming activity. Such cells include, for example, COST and NIH3T3 cells.

In some embodiments of the present invention, Sec7 domain is conserved in a functional equivalent of A7332 to maintain the biological activity of A7332 polypeptide. Sec7 domain of A7332 polypeptide corresponds to positions 139 (Ala) to 209 (Val) of the amino acid sequence of SEQ ID NO: 80 which is encoded by codon 586 and 798 of the nucleotide sequence of SEQ ID NO: 79. In the present invention, the biological activity of A7332 or F3374V1 polypeptide includes cell proliferative activity. Accordingly, functional equivalents of the present invention have cell proliferative activity.

In some embodiments of the present invention, functional equivalents are also included in the A7322 polypeptide. Herein, a "functional equivalent" of a protein is a polypeptide that has a biological activity, in particular, has binding activity to PHB2/REA and has an activity of nuclear-translocation of the PHB2/REA protein. Namely, any polypeptide that retains the PHB2/REA binding domain of the A7322 protein may be used as such a functional equivalent in the present invention. Such functional equivalents include those wherein one or more amino acids are substituted, deleted, added, or inserted to the natural occurring amino acid sequence of the A7322 protein.

Alternatively, functional equivalents are also included in the PHB2/REA polypeptide. Herein, a "functional equivalent" of a protein is a polypeptide that has a biological activity, in particular, the binding activity to A7322 equivalent to the protein. Namely, any polypeptide that retains the A7322 binding domain of PHB2/REA protein may be used as such a functional equivalent in the present invention. Such functional equivalents include those wherein one or more amino acids are substituted, deleted, added, or inserted to the natural occurring amino acid sequence of the PHB2/REA protein.

In preferable embodiments of the present invention, functional equivalents are also included in the F3374V1 polypeptide. Herein, a "functional equivalent" of a protein is a polypeptide that has a biological activity, in particular, has binding activity to AURKB and is phosphorylated by AURKB. Namely, any polypeptide that retains the binding domain and phosphorylated site of the F3374V1 protein may be used as such a functional equivalent in the present invention. Such functional equivalents include those wherein one or more amino acids are substituted, deleted, added, or inserted to the natural occurring amino acid sequence of the F3374V1 protein.

Alternatively, functional equivalents are also included in the AURKB polypeptide. Herein, a "functional equivalent" of a protein is a polypeptide that has a biological activity, in particular, the binding and phosphorylating activity against F3374V1 equivalent to the protein. Namely, any polypeptide that retains the binding and phosphorylating activity against F3374V1 of the AURKB protein may be used as such a functional equivalent in the present invention. Such functional equivalents include those wherein one or more amino acids are substituted, deleted, added, or inserted to the natural occurring amino acid sequence of the AURKB protein.

In preferable embodiments of the present invention, functional equivalents are also includes in the PBK/TOPK polypeptide. Herein, a "functional equivalent" of a protein is a polypeptide that has a biological activity, in particular, the phosphorylating activity equivalent to the protein. Namely, any polypeptide that retains the phosphorylating activity of the PBK/TOPK protein may be used as such a functional equivalent in the present invention. Such functional equivalents include those wherein one or more amino acids are substituted, deleted, added, or inserted to the natural occurring amino acid sequence of the PBK/TOPK protein.

Mutated or modified proteins, proteins having amino acid sequences modified by substituting, deleting, inserting, and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

Conservative substitution tables providing functionally similar amino acids are well known in the art. Such conservatively modified variants are in addition to and do not exclude polymorphic variants, interspecies homologs, and alleles of the invention. For example, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

Such conservatively modified polypeptides are included in the present BC proteins and AURKB protein. However, the present invention is not restricted thereto and the BC proteins and AURKB protein includes non-conservative modifications so long as they retain the phsphorylating activity of the BC proteins and AURKB. The number of amino acids to be mutated in such a modified protein is generally 10 amino acids of less, preferably 6 amino acids of less, and more preferably 3 amino acids or less.

An example of a polypeptide to which one or more amino acids residues are added to the amino acid sequence of human BC proteins or AURKB protein is a fusion protein containing the human BC proteins or AURKB protein. Fusion proteins, fusions of the human BC proteins or AURKB protein and other peptides or proteins, are included in the present invention. Fusion proteins can be made by techniques well known to a person skilled in the art, such as by linking a DNA encoding a human BC proteins or AURKB protein of the present invention with DNA encoding another peptide or protein, so that the frames match, inserting the fusion DNA into an expression vector, and expressing it in a host. There is no restriction as to the peptides or proteins fused to the protein of the present invention.

Known peptides that can be used as peptides that are fused to the protein of the present invention include, for example, FLAG (Hopp et al., Biotechnology 6: 1204-10 (1988)), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, β-tubulin fragment, B-tag, Protein C fragment, and the like. Examples of proteins that may be fused to a protein of the invention include GST (glutathione-5-transferase), Influenza agglutinin (HA), immunoglobulin constant region, β-galactosidase, MBP (maltose-binding protein), and such.

Fusion proteins can be prepared by fusing commercially available DNA, encoding the fusion peptides or proteins discussed above, with the DNA encoding the polypeptide of the present invention and expressing the fused DNA prepared.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with a whole or part of the DNA sequence encoding the human BC proteins or AURKB protein (i.e., SEQ ID NO: 80, 82, 90, 92 or 88), and isolate functionally equivalent polypeptides to the human BC proteins or AURKB protein from the isolated DNA. The polypeptides of the present invention include those that are encoded by DNA that hybridize with a whole or part of the DNA sequence encoding the human BC proteins or AURKB protein and are functionally equivalent to the human BC proteins or AURKB protein. These polypeptides include mammal homologues corresponding to the protein derived from human (for example, a polypeptide encoded by a monkey, rat, rabbit and bovine gene). For example, in isolating a cDNA highly homologous to a DNA encoding the human A7322 protein from animals, it is particularly preferable to use tissues from testis or breast cancer cell line. Alternatively, in isolating a cDNA highly homologous to a DNA encoding the human F3374V1 protein from animals, it is particularly preferable to use tissues from breast cancer cell line.

The condition of hybridization for isolating a DNA encoding a protein functional equivalent to the human BC proteins or AURKB protein can be routinely selected by a person skilled in the art. The phrase "stringent (hybridization) conditions" refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology*-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times of background, preferably 10 times of background hybridization.

For example, hybridization may be performed by conducting pre-hybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringency condition is, for example, 42° C., 2×SSC, 0.1% SDS, or preferably 50° C., 2×SSC, 0.1% SDS. More preferably, high stringency conditions are used. An example of a high stringency condition includes washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human BC proteins or AURKB protein, using a primer synthesized based on the sequence information of the protein encoding DNA (SEQ ID NO: 79, 81, 89, 91 or 87).

Polypeptides that are functionally equivalent to the human BC proteins or AURKB protein encoded by the DNA isolated through the above hybridization techniques or gene amplification techniques, normally have a high homology to the amino acid sequence of the human BC proteins or AURKB protein. "High homology" or "high sequence identity" interchangeably refer to a homology (sequence identity) of 40% or higher, preferably 60% or higher, more preferably 80% or higher, even more preferably 95% or higher. The homology of a polypeptide can be determined by following the algorithm in "Wilbur and Lipman, Proc Natl Acad Sci USA 80: 726-30 (1983)". Additional examples of algorithms that are suitable for determining percent sequence identity are described herein.

A polypeptide of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human BC proteins or AURKB protein of the present invention, it is within the scope of the present invention.

The present invention also encompasses the use of partial peptides of the BC protein or AURKB protein. A partial peptide has an amino acid sequence specific to the protein of the BC or AURKB and consists of less than about 400 amino acids, usually less than about 200 and often less than about 100 amino acids, and at least about 7 amino acids, preferably about 8 amino acids or more, and more preferably about 9 amino acids or more. A partial peptide of the invention can be produced by genetic engineering, by known methods of peptide synthesis, or by digesting the polypeptide of the invention with an appropriate peptidase. For peptide synthesis, for example, solid phase synthesis or liquid phase synthesis may be used.

A partial peptide used for the screenings of the present invention suitably contains at least the PHB2/REA binding site or the active center for nuclear-translocation activity of the A7322 protein. Such partial peptides are also encompassed by the phrase "functional equivalent" of the A7322 protein.

A partial peptide used for the screenings of the present invention suitably contains at least the A7322 binding site of the PHB2/REA protein. Such partial peptides are also encompassed by the phrase "functional equivalent" of the PHB2/REA protein.

A partial peptide used for the screenings of the present invention suitably contains at least the AURKB binding site or the phosphorylated site of the F3374V1 protein (591α-730aa of SEQ ID NO: 88) by AURKB protein. Such partial peptides are also encompassed by the phrase "functional equivalent" of the F3374V1 protein.

A partial peptide used for the screenings of the present invention suitably contains at least the binding site to F3374V1 protein or the catalytic domain of the AURKB protein. Such partial peptides are also encompassed by the phrase "functional equivalent" of the PBK/TOPK protein.

A partial peptide used for the screenings of the present invention using a kinase activity level of PBK/TOPK as index suitably contains at least a kinase domain (32α-318aa of SEQ ID NO: 92), especially conserves the catalytic site of the PBK/TOPK protein (Lys64 and Lys65 of SEQ ID NO: 92). Such partial peptides are also encompassed by the phrase "functional equivalent" of the PBK/TOPK protein. Furthermore a partial peptide used for the screenings of the present invention using phosphorylated level of PBK/TOPK as index suitably contains at least the phosphorylated site of the PBK/TOPK protein (Thr9 of SEQ ID NO: 92). Such partial peptides are also encompassed by the phrase "functional equivalent" of the PBK/TOPK protein.

Such partial peptides can be produced by genetic engineering, by known methods of peptide synthesis, or by digesting the natural BC protein with an appropriate peptidase. For peptide synthesis, for example, solid phase synthesis or liquid phase synthesis may be used. Conventional peptide synthesis methods that can be adopted for the synthesis include:

1) Peptide Synthesis, Interscience, New York, 1966;
2) The Proteins, Vol. 2, Academic Press, New York, 1976;
3) Peptide Synthesis (in Japanese), Maruzen Co., 1975;
4) Basics and Experiment of Peptide Synthesis (in Japanese), Maruzen Co., 1985;
5) Development of Pharmaceuticals (second volume) (in Japanese), Vol. 14 (peptide synthesis), Hirokawa, 1991;
6) WO99/67288; and
7) Barany G. & Merrifield R. B., Peptides Vol. 2, "Solid Phase Peptide Synthesis", Academic Press, New York, 1980, 100-118.

The polypeptide or fragments thereof may be further linked to other substances so long as the polypeptide and fragments retains its original ability to biological activity, e.g. phosphorylate a substrate or phosphorylated by a kinase. Usable substances include: peptides, lipids, sugar and sugar chains, acetyl groups, natural and synthetic polymers, etc. These kinds of modifications may be performed to confer additional functions or to stabilize the polypeptide and fragments.

The polypeptides of the present invention can be prepared as recombinant proteins or natural proteins, by methods well known to those skilled in the art. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all.

By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e., through the expression of a recombinant nucleic acid as depicted above. Thus, a recombinant protein can be prepared by inserting a DNA, which encodes a polypeptide of the present invention (for example, a DNA comprising the nucleotide sequence of SEQ ID NO: 79, 81, 89, 91 or 87), into an appropriate expression vector, introducing the vector into an appropriate host cell, obtaining the extract, and purifying the polypeptide by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

Also when the polypeptide of the present invention is expressed within host cells (for example, animal cells and $E. coli$) as a fusion protein with glutathione-5-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines, or FLAG, it can be detected and purified using antibodies to c-myc, H is, or FLAG, respectively.

After purifying the fusion protein, it is also possible to exclude regions other than the objective polypeptide by cutting with thrombin or factor-Xa as required.

A natural protein can be isolated by methods known to a person skilled in the art, for example, by contacting the affinity column, in which antibodies binding to the BC proteins described below are bound, with the extract of tissues or cells expressing the polypeptide of the present invention. The antibodies can be polyclonal antibodies or monoclonal antibodies.

Furthermore, the present invention provides polynucleotides encoding a polypeptide of the present invention. The polynucleotides of the present invention can be used for the in vivo or in vitro production of a polypeptide of the present invention as described above. Any form of the polynucleotide of the present invention can be used, so long as it encodes a polypeptide of the present invention, including mRNA, RNA, cDNA, genomic DNA, chemically synthesized polynucleotides. The polynucleotides of the present invention include a DNA comprising a given nucleotide sequences as well as its degenerate sequences, so long as the resulting DNA encodes a polypeptide of the present invention.

The polynucleotides of the present invention can be prepared by methods known to a person skilled in the art. For example, the polynucleotide of the present invention can be from a cDNA library from cells which express a polypeptide of the present invention, by conducting hybridization using a partial sequence of the DNA of the present invention (for example, SEQ ID NO: 79, 81, 89, 91 or 87) as a probe. A cDNA library can be prepared, for example, by the method described in Sambrook et al., Molecular Cloning, $3^{rd}$ Edition, Cold Spring Harbor Laboratory Press (2001); alternatively, commercially available cDNA libraries may be used. A cDNA library can be also prepared by extracting RNAs from cells expressing the polypeptide of the present invention, synthesizing oligo DNAs based on the sequence of a DNA of the present invention (for example, SEQ ID NO: 79, 81, 89, 91 or 87), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained. Moreover, by screening the genomic DNA library using the obtained cDNA or parts thereof as a probe, the genomic DNA can be isolated.

More specifically, mRNAs may first be prepared from a cell, tissue, or organ (e.g., brain or breast cancer cell line for A7322; testis or breast cancer cell line for F3374V1; breast cancer cell line for PHB2/REA; and testis or breast cancer cell line for PBK/TOPK) in which an object polypeptide of the present invention is expressed. Known methods can be used to isolate mRNAs; for instance, total RNA may be prepared by guanidine ultracentrifugation (Chirgwin et al., Biochemistry 18:5294-9 (1979)) or AGPC method (Chomczynski and Sacchi, Anal Biochem 162:156-9 (1987)). In addition, mRNA may be purified from total RNA using mRNA Purification Kit (Pharmacia) and such or, alternatively, mRNA may be directly purified by QuickPrep mRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc Natl Acad Sci USA 85: 8998-9002 (1988); Belyaysky et al., Nucleic Acids Res 17: 2919-32 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform E. coli and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., Nucleic Acids Res 9: 43-74 (1981)). In addition, the sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA, or TAG).

In a particularly preferred embodiment, the polynucleotide of the present invention encompasses DNA comprising the nucleotide sequence of SEQ ID NO: 79, 81, 89, 91 or 87.

Furthermore, the present invention provides a polynucleotide that hybridizes under stringent conditions with a polynucleotide having a nucleotide sequence of SEQ ID NO: 79, 81, 89, 91 or 87 and encodes a polypeptide functionally equivalent to the BC proteins or AURKB protein of the invention described above. As discussed above, one skilled in the art may appropriately choose stringent conditions. For example, low stringency conditions can be used. More preferably, high stringency conditions are used. These conditions are as described above. The hybridizing DNA above is preferably a cDNA or a chromosomal DNA.

The present invention also provides a vector into which a polynucleotide of the present invention is inserted. A vector of the present invention is useful to keep a polynucleotide, especially a DNA, of the present invention in host cell, to express the polypeptide of the present invention.

When E. coli is selected as the host cell and the vector is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT, and pT7 can also be used for subcloning and extracting cDNA as well as the vectors described above. When a vector is used to produce a protein of the present invention, an expression vector is especially useful.

For example, an expression vector to be expressed in E. coli should have the above characteristics to be amplified in E. coli. When E. coli, such as JM109, DH5α, HB101, or XL1Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), or T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the E. coli is the pelB signal sequence (Lei et al., J Bacteriol 169: 4379-83 (1987)). Means for introducing of the vectors into the target host cells include, for example, the calcium chloride method, and the electroporation method.

In addition to E. coli, for example, expression vectors derived from mammalian cells (for example, pcDNA3 (Invitrogen) and pEGF-BOS (Mizushima S., Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01), and expression vectors derived from *Bacillus subtilis* (e.g., pPL608, pKTH50) can be used for producing the polypeptide of the present invention.

In order to express a vector in animal cells, such as CHO, COS, or NIH3T3 cells, the vector should have a promoter necessary for expression in such cells, for example, the SV40 promoter (Mulligan et al., Nature 277: 108-14 (1979)), the MMLV-LTR promoter, the EF1α promoter (Mizushima et al., Nucleic Acids Res 18: 5322 (1990)), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, methods may be used to express a gene stably and, at the same time, to amplify the copy number of the gene in cells. For example, a vector comprising the complementary DHFR gene (e.g., pCHOI) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells, and purified as a substantially pure homogeneous polypeptide. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified polypeptides prepared by the above methods.

In the context of the present invention, a "percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity", in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length, or over the full-length of the amino acid or nucleic acid sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981) Adv. Appl. Math. 2:482-9, by the homology alignment algorithm of Needleman and Wunsch (1970) J. Mol. Biol. 48:443-53, by the search for similarity method of Pearson and Lipman (1988) Proc. Nat'l. Acad. Sci. USA 85:2444-8, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-402, and Altschul et al. (1990) J. Mol. Biol. 215:403-10, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-7). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

A polypeptide of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase, and the like.

Antibodies and Non-Antibody Binding Proteins

The present invention also provides antibodies and non-antibody binding protein that specifically bind to a polypeptide of the invention. An antibody and non-antibody binding protein of the present invention can be used in any form, including monoclonal or polyclonal antibodies, and includes antiserum obtained by immunizing an animal such as a rabbit with the polypeptide of the invention, all classes of polyclonal and monoclonal antibodies, human antibodies, and humanized antibodies produced by genetic recombination.

The terms "bind(s) specifically" or "specifically bind(s)" or "attached" or "attaching" in the context of antibodies or non-antibody binding proteins refers to the preferential association of an agent or ligand, in whole or part, with a target epitope (e.g. A7322, F3374 or PBK/TOPK) that binds or competes with another agent or ligand for binding to A7322, F3374 or PBK/TOPK expressed in or on a cell or tissue. It is, of course, recognized that a certain degree of non-specific interaction may occur between an antibody and a non-target epitope. Nevertheless, specific binding, can be distinguished as mediated through specific recognition of the target epitope. Typically specific binding results in a much stronger association between the delivered molecule and an entity (e.g., an assay well or a cell) bearing the target epitope than between the bound antibody and an entity (e.g., an assay well or a cell) lacking the target epitope. Specific binding typically results in at least about a 2-fold increase over background, preferably greater than about 10-fold and most preferably greater than 100-fold increase in amount of bound agent or ligand (per unit time) to a cell or tissue bearing the target epitope (i.e. REG4) as compared to a cell or tissue lacking the target epitope. Specific binding between two entities generally means an affinity of at least $10^6$ $M^{-1}$. Affinities greater than $10^8$ $M^{-1}$ or greater are preferred. Specific binding can be determined for nucleic acid as well as protein agents and ligands. Specific binding for nucleic acid agents can be determined using any assay known in the art, including but not limited to northern blots, gel shift assays and in situ hybridization. Specific binding for protein agents and ligands can be determined using any binding assay known in the art, including but not limited to gel electrophoresis, western blot, ELISA, flow cytometry, and immunohistochemistry.

Antibodies

The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')$_2$, Fab, Fv and rIgG). See also, Pierce Catalog and Handbook, 1994-1995 (Pierce Chemical Co., Rockford, Ill.). See also, e.g., Kuby, J., Immunology, 3rd Ed., W.H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275-81 (1989), which is incorporated herein by reference. These and other methods of making, for example, chimeric, humanized, CDR-grafted, single chain, and bifunctional antibodies are well known to those skilled in the art (Winter and Harris, Immunol. Today 14:243-6 (1993); Ward et al., Nature 341:544-6 (1989); Harlow and Lane, Antibodies, 511-52, Cold Spring Harbor Laboratory publications, New York, 1988; Hilyard et al., Protein Engineering: A practical approach (IRL Press 1992); Borrebaeck, Antibody Engineering, 2d ed. (Oxford University Press 1995); each of which is incorporated herein by reference).

The term "antibody" includes both polyclonal and monoclonal antibodies. The term also includes genetically engineered forms such as chimeric antibodies (e.g., humanized murine antibodies) and heteroconjugate antibodies (e.g., bispecific antibodies). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547-53; Pack and Pluckthun (1992) Biochemistry 31:1579-84; Holliger et al. (1993) Proc Natl Acad Sci USA. 90:6444-8; Gruber et al. (1994) J Immunol: 5368-74; Zhu et al. (1997) Protein Sci 6:781-8; Hu et al. (1997) Cancer Res. 56:3055-61; Adams et al. (1993) Cancer Res. 53:4026; and McCartney, et al. (1995) Protein Eng. 8:301-14.

Typically, an antibody has a heavy and light chain. Each heavy and light chain contains a constant region and a variable region, (the regions are also known as "domains"). Light and heavy chain variable regions contain four "framework" regions interrupted by three hyper-variable regions, also called "complementarity-determining regions" or "CDRs". The extent of the framework regions and CDRs has been defined. The sequences of the framework regions of different light or heavy chains are relatively conserved within a species. The framework region of an antibody, that is the combined framework regions of the constituent light and heavy chains, serves to position and align the CDRs in three dimensional spaces.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

A polypeptide of the present invention used as an antigen to obtain an antibody may be derived from any animal species, but preferably is derived from a mammal such as a human, mouse, or rat, more preferably from a human. A human-derived polypeptide may be obtained from the nucleotide or amino acid sequences disclosed herein.

According to the present invention, the polypeptide to be used as an immunization antigen may be a complete protein or a partial peptide of the protein. A partial peptide may comprise, for example, the amino (N)-terminal or carboxy (C)-terminal fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates, or a chemically synthesized polypeptide may be used as the antigen.

Any mammalian animal may be immunized with the antigen, but preferably the compatibility with parental cells used for cell fusion is taken into account. In general, animals of the orders Rodentia, Lagomorpha, or Primates are used. Animals of the order Rodentia include, for example, mouse, rat, and hamster. Animals of the order Lagomorpha include, for example, rabbit. Animals of the Primate order include, for example, a monkey of Catarrhini (old world monkey) such as *Macaca fascicularis*, rhesus monkey, sacred baboon, and chimpanzees.

Methods for immunizing animals with antigens are known in the art. For example, intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as fractions containing the polyclonal antibodies isolated from the serum Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells, or their lysates in vitro. Then, the immunized lymphocytes are fused with human-derived myeloma cells that are capable of indefinitely dividing, such as U266, to yield a hybridoma producing a desired human antibody that is able to bind to the polypeptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography, or an affinity column to which the polypeptide of the present invention is coupled. The antibody of the present invention can be used not only for purification and detection of the polypeptide of the present invention, but also as a candidate for agonists and antagonists of the polypeptide of the present invention. In addition, this antibody can be applied to the antibody treatment for diseases related to the polypeptide of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a polypeptide, polypeptide expressing cells, or their lysates. Antibody producing cells are then collected from the animals and fused with myeloma cells to obtain hybridoma, from which human antibodies against the polypeptide can be prepared (see WO92-03918, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, F(ab')$_2$, Fv, or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co et al., J Immunol 152: 2968-76 (1994); Better and & Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-5 (1986); Riechmann et al., Nature 332:323-7 (1988); and Presta, Curr. Op. Struct. Biol. 2:593-6 (1992)).

Humanization can be essentially performed following the method of Winter and co-workers (Jones et al., Nature 321: 522-5 (1986); Riechmann et al., Nature 332:323-7 (1988); Verhoeyen et al., Science 239:1534-6 (1988)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species.

The terms "epitope" and "antigenic determinant" refer to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) and the constant region derived from human antibody. Such antibodies can be prepared by using known technology.

Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, J Mol Biol 1991, 227: 381), Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Non-Antibody Binding Proteins

The present invention also includes antigen binding proteins or non-antibody binding proteins (e.g., ligands) that specifically bind to a polypeptide of the invention. Non-antibody ligands include antibody mimics that use non-immunoglobulin protein scaffolds, including adnectins, avimers, single chain polypeptide binding molecules, and antibody-like binding peptidomimetics, as discussed in more detail below.

Other compounds have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (Proc. Natl. Acad. Sci. U.S.A. 92(14):6552-6556 (1995)) discloses an alternative to antibodies based on cytochrome b562. Ku et al. (1995) generated a library in which two of the loops of cytochrome b562 were randomized and selected for binding against bovine serum albumin. The individual mutants were found to bind selectively with BSA similarly with anti-BSA antibodies.

Lipovsek et al. (U.S. Pat. Nos. 6,818,418 and 7,115,396) discloses an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. Any technique for evolving new or improved binding proteins can be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling can be employed in vitro that is similar to the process of affinity maturation of antibodies in vivo.

Beste et al. (Proc. Natl. Acad. Sci. U.S.A. 96(5):1898-1903 (1999)) discloses an antibody mimic based on a lipocalin scaffold (Anticalin®). Lipocalins are composed of a β-barrel with four hypervariable loops at the terminus of the protein.

Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies.

Anticalins® are small, single chain peptides, typically between 160 and 180 residues, which provides several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (Cell. Mol. Biol. 49(2):209-216 (2003)) discusses a methodology for reducing antibodies into smaller peptidomimetics, they term "antibody like binding peptidomemetics" (ABiP) which can also be useful as an alternative to antibodies.

Silverman et al. (Nat. Biotechnol. (2005), 23: 1556-1561) discloses fusion proteins that are single-chain polypeptides comprising multiple domains termed "avimers." Developed from human extracellular receptor domains by in vitro exon shuffling and phage display the avimers are a class of binding proteins somewhat similar to antibodies in their affinities and specificities for various target molecules. The resulting multidomain proteins can comprise multiple independent binding domains that can exhibit improved affinity (in some cases sub-nanomolar) and specificity compared with single-epitope binding proteins. Additional details concerning methods of construction and use of avimers are disclosed, for example, in U.S. Patent App. Pub. Nos. 20040175756, 20050048512, 20050053973, 20050089932 and 20050221384.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics) all of which are suitable for use with the present invention.

Antibodies and non-antibody binding proteins obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS, and Sepharose F.F. (Pharmacia).

Examples of chromatography, with the exception of affinity include ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC, and FPLC.

For example, absorbance assays, enzyme-linked immunosorbent assays (ELISA), enzyme immunoassays (ETA), radioimmunoassays (RIA), and/or immunofluorescence assays may be used to measure the antigen binding activity of the antibody of the invention. In ELISA, an antibody or non-antibody binding protein of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the polypeptide of the invention, by exposing the antibody or non-antibody binding protein of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

Antisense Oligonucleotides

As noted above, the present invention also provides a polynucleotide which hybridizes with a polynucleotide encoding human A7322 or F3374V1 protein (SEQ ID NO: 79 or 81) or the complementary strand thereof, and which comprises at least 15 nucleotides. For instance, antisense oligonucleotides complyment to the contiguous nucleotide sequence selected from positions 1 to 384 of SEQ ID NO: 79 (A7322) are preferable. Generally, nucleotide sequence comprising start codon is preferable to design an effective antisense oligonucleotide. The start codon (172-174) of A7332 locates within the positions of 1 to 384 of SEQ ID NO: 79 (A7322). The polynucleotide of the present invention is preferably a polynucleotide which specifically hybridizes with the DNA encoding the polypeptide of the present invention.

The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the polypeptide of the invention or its complementary strand. Moreover, such polynucleotide can be utilized for the preparation of DNA chip.

The term "antisense oligonucleotides" as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO: 79 or 81.

Such polynucleotides are contained as those having, in the "at least 15 continuous nucleotide sequence region", a homology of at least 70% or higher, preferably at 80% or higher, more preferably 90% or higher, even more preferably 95% or higher. The algorithm stated herein can be used to determine the homology. Such polynucleotides are useful as probes for the isolation or detection of DNA encoding the polypeptide of the invention as stated in a later example or as a primer used for amplifications.

Derivatives or modified products of antisense oligonucleotides can be used as antisense oligonucleotides of the present invention. Examples of such modified products include lower alkyl phosphonate modifications, such as methyl-phosphonate-type or ethyl-phosphonate-type, phosphorothioate modifications and phosphoroamidate modifications.

The antisense oligonucleotide derivatives of the present invention act upon cells producing the polypeptide of the invention by binding to the DNA or mRNA encoding the polypeptide, inhibiting its transcription or translation, promoting the degradation of the mRNA, and inhibiting the expression of the polypeptide of the invention, thereby resulting in the inhibition of the polypeptide's function.

An antisense oligonucleotide derivative of the present invention can be made into an external preparation, such as a liniment or a poultice, by mixing with a suitable base material which is inactive against the derivatives.

Also, as needed, the derivatives can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following usual methods.

The antisense oligonucleotide derivative may be given to the patient by directly applying onto the ailing site or by injecting into a blood vessel so that it will reach the site of ailment. An antisense-mounting medium can also be used to increase durability and membrane-permeability. Examples include, but are not limited to, liposome, poly-L-lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

siRNA

The term "siRNA" refers to a double stranded RNA molecule which prevents translation of a target mRNA. Standard techniques are used for introducing siRNA into cells, including those wherein DNA is used as the template to transcribe RNA. An siRNA of the present invention comprises a sense nucleic acid sequence and an anti-sense nucleic acid sequence of a polynucleotide encoding human A7322, F3374V1, PBK/TOPK or AURKB protein (SEQ ID NO: 79, 81, 92 or 88). The siRNA is constructed such that a single transcript (double stranded RNA) has both the sense and complementary antisense sequences from the target gene, e.g., a hairpin. The siRNA may either be a dsRNA or shRNA.

As used herein, the term "dsRNA" refers to a construct of two RNA molecules comprising complementary sequences to one another and that have annealed together via the complementary sequences to form a double-stranded RNA molecule. The nucleotide sequence of two strands may comprise not only the "sense" or "antisense" RNAs selected from a protein coding sequence of target gene sequence, but also RNA molecule having a nucleotide sequence selected from non-coding region of the target gene.

The term "shRNA", as used herein, refers to an siRNA having a stem-loop structure, comprising first and second regions complementary to one another, i.e., sense and antisense strands. The degree of complementarity and orientation of the regions being sufficient such that base pairing occurs between the regions, the first and second regions being joined by a loop region, the loop resulting from a lack of base pairing between nucleotides (or nucleotide analogs) within the loop region. The loop region of an shRNA is a single-stranded region intervening between the sense and antisense strands and may also be referred to as "intervening single-strand".

As use herein, the term "siD/R-NA" refers to a double-stranded polynucleotide molecule which is composed of both RNA and DNA, and includes hybrids and chimeras of RNA and DNA and prevents translation of a target mRNA. Herein, a hybrid indicates a molecule wherein a polynucleotide composed of DNA and a polynucleotide composed of RNA hybridize to each other to form the double-stranded molecule; whereas a chimera indicates that one or both of the strands composing the double stranded molecule may contain RNA and DNA. Standard techniques of introducing siD/R-NA into the cell are used. The siD/R-NA includes a CX sense nucleic acid sequence (also referred to as "sense strand"), a CX antisense nucleic acid sequence (also referred to as "antisense strand") or both. The siD/R-NA may be constructed such that a single transcript has both the sense and complementary antisense nucleic acid sequences from the target gene, e.g., a hairpin. The siD/R-NA may either be a dsD/R-NA or shD/R-NA.

As used herein, the term "dsD/R-NA" refers to a construct of two molecules comprising complementary sequences to one another and that have annealed together via the complementary sequences to form a double-stranded polynucleotide molecule. The nucleotide sequence of two strands may comprise not only the "sense" or "antisense" polynucleotides sequence selected from a protein coding sequence of target gene sequence, but also polynucleotide having a nucleotide sequence selected from non-coding region of the target gene. One or both of the two molecules constructing the dsD/R-NA are composed of both RNA and DNA (chimeric molecule), or alternatively, one of the molecules is composed of RNA and the other is composed of DNA (hybrid double-strand).

The term "shD/R-NA", as used herein, refers to an siD/R-NA having a stem-loop structure, comprising a first and second regions complementary to one another, i.e., sense and antisense strands. The degree of complementarity and orientation of the regions being sufficient such that base pairing occurs between the regions, the first and second regions being joined by a loop region, the loop resulting from a lack of base pairing between nucleotides (or nucleotide analogs) within the loop region. The loop region of an shD/R-NA is a single-stranded region intervening between the sense and antisense strands and may also be referred to as "intervening single-strand".

The siRNA of A7322, F3374V1, PBK/TOPK or AURKB is directed to a single target of A7322, F3374V1, PBK/TOPK or AURKB gene sequence. Alternatively, the siRNA is directed to multiple targets of A7322, F3374V1, PBK/TOPK or AURKB gene sequences. For example, the composition contains siRNA of A7322, F3374V1, PBK/TOPK or AURKB directed to two, three, four, or five or more target sequences of A7322, F3374V1, PBK/TOPK or AURKB. By A7322, F3374V1, PBK/TOPK or AURKB target sequence is meant a nucleotide sequence that is identical to a portion of the A7322, F3374V1, PBK/TOPK or AURKB gene.

The target sequence can include the 5' untranslated (UT) region, the open reading frame (ORF) or the 3' untranslated region of the human A7322, F3374V1, PBK/TOPK or AURKB gene. siRNA of A7322, F3374V1, PBK/TOPK or AURKB which hybridize to target mRNA decrease or inhibit production of the A7322, F3374V1, PBK/TOPK or AURKB polypeptide product encoded by the A7322, F3374V1, PBK/TOPK or AURKB gene by associating with the normally single-stranded mRNA transcript, thereby interfering with translation and thus, expression of the protein. Thus, siRNA molecules of the invention can be defined by their ability to hybridize specifically to mRNA or cDNA from an A7322, F3374V1, PBK/TOPK or AURKB gene under stringent conditions.

Binding of the siRNA to a transcript corresponding to A7322, F3374V1, PBK/TOPK or AURKB in the target cell results in a reduction in the protein production by the cell. The length of the oligonucleotide is at least 10 nucleotides and may be as long as the naturally-occurring the transcript. Preferably, the oligonucleotide is less than 100, 75, 50, 25 nucleotides in length. Most preferably, the oligonucleotide is 19-25 nucleotides in length. Examples of A7322, F3374V1, PBK/TOPK or AURKB siRNA oligonucleotides which inhibit the growth of the cancer cell include the target sequence containing SEQ ID NO: 34 or 35 for A7322, SEQ ID NO: 37, 38 or 67 for F3374V1, SEQ ID NO: 39 or 40 for PBK/TOPK or SEQ ID NO: 68 for AURKB.

Furthermore, in order to enhance the inhibition activity of the siRNA, nucleotide "u" can be added to 3' end of the antisense strand of the target sequence. The number of "u"s to be added is at least 2, generally 2 to 10, preferably 2 to 5. The added "u"s form single strand at the 3' end of the antisense strand of the siRNA.

A7322, F3374V1, TBP/TOPK or AURKB siRNA may be directly introduced into the cells in a form that is capable of binding to the mRNA transcripts. In these embodiments, the siRNA molecules of the invention are typically modified as described above for antisense molecules. Other modifications are also possible, for example, cholesterol-conjugated siRNAs have shown improved pharmacological properties (Song et al. Nature Med. 9:347-51 (2003)). Alternatively, the DNA encoding the A7322, F3374V1, PBK/TOPK or AURKB siRNA may be contained in a vector.

Vectors are produced, for example, by cloning a A7322, F3374V1, PBK/TOPK or AURKB target sequence into an expression vector operatively-linked regulatory sequences flanking the A7322, F3374V1, PBK/TOPK or AURKB sequence in a manner that allows for expression (by transcription of the DNA molecule) of both strands (Lee, N. S. et al., (2002) Nature Biotechnology 20:500-5.). An RNA molecule that is antisense to a A7322, F3374V1, PBK/TOPK or AURKB mRNA is transcribed by a first promoter (e.g., a promoter sequence 3' of the cloned DNA) and an RNA molecule that is the sense strand for a A7322, F3374V1, PBK/TOPK or AURKB mRNA is transcribed by a second promoter (e.g., a promoter sequence 5' of the cloned DNA). The sense and antisense strands hybridize in vivo to generate siRNA constructs for silencing of the A7322, F3374V1, PBK/TOPK or AURKB gene. Alternatively, two constructs may be utilized to create the sense and anti-sense strands of the siRNA construct. Cloned A7322, F3374V1, PBK/TOPK or AURKB can encode a construct having secondary structure, e.g., hairpins, wherein a single transcript has both the sense and complementary antisense sequences from the target gene.

Furthermore, a loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence of nucleotides SEQ ID NO: 34, 35, 37, 38, 39, 40, 67 or 68 [B] is a ribonucleotide sequence consisting of 3 to 23 nucleotides, and [A'] is a ribonucleotide sequence consisting of the complementary sequence of [A]. The loop sequence may consist of an arbitrary sequence preferably 3 to 23 nucleotides in length. The loop sequence, for example, can be selected from group consisting of following sequences (on the Worldwide Web at ambion.com/techlib/tb/tb_506.html). In the siRNA of the present invention, the nucleotide "u" can be added to the 3' end of [A'], in order to enhance the inhibiting activity of the siRNA. The number of "u"s to be added is at least 2, generally 2 to 10, preferably 2 to 5. Furthermore, loop sequence consisting of 23 nucleotides also provides active siRNA (Jacque J M, et al., Nature 418: 435-8 (2002)):

CCC, CCACC or CCACACC: Jacque J M et al., Nature, Vol. 418: 435-8 (2002);

UUCG: Lee, N S. et al., Nature Biotechnology 20:500-5; Fruscoloni P., et al., Proc. Natl. Acad. Sci. USA 100(4): 1639-44 (2003); and UUCAAGAGA: Dykxhoorn D M et al., Nature Reviews Molecular Cell Biology 4: 457-67 (2003).

Examples of preferred siRNAs having hairpin structure of the present invention are shown below. In the following structure, the loop sequence can be selected from group consisting of CCC, UUCG, CCACC, CCACACC, and UUCAAGAGA. A preferred loop sequence is UUCAAGAGA ("ttcaagaga" in DNA).

```
               (for target sequence of SEQ ID NO: 34)
aagaaagcaucgcagucucag-[B]-cugagacugcgaugcuuucuu (for target sequence of SEQ ID NO: 35)
aagaugcguucucugccacac-[B]-guguggcagagaacgcaucuu (for target sequence of SEQ ID NO: 37)
gaucaugucuccgagaaaa-[B]-uuuucucggagacaugauc (for target sequence of SEQ ID NO: 38)
ggaagccauagaauugcuc-[B]-gagcaauucuauggcuucc (for target sequence of SEQ ID NO: 39)
cuggaugaaucauaccaga-[B]-ucugguaugauucauccag (for target sequence of SEQ ID NO: 40)
guguggcuugcguaaauaa-[B]-uuauuuacgcaagccacac (for target sequence of SEQ ID NO: 67)
acuccuacguucucuauua-[B]-uaauagagaacguaggagu (for target sequence of SEQ ID NO: 68)
aaggugauggagaauagcagu-[B]-acugcuauucuccaucaccuu
```

The regulatory sequences flanking the A7322, F3374V1, PBK/TOPK or AURKB sequence are identical or different, such that their expression can be modulated independently, or in a temporal or spatial manner. siRNAs are transcribed intracellularly by cloning the A7322, F3374V1, PBK/TOPK or AURKB gene templates into a vector containing, e.g., a RNA polymerase III transcription unit from the small nuclear RNA (snRNA) U6 or the human H1 RNA promoter. For introducing the vector into the cell, transfection-enhancing agent can be used. FuGENE (Roche Diagnostics), Lipofectamine 2000

(Invitrogen), Oligofectamine (Invitrogen), and Nucleofector (Wako pure Chemical) are useful as the transfection-enhancing agent.

The nucleotide sequences of siRNAs may be designed using an siRNA design computer program available from the Ambion website on the Worldwide Web at ambion.com/techlib/misc/siRNA_finder.html. Nucleotide sequences for the siRNA are selected by the computer program based on the following protocol:

Selection of siRNA Target Sites:

1. Beginning with the AUG start codon of the object transcript, scan downstream for AA dinucleotide sequences. Record the occurrence of each AA and the 3' adjacent 19 nucleotides as potential siRNA target sites. Tuschl, et al., Genes Dev 13(24):3191-7 (1999), not to recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.

2. Compare the potential target sites to the human genome database and eliminate from consideration any target sequences with significant homology to other coding sequences. The homology search can be performed using BLAST (Altschul S F, et al., J Mol. Biol. 1990; 215:403-10; Altschul S F, et al., Nucleic Acids Res. 1997; 25:3389-402), which can be found on the NCBI server on the Worldwide Web at ncbi.nlm.nih.gov/BLAST/.

3. Select qualifying target sequences for synthesis. At Ambion, preferably several target sequences can be selected along the length of the gene for evaluation.

Oligonucleotides and oligonucleotides complementary to various portions of A7322, F3374V1, PBK/TOPK or AURKB mRNA were tested in vitro for their ability to decrease production of A7322, F3374V1, PBK/TOPK or AURKB in tumor cells (e.g., using breast cancer cell line, as the BT-549; BT-474 for A7322, D47T and HBC4 for F3374; T47D and BT-20 for PBK/TOPK) according to standard methods. A reduction in A7322, F3374V1, PBK/TOPK or AURKB gene product in cells contacted with the candidate siRNA composition as compared to cells cultured in the absence of the candidate composition can be detected using A7322, F3374V1, PBK/TOPK or AURKB-specific antibodies or other detection strategies. Sequences which decrease the production of A7322, F3374V1, PBK/TOPK or AURKB in in vitro cell-based or cell-free assays can then be tested for there inhibitory effects on cell growth. Sequences which inhibit cell growth in in vitro cell-based assay are tested in vivo in rats or mice to confirm decreased A7322, F3374V1, PBK/TOPK or AURKB production and decreased tumor cell growth in animals with malignant neoplasms.

Also included in the invention are double-stranded molecules that include the nucleic acid sequence of target sequences, for example, nucleotides SEQ ID NO: 34, 35, 37, 38, 38, 39, 67 or 68. In the present invention, the double-stranded molecule comprising a sense strand and an antisense strand, wherein the sense strand comprises a ribonucleotide sequence corresponding to SEQ ID NO: 34, 35, 37, 38, 38, 39, 67 or 68, and wherein the antisense strand comprises a ribonucleotide sequence which is complementary to said sense strand, wherein said sense strand and said antisense strand hybridize to each other to form said double-stranded molecule, and wherein said double-stranded molecule, when introduced into a cell expressing the A7322, F3374V1 or AURKB gene, inhibits expression of said gene.

In the present invention, when the isolated nucleic acid is RNA or derivatives thereof, base "t" should be replaced with "u" in the nucleotide sequences. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. When the polynucleotide comprises modified nucleotides and/or non-phosphodiester linkages, these polynucleotides may also bind each other as same manner.

Complementary nucleic acid sequences hybridize under appropriate conditions to form stable duplexes containing few or no mismatches. Furthermore, the sense strand and antisense strand of the isolated nucleotide of the present invention can form double stranded nucleotide or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches.

For example, the nucleic acid molecule is less than 500, 100, 200, or 75 nucleotides in length. Also included in the invention is a vector containing one or more of the nucleic acids described herein, and a cell containing the vectors. The isolated nucleic acids of the present invention are useful for siRNA against A7322 or F3374V1 or DNA encoding the siRNA. When the nucleic acids are used for siRNA or coding DNA thereof, the sense strand is preferably longer than 19 nucleotides, and more preferably longer than 21 nucleotides.

The double-stranded molecules of the invention may contain one or more modified nucleotides and/or non-phosphodiester linkages. Chemical modifications well known in the art are capable of increasing stability, availability, and/or cell uptake of the double-stranded molecule. The skilled person will be aware of other types of chemical modification which may be incorporated into the present molecules (WO03/070744; WO2005/045037). In one embodiment, modifications can be used to provide improved resistance to degradation or improved uptake. Examples of such modifications include phosphorothioate linkages, 2'-β-methyl ribonucleotides (especially on the sense strand of a double-stranded molecule), 2'-deoxy-fluoro ribonucleotides, 2'-deoxy ribonucleotides, "universal base" nucleotides, 5'-C-methyl nucleotides, and inverted deoxyabasic residue incorporation (US20060122137).

In another embodiment, modifications can be used to enhance the stability or to increase targeting efficiency of the double-stranded molecule. Modifications include chemical cross linking between the two complementary strands of a double-stranded molecule, chemical modification of a 3' or 5' terminus of a strand of a double-stranded molecule, sugar modifications, nucleobase modifications and/or backbone modifications, 2-fluoro modified ribonucleotides and 2'-deoxy ribonucleotides (WO2004/029212). In another embodiment, modifications can be used to increased or decreased affinity for the complementary nucleotides in the target mRNA and/or in the complementary double-stranded molecule strand (WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyi purine. In another embodiment, when the double-stranded molecule is a double-stranded molecule with a 3' overhang, the 3'-terminal nucleotide overhanging nucleotides may be replaced by deoxyribonucleotides (Elbashir S M et al., Genes Dev 2001 Jan. 15, 15(2): 188-

200). For further details, published documents such as US20060234970 are available. The present invention is not limited to these examples and any known chemical modifications may be employed for the double-stranded molecules of the present invention so long as the resulting molecule retains the ability to inhibit the expression of the target gene.

Furthermore, the double-stranded molecules of the invention may comprise both DNA and RNA, e.g., dsD/R-NA or shD/R-NA. Specifically, a hybrid polynucleotide of a DNA strand and an RNA strand or a DNA-RNA chimera polynucleotide shows increased stability. Mixing of DNA and RNA, i.e., a hybrid type double-stranded molecule consisting of a DNA strand (polynucleotide) and an RNA strand (polynucleotide), a chimera type double-stranded molecule comprising both DNA and RNA on any or both of the single strands (polynucleotides), or the like may be formed for enhancing stability of the double-stranded molecule. The hybrid of a DNA strand and an RNA strand may be the hybrid in which either the sense strand is DNA and the antisense strand is RNA, or the opposite so long as it has an activity to inhibit expression of the target gene when introduced into a cell expressing the gene. Preferably, the sense strand polynucleotide is DNA and the antisense strand polynucleotide is RNA. Also, the chimera type double-stranded molecule may be either where both of the sense and antisense strands are composed of DNA and RNA, or where any one of the sense and antisense strands is composed of DNA and RNA so long as it has an activity to inhibit expression of the target gene when introduced into a cell expressing the gene.

In order to enhance stability of the double-stranded molecule, the molecule preferably contains as much DNA as possible, whereas to induce inhibition of the target gene expression, the molecule is required to be RNA within a range to induce sufficient inhibition of the expression. As a preferred example of the chimera type double-stranded molecule, an upstream partial region (i.e., a region flanking to the target sequence or complementary sequence thereof within the sense or antisense strands) of the double-stranded molecule is RNA. Preferably, the upstream partial region indicates the 5' side (5'-end) of the sense strand and the 3' side (3'-end) of the antisense strand. That is, in preferable embodiments, a region flanking to the 3'-end of the antisense strand, or both of a region flanking to the 5'-end of sense strand and a region flanking to the 3'-end of antisense strand consists of RNA. For instance, the chimera or hybrid type double-stranded molecule of the present invention comprise following combinations.

```
sense strand:    5'-[DNA]-3'
                 3'-(RNA)-[DNA]-5': antisense strand,
sense strand:    5'-(RNA)-[DNA]-3'
                 3'-(RNA)-[DNA]-5': antisense strand,
and
sense strand:    5'-(RNA)-[DNA]-3'
                 3'-(RNA)-5': antisense strand.
```

The upstream partial region preferably is a domain consisting of 9 to 13 nucleotides counted from the terminus of the target sequence or complementary sequence thereto within the sense or antisense strands of the double-stranded molecules. Moreover, preferred examples of such chimera type double-stranded molecules include those having a strand length of 19 to 21 nucleotides in which at least the upstream half region (5' side region for the sense strand and 3' side region for the antisense strand) of the polynucleotide is RNA and the other half is DNA. In such a chimera type double-stranded molecule, the effect to inhibit expression of the target gene is much higher when the entire antisense strand is RNA (US20050004064).

In the present invention, the double-stranded molecule may form a hairpin, such as a short hairpin RNA (shRNA) and short hairpin consisting of DNA and RNA (shD/R-NA). The shRNA or shD/R-NA is a sequence of RNA or mixture of RNA and DNA making a tight hairpin turn that can be used to silence gene expression via RNA interference. The shRNA or shD/R-NA comprises the sense target sequence and the antisense target sequence on a single strand wherein the sequences are separated by a loop sequence. Generally, the hairpin structure is cleaved by the cellular machinery into dsRNA or dsD/R-NA, which is then bound to the RNA-induced silencing complex (RISC). This complex binds to and cleaves mRNAs which match the target sequence of the dsRNA or dsD/R-NA.

Diagnosing Breast Cancer

An inhibitory polynucleotide (e.g., antisense oligonucleotide or siRNA) of the present invention inhibits the expression of a polypeptide of the invention and is thereby useful for suppressing the biological activity of the polypeptide of the invention. Also, expression-inhibitors, comprising the antisense oligonucleotide or siRNA of the invention, are useful for inhibiting the biological activity of the polypeptide of the invention. Therefore, a composition comprising one or more inhibitory polynucleotides (e.g., antisense oligonucleotide or siRNA) of the present invention is useful in the treatment of breast cancer. Moreover, the present invention provides a method for providing prognosis, diagnosing, detecting, or testing breast cancer using the expression level of the polypeptides of the present invention as a prognostic and/or diagnostic marker.

The diagnostic methods of the present invention comprise the steps of:
  (a) detecting the expression level of the A7322 or F3374V1 gene of the present invention; and
  (b) correlating an elevation in the expression (e.g., transcription and/or translation) level of A7322 and/or F3374V1 to a diagnosis or prognosis of breast cancer.

The expression level of the A7322 or F3374V1 gene in a particular specimen can be estimated by quantifying mRNA corresponding to or protein encoded by the A7322 or F3374V1 gene. Quantification methods for mRNA are known to those skilled in the art. For example, the levels of mRNAs corresponding to the A7322 or F3374V1 gene can be estimated by Northern blotting or RT-PCR (e.g., using quantitative or real-time PCR). Since the full-length nucleotide sequences of the A7322 or F3374V1 genes are shown in SEQ ID NO: 79 or 81, anyone skilled in the art can design the nucleotide sequences for probes or primers to quantify the A7322 or F3374V1 gene.

Also the expression level of the A7322 or F3374V1 gene can be analyzed based on the activity or quantity of protein encoded by the gene. A method for determining the quantity of the A7322 or F3374V1 protein is shown in below. For example, an immunoassay method is useful for determining proteins in biological materials. Any biological materials can be used for the determination of the protein or its activity. For example, a blood sample may be analyzed for estimation of the protein encoded by a serum marker. On the other hand, a suitable method can be selected for the determination of the activity of a protein encoded by the A7322 or F3374V1 gene according to the activity of each protein to be analyzed.

As another method to detect the expression level of the A7322 or F3374V1 gene based on its translation product, the intensity of staining may be observed via immunohistochemical analysis using an antibody against A7322 or F3374V1 protein. Namely, the observation of strong staining indicates increased presence of the A7322 or F3374V1 protein and at the same time high expression level of the A7322 or F3374V1 gene. Breast cancer tissue can be preferably used as a test material for immunohistochemical analysis.

In accordance with the methods of the present invention, expression levels of the A7322 or F3374V1 gene in a specimen (test sample) are estimated and compared with those in a normal sample. When such a comparison shows that the expression level of the target gene is higher than that of the normal sample, the subject is judged to be affected with breast cancer. The expression level of the A7322 or F3374V1 gene in the specimens from the normal sample and subject may be determined at the same time. Alternatively, normal ranges of the expression levels can be determined by a statistical method based on the results obtained from analyzing specimens previously collected from a control group. A result obtained from a subject sample is compared with the normal range; when the result does not fall within the normal range, the subject is judged to be affected with the breast cancer. Expression levels of the A7322 or F3374V1 gene in a specimen (test sample) can also be compared to those in one or more breast cancer samples. The breast cancer samples can be representative of different stages of breast cancer. When such a comparison shows that the expression level of the target gene is about equal than that of the breast cancer sample, the subject is judged to be affected with breast cancer. Comparison with breast cancer samples from different stages of the disease can also allow for prognosis and/or diagnosis of the extent of advancement of the disease in the test sample.

According to the present invention, an intermediate result for examining the condition of a subject may be provided. Such intermediate result may be combined with additional information to assist a doctor, nurse, or other practitioner to diagnose that a subject suffers from the disease. Alternatively, the present invention may be used to detect cancerous cells in a subject-derived tissue, and provide a doctor with useful information to diagnose that the subject suffers from the disease.

In the present invention, a diagnostic agent for diagnosing breast cancer is also provided. The diagnostic agent of the present invention comprises a compound that binds to a polynucleotide or a polypeptide of the present invention. Preferably, an oligonucleotide that hybridizes to the polynucleotide of the present invention, or an antibody or non-antibody binding protein that binds to the polypeptide of the present invention may be used as such a compound.

For instance, an oligonucleotide comprising at least 15 continuous nucleotide bases selected from the nucleotide sequence of the A7322 or F337V14 genes, or complement thereof can be used as preferable diagnostic agent of the present invention. Such oligonucleotides are useful as probes for the isolation or detection of the A7322 or F3374V1 genes. Alternatively, an antibody or non-antibody binding protein specifically recognizing a polypeptide encoded by the A7322 or F3374V1 genes also finds use as a diagnostic agent of the present invention.

Monitoring Breast Cancer Treatment

The expression levels of the A7322 or F3374V1 genes also allow for the course of treatment of breast cancer to be monitored. In this method, a test cell population is provided from a subject undergoing treatment for breast cancer. If desired, test cell populations are obtained from the subject at various time points, before, during, and/or after treatment. Expression of one or more of the A7322 or F3374V1 genes in the cell population is then determined and compared to a reference cell population which includes cells whose breast cancer state is known. In the context of the present invention, the reference cells should have not been exposed to the treatment of interest.

If the reference cell population contains no breast cancer cells, a similarity in the expression one or more of the A7322 or F3374V1 genes in the test cell population and the reference cell population indicates that the treatment of interest is efficacious. However, a difference in the expression of these genes in the test population and a normal control reference cell population indicates a less favorable clinical outcome or prognosis. Similarly, if the reference cell population contains breast cancer cells, a difference between the expression of one or more of the genes of the present invention in the test cell population and the reference cell population indicates that the treatment of interest is efficacious, while a similarity in the expression of such genes in the test population and a reference cell population indicates a less favorable clinical outcome or prognosis.

Additionally, the expression level of the genes of the present invention determined in a subject-derived biological sample obtained after treatment (i.e., post-treatment levels) can be compared to the expression level of the one or more of the A7322 or F3374V1 genes determined in a subject-derived biological sample obtained prior to treatment onset (i.e., pre-treatment levels). A decrease in the expression level in a post-treatment sample indicates that the treatment of interest is efficacious while an increase or maintenance in the expression level in the post-treatment sample indicates a less favorable clinical outcome or prognosis.

As used herein, the term "efficacious" indicates that the treatment leads to a reduction in the expression of a pathologically up-regulated gene, an increase in the expression of a pathologically down-regulated gene or a decrease in size, prevalence, or metastatic potential of breast cancer (e.g., breast ductal carcinoma) in a subject. When a treatment of interest is applied prophylactically, the term "efficacious" means that the treatment retards or prevents a breast tumor from forming or retards, prevents, or alleviates a symptom of clinical breast cancer. Assessment of breast tumors can be made using standard clinical protocols.

In addition, efficaciousness can be determined in association with any known method for diagnosing or treating breast cancer. Breast cancer can be diagnosed, for example, by identifying symptomatic anomalies, e.g., weight loss, abdominal pain, back pain, anorexia, nausea, vomiting and generalized malaise, weakness, and jaundice.

Screening Method (1) Test Compounds for Screening

In the context of the present invention, agents to be identified through the present screening methods can be any compound or composition including several compounds. Furthermore, the test agent exposed to a cell or protein according to the screening methods of the present invention can be a single compound or a combination of compounds. When a combination of compounds is used in the methods, the compounds can be contacted sequentially or simultaneously.

Any test agent, for example, cell extracts, cell culture supernatant, products of fermenting microorganism, extracts from marine organism, plant extracts, purified or crude proteins, peptides, non-peptide compounds, synthetic micro-molecular compounds (including nucleic acid constructs, such as antisense RNA, siRNA, ribozymes, etc.) and natural compounds can be used in the screening methods of the present invention. The test agent of the present invention can be also obtained using any of the numerous approaches in combinatorial library methods known in the art, including (1) biological libraries,
(2) spatially addressable parallel solid phase or solution phase libraries,
(3) synthetic library methods requiring deconvolution,
(4) the "one-bead one-compound" library method and
(5) synthetic library methods using affinity chromatography selection.

The biological library methods using affinity chromatography selection is limited to peptide libraries, while the other four approaches are applicable to peptide, non-peptide oligomer or small molecule libraries of compounds (Lam, Anticancer Drug Des 1997, 12: 145-67). Examples of methods for the synthesis of molecular libraries can be found in the art (DeWitt et al., Proc Natl Acad Sci USA 1993, 90: 6909-13; Erb et al., Proc Natl Acad Sci USA 1994, 91: 11422-6; Zuckermann et al., J Med Chem 37: 2678-85, 1994; Cho et al., Science 1993, 261: 1303-5; Carell et al., Angew Chem Int Ed Engl 1994, 33: 2059; Carell et al., Angew Chem Int Ed Engl 1994, 33: 2061; Gallop et al., J Med Chem 1994, 37: 1233-51). Libraries of compounds can be presented in solution (see Houghten, Bio/Techniques 1992, 13: 412-21) or on beads (Lam, Nature 1991, 354: 82-4), chips (Fodor, Nature 1993, 364: 555-6), bacteria (U.S. Pat. No. 5,223,409), spores (U.S. Pat. Nos. 5,571,698; 5,403,484 and 5,223,409), plasmids (Cull et al., Proc Natl Acad Sci USA 1992, 89: 1865-9) or phage (Scott and Smith, Science 1990, 249: 386-90; Devlin, Science 1990, 249: 404-6; Cwirla et al., Proc Natl Acad Sci USA 1990, 87: 6378-82; Felici, J Mol Biol 1991, 222: 301-10; US Pat. Application 2002-103360).

A compound in which a part of the structure of the compound screened by any of the present screening methods is converted by addition, deletion and/or replacement, is included in the agents obtained by the screening methods of the present invention.

Furthermore, when the screened test agent is a protein, for obtaining a DNA encoding the protein, either the whole amino acid sequence of the protein may be determined to deduce the nucleic acid sequence coding for the protein, or partial amino acid sequence of the obtained protein may be analyzed to prepare an oligo DNA as a probe based on the sequence, and screen cDNA libraries with the probe to obtain a DNA encoding the protein. The obtained DNA finds use in preparing the test agent which is a candidate for treating or preventing cancer.

Test agents useful in the screening described herein can also be antibodies or non-antibody binding proteins that specifically bind to the BC protein or partial BC peptides that lack the activity to binding for partner or the activity to phosphorylate a substrate or phosphorylated by kinases in vivo. Such partial protein or antibody can be prepared by the methods described herein (see Nucleotides, polypeptides, vectors and host cells or Antibodies) and can be tested for their ability to block phosphorylation of the BC protein or binding of the protein (e.g., A7322, F3374 or PBK/TOPK) with its binding partners.

(2) General Screening Method

For screening of compounds that bind to a BC protein, in immunoprecipitation, an immune complex is formed by adding these antibodies or non-antibody binding proteins to a cell lysate prepared using an appropriate detergent. The immune complex consists of a polypeptide, a polypeptide having a binding affinity for the polypeptide, and an antibody or non-antibody binding protein Immunoprecipitation can be also conducted using antibodies against a polypeptide, in addition to using antibodies against the above epitopes, which antibodies can be prepared as described above (see Antibodies).

An immune complex can be precipitated, for example, by Protein A sepharose or Protein G sepharose when the antibody is a mouse IgG antibody. If the polypeptide of the present invention is prepared as a fusion protein with an epitope, such as GST, an immune complex can be formed in the same manner as in the use of the antibody against the polypeptide, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the polypeptide is difficult to detect by a common staining method, such as Coomassie staining or silver staining, the detection sensitivity for the protein can be improved by culturing cells in culture medium containing radioactive isotope, $^{35}$S-methionine or $^{35}$S-cysteine, labeling proteins in the cells, and detecting the proteins. The target protein can be purified directly from the SDS-polyacrylamide gel and its sequence can be determined, when the molecular weight of a protein has been revealed.

As a method for screening for proteins that bind to the BC polypeptide using the polypeptide, for example, West-Western blotting analysis (Skolnik et al., Cell 65: 83-90 (1991)) can be used. Specifically, a protein binding to the BC polypeptide can be obtained by preparing a cDNA library from cells, tissues, organs (see Nucleotides, polypeptides, vectors and host cells), or cultured cells expected to express a protein binding to the BC polypeptide using a phage vector (e.g., ZAP), expressing the protein on LB-agarose, fixing the protein expressed on a filter, reacting the purified and labeled BC polypeptide with the above filter, and detecting the plaques expressing proteins bound to the BC polypeptide according to the label. The BC polypeptide may be labeled by utilizing the binding between biotin and avidin, or by utilizing an antibody that specifically binds to the BC polypeptide, or a peptide or polypeptide (for example, GST) that is fused to the BC polypeptide. Methods using radioisotope or fluorescence and such may be also used.

The terms "label" and "detectable label" are used herein to refer to any composition detectable by spectroscopic, photochemical, biochemical, immunochemical, electrical, optical or chemical means. Such labels include biotin for staining with labeled streptavidin conjugate, magnetic beads (e.g., DYNABEADS™), fluorescent dyes (e.g., fluorescein, Texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,275,149; and 4,366,241. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to *E. coli* and expressing the protein.

As a reporter gene, for example, Ade2 gene, lacZ gene, CAT gene, luciferase gene and such can be used in addition to the HIS3 gene.

A compound binding to BC polypeptide can also be screened using affinity chromatography. For example, the BC polypeptide can be immobilized on a carrier of an affinity column, and a test compound, containing a protein capable of binding to the BC polypeptide, is applied to the column. A test compound herein can be, for example, cell extracts, cell lysates, etc. After loading the test compound, the column is washed, and compounds bound to the BC polypeptide can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon can be used as a means for detecting or quantifying the bound compound in the present invention. When such a biosensor is used, the interaction between the BC polypeptide and a test compound can be observed real-time as a surface plasmon resonance signal, using only a minute amount of polypeptide and without labeling (for example, BIAcore, Pharmacia). Therefore, it is possible to evaluate the binding between the BC polypeptide and a test compound using a biosensor such as BIAcore.

As a method of screening for compounds that inhibit the binding between a BC protein (e.g., A7322, F3374 or PBK/TOPK) and a binding partner thereof, many methods well known by one skilled in the art can be used. For example, screening can be carried out as an in vitro assay system, such as a cellular system. More specifically, first, either the BC protein or the binding partner thereof is bound to a support, and the other protein is added together with a test compound thereto. Next, the mixture is incubated, washed and the other protein bound to the support is detected and/or measured.

In the context of the present invention, "inhibition of binding" between two proteins refers to at least reducing binding between the proteins. Thus, in some cases, the percentage of binding pairs in a sample in the presence of a test agent will be decreased compared to an appropriate (e.g., not treated with test compound or from a non-cancer sample, or from a cancer sample) control. The reduction in the amount of proteins bound may be, e.g., less than 90%, 80%, 70%, 60%, 50%, 40%, 25%, 10%, 5%, 1% or less (e.g., 0%), than the pairs bound in a control sample.

Examples of supports that may be used for binding proteins include, for example, insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they may be filled into a column. Alternatively, the use of magnetic beads is also known in the art, and enables one to readily isolate proteins bound on the beads via magnetism.

The binding of a protein to a support may be conducted according to routine methods, such as chemical bonding and physical adsorption, for example. Alternatively, a protein may be bound to a support via antibodies that specifically recognize the protein. Moreover, binding of a protein to a support can be also conducted by means of avidin and biotin.

The methods of screening for molecules that bind when the immobilized polypeptide is exposed to synthetic chemical compounds, or natural substance banks, or a random phage peptide display library, and the methods of screening using high-throughput based on combinatorial chemistry techniques (Wrighton et al., Science 273: 458-63 (1996); Verdine, Nature 384: 11-3 (1996)) to isolate not only proteins but chemical compounds that bind to the protein (including agonist and antagonist) are well known to one skilled in the art.

Furthermore, the phosphorylation level of a polypeptide or functional equivalent thereof may be detected according to any method known in the art. For example, a test compound is contacted with the polypeptide expressing cell, the cell is incubated for a sufficient time to allow phosphorylation of the polypeptide, and then, the amount of phosphorylated polypeptide may be detected. Alternatively, a test compound is contacted with the polypeptide in vitro, the polypeptide is incubated under condition that allows phosphorylation of the polypeptide, and then, the amount of phosphorylated polypeptide may be detected (see (17) In vitro and in vivo kinase assay.).

In the present invention, the conditions suitable for the phosphorylation may be provided with an incubation of substrate and enzyme protein in the presence of phosphate donor, e.g. ATP. The conditions suitable for the phosphorylation also include conditions in culturing cells expressing the polypeptides. For example, the cell is a transformant cell harboring an expression vector comprising a polynucleotide encoding the BC polypeptide (see Nucleotides, polypeptides, vectors and host cells). After the incubation, the phosphorylation level of the substrate can be detected, for example, with an antibody recognizing phosphorylated substrate or by detecting labeled gamma-phosphate transferred by the ATP phosphate donor. Prior to the detection of phosphorylated substrate, substrate may be separated from other elements, or cell lysate of transformant cells. For instance, gel electrophoresis may be used for separation of substrate. Alternatively, substrate may be captured by contacting with a carrier having an antibody against substrate.

For detection of phosphorylated protein, SDS-PAGE or immunoprecipitation can be used. Furthermore, an antibody that recognizes a phosphorylated residue or transferred labeled phosphate can be used for detecting phosphorylated protein level. Any immunological techniques using an antibody recognizing the phosphorylated polypeptide can be used for the detection. ELISA or immunoblotting with antibodies recognizing phosphorylated polypeptide can be used for the present invention. When a labeled phosphate donor is used, the phosphorylation level of the substrate can be detected via tracing the label. For example, radio-labeled ATP (e.g. $^{32}$P-ATP) can be used as phosphate donor, wherein radioactivity of the separated substrate correlates with the phosphorylation level of the substrate. Alternatively, an antibody specifically recognizing a phosphorylated substrate from un-phosphorylated substrate can be used for detection phosphorylated substrate.

If the detected amount of phosphorylated BC polypeptide contacted with a test compound is decreased to the amount detected in not contacted with the test compound, the test compound is deemed to inhibit polypeptide phosphorylation of a BC protein and thus have breast cancer suppressing ability. Herein, a phosphorylation level can be deemed to be "decreased" when it decreases by, for example, 10%, 25%, or 50% from, or at least 0.1 fold, at least 0.2 fold, at least 1 fold, at least 2 fold, at least 5 fold, or at least 10 fold or more compared to that detected for cells not contacted with the test agent. For example, Student's t-test, the Mann-Whitney U-test, or ANOVA may be used for statistical analysis.

Furthermore, the expression level of a polypeptide or functional equivalent thereof may be detected according to any method known in the art. For example, a reporter assay can be used. Suitable reporter genes and host cells are well known in the art. The reporter construct required for the screening can be prepared by using the transcriptional regulatory region of BC gene or downstream gene thereof. When the transcriptional regulatory region of the gene has been known to those skilled in the art, a reporter construct can be prepared by using the previous sequence information. When the transcriptional regulatory region remains unidentified, a nucleotide segment containing the transcriptional regulatory region can be isolated from a genome library based on the nucleotide sequence information of the gene. The transcriptional regulatory region of the gene herein is the region from start codon to at least 500 bp upstream, preferably 1000 bp, more preferably 5000 or 10000 bp upstream. A nucleotide segment containing the transcriptional regulatory region can be isolated from a genome library or can be propagated by PCR. Methods for identifying a transcriptional regulatory region, and also assay protocol are well known (Molecular Cloning third edition chapter 17, 2001, Cold Springs Harbor Laboratory Press).

Various low-throughput and high-throughput enzyme assay formats are known in the art and can be readily adapted for detection or measuring of the phosphorylation level of the BC polypeptide. For high-throughput assays, the substrate can conveniently be immobilized on a solid support. Following the reaction, the phosphorylated substrate can be detected on the solid support by the methods described above. Alternatively, the contact step can be performed in solution, after which the substrate can be immobilized on a solid support, and the phosphorylated substrate detected. To facilitate such assays, the solid support can be coated with streptavidin and the substrate labeled with biotin, or the solid support can be coated with antibodies against the substrate. The skilled person can determine suitable assay formats depending on the desired throughput capacity of the screen.

The assays of the invention are also suitable for automated procedures which facilitate high-throughput screening. A number of well-known robotic systems have been developed for solution phase chemistries. These systems include automated workstations like the automated synthesis apparatus developed by Takeda Chemical Industries, Ltd. (Osaka, Japan) and many robotic systems utilizing robotic arms (Zymate II, Zymark Corporation, Hopkinton, Mass.; Orca, Hewlett Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

(3) Screening Using the Binding Activity for A7322 or F3374 as Index

The present invention further provides a method of screening for a compound useful in the treatment of breast cancer using a polypeptide of the present invention. The present invention further provides a method of screening for a compound has a binding abirity to the protein of the present invention. An embodiment of such a screening method comprises the steps of:

(a) contacting a test compound with a polypeptide selected from the group consisting of:
(1) a polypeptide comprising the amino acid sequence of SEQ ID NO: 80 or 82;
(2) a polypeptide that comprises the amino acid sequence of SEQ ID NO: 80 or 82 in which one or more amino acids are substituted, deleted, inserted, and/or added and that has a biological activity equivalent to a protein consisting of the amino acid sequence of SEQ ID NO: 80 or 82
(3) a polypeptide that shares at least 90%, 93%, 95%, 96%, 97%, 98% or 99% sequence identity with a polypeptide comprising the amino acid sequence of SEQ ID NO:80 or 82 wherein the polypeptide has a biological activity equivalent to a polypeptide of the amino acid sequence of SEQ ID NO: 80 or 82; and
(4) a polypeptide encoded by a polynucleotide that hybridizes under stringent conditions to a polynucleotide consisting of the nucleotide sequence of SEQ ID NO: 79 or 81, wherein the polypeptide has a biological activity equivalent to a polypeptide consisting of the amino acid sequence of SEQ ID NO: 80 or 82;
(b) detecting the binding activity between the polypeptide and the test compound; and
(c) selecting the test compound that binds to the polypeptide.

A polypeptide to be used for screening may be a recombinant polypeptide or a protein derived from natural sources, or a partial peptide thereof. Any test compound aforementioned may used for screening.

As a method of screening for proteins, for example, that bind to a polypeptide using A7322 or F3374V1 polypeptide (or functionally equivalent thereof, see Nucleotides, polypeptides, vectors and host cells), many methods well known by a person skilled in the art can be used. Such a screening can be conducted using, for example, an immunoprecipitation, West-Western blotting analysis (Skolnik et al., Cell 65: 83-90 (1991)), a two-hybrid system utilizing cells ("MATCH-MAKER Two-Hybrid system", "Mammalian MATCH-MAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)"), affinity chromatography and A biosensor using the surface plasmon resonance phenomenon (see (2) General screening Method).

Any aforementioned test compound may used (see (1) Test compounds for screening).

(4) Screening Using the Expression Level of A7322 or F3374 as Index

Alternatively, the screening methods of the present invention may comprise the following steps:
(a) contacting a candidate compound with a cell into which a vector comprising the transcriptional regulatory region of A7322 or F3374V1 gene and a reporter gene that is expressed under the control of the transcriptional regulatory region has been introduced,
(b) measuring the expression or activity level of said reporter gene; and
(c) selecting the compound that reduces the expression or activity level of said reporter gene as compared to the expression or activity level of said reporter gene detected in the absence of the test compound.

Suitable reporter genes and host cells are well known in the art. The reporter construct required for the screening can be prepared by the methods mentioned above (see (2) General screening Method).

A compound isolated by the screening is a candidate for drugs which inhibit the activity of A7322 or F3374V1 polypeptide, which, in turn, finds use to treat or prevent breast cancer. A compound in which a part of the structure of the compound obtained by the present screening method having the activity of binding to A7322 or F3374V1 polypeptide is converted by addition, deletion and/or replacement, is included in the compounds obtained by the screening method of the present invention.

In a further embodiment, the present invention provides methods for screening candidate compounds which are targets in the treatment of breast cancer. As discussed in detail above, by controlling the expression level of the A7322 or F3374V1 protein, one can control the onset and progression of breast cancer. Thus, candidate compounds, which are targets in the treatment of breast cancer, can be identified through screenings that use the expression levels and activities of A7322 or F3374V1 as indices. In the context of the present invention, such screening may comprise, for example, the following steps:
(a) contacting a candidate compound with a cell expressing the A7322 or F3374V1 protein and
(b) selecting a compound that reduces the expression level of A7322 or F3374V1 in comparison with the expression level detected in the absence of the test compound.

Cells expressing at least one of the A7322 or F3374V1 proteins include, for example, cell lines established from breast cancer; such cells can be used for the above screening of the present invention. Expression levels can be estimated by methods well known to one skilled in the art. In the methods of screening, a compound that reduces the expression level of at least one of A7322 or F3374V1 can be selected as candidate compound.

In another embodiment of the methods for screening a compound useful in the treatment of breast cancer of the present invention, the method utilizes the biological activity of a polypeptide of the present invention as an index. Since the A7322 or F3374V1 proteins have the activity of promoting cell proliferation, a compound which inhibits the activity of one of these proteins of the present invention can be screened using this activity as an index.

Any polypeptides can be used for screening so long as they comprise the biological activity of the A7322 or F3374V1 protein (e.g., binding to PHB2/REA or AURKB, respectively, and promoting cell proliferation). Such biological activity includes cell-proliferating activity of the human A7322 or F3374V1 protein. For example, a human A7322 or F3374V1 protein can be used and polypeptides functionally equivalent to these proteins can also be used. Such polypeptides may be expressed endogenously or exogenously by cells.

(5) Screening Using the Binding of A7322 and PHB2/REA as Index

In the present invention, it was confirmed that the A7322 protein interacts with PHB/REA protein, and inhibits a nuclear-translocation of the PHB2/REA protein (FIG. 10A). In addition, suppression of reactivation of ERα (FIG. 11A to B) in the presence of A7322 protein was also confirmed. PHB2/REA is known to be an estrogen receptor α (ERα)-selective co-regulator and represses the transcriptional activity of the estradiol-liganded ERα. Hence, the present inventors revealed that A7322 activates the transcriptional activity of ERα through inhibition of the interaction of ERα and PHB2/REA (FIG. 11C). Thus, a compound that inhibits the binding between A7322 protein and PHB2/REA can be screened using such a binding of A7322 protein and PHB2/REA, cellular localization of PHB2/REA or the transcriptional activity of ERα as an index. Therefore, the present invention also provides a method for screening a compound for inhibiting the binding between A7322 protein and PHB2/REA can be screened using such a binding of A7322 protein and PHB2/REA, cellular localization of PHB2/REA or the transcriptional activity of ERα. Furthermore, the present invention also provides a method for screening a compound for treating or preventing breast cancer. The method is particularly suited for screening agents that may be used in treating or preventing breast cancer. More specifically, the method comprises the steps of:
(a) contacting an A7322 polypeptide or functional equivalent thereof with a PHB2/REA polypeptide or functional equivalent thereof in the presence of a test compound;
(b) detecting the binding between the polypeptides of step (a); and
(c) selecting the test compound that inhibits the binding between the A7322 and PHB2/REA polypeptides.

In the context of the present invention, a functional equivalent of an A7322 or PHB2/REA polypeptide is a polypeptide that has a biological activity equivalent to an A7322 polypeptide (SEQ ID NO: 79) or PHB2/REA polypeptide (SEQ ID NO: 90), respectively (see Nucleotides, polypeptides, vectors and host cells).

As a method of screening for compounds that inhibit the binding of A7322 to PHB2/REA, many methods well known by one skilled in the art can be used. A polypeptide to be used for screening may be a recombinant polypeptide or a protein derived from natural sources, or a partial peptide thereof. Any test compound aforementioned may used for screening.

As a method of screening for proteins, for example, that bind to a polypeptide using A7322 or PHB2/REA polypeptide (or functionally equivalent thereof, see Nucleotides, polypeptides, vectors and host cells), many methods well known by a person skilled in the art can be used. Such a screening can be conducted using, for example, an immunoprecipitation, West-Western blotting analysis (Skolnik et al., Cell 65: 83-90 (1991)), a two-hybrid system utilizing cells ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Steprnglanz, Trends Genet. 10: 286-92 (1994)"), affinity chromatography and A biosensor using the surface plasmon resonance phenomenon (see (2) General screening Method).

Any aforementioned test compound may used (see (1) Test compounds for screening).

Furthermore, the present invention provides a method for a compound that inhibits an interaction of A7322 and PHB2/REA using cellular localization of PHB2/REA as an index. More specifically, the method comprises the steps of:
- (a) contacting a candidate compound with cells expressing A7322 and PHB2/REA proteins,
- (b) detecting the subcellular localization of PHB2/REA protein; and
- (c) selecting the compound that reduces the level of PHB2/REA protein in nucleus as compared to the level of said protein detected in the absence of the test compound.

In some embodiments, this method further comprises the step of detecting the binding of the candidate compound to A7322 or PHB2/REA, or detecting the level of binding A7322 to PHB2/REA. Cells expressing A7322 and PHB2/REA proteins include, for example, cell lines established from breast cancer, such cells can be used for the above screening of the present invention so long as the cells express these two genes. Alternatively cells may be transfected both or either of expression vectors of A7322 and PHB2/REA, so as to express these two genes. The subcellular localization of PHB2/REA protein can be detected by immunocytochemical staining using an anti-PHB2/REA antibody (see (8) Immunocytochemical staining), a combination of fractionation method and western blot or PHB2/REA proteins labeling with isotope or fluorescence (see Nucleotides, polypeptides, vectors and host cells).

In another embodiment, the present invention provides a method for a compound that inhibits an interaction of A7322 and PHB2/REA using the transcriptional activity of ERα as an index. More specifically, the method comprises the steps of:
- (a) contacting a candidate compound with cells expressing A7322, PHB2/REA and ERα proteins, into which a vector comprising the estrogen responsive transcriptional regulatory region and a reporter gene that is expressed under the control of the transcriptional regulatory region has been introduced under E2 treatment,
- (b) measuring the expression or activity level of said reporter gene; and
- (c) selecting the compound that reduces the expression or activity level of said reporter gene as compared to the expression or activity level of said reporter gene detected in the absence of the test compound.

Cells expressing A7322, PHB2/REA and ERα proteins include, for example, cell lines established from breast cancer, such cells can be used for the above screening of the present invention so long as the cells express these three genes. Alternatively the cells may be transfected each or either of expression vectors of A7322, PHB2/REA and ERα, so as to express these three genes. Suitable reporter genes and host cells are well known in the art. The reporter construct required for the screening can be prepared by the methods mentioned above and below (see (2) General screening Method and (19) Estrogen responsive element (ERE) reporter gene assays).

(6) Screening Using the Phosphorylation Level of F3374V1 as Index

Furthermore, in the present invention, it was confirmed that the F3374V1 proteins were modified by phosphorylation at C-terminal region (591-730 amino-acid). Thus, a compound that inhibits the phosphorylation of F3374V1 protein can be screened using such modification as an index. Therefore, the present invention also provides a method for screening a compound for inhibits the phosphorylation of F3374V1 protein. Furthermore, the present invention also provides a method for screening a compound for treating or preventing breast cancer. The method is particularly suited for screening agents that may be used in treating or preventing breast cancer. More specifically, the method comprises the steps of:
- (a) contacting a cell that expresses a polypeptide selected from the group consisting of:
  - (1) a polypeptide comprising the amino acid sequence of SEQ ID NO: 82;
  - (2) a polypeptide that comprises the amino acid sequence of SEQ ID NO: 82 in which one or more amino acids are substituted, deleted, inserted, and/or added and that has a biological activity equivalent to a protein consisting of the amino acid sequence of SEQ ID NO: 82
  - (3) a polypeptide that shares at least 90%, 93%, 95%, 96%, 97%, 98% or 99% sequence identity with a polypeptide comprising the amino acid sequence of SEQ ID NO: 82 wherein the polypeptide has a biological activity equivalent to a polypeptide of the amino acid sequence of SEQ ID NO: 82; and
  - (4) a polypeptide encoded by a polynucleotide that hybridizes under stringent conditions to a polynucleotide consisting of the nucleotide sequence of SEQ ID NO: 81, wherein the polypeptide has a biological activity equivalent to a polypeptide consisting of the amino acid sequence of SEQ ID NO: 82; with a test compound;
- (b) detecting the phosphorylation level of the polypeptide;
- (c) comparing the phosphorylation level of the polypeptide with the phosphorylation level of the polypeptide detected in the absence of the compound; and
- (d) selecting the compound that reduced the phosphorylation level of the polypeptide as an inhibitor of the phosphorylation of the polypeptide or a compound for treating or preventing breast cancer.

Herein, any cell may be used so long as it expresses the F3374V1 polypeptide or functional equivalents thereof (see Nucleotides, polypeptides, vectors and host cells). The cell used in the present screening may be a cell naturally expressing the F3374V1 polypeptide including, for example, cells derived from and cell-lines established from breast cancer and testis. Cell-lines of breast cancer such as HBC4, HBC5, HBL100, HCC1937, MCF-7, MDA-MB-231, MDA-MB-4355, SKBR3, T47D, and YMB1 can be employed.

Alternatively, the cell used in the screening may be a cell that naturally does not express the F3374V1 polypeptide and which is transfected with an F3374V1 polypeptide- or an F3374V1 functional equivalent-expressing vector. Such recombinant cells can be obtained through known genetic engineering methods (e.g., Morrison D A., J Bacteriology 1977, 132: 349-51; Clark-Curtiss & Curtiss, Methods in Enzymology (eds. Wu et al.) 1983, 101: 347-62) as mentioned above (see Nucleotides, polypeptides, vectors and host cells).

Any of the aforementioned test compounds may be used for the present screening. However, it is preferred to select compounds that can permeate into a cell. Alternatively, when the test compound is a polypeptide, the contact of a cell and the test agent in the present screening can be performed by transforming the cell with a vector that comprises the nucleotide sequence coding for the test agent and expressing the test agent in the cell.

In another embodiment, conditions suitable for phosphorylation of F3374V1 polypeptide or functional equivalents thereof can be provided in vitro. This screening method includes the steps of:

(a) contacting a test compound with the polypeptide of the present invention or fragment thereof (e.g. C-terminal region (591-730 amino-acid));
(b) detecting the phosphorylation of the polypeptide of step (a); and
(c) selecting a compound that suppresses the phosphorylation of the polypeptide in comparison with the biological activity detected in the absence of the test compound.

In the present invention, as mentioned above, the biological activity of the F3374V1 protein is preferably phosphorylated activity. The skilled artisan can estimate phosphorylation level as mentioned above (see (2) General screening Method).

Accordingly, in these embodiments, the present invention provides a method of screening an agent for inhibiting the phosphorylation of F3374V1 or preventing or treating breast cancer comprising the steps of:
(a) contacting a polypeptide selected from the group consisting of:
  (1) a polypeptide comprising the amino acid sequence of SEQ ID NO: 82;
  (2) a polypeptide that comprises the amino acid sequence of SEQ ID NO: 82 in which one or more amino acids are substituted, deleted, inserted, and/or added and that has a biological activity equivalent to a protein consisting of the amino acid sequence of SEQ ID NO: 82
  (3) a polypeptide that shares at least 90%, 93%, 95%, 96%, 97%, 98% or 99% sequence identity with a polypeptide comprising the amino acid sequence of SEQ ID NO: 82 wherein the polypeptide has a biological activity equivalent to a polypeptide of the amino acid sequence of SEQ ID NO: 82; and
  (4) a polypeptide encoded by a polynucleotide that hybridizes under stringent conditions to a polynucleotide consisting of the nucleotide sequence of SEQ ID NO: 81, wherein the polypeptide has a biological activity equivalent to a polypeptide consisting of the amino acid sequence of SEQ ID NO: 82; or a fragment thereof comprising a phosphorylation site
with a test compound under a condition that allows phosphorylation of the polypeptide;
(b) detecting the phosphorylation level of the polypeptide or the fragment thereof;
(c) comparing the phosphorylation level of the substrate with the phosphorylation level of the polypeptide detected in the absence of the test compound; and
(d) selecting the compound that reduced the phosphorylation level of the polypeptide as a compound for inhibiting the phosphorylation of the polypeptide or treating or preventing breast cancer.

In these embodiments, a condition that allows phosphorylation of F3374V1 polypeptide can be provided by incubating the polypeptide with suitable kinase for phosphorylation the F3374V1 polypeptide and ATP. In some embodiments, the F3374V1 polypeptide is further contacted with an AURKB polypeptide. Further, in the preferable embodiments, a substance enhancing phosphorylation of the F3374V1 polypeptide can be added to the reaction mixture of screening. When phosphorylation of the polypeptide is enhanced by the addition of the substance, the phosphorylation level can be determined with higher sensitivity.

The phosphorylation level of F3374V1 polypeptide or functional equivalent thereof may be detected according to any method known in the art (see (2) General screening Method).

Furthermore, the present inventors revealed that F3374V1 interacts with AURKB in breast cancer cells (FIG. 13). Accordingly, it is believed that the interaction of both polypeptides plays a crucial role in carcinogenesis or cell proliferation, in particular cell proliferation of breast cancer. Hence, it is intended to screen for a compound useful in treating or preventing breast cancer, that inhibits an interaction between an F3374V1 polypeptide and an AURKB polypeptide or a vice versa interaction. Thus, the present invention provides methods of screening for a compound for inhibiting an interaction between an F3374V1 polypeptide and an AURKB polypeptide. Furthermore, the present invention provides methods of screening for a compound for treating or preventing breast cancer. The methods include the steps of:
(a) contacting an AURKB polypeptide or functional equivalent thereof with an F3374V1 polypeptide or functional equivalent thereof in the presence of a test compound;
(b) detecting the binding between the polypeptides of step (a); and
(c) selecting the test compound that inhibits the binding between the AURKB and F3374V1 polypeptides.

In the context of the present invention, a functional equivalent of an F3374V1 or AURKB polypeptide is a polypeptide that has a biological activity equivalent to an F3374V1 polypeptide (SEQ ID NO: 82) or AURKB polypeptide (SEQ ID NO: 88), respectively (see Nucleotides, polypeptides, vectors and host cells).

As a method of screening for compounds that inhibit the phosphorylation of F3374V1 by AURKB, many methods well known by one skilled in the art can be used. For example, screening can be carried out as an in vitro assay system, such as a cellular system.

The present invention is also based on the finding that AURKB has the kinase activity for F3374V1. For example, phosphorylation sites of F3374V1 by AURKB are located in the C-terminal portion of the F3374 protein (591-730 amino-acid) (SEQ ID NO: 122). These findings suggest that phosphorylation of F3374V1 by AURKB plays key roles in tumor cell growth proliferation, and inhibiting the phosphorylation of F3374V1 by AURKB is a promising target for development of anti-cancer drugs. To that end, one aspect of the invention involves identifying test compounds that regulate AURKB-mediated phosphorylation of F3374V1. Accordingly, the present invention provides a method of screening for compounds for inhibiting AURKB-mediated phosphorylation of F3374V1. Furthermore, the present invention provides a method of screening for compounds for treating or preventing breast cancer. The method comprising the steps of:
(a) incubating F3374V1 and AURKB in the presence of a test compound under conditions suitable for the phosphorylation of F3374V1 by AURKB, wherein the F3374V1 is a polypeptide selected from the group consisting of:
  (1) a polypeptide comprising the amino acid sequence of SEQ ID NO: 82 (F3374V1);
  (2) a polypeptide comprising the amino acid sequence of SEQ ID NO: 82 wherein one or more amino acids are substituted, deleted, or inserted, provided the polypeptide has a biological activity equivalent to the polypeptide consisting of the amino acid sequence of SEQ ID NO: 82;
  (3) a polypeptide that shares at least 90%, 93%, 95%, 96%, 97%, 98% or 99% sequence identity with a polypeptide comprising the amino acid sequence of SEQ ID NO: 82 wherein the polypeptide has a biological activity equivalent to a polypeptide of the amino acid sequence of SEQ ID NO: 82

(4) a polypeptide encoded by a polynucleotide that hybridizes under stringent conditions to a polynucleotide consisting of the nucleotide sequence of SEQ ID NO: 81, provided the polypeptide has a biological activity equivalent to a polypeptide consisting of the amino acid sequence of SEQ ID NO: 82;

(b) detecting a phosphorylation level of the F3374V1;

(c) comparing the phosphorylation level of the F3374V1 to a control level; and (d) selecting a compound that decreases the phosphorylation level of the F3374V1 as compared to the control level that detect in the absence of the test compound.

Herein, the method of screening for a compound for inhibiting AURKB-mediated phosphorylation of F3374V1 or treating and/or preventing breast cancer includes the detection of the phosphorylated level of the F3374V1 at C-terminal F3374 protein (591-730 amino-acid) (SEQ ID NO: 122), or homologous positions of the polypeptide.

In another aspect of the invention, a kit for screening for compounds for inhibiting AURKB-mediated phosphorylation of F3374V1 or treating or preventing breast cancer is also provided. The kit comprises the components of:

(a) a polypeptide selected from the group consisting of:
  (1) a polypeptide comprising the amino acid sequence of SEQ ID NO: 82 (F3374V1);
  (2) a polypeptide comprising the amino acid sequence of SEQ ID NO: 82 wherein one or more amino acids are substituted, deleted, or inserted, provided the polypeptide has a biological activity equivalent to the polypeptide consisting of the amino acid sequence of SEQ ID NO: 82;
  (3) a polypeptide that shares at least 90%, 93%, 95%, 96%, 97%, 98% or 99% sequence identity with a polypeptide comprising the amino acid sequence of SEQ ID NO: 82 wherein the polypeptide has a biological activity equivalent to a polypeptide of the amino acid sequence of SEQ ID NO: 82; and
  (4) a polypeptide encoded by a polynucleotide that hybridizes under stringent conditions to a polynucleotide consisting of the nucleotide sequence of SEQ ID NO: 81 provided the polypeptide has a biological activity equivalent to a polypeptide consisting of the amino acid sequence of SEQ ID NO: 82 and (b) a polypeptide selected from the group consisting of:
  (1) a polypeptide comprising the amino acid sequence of SEQ ID NO: 88 (AURKB);
  (2) a polypeptide comprising the amino acid sequence of SEQ ID NO: 88 wherein one or more amino acids are substituted, deleted, or inserted, provided the polypeptide has a biological activity equivalent to the polypeptide consisting of the amino acid sequence of SEQ ID NO: 88;
  (3) a polypeptide that shares at least 90%, 93%, 95%, 96%, 97%, 98% or 99% sequence identity with a polypeptide comprising the amino acid sequence of SEQ ID NO:88 wherein the polypeptide has a biological activity equivalent to a polypeptide of the amino acid sequence of SEQ ID NO: 88; and
  (4) a polypeptide encoded by a polynucleotide that hybridizes under stringent conditions to a polynucleotide consisting of the nucleotide sequence of SEQ ID NO: 87, provided the polypeptide has a biological activity equivalent to a polypeptide consisting of the amino acid sequence of SEQ ID NO: 88; and (c) a reagent for detecting a phosphorylation level of F3374V1.

Further, this invention also provides a kit for screening for a compound for treating or preventing breast cancer. The kit comprises the components of:

(a) a cell expressing a polypeptide selected from the group consisting of:
  (1) a polypeptide comprising the amino acid sequence of SEQ ID NO: 82 (F3374V1);
  (2) a polypeptide comprising the amino acid sequence of SEQ ID NO: 82 wherein one or more amino acids are substituted, deleted, or inserted, provided the polypeptide has a biological activity equivalent to the polypeptide consisting of the amino acid sequence of SEQ ID NO: 82;
  (3) a polypeptide that shares at least 90%, 93%, 95%, 96%, 97%, 98% or 99% sequence identity with a polypeptide comprising the amino acid sequence of SEQ ID NO: 82 wherein the polypeptide has a biological activity equivalent to a polypeptide of the amino acid sequence of SEQ ID NO: 82
  (4) a polypeptide encoded by a polynucleotide that hybridizes under stringent conditions to a polynucleotide consisting of the nucleotide sequence of SEQ ID NO: 81, provided the polypeptide has a biological activity equivalent to a polypeptide consisting of the amino acid sequence of SEQ ID NO: 82; and (b) a reagent for detecting a phosphorylation level of F3374V1.

Furthermore, the kit for screening for compounds for inhibiting AURKB-mediated phosphorylation of F3374V1 or treating or preventing breast cancer includes cells further expressing a polypeptide selected from the group consisting of:

(a) a polypeptide comprising the amino acid sequence of SEQ ID NO: 88 (AURKB);

(b) a polypeptide comprising the amino acid sequence of SEQ ID NO: 88 wherein one or more amino acids are substituted, deleted, or inserted, provided the polypeptide has a biological activity equivalent to the polypeptide consisting of the amino acid sequence of SEQ ID NO: 88;

(c) a polypeptide that shares at least 90%, 93%, 95%, 96%, 97%, 98% or 99% sequence identity with a polypeptide comprising the amino acid sequence of SEQ ID NO: 88 wherein the polypeptide has a biological activity equivalent to a polypeptide of the amino acid sequence of SEQ ID NO: 88; and (d) a polypeptide encoded by a polynucleotide that hybridizes under stringent conditions to a polynucleotide consisting of the nucleotide sequence of SEQ ID NO: 81, provided the polypeptide has a biological activity equivalent to a polypeptide consisting of the amino acid sequence of SEQ ID NO: 88.

In another aspect, the cell used in the kit is breast cancer cells.

In the present invention, the kit may further comprise phosphate donor. The kit of the present invention may also comprise an antibody which recognizes phosphorylated C-terminal F3374 protein (591-730 amino-acid) (SEQ ID NO: 122) as a reagent for detecting a phosphorylated F3374V1. Consequently, this invention also provides the kit for screening for a compound for treating or preventing breast cancer, wherein the reagent for detecting a phosphorylation level of F3374V1 is an antibody that recognises the phosphorylation at C-terminal F3374 protein (591-730 amino-acid) (SEQ ID NO: 122). Whether or not a subject protein is the target for phosphorylation can be determined in accordance with the present invention. For example, kinase activity for F3374V1 can be determined by incubating a polypeptide under conditions suitable for phosphorylation of F3374V1 and detecting the phosphorylated F3374V1 level. For example, the phosphorylated sites of F3374V1 by AURKB are C-terminal F3374 protein (591-730 amino-acid) (SEQ ID NO: 122).

In the present invention, the conditions suitable for the phosphorylation of F3374V1 by AURKB may be provided with an incubation of F3374V1 and AURKB in the presence of phosphate donor, e.g. ATP. The conditions suitable for the F3374V1 phosphorylation by AURKB also were a condition in culturing cells expressing the polypeptides (see (2) General screening Method).

Methods for preparing polypeptides functionally equivalent to a given protein are well known by a person skilled in the art and include known methods of introducing mutations into the protein as mentioned above (see Nucleotides, polypeptides, vectors and host cells).

In some preferred embodiments, the functional equivalent of the F3374V1 polypeptide can include an amino acid sequence corresponding to the AURKB binding domain, for example the amino acid sequence of SEQ ID NO: 122. Similarly, the functional equivalent of AURKB polypeptide can include an amino acid sequence corresponding to the F3374V1 binding domain.

As discussed above, the inhibition of binding between F3374V1 and AURKB leads to the suppression of cell proliferation. Furthermore, the inhibition of phosphorylation of F3374V1 by AURKB leads to the suppression of cell proliferation. Accordingly, compounds that inhibit this binding or phosphorylation may serve as pharmaceuticals for treating or preventing breast cancers. The F3374V1 and AURKB polypeptides to be used for the screening methods of the present invention may be a recombinant polypeptide or a protein derived from the nature, or may also be a partial peptide thereof, so long as it retains the binding ability or phosphorylation activity of the full-length protein. Such partial peptides retaining the binding ability or phosphorylation activity are herein referred to as "functional equivalents". The F3374V1 and AURKB polypeptides to be used in the screening methods can be, for example, a purified polypeptide, a soluble protein, a form bound to a carrier or a fusion protein fused with other polypeptides.

As a method of screening for compounds that inhibit the binding between F3374V1 and AURKB, many methods well known by one skilled in the art can be used. The binding between proteins is preferably carried out in buffer, examples of which include, but are not limited to, phosphate buffer and Tris buffer. However, the selected buffer must not inhibit binding between the proteins. Any of the aforementioned detected method may be used for the present screening (see (2) General screening Method). And any of the aforementioned test compounds may be used for the present screening (see (1) Test compounds for screening).

A compound isolated by the screening methods of the present invention is a candidate for drugs which inhibit the activity of F3374V1 or AURKB, for treating or preventing diseases attributed to, for example, cell proliferative diseases, such as breast cancer. A compound in which a part of the structure of the compound obtained by the present screening methods of the present invention is converted by addition, deletion and/or replacement, is included in the compounds obtained by the screening methods of the present invention. A compound effective in suppressing the expression of over-expressed genes, i.e., the F3374V1 and AURKB genes, is deemed to have a clinical benefit and can be further tested for its ability to reduce or prevent cancer cell growth in animal models or test subjects.

The present invention may also include screening for proteins that bind to an F3374V1 or AURKB polypeptide to inhibit the interaction thereof. To that end, many methods well known to those skilled in the art can be used. Such a screening can be conducted by, for example, an immunoprecipitation assay using methods well known in the art. The proteins of the invention can be recombinantly produced using standard procedures mentioned above (see (2) General screening Method). A compound binding to the F3374V1 or AURKB polypeptide can also be screened using affinity chromatography mentioned above (see (1) Test compounds for screening).

(7) Screening Using the Phosphorylation Level of PBK/TOPK as Index

The present invention provides a method of screening for an agent that induces apoptosis or cell cycle arrest in breast cancer cells. An agent that induces apoptosis or cell cycle arrest of cells expressing TOPK, e.g. breast cancer cells, are expected to be useful for treating or preventing breast cancer. Therefore, the present invention also provides a method for screening an agent for treating or preventing breast cancer. The method is particularly suited for screening agents that may be used in treating or preventing invasive ductal carcinoma ("IDC").

More specifically, the method comprises the steps of:
(a) contacting a cell that expresses the PBK/TOPK polypeptide or functional equivalents thereof with an agent;
(b) detecting the phosphorylation level of the PBK/TOPK polypeptide;
(c) comparing the phosphorylation level of the polypeptide with the phosphorylation level of the polypeptide detected in the absence of the agent; and
(d) selecting the agent that reduced the phosphorylation level of the polypeptide as an agent that induces apoptosis or cell cycle arrest of cells expressing TOPK, e.g. breast cancer cells or as an agent for treating or preventing breast cancer.

In another embodiment, the method comprises the steps of:
(a) contacting a cell that expresses PP1α polypeptide and the PBK/TOPK polypeptide or functional equivalents thereof with an agent;
(b) detecting the phosphorylation level of the PBK/TOPK polypeptide;
(c) comparing the phosphorylation level of the polypeptide with the phosphorylation level of the polypeptide detected in the absence of the agent; and
(d) selecting the agent that reduced the phosphorylation level of the polypeptide as an agent that induces apoptosis or cell cycle arrest of breast cancer cells or as an agent for treating or preventing cells expressing TOPK, e.g. breast cancer.

Herein, any cell may be used so long as it expresses the PBK/TOPK polypeptide or functional equivalents thereof. The cell used in the present screening may be a cell naturally expressing the PBK/TOPK polypeptide including, for example, cells derived from and cell-lines established from breast cancer (e.g., IDC), thymus, and testis. Cell-lines of breast cancer such as HBC4, HBC5, HBL100, HCC1937, MCF-7, MDA-MB-231, MDA-MB-435S, SKBR3, T47D, and YMB1 can be employed.

Alternatively, the cell used in the screening may be a cell that naturally does not express the PBK/TOPK polypeptide or PP1α and which is transfected with a PBK-TOPK polypeptide- or a PBK/TOPK functional equivalent-expressing or PP1α expressing vector. Such recombinant cells can be obtained through known genetic engineering methods (e.g., Morrison D A., J Bacteriology 1977, 132: 349-51; Clark-Curtiss & Curtiss, Methods in Enzymology (eds. Wu et al.) 1983, 101: 347-62) mentioned above (see Nucleotides, polypeptides, vectors and host cells).

Any of the aforementioned test agents may be used for the present screening (see (1) Test compounds for screening). However, it is preferred to select agents that can permeate into a cell. Alternatively, when the test agent is a polypeptide, the contact of a cell and the test agent in the present screening can be performed by transforming the cell with a vector that comprises the nucleotide sequence coding for the test agent and expressing the test agent in the cell.

In the present invention, a substance enhancing phosphorylation of the PBK/TOPK polypeptide can be added to the reaction mixture of screening. When phosphorylation of the polypeptide is enhanced by the addition of the substance, the phosphorylation level can be determined with higher sensitivity.

The phosphorylation level of PBK/TOPK polypeptide or functional equivalent thereof may be detected according to any method known in the art (see (2) General screening Method).

Alternatively, the phosphorylation level of PBK/TOPK polypeptide or functional equivalent thereof may be detected by detecting the cell cycle of the cell. Specifically, the cell cycle of a cell can be determined by using conventional methods known in the art including FACS and so on. When detecting the cell cycle of a cell for determining the phosphorylation level of the polypeptide, after the contact of the cell with a test agent, it is preferred to incubate the cell for a sufficient time, for example, for 12 h or more, until normal cells path through the G2/M phase. According to this procedure, a test agent can be determined to have the ability to induce apoptosis of breast cancer cells, when the cell cycle is detected to be trapped at the G2/M phase.

In another embodiment the method comprises the steps of:
(a) contacting CDK1, CyclinB1 and PBK/TOPK polypeptide or a functional equivalent thereof with a substrate that is phosphorylated by the polypeptide and an agent under a condition that allows phosphorylation of the substrate;
(b) detecting the phosphorylation level of the PBK/TOPK polypeptide;
(c) comparing the phosphorylation level of the PBK/TOPK polypeptide with the phosphorylation level detected in the absence of the agent; and
(d) selecting the agent that reduced the phosphorylation level of the PBK/TOPK polypeptide as an agent that induces apoptosis of breast cancer cells or as an agent for inhibiting phosphorylation of the PBK/TOPK polypeptide or treating or preventing breast cancer.

Herein, the CDK1, CyclinB1 and PBK/TOPK polypeptide or functional equivalents thereof used in the screening can be prepared as a recombinant protein or natural protein, by methods well known to those skilled in the art. The polypeptides may be obtained adopting any known genetic engineering methods for producing polypeptides (e.g., Morrison J., J Bacteriology 1977, 132: 349-51; Clark-Curtiss & Curtiss, Methods in Enzymology (eds. Wu et al.) 1983, 101: 347-62) as mentioned above (see Nucleotides, polypeptides, vectors and host cells).

Further, the CDK1 and CyclinB1 protein complex may also be used for the invention so long as it retains the kinase activity for the PBK/TOPK protein. Such partial peptides can be produced by genetic engineering, by known methods of peptide synthesis, or by digesting the natural CDK1 and CyclinB1 protein with an appropriate peptidase (see Nucleotides, polypeptides, vectors and host cells).

The PBK/TOPK polypeptide or functional equivalent thereof to be contacted with the CDK1 and CyclinB1 protein complex can be, for example, a purified polypeptide, a soluble protein, or a fusion protein fused with other polypeptides.

In these embodiments, a condition that allows having kinase activity of the CDK1 and CyclinB1 polypeptides can be provided by incubating the CDK1 and CyclinB1 polypeptide with the PBK/TOPK polypeptide to phosphorylate the PBK/TOPK polypeptide and ATP. Further, in the present invention, a substance enhancing phosphorylation of the PBK/TOPK polypeptide can be added to the reaction mixture of screening. When phosphorylation of the PBK/TOPK polypeptide is enhanced by the addition of the substance, phosphorylation level of the PBK/TOPK polypeptide can be determined with higher sensitivity.

The contact of the CDK1, CyclinB1 and PBK/TOPK polypeptide or functional equivalent thereof and a test agent may be conducted in vivo or in vitro. The screening in vitro can be carried out in buffer, for example, but are not limited to, phosphate buffer and Tris buffer, so long as the buffer does not inhibit the phosphorylation of the PBK/TOPK polypeptide or functional equivalent thereof.

According to an aspect of the present invention, the components necessary for the present screening methods may be provided as a kit for screening agents that induces apoptosis or cell cycle arrest of breast cancer cells or agents for treating or preventing breast cancer. The kit may contain, for example, a cell expressing PBK/TOPK polypeptide or a function equivalent thereof, or PBK/TOPK polypeptide and/or PP1α or functional equivalents thereof, or polypeptide of PBK/TOPK, CDK1 and CyclinB1 or function equivalents thereof. Further, the kit may include control reagents (positive and/or negative), detectable labels, cell culture medium or buffer solution, containers required for the screening, instructions (e.g., written, tape, VCR, CD-ROM, etc.) for carrying out the method, and so on. The components and reagents may be packaged in separate containers.

(8) Screening Using the Kinase Activity of PBK/TOPK for a Substrate as Index

According to another aspect of the invention, agents that induce apoptosis of breast cancer cells or that can be used for treating or preventing breast cancer (e.g., IDC) are screened using the phosphorylation level of a PBK/TOPK substrate as an index. Specifically, the method comprises the steps of:
(a) contacting PBK/TOPK polypeptide or a functional equivalent thereof with a substrate that is phosphorylated by the polypeptide and an agent under a condition that allows phosphorylation of the substrate;
(b) detecting the phosphorylation level of the substrate;
(c) comparing the phosphorylation level of the substrate with the phosphorylation level of the substrate detected in the absence of the agent; and
(d) selecting the agent that reduced the phosphorylation level of the substrate as an agent that inhibits the kinase activity of PBK/TOPK polypeptide, induces apoptosis of breast cancer cells or as an agent for treating or preventing breast cancer.

In some embodiments, the substrate is a Histone H3 polypeptide. The PBK/TOPK polypeptide or functional equivalents thereof used in the screening can be prepared as a recombinant protein or natural protein, by methods well known to those skilled in the art. The polypeptides may be obtained adopting any known genetic engineering methods for producing polypeptides (e.g., Morrison J., J Bacteriology 1977, 132: 349-51; Clark-Curtiss & Curtiss, Methods in Enzymology (eds. Wu et al.) 1983, 101: 347-62) as mentioned above (see Nucleotides, polypeptides, vectors and host cells).

Further, a partial peptide of the PBK/TOPK protein may also be used for the invention so long as it retains the kinase activity of the protein. Such partial peptides can be produced by genetic engineering, by known methods of peptide synthesis, or by digesting the natural PBK/TOPK protein with an appropriate peptidase (see Nucleotides, polypeptides, vectors and host cells).

The PBK/TOPK polypeptide or functional equivalent thereof to be contacted with a test agent and substrate can be, for example, a purified polypeptide, a soluble protein, or a fusion protein fused with other polypeptides.

The substrate is any compound capable of accepting a phosphor group such as a protein, a nucleic acid (RNA or DNA) or a small molecule. For example, the substrate can be a histone or a fragment of a histone containing the phosphorylation site. It is confirmed that Ser 10 of histone H3 can be phosphorylated by the PBK/TOPK protein. Therefore, histone H3, or a fragment thereof containing Ser 10, is useful as the substrate.

Similarly to the PBK/TOPK polypeptide, histone H3 for the present screening can be prepared as a recombinant protein or natural protein. Furthermore, similarly to the PBK/TOPK polypeptide, histone H3 may be prepared as a fusion protein so long as the resulting fusion protein can be phosphorylated by the PBK/TOPK polypeptide. The nucleotide sequence of histone H3 is well known in the art. Further, histone H3 is also commercially available (e.g., product of Roche).

In these embodiments, a condition that allows phosphorylation of histone H3 polypeptide can be provided by incubating the histone H3 polypeptide with PBK/TOPK polypeptide to be phosphorylated the histone H3 polypeptide and ATP. Further, in the present invention, a substance enhancing kinase activity of the PBK/TOPK polypeptide can be added to the reaction mixture of screening. When phosphorylation of the substrate is enhanced by the addition of the substance, phosphorylation level of a substrate can be determined with higher sensitivity.

The contact of the PBK/TOPK polypeptide or functional equivalent thereof, its substrate, and a test agent may be conducted in vivo or in vitro. The screening in vitro can be carried out in buffer, for example, but are not limited to, phosphate buffer and Tris buffer, so long as the buffer does not inhibit the phosphorylation of the substrate by the PBK/TOPK polypeptide or functional equivalent thereof.

In the present invention, the phosphorylation level of a substrate can be determined by methods known in the art (see (2) General screening Method).

(9) Screening Using the Binding of PBK/TOPK and p47 or Phosphorylation of p97 as Index In the present invention, it was confirmed that the PBK/TOPK protein interacts with the p97 protein through the p47 protein as adapter, and inhibits cell division. Thus, a compound that inhibits the binding between the PBK/TOPK protein and the p47 protein or the phosphorylation of p97 can be screened using such a binding of the PBK/TOPK protein and the p47 protein or phosphorylation level of p97 as an index. Therefore, the present invention also provides a method for screening a compound for inhibiting the binding between PBK and reducing p47 or phosphorylation level of p97. Furthermore, the present invention also provides a method for screening a compound for treating or preventing breast cancer. The method is particularly suited for screening agents that may be used in treating or preventing breast cancer. More specifically, the method comprises the steps of:

(a) contacting the PBK/TOPK polypeptide or functional equivalent thereof with the p47 polypeptide or functional equivalent thereof and the p97 polypeptide or functional equivalent thereof in the presence of a test compound;

(b) detecting the binding between the PBK/TOPK polypeptide and the p47 polypeptide or the phosphorylation level of p97; and (c) selecting the test compound that inhibits the binding between the PBK/TOPK polypeptide and the p47 polypeptide or reduces the phosphorylation of p97.

In the context of the present invention, a functional equivalent of the PBK/TOPK or p47 or p97 polypeptide is a polypeptide that has a biological activity equivalent to the PBK/TOPK (SEQ ID NO: 92) or p47 (SEQ ID NO: 118) or p97 (SEQ ID NO: 120), respectively (see Nucleotides, polypeptides, vectors and host cells).

As a method of screening for compounds that inhibit the binding of the PBK/TOPK polypeptide to the p47 polypeptide, many methods well known by one skilled in the art can be used.

A polypeptide to be used for screening may be a recombinant polypeptide or a protein derived from natural sources, or a partial peptide thereof. Any test compound aforementioned may used for screening.

As a method of screening for proteins, for example, that bind to a polypeptide using the PBK/TOPK polypeptide and the p47 polypeptide (or functionally equivalent thereof, see Nucleotides, polypeptides, vectors and host cells), many methods well known by a person skilled in the art can be used. Such a screening can be conducted using, for example, an immunoprecipitation, West-Western blotting analysis (Skolnik et al., Cell 65: 83-90 (1991)), a two-hybrid system utilizing cells ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)"), affinity chromatography and A biosensor using the surface plasmon resonance phenomenon (see (2) General screening Method).

Any aforementioned test compound may used (see (1) Test compounds for screening).

Furthermore, in the present invention the method of screening allows detecting the phosphorylation of the p97 peptide. Thus, a condition that allows phosphorylation of p97 polypeptide can be provided by incubating the p97 polypeptide with the PBK/TOPK polypeptide and p47 polypeptide to phosphorylate the p97 polypeptide and ATP. Further, in the present invention, a substance enhancing a kinase activity of the PBK/TOPK polypeptide or a phosphorylation of the p97 polypeptide can be added to the reaction mixture of screening. When phosphorylation of the p97 is enhanced by the addition of the substance, phosphorylation level of a p97 can be determined with higher sensitivity.

The contact of the PBK/TOPK polypeptide or functional equivalent thereof, p97 or functional equivalent thereof, and a test agent may be conducted in vivo or in vitro. The screening in vitro can be carried out in buffer, for example, but are not limited to, phosphate buffer and Tris buffer, so long as the buffer does not inhibit the phosphorylation of the substrate by the PBK/TOPK polypeptide or functional equivalent thereof.

In the present invention, the phosphorylation level of a substrate can be determined by methods known in the art (see (2) General screening Method).

(10) Screening Using the Cell Cycle Structure and G2/M Population of PBK/TOPK Expressing Cells as Index The present invention provides a method of screening for an agent that induces cell cycle arrest in breast cancer cells. An agent that induces cell cycle arrest of breast cancer cells are expected to be useful for treating or preventing breast cancer. Therefore, the present invention also provides a method for screening an agent for treating or preventing breast cancer. The method is particularly suited for screening agents that may be used in treating or preventing invasive ductal carcinoma ("IDC").

More specifically, the method comprises the steps of:
(a) contacting a candidate agent with a cell which expresses the PBK/TOPK polypeptide or functional equivalents thereof,
(b) observing the cell structure and/or G2/M population on cell cycle; and
(c) selecting the compound that alters the intercellular junction to the long intercellular bridges and/or increase the G2/M population of the cell.

Herein, any cell may be used so long as it expresses the PBK/TOPK polypeptide or functional equivalents thereof. The cell used in the present screening may be a cell naturally expressing the PBK/TOPK polypeptide including, for example, cells derived from and cell-lines established from breast cancer (e.g., IDC), thymus, and testis. Cell-lines of breast cancer such as HBC4, HBC5, HBL100, HCC1937, MCF-7, MDA-MB-231, MDA-MB-435S, SKBR3, T47D, and YMB1 can be employed.

Alternatively, the cell used in the screening may be a cell that naturally does not express the PBK/TOPK polypeptide or PP1α and which is transfected with a PBK-TOPK polypeptide- or a PBK/TOPK functional equivalent-expressing or PP1α-expressing vector. Such recombinant cells can be obtained through known genetic engineering methods (e.g., Morrison D A., J Bacteriology 1977, 132: 349-51; Clark-Curtiss & Curtiss, Methods in Enzymology (eds. Wu et al.) 1983, 101: 347-62) mentioned above (see Nucleotides, polypeptides, vectors and host cells).

Any of the aforementioned test agents may be used for the present screening (see (1) Test compounds for screening). However, it is preferred to select agents that can permeate into a cell. Alternatively, when the test agent is a polypeptide, the contact of a cell and the test agent in the present screening can be performed by transforming the cell with a vector that comprises the nucleotide sequence coding for the test agent and expressing the test agent in the cell.

In the present invention, a substance getting a good view of cell can be added to the reaction mixture of screening, for example DAPI, anti-cell membrane protein antibody. The cell structure can be observed by a phase contrast microscopy or a Time-lapse microscopy 2 days after contacting with the test agents.

The cell cycle of a cell can be determined by using conventional methods known in the art including FACS and so on. When the cell cycle of a cell was detected, after the contact of the cell with a test agent, it is preferred to incubate the cell for a sufficient time, for example, for 12 h or more, until normal cells path through the G2/M phase. According to this procedure, a test agent can be determined to have the ability to inhibit proliferation of breast cancer cells, when the cell cycle is detected to be trapped at the G2/M phase.

According to an aspect of the present invention, the components necessary for the present screening methods may be provided as a kit for screening agents that induces apoptosis or cell cycle arrest of breast cancer cells or agents for treating or preventing breast cancer. The kit may contain, for example, a cell expressing A7322 or F3374V1 or PBK/TOPK and/or PP1α polypeptide or function equivalents thereof, or A7322 or AURKB or F3374V1 or PHB2/REA or ERα or PBK/TOPK or histone H3 or CDK1 or CyclinB1 or p47 or p97 polypeptide or functional equivalents thereof. Further, the kit may include control reagents (positive and/or negative), detectable labels, cell culture medium, containers required for the screening, instructions (e.g., written, tape, VCR, CD-ROM, etc.) for carrying out the method, and so on. The components and reagents may be packaged in separate containers.

A compound isolated by the screening methods of the present invention is a candidate for drugs which inhibit the expression or activity of A7322, F3374V1, PBK/TOPK or AURKB, for treating or preventing diseases attributed to, for example, cell proliferative diseases, such as breast cancer.

The compound isolated by this screening is a candidate for antagonists of the polypeptide of the present invention. Likewise, the term "antagonist" refers to molecules that inhibit the function of the polypeptide of the present invention by binding thereto. Moreover, a compound isolated by this screening is a candidate for compounds which inhibit the in vivo interaction of the polypeptide of the present invention with molecules (including DNAs and proteins).

When the biological activity to be detected in the present method is cell proliferation, it can be detected, for example, by preparing cells which express the polypeptide of the present invention, culturing the cells in the presence of a test compound, and determining the speed of cell proliferation, measuring the cell cycle and such, as well as by measuring the colony forming activity as described in the Examples.

Unless otherwise defined, all technical and scientific terms used herein have the same meaning as commonly understood by one of ordinary skill in the art to which this invention belongs. In case of conflict, the present specification, including definitions, will control.

Isolated Compounds and Pharmaceutical Compositions

A compound isolated by the above screenings is a candidate for drugs which inhibit the activity of the BC polypeptides of the present invention and finds use in the treatment of breast cancer. More particularly, when the biological activity of the BC proteins is used as the index, compounds screened by the present method serve as a candidate for drugs for the treatment of breast cancer. For instance, the present invention provides a composition for treating or preventing breast cancer, said composition comprising a pharmaceutically effective amount of an inhibitor having at least one function selected from the group consisting of:
(a) inhibiting binding between A7322 and PHB2/REA, F3374V1 and AURKB, or PBK/TOPK and histone H3;
(b) inhibiting phosphorylation of F3374V1 by AURKB or histone H3 by PBK/TOPK;
(c) inhibiting expression of a gene selected from the group consisting of A7322 or F3374; and
(d) inhibiting nuclear-translocation of the PHB2/REA protein.

A "pharmaceutically effective amount" of a compound is a quantity that is sufficient to treat and/or ameliorate cancer in an individual. An example of a pharmaceutically effective amount includes an amount needed to decrease the expression or biological activity of A7322 or F3374V1 when administered to an animal. The decrease may be, e.g., at least a 5%, 10%, 20%, 30%, 40%, 50%, 75%, 80%, 90%, 95%, 99%, or 100% change in expression.

Such active ingredient inhibiting an expression of any one gene selected from the group consisting of BC genes and AURKB (c) can also be an inhibitory oligonucleotide (e.g., antisense-oligonucleotide, siRNA or ribozyme) against the gene, or derivatives, such as expression vector, of the antisense-oligonucleotide, siRNA or ribozyme, as described above (see Antisense Oligonucleotides, siRNA). Alternatively, an active ingredient inhibiting phosphorylation of F3374V1 by AURKB (b) can be, for example, a dominant negative mutant of F3374V1 or PBK/TOPK. Further, an antagonist of F3374V1 can be used as an active ingredient inhibiting binding between F3374V1 and AURKB, or an antagonist of PBK/TOPK can be used as an active ingredient inhibiting binding between PBK/TOPK and histone H3 (a). Alternatively, such active ingredient may be selected by the screening method as described above (see Screening Method).

Moreover, compounds in which a part of the structure of the compound inhibiting the activity of one of the BC proteins is converted by addition, deletion and/or replacement are also included in the compounds obtainable by the screening method of the present invention.

An agent isolated by any of the methods of the invention can be administered as a pharmaceutical or can be used for the manufacture of pharmaceutical (therapeutic or prophylactic) compositions for humans and other mammals, such as mice, rats, guinea-pigs, rabbits, cats, dogs, sheep, pigs, cattle, monkeys, baboons, and chimpanzees for treating or preventing breast cancer. Preferred cancers to be treated or prevented by the agents screened through the present methods include invasive ductal carcinoma (IDC) and such.

The isolated agents can be directly administered or can be formulated into dosage form using known pharmaceutical preparation methods. Pharmaceutical formulations may include those suitable for oral, rectal, nasal, topical (including buccal and sub-lingual), vaginal or parenteral (including intramuscular, sub-cutaneous and intravenous) administration, or for administration by inhalation or insufflation. For example, according to the need, the agents can be taken orally, as sugar-coated tablets, capsules, elixirs and microcapsules; or non-orally, in the form of injections of sterile solutions or suspensions with water or any other pharmaceutically acceptable liquid. For example, the agents can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

The phrase "pharmaceutically acceptable carrier" refers to an inert substance used as a diluent or vehicle for a drug.

Examples of additives that can be mixed to tablets and capsules are, binders such as gelatin, corn starch, tragacanth gum and Arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the compounds obtained by the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflators.

When desired, the above described formulations, adapted to give sustained release of the active ingredient, may be employed. The pharmaceutical compositions may also contain other active ingredients such as antimicrobial agents, immunosuppressants or preservatives.

Preferred unit dosage formulations are those containing an effective dose, as recited below, or an appropriate fraction of the active ingredient.

Methods well known to one skilled in the art may be used to administer the inventive pharmaceutical compound to patients, for example as intra-arterial, intravenous, percutaneous injections and also as intranasal, transbronchial, intramuscular or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

The agents are preferably administered orally or by injection (intravenous or subcutaneous), and the precise amount administered to a subject will be determined under the responsibility of the attendant physician, considering a number of factors, including the age and sex of the subject, the precise disorder being treated, and its severity. Also the route of administration may vary depending upon the condition and its severity.

Moreover, the present invention provides a method for treating or preventing breast cancer using an antibody against a polypeptide of the present invention. According to the method, a pharmaceutically effective amount of an antibody against the polypeptide of the present invention is administered. Since the expression of the BC protein is up-regulated in cancer cells, and the suppression of the expression of these proteins leads to the decrease in cell proliferating activity, it is expected that breast cancer can be treated or prevented by binding the antibody and these proteins. Thus, an antibody against a polypeptide of the present invention may be administered at a dosage sufficient to reduce the activity of the protein of the present invention, which is in the range of 0.1 to about 250 mg/kg per day. The dose range for adult humans is generally from about 5 mg to about 17.5 g/day, preferably about 5 mg to about 10 g/day, and most preferably about 100 mg to about 3 g/day.

Generally, an efficacious or effective amount of one or more BC protein inhibitors is determined by first administering a low dose or small amount of a BC protein inhibitor and then incrementally increasing the administered dose or dosages, and/or adding a second BC protein inhibitor as needed, until a desired effect of inhibiting or preventing breast cancer is observed in the treated subject, with minimal or no toxic side effects. Applicable methods for determining an appropriate dose and dosing schedule for administration of a pharmaceutical composition of the present invention is described, for example, in Goodman and Gilman's The Pharmacological Basis of Therapeutics, 11th Ed., Brunton, et al., Eds., McGraw-Hill (2006), and in Remington: The Science and Practice of Pharmacy, 21st Ed., University of the Sciences in Philadelphia (USIP), Lippincott Williams & Wilkins (2005), both of which are hereby incorporated herein by reference.

The agents screened by the present methods further can be used for treating or preventing breast cancer, for example, invasive ductal carcinoma (IDC), in a subject. Administration can be prophylactic or therapeutic to a subject at risk of (or susceptible to) a disorder or having a disorder associated with aberrant phosphorylation activity of the BC protein. The method includes decreasing the function of BC protein in breast cancer cells. The function can be inhibited through the administration of an agent obtained by the screening method of the present invention.

Herein, the term "preventing" means that the agent is administered prophylactically to retard or suppress the forming of tumor or retards, suppresses, or alleviates at least one clinical symptom of cancer. Assessment of the state of tumor in a subject can be made using standard clinical protocols.

Alternatively, an antibody binding to a cell surface marker specific for tumor cells can be used as a tool for drug delivery. For example, the antibody conjugated with a cytotoxic agent is administered at a dosage sufficient to injure tumor cells.

Methods of Inducing Anti-Tumor Immunity and Tumor Vaccines

The present invention also relates to a method of inducing anti-tumor immunity comprising the step of administering an A7322 or F3374V1 protein or an immunologically active fragment thereof, or a polynucleotide encoding the protein or fragments thereof. The A7322 or F3374V1 protein or the immunologically active fragments thereof is useful as vaccines against breast cancer. In some cases the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the present invention, a vaccine against breast cancer refers to a substance that has the function to induce anti-tumor immunity upon inoculation into animals. In general, anti-tumor immunity includes immune responses such as follows:
    induction of cytotoxic lymphocytes against breast cancer,
    induction of antibodies that recognize breast cancer, and induction of anti-tumor cytokine production.

Therefore, when a certain protein induces any one of these immune responses upon inoculation into an animal, the protein is deemed to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to T cell by APC, and detecting the induction of CTL. Furthermore, APC has the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC, and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^{3}$H-thymidine uptake activity or LDH (lactose dehydrogenase)-release as the indicator is also well known.

Apart from DC, peripheral blood mononuclear cells (PBMCs) may also be used as the APC. The induction of CTL is reported that it can be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against tumors. Furthermore, APC that acquired the ability to induce CTL against tumors by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of breast cancer. Therapy against cancer or prevention of the onset of cancer includes any of the steps, such as inhibition of the growth of cancerous cells, involution of cancer, and suppression of occurrence of cancer. Decrease in mortality of individuals having cancer, decrease of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against breast cancer is compared to a control without vaccine administration. For example, Student's t-test, the Mann-Whitney U-test, or ANOVA may be used for statistical analyses.

The above-mentioned protein having immunological activity or a vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum, and such, but are not limited thereto. Furthermore, the vaccine of this invention may be combined appropriately with a pharmaceutically acceptable carrier. Examples of such carriers are sterilized water, physiological saline, phosphate buffer, culture fluid, and such. Furthermore, the vaccine may contain as necessary, stabilizers, suspensions, preservatives, surfactants, and such. The vaccine is administered systemically or locally. Vaccine administration may be performed by single administration, or boosted by multiple administrations.

When using APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of tumors from other individuals.

Furthermore, a pharmaceutical composition for treating or preventing breast cancer, comprising a pharmaceutically effective amount of the polypeptide of the present invention is provided. The pharmaceutical composition may be used for raising anti-tumor immunity. In the normal tissues, expression of A7322 is restricted to brain; expression of F3374V1 in normal organ is restricted to testis, thymus, placenta and bone marrow. Therefore, suppression of these genes may not adversely affect other organs. Thus, the A7322 and F3374V1 polypeptides are preferable for treating breast cancer. In the present invention, the polypeptide or fragment thereof is administered at a dosage sufficient to induce anti-tumor immunity, which is in the range of 0.1 mg to 10 mg, preferably 0.3 mg to 5 mg, more preferably 0.8 mg to 1.5 mg. The administrations are repeated. For example, 1 mg of the peptide or fragment thereof may be administered 4 times in every two weeks for inducing the anti-tumor immunity.

Dominant Negative Protein that Inhibits

The present invention relates to inhibitory polypeptides that contain MEGISNFKTPSKLSEKKK (SEQ ID NO: 98). In some preferred embodiments, the inhibitory polypeptide comprises MEGISNFKTPSKLSEKKK (SEQ ID NO: 98); a polypeptide functionally equivalent to the polypeptide; or polynucleotide encoding those polypeptides, wherein the polypeptide lacks the biological function of a peptide consisting of SEQ ID NO: 92. The amino acid sequence set forth in SEQ ID NO: 92 is disclosed in WO2005/028676. It has been known that cancer cell proliferation can be controlled by inhibiting the expression of the amino acid sequence. However, it is a novel finding proved by the present inventors that a fragment containing a sequence with a specific mutation in the above amino acid sequence inhibits the cancer cell proliferation.

The polypeptides comprising the selected amino acid sequence of the present invention, can be of any length, so long as the polypeptide inhibits cancer cell proliferation. Specifically, the length of the amino acid sequence may range from 8 to 70 residues, for example, from 8 to 50, preferably from 8 to 30, more specifically from 8 to 20, further more specifically from 8 to 16 residues.

The polypeptides of the present invention may contain two or more "selected amino acid sequences". The two or more "selected amino acid sequences" may be the same or different amino acid sequences. Furthermore, the "selected amino acid sequences" can be linked directly. Alternatively, they may be disposed with any intervening sequences among them.

Furthermore, the present invention relates to polypeptides homologous (i.e., share sequence identity) to the MEGISNFKTPSKLSEKKK/SEQ ID NO: 98 polypeptide specifically disclosed here. In the present invention, polypeptides homologous to the MEGISNFKTPSKLSEKKK/SEQ ID NO: 98 polypeptide are those which contain any mutations selected from addition, deletion, substitution and insertion of one or several amino acid residues and are functionally equivalent to the MEGISNFKTPSKLSEKKK/SEQ ID NO: 98 polypeptide. The phrase "functionally equivalent to the MEGISNFKTPSKLSEKKK/SEQ ID NO: 98 polypeptide" refers to having the function to inhibit the binding of CDK1 and CyclinB1 complex to PBK/TOPK. The MEGISNFKTPSKLSEKKK/SEQ ID NO: 98 sequence is preferably conserved in the amino acid sequences constituting polypeptides functionally equivalent to MEGISNFKTPSKLSEKKK/SEQ ID NO: 98 polypeptide. Therefore, polypeptides functionally equivalent to the MEGISNFKTPSKLSEKKK/SEQ ID NO: 98 peptide in the present invention preferably have amino acid mutations in sites other than the MEGISNFKTPSKLSEKKK/SEQ ID NO: 98 sequence. Amino acid sequences of polypeptides functionally equivalent to the MEGISNFKTPSKLSEKKK/SEQ ID NO: 98 peptide in the present invention conserve the MEGISNFKTPSKLSEKKK/SEQ ID NO: 98 sequence, and have 60% or higher, usually 70% or higher, preferably 80% or higher, more preferably 90% or higher, or 95% or higher, and further more preferably 98% or higher homology to a "selected amino acid sequence" Amino acid sequence homology can be determined using algorithms well known in the art, for example, BLAST or ALIGN set to their default settings.

Alternatively, the number of amino acids that may be mutated is not particularly restricted, so long as the MEGISNFKTPSKLSEKKK/SEQ ID NO: 98 peptide activity is maintained. Generally, up to about 10 amino acids, and even more preferably up to about 3 amino acids. Likewise, the site of mutation is not particularly restricted, so long as the mutation does not result in the disruption of the MEGISNFKTPSKLSEKKK/SEQ ID NO: 98 peptide activity.

In a preferred embodiment, the activity of the MEGISNFKTPSKLSEKKK/SEQ ID NO: 98 peptide comprises cell cycle arrest inducing effect in a PBK/TOPK expressing cell, i.e. breast cancer cell. Cell cycle arrest means stopping at check point of DNA replication and mitosis. Methods for detecting cell cycle arrest are well known. For instance, cell cycle arrest may be confirmed by using FACS (Flow cytometory).

In a another embodiment, the activity of the MEGISNFKTPSKLSEKKK/SEQ ID NO: 98 peptide comprises apoptosis inducing effect in a PBK/TOPK expressing cell, i.e. breast cancer cell. Apoptosis means cell death caused by the cell itself and is sometimes referred to as programmed cell death. Aggregation of nuclear chromosome, fragmentation of nucleus, or condensation of cytoplasm is observed in a cell undergoing apoptosis. Methods for detecting apoptosis are well known. For instance, apoptosis may be confirmed by TUNEL staining (Terminal deoxynucleotidyl Transferase Biotin-dUTP Nick End Labeling; Gavrieli et al., (1992) J. Cell Biol. 119: 493-501, Mori et al., (1994) Anat. & Embryol. 190: 21-28). Alternatively, DNA ladder assays, Annexin V staining, caspase assay, electron microscopy, or observation of conformational alterations on nucleus or cell membrane may be used for detecting apoptosis. Any commercially available kits may be used for detecting these behaviors in cells which are induced by apoptosis. For example, such apoptosis detection kits may be commercially available from the following providers:

LabChem. Inc.,
Promega,
BD Biosciences Pharmingen,
Calbiochem,
Takara Bio Company (CLONTECH Inc.),
CHEMICON International, Inc,
Medical & Biological Laboratories Co., Ltd. etc.

The polypeptides of the present invention can be chemically synthesized from any position based on selected amino acid sequences. Methods used in the ordinary peptide chemistry can be used for the method of synthesizing polypeptides. Specifically, the methods include those described in the following documents and Japanese Patent publications:

Peptide Synthesis, Interscience, New York, 1966; The Proteins, Vol. 2, Academic Press Inc., New York, 1976;
Peputido gousei (Peptide Synthesis), Maruzen (Inc.), 1975;
Peputido gousei no kiso to jikken (Fundamental and Experimental Peptide Synthesis), Maruzen (Inc.), 1985;
Iyakuhin no kaihatsu (Development of Pharmaceuticals), Sequel, Vol. 14: Peputido gousei (Peptide Synthesis), Hirokawa Shoten, 1991;
International Patent Publication WO99/67288.

The polypeptides of the present invention can be also synthesized by known genetic engineering techniques. An example of genetic engineering techniques is as follows. Specifically, DNA encoding a desired peptide is introduced into an appropriate host cell to prepare a transformed cell. The polypeptides of the present invention can be obtained by recovering polypeptides produced by this transformed cell. Alternatively, a desired polypeptide can be synthesized with an in vitro translation system, in which necessary elements for protein synthesis are reconstituted in vitro.

When genetic engineering techniques are used, the polypeptide of the present invention can be expressed as a fused protein with a peptide having a different amino acid sequence. A vector expressing a desired fusion protein can be obtained by linking a polynucleotide encoding the polypeptide of the present invention to a polynucleotide encoding a different peptide so that they are in the same reading frame, and then introducing the resulting nucleotide into an expression vector. The fusion protein is expressed by transforming an appropriate host with the resulting vector. Different peptides to be used in forming fusion proteins include the following peptides:

FLAG (Hopp et al., (1988) BioTechnology 6, 1204-10),
6×His consisting of six H is (histidine) residues, 10×His,
Influenza hemagglutinin (HA),
Human c-myc fragment,
VSV-GP fragment,
p18 HIV fragment,
T7-tag,
HSV-tag,
E-tag,
SV40T antigen fragment,
lck tag,
α-tubulin fragment,
B-tag,
Protein C fragment,
GST (glutathione-S-transferase),
HA (Influenza hemagglutinin),
Immunoglobulin constant region,
β-galactosidase, and
MBP (maltose-binding protein).

The polypeptide of the present invention can be obtained by treating the fusion protein thus produced with an appropriate protease, and then recovering the desired polypeptide. To purify the polypeptide, the fusion protein is captured in advance with affinity chromatography that binds with the fusion protein, and then the captured fusion protein can be treated with a protease. With the protease treatment, the desired polypeptide is separated from affinity chromatography, and the desired polypeptide with high purity is recovered.

The polypeptides of the present invention include modified polypeptides. In the present invention, the term "modified" refers, for example, to binding with other substances. Accordingly, in the present invention, the polypeptides of the present invention may further comprise other substances such as cell-membrane permeable substance. The other substances include organic compounds such as peptides, lipids, saccharides, and various naturally-occurring or synthetic polymers. The polypeptides of the present invention may have any modifications so long as the polypeptides retain the desired activity of inhibiting the binding of CDK1 and CyclinB1 complex to PBK/TOPK. In some embodiments, the inhibitory polypeptides can directly compete with PBK/TOPK binding to CDK1 and CyclinB1 complex. Modifications can also confer additive functions on the polypeptides of the invention. Examples of the additive functions include targetability, deliverability, and stabilization.

Preferred examples of modifications in the present invention include, for example, the introduction of a cell-membrane permeable substance. Usually, the intracellular structure is cut off from the outside by the cell membrane. Therefore, it is difficult to efficiently introduce an extracellular substance into cells. Cell membrane permeability can be conferred on the polypeptides of the present invention by modifying the polypeptides with a cell-membrane permeable substance. As a result, by contacting the polypeptide of the present invention with a cell, the polypeptide can be delivered into the cell to act thereon.

The "cell-membrane permeable substance" refers to a substance capable of penetrating the mammalian cell membrane to enter the cytoplasm. For example, a certain liposome fuses with the cell membrane to release the content into the cell. Meanwhile, a certain type of polypeptide penetrates the cytoplasmic membrane of mammalian cell to enter the inside of the cell. For polypeptides having such a cell-entering activity, cytoplasmic membranes and such in the present invention are preferable as the substance. Specifically, the present invention includes polypeptides having the following general formula.

[R]-[D];

wherein,
[R] represents a cell-membrane permeable substance; [D] represents a fragment sequence containing MEGISNFKTPSKLSEKKK/SEQ ID NO: 98. In the above-described general formula, [R] and [D] can be linked directly or indirectly through a linker. Peptides, compounds having multiple functional groups, or such can be used as a linker. Specifically, amino acid sequences containing -G- can be used as a linker. Alternatively, a cell-membrane permeable substance and a polypeptide containing a selected sequence can be bound to the surface of a minute particle. [R] can be linked to any positions of [D]. Specifically, [R] can be linked to the N terminal or C terminal of [D], or to a side chain of amino acids constituting [D]. Furthermore, more than one [R] molecule can be linked to one molecule of [D]. The [R] molecules can be introduced to different positions on the [D] molecule. Alternatively, [D] can be modified with a number of [R]s linked together.

For example, there have been reported a variety of naturally-occurring or artificially synthesized polypeptides having cell-membrane permeability (Joliot A. & Prochiantz A., Nat Cell Biol. 2004; 6: 189-96). All of these known cell-membrane permeable substances can be used for modifying polypeptides in the present invention. In the present invention, for example, any substance selected from the following group can be used as the above-described cell-permeable substance:

poly-arginine; Matsushita et al., (2003) J. Neurosci.; 21, 6000-7.
[Tat/RKKRRQRRR] (SEQ ID NO: 100) Frankel et al., (1988) Cell 55, 1189-93.
Green & Loewenstein (1988) Cell 55, 1179-88.
[Penetratin/RQIKIWFQNRRMKWKK] (SEQ ID NO: 101)
Derossi et al., (1994) J. Biol. Chem. 269, 10444-50.
[Buforin II/TRSSRAGLQFPVGRVHRLLRK] (SEQ ID NO: 102)
Park et al., (2000) Proc. Natl. Acad. Sci. USA 97, 8245-50.
[Transportan/GWTLNSAGYLLGKINLKALAALAKKIL] (SEQ ID NO: 103)
Pooga et al., (1998) FASEB J. 12, 67-77.
[MAP (model amphipathic peptide)/KLALKLALKALKAALKLA] (SEQ ID NO: 104)
Oehlke et al., (1998) Biochim. Biophys. Acta. 1414, 127-39.
[K-FGF/AAVALLPAVLLALLAP] (SEQ ID NO: 105)
Lin et al., (1995) J. Biol. Chem. 270, 14255-8.
[Ku70/VPMLK] (SEQ ID NO: 106)
Sawada et al., (2003) Nature Cell Biol. 5, 352-7.
[Ku70/PMLKE] (SEQ ID NO: 114)
Sawada et al., (2003) Nature Cell Biol. 5, 352-7.
[Prion/MANLGYWLLALFVTMWTDVGLCKKRPKP] (SEQ ID NO: 107)

Lundberg et al., (2002) Biochem. Biophys. Res. Commun. 299, 85-90.
[pVEC/LLIILRRRIRKQAHAHSK] (SEQ ID NO: 108)
Elmquist et al., (2001) Exp. Cell Res. 269, 237-44.
[Pep-1/KETWWETWWTEWSQPKKKRKV] (SEQ ID NO: 109)
Morris et al., (2001) Nature Biotechnol. 19, 1173-6.
[SynB1/RGGRLSYSRRRFSTSTGR] (SEQ ID NO: 110)
Rousselle et al., (2000) Mol. Pharmacol. 57, 679-86.
[Pep-7/SDLWEMMMVSLACQY] (SEQ ID NO: 111)
Gao et al., (2002) Bioorg. Med. Chem. 10, 4057-65.
[HN-1/TSPLNIHNGQKL] (SEQ ID NO: 112)
Hong & Clayman (2000) Cancer Res. 60, 6551-6.

In the present invention, the poly-arginine, which is listed above as an example of cell-membrane permeable substances, is constituted by any number of arginine residues. Specifically, for example, it is constituted by consecutive 5-20 arginine residues. The preferable number of arginine residues is 11 (SEQ ID NO: 113).

Pharmaceutical Compositions Comprising MEGISNFK-TPSKLSEKICK/SEQ ID NO: 98

The polypeptides of the present invention inhibit proliferation of cancer cells. Therefore, the present invention provides therapeutic and/or preventive agents for cancer which comprise as an active ingredient a polypeptide which comprises MEGISNFKTPSKLSEKKK/SEQ ID NO: 98; or a polynucleotide encoding the same. Alternatively, the present invention relates to methods for treating and/or preventing cancer comprising the step of administering a polypeptide of the present invention. Furthermore, the present invention relates to the use of the polypeptides of the present invention in manufacturing pharmaceutical compositions for treating and/or preventing cancer. Cancers which can be treated or prevented by the present invention are not limited, so long as expression of PBK/TOPK is up-regulated in the cancer cells. For example, the polypeptides of the present invention are useful for treating breast cancer.

Alternatively, the inhibitory polypeptides of the present invention can be used to induce cell cycle arrest of cancer cells. Therefore, the present invention provides cell cycle arrest inducing agents for cells, which comprise as an active ingredient a polypeptide which comprises MEGISNFK-TPSKLSEKKK/SEQ ID NO: 98; or a polynucleotide encoding the same. The cell cycle arrest inducing agents of the present invention may be used for treating cell proliferative diseases such as cancer. Cancers which can be treated or prevented by the present invention are not limited, so long as expression of PBK/TOPK is up-regulated in the cancer cells. For example, the polypeptides of the present invention are useful in treating breast cancer. Alternatively, the present invention relates to methods for inducing apoptosis of cells which comprise the step of administering the polypeptides of the present invention. Furthermore, the present invention relates to the use of polypeptides of the present invention in manufacturing pharmaceutical compositions for inducing cell cycle arrest in cells.

The inhibitory polypeptides of the present invention induce cell cycle arrest in PBK/TOPK-expressing cells such as breast cancer. In the meantime, PBK/TOPK expression has not been observed in most of normal organs. In some normal organs, the expression level of PBK/TOPK is relatively low as compared with cancer tissues. Accordingly, the polypeptides of the present invention may induce cell cycle arrest specifically in cancer cells.

When the polypeptides of the present invention are administered, as a prepared pharmaceutical, to human and other mammals such as mouse, rat, guinea pig, rabbit, cat, dog, sheep, pig, cattle, monkey, baboon and chimpanzee for treating cancer or inducing cell cycle arrest in cells, isolated compounds can be administered directly, or formulated into an appropriate dosage form using known methods for preparing pharmaceuticals. For example, if necessary, the pharmaceuticals can be orally administered as a sugar-coated tablet, capsule, elixir, and microcapsule, or alternatively parenterally administered in the injection form that is a sterilized solution or suspension with water or any other pharmaceutically acceptable liquid. For example, the compounds can be mixed with pharmacologically acceptable carriers or media, specifically sterilized water, physiological saline, plant oil, emulsifier, suspending agent, surfactant, stabilizer, corrigent, excipient, vehicle, preservative, and binder, in a unit dosage form necessary for producing a generally accepted pharmaceutical. Depending on the amount of active ingredient in these formulations, a suitable dose within the specified range can be determined.

Examples of additives that can be mixed in tablets and capsules are binders such as gelatin, corn starch, tragacanth gum, and gum arabic; media such as crystalline cellulose; swelling agents such as corn starch, gelatin, and alginic acid; lubricants such as magnesium stearate; sweetening agents such as sucrose, lactose or saccharine; and corrigents such as peppermint, wintergreen oil and cherry. When the unit dosage from is capsule, liquid carriers such as oil can be further included in the above-described ingredients. Sterilized mixture for injection can be formulated using media such as distilled water for injection according to the realization of usual pharmaceuticals.

Physiological saline, glucose, and other isotonic solutions containing adjuvants such as D-sorbitol, D-mannose, D-mannitol, and sodium chloride can be used as an aqueous solution for injection. They can be used in combination with a suitable solubilizer, for example, alcohol, specifically ethanol and polyalcohols such as propylene glycol and polyethylene glycol, non-ionic surfactants such as Polysorbate 80™ and HCO-50.

Sesame oil or soybean oil can be used as an oleaginous liquid, and also used in combination with benzyl benzoate or benzyl alcohol as a solubilizer. Furthermore, they can be further formulated with buffers such as phosphate buffer and sodium acetate buffer; analgesics such as procaine hydrochloride; stabilizers such as benzyl alcohol and phenol; and antioxidants. Injections thus prepared can be loaded into appropriate ampoules.

Methods well-known to those skilled in the art can be used for administering pharmaceutical compounds of the present invention to patients, for example, by intraarterial, intravenous, or subcutaneous injection, and similarly, by intranasal, transtracheal, intramuscular, or oral administration. Doses and administration methods are varied depending on the body weight and age of patients as well as administration methods. However, those skilled in the art can routinely select them. DNA encoding a polypeptide of the present invention can be inserted into a vector for the gene therapy, and the vector can be administered for treatment. Although doses and administration methods are varied depending on the body weight, age, and symptoms of patients, those skilled in the art can appropriately select them. For example, a dose of the compound which bind to the polypeptides of the present invention so as to regulate their activity is, when orally administered to a normal adult (body weight 60 kg), about 0.1 mg to about 100 mg/day, preferably about 1.0 mg to about 50 mg/day, more preferably about 1.0 mg to about 20 mg/day, although it is slightly varied depending on symptoms.

When the compound is parenterally administered to a normal adult (body weight 60 kg) in the injection form, it is convenient to intravenously inject a dose of about 0.01 mg to about 30 mg/day, preferably about 0.1 mg to about 20 mg/day, more preferably about 0.1 mg to about 10 mg/day, although it is slightly varied depending on patients, target organs, symptoms, and administration methods. Similarly, the compound can be administered to other animals in an amount converted from the dose for the body weight of 60 kg.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of non-critical parameters that could be changed or modified to yield essentially similar results.

The present invention is illustrated in details by following Examples, but is not restricted to these Examples.

Example 1

Materials and Methods (1) Cell Lines and Clinical Materials

Human-breast cancer cell lines HBL100, HCC1937, MCF-7, MDA-MB-4355, SKBR3, T47D, BT-549, YMB1, ZR-75-1, OCUB-F, MDA-MB-453, MDA-MB-157, HCC1599, HCC1500, HCC1395, HCC1143, BT-474 and BT-20 as well as human embryonic kidney cell-line HEK293T cells, BTL100 and COS7 were purchased from American Type Culture Collection (ATCC, Rockville, Md.). HBC4, HBC5, BSY-1 and MDA-MB-231 cells lines were kind gifts from Dr. Yamori of Division of Molecular Pharmacology, Cancer Chemotherapy Center, Japanese Foundation for Cancer Research. All cells were cultured under their respective depositors' recommendation; i.e. RPMI-1640 (Sigma-Aldrich, St. Louis, Mo.) for HBC4, HBC5, BT-483, SKBR3, BT-549, HCC1143, HCC1599, HCC1500, HCC1395, T47D, YMB1, HCC1937, BSY-1 and ZR-75-1 (with 2 mM L-glutamine); Dulbecco's modified Eagle's medium (Invitrogen, Carlsbad, Calif.) for HBL100 BT-474 and OCUB-F; EMEM (Sigma-Aldrich) with 0.1 mM essential amino acid (Roche, Basel, Switzerland), 1 mM sodium pyruvate (Roche), 0.01 mg/ml Insulin (Sigma-Aldrich) for MCF-7 and BT-20; L-15 (Roche) for MDA-MB-231 and MDA-MB-4355, MDA-MB-453 and MDA-MB-157. Each medium was supplemented with 10% fetal bovine serum (Cansera) and 1% antibiotic/antimycotic solution (Sigma-Aldrich). MDA-MB-231 and MDA-MB-4355 cells were maintained at 37° C. in humidified air without $CO_2$. Other cell-lines were maintained at 37° C. in humidified air with 5% $CO_2$. Tissue samples from surgically-resected breast cancers, and their corresponding clinical information were obtained after obtaining written informed consent.

(2) Semi-Quantitative RT-PCR Analysis

These inventors extracted total RNA from each of breast cancer clinical samples. Inventors extracted total RNAs from microdissected cells, and then performed T7-based amplification and reverse transcription as described previously (Nishidate T et al. Int J Oncol 2004; 25:797-819.). Inventors prepared appropriate dilutions of each single-stranded cDNA for subsequent PCR by monitoring the glyceraldehyde-3-phosphate dehydrogenase (β2MG), glyceraldehyde-3-phosphate dehydrogenase (GAPDH) and Farnesyl-diphosphate farnesyltransferase 1 (FDFT1) as a quantitative internal control. The PCR primer sequences were follows:

```
5'-AACTTAGAGGTGGGAGCAG-3'      (SEQ ID NO: 1)
and

5'-CACAACCATGCCTTACTTTATC-3'   (SEQ ID NO: 2)
for β2MG;

5'-CTTGACAAGGCCTTTGGAGT-3'     (SEQ ID NO: 3)
and

5'-CAATATGCTTTTCCCGCTTT-3'     (SEQ ID NO: 4)
for A7322;

5'-AACCAAGCACACCATAGCCTTA-3'   (SEQ ID NO: 5)
and

5'-GGAGATGGGTAGGGATACAAAC-3'   (SEQ ID NO: 6)
for F3374,

5'-GGGAGAGCTGAAGATTGCTG-3'     (SEQ ID NO: 7)
and

5'-GACAGATTGAAGGGCAGAGG-3'     (SEQ ID NO: 8)
for AURKB;

5'-CGACCACTTTGTCAAGCTCA-3'     (SEQ ID NO: 9)
and

5'-GGTTGAGCACAGGGTACTTTATT-3'  (SEQ ID NO: 10)
for GAPDH;

5'-AGTGAAATGCAGGTGAGAAGAAC-3'  (SEQ ID NO: 11)
and

5'-TCATTCTAGCCAGGATCATACTAAG-3'(SEQ ID NO: 12)
for FDFT1;

5'-AGACCCTAAAGATCGTCCTTCTG-3'  (SEQ ID NO: 13)
and

5'-GTGTTTTAAGTCAGCATGAGCAG-3'  (SEQ ID NO: 14)
for PBK/TOPK;
and

5'-GCTGACAACCTTGTGCTGAA-3'     (SEQ ID NO: 15)
and

5'-TGAGAAATCACGCACTGTCC-3'     (SEQ ID NO: 16)
for PHB2/REA.
```

(3) Northern-Blot Analysis

Total RNAs were extracted from all breast cancer cell-lines using RNeasy kit (Qiagen, Valencia, Calif.) according to the manufacturer's instructions. After treatment with DNase I (Nippon Gene, Osaka, Japan), mRNA was isolated with mRNA purification kit (GE Healthcare, Buckinghamshire, United Kingdom) following the manufacturer's instructions. A 1-μg aliquot of each mRNA isolated from normal adult human mammary gland (Biochain, Hayward, Calif.), lung, heart, liver, kidney and bone marrow (BD Biosciences, San Jose, Calif.) was separated on 1% denaturing agarose gels and transferred to nylon membranes (Breast cancer Northern blots). Human multiple-tissue northern blots (BD Biosciences) were hybridized with [$\alpha^{32}P$]-dCTP-labeled PCR products of A7322 prepared by RT-PCR (see below). Prehybridization, hybridization and washing were performed according to the supplier's recommendations. The blots were autoradiographed with intensifying screens at −80° C. for 14 days. Specific probes for A7322 (459 bp) and F3374 were prepared by RT-PCR using the following primer set;

```
5'-CAAGCTTGCTTACAGAGACCTG-3'    (SEQ ID NO: 17)
and

5'-GGGCCAAACCTACCAAAGTT-3'      (SEQ ID NO: 18)
within 3'UTR of A7322;

5'-GCAATCTGCTATGTCAGCCAAC-3'    (SEQ ID NO: 19)
and

5'-CAGGATCAGCTCAAAGTCTGACA-3'   (SEQ ID NO: 20)
for F3374;

5'-AGACCCTAAAGATCGTCCTTCTG-3'   (SEQ ID NO: 13)
and

5'-GTGTTTTAAGTCAGCATGAGCAG-3',  (SEQ ID NO: 14)
``` and radioactively labeled with megaprime DNA labeling system (GE Healthcare).

(4) 5' Rapid Amplification of cDNA Ends (5' RACE)

5' RACE experiments were carried out using SMART RACE cDNA amplification kit (Takara Clontech) according to the manufacturer's instructions. For the amplification of the 5' part of A7322 cDNA, a gene-specific primer as follows:

```
5'-GCCTCCTTCTGCAGCTTCCTCAGGATTT-   (SEQ ID NO: 21)
3'
``` and universal primer mix supplied in the kit were used. The cDNA template was synthesized from mRNA extracted and purified from MDA-MB-453 breast cancer cells, using Superscript III Reverse Transcriptase (Invitrogen). The PCR products were cloned using TA cloning kit (Invitrogen) and sequences were determined by DNA sequencing (ABI3700; PE Applied Biosystems, Foster, Calif.).

(5) Construction of Expression Vectors

For constructing of A7322, PHB2/REA or F3374 expression vectors, the entire coding sequence of A7322 or cDNA was amplified by the PCR using KOD-Plus DNA polymerase (Toyobo, Osaka, Japan). Primer sets were A7322-forward; 5'-CG<u>GAATTC</u>ATGGAAGAAATCCTGAGGAAGC-3' (SEQ ID NO: 22) (the underline indicates EcoRI site) and A7322-reverse; 5'-ATAGTTTA<u>GCGGCCGC</u>ACAATGATGTCATAGACACGG-3' (SEQ ID NO: 23) (the underline indicates NotI site); PHB2/REA-forward; 5'-CG<u>GAATTC</u>CAGACCGTGCATCATGGCCC-AGAACTTGAAGGA-3' (SEQ ID NO: 24) (the underline indicates EcoRI site) and PHB2/REA-reverse; 5'-CCG<u>CTCGAG</u>TTTCTTACCCTTGATGAGGCTGT-3' (SEQ ID NO: 25) (the underline indicates XhoI site); ERα-forward; 5'-CG<u>GAATTC</u>ATGACCATGACCCTCCACACCAAAG-CATCC-3' (SEQ ID NO: 26) and ERα-reverse; 5'-CCG<u>CTCGAG</u>GACCGTGGCAGGGAAACCCTCT-3' (SEQ ID NO: 27) (Underlines indicate recognition sites of restriction enzymes); F3374-forward; 5'-AAGGAAAAAA<u>GCGGCCGC</u>GATGCTCTTCAATTCGGTGCT-3' (SEQ ID NO: 28) (the underline indicates NotI site) and F3374-reverse; 5'-CCG<u>CTCGAG</u>TAATTCTGTTGAGTGTTCAGGACC-3' (SEQ ID NO: 29) (the underline indicates XhoI site).

The PCR product was inserted into the EocRI and NotI sites (for A7322), EocRI and XhoI sites (for PHB2/REA), EocRI and XhoI sites (for ERα) or the NotI and XhoI sites (for B3374) of pCAGGS-nH3F expression vector in frame with N-terminal HA-tag and C-terminal Flag-tag. The construct was confirmed by DNA sequencing (ABI3700, PE Applied Biosystems, Foster, Calif.).

(6) Generation of Anti-A7322 Polyclonal Antibody and Anti-F3374 Polyclonal Antibody Plasmids designed to express two fragments of A7322 (codons 459-572 and 799-1200) using pET21a (+) vector in frame with T7-tag at the N-terminus and histidine (His)-tag at the C-terminus (Novagen, Madison, Wis.). The two recombinant peptides were expressed in *Escherichia coli*, BL21 codon-plus strain (Stratagene, La Jolla, Calif.), respectively, and purified using Ni-NTA resin agarose (QIAGEN) according to the supplier's protocols. The purified recombinant proteins were mixed together and then used for immunization of rabbits (Medical and Biological Laboratories, Nagoya, Japan). The immune sera subsequently were purified on anti-gen affinity columns using Affigel 15 gel (Bio-Rad Laboratories, Hercules, Calif.) according to supplier's instructions. The present inventors confirmed that this antibody could specifically recognize endogenous A7322 protein in breast cancer cell line, SK-BR-3 cells. An affinity-purified anti-A7322 antibody was used for Western blot, immunocytochemical staining and immunohistochemical staining analyses as described below.

Plasmid designed to express a part of F3374 (437-730 amino acids) with His-tag at its C-terminus was prepared using pET21 vector (Merck, Novagen, Madison, Wis.). The recombinant peptide (36 kDa) was expressed in *Escherichia coli*, BL21 codon-plus (Stratagene, La Jolla, Calif.), and purified using Ni-NTA resin (Qiagen) according to the supplier's protocol. To remove *E. coli*'s proteins as contaminations, F3374 fragment protein was cut from SDS-PAGE gel, and extracted by using electro-eluter (Bio-Rad, Hercules, Calif.). The extracted protein was inoculated into rabbits, and subsequently the immune sera were purified on antigen affinity columns using Affigel 15 gel (Bio-Rad), according to supplier's instructions. Affinity-purified anti-F3374 antibodies were used for western blot, immunohistochemical, and immunocytochemical analyses as described below.

(7) Cloning and Mutagenesis

To construct PBK/TOPK expression vectors, the entire coding sequence of PBK/TOPK cDNA was amplified by PCR using KOD-Plus DNA polymerase (Toyobo, Osaka, Japan). Primer sets were 5'-CCG<u>GAATTC</u>ATGGAAGGGATCAGTAATTTC-3' (SEQ ID NO: 30) and 5'-CCG<u>CTCGAG</u>TCAGACATCTGTTTCCAGAGCTTC-3' (SEQ ID NO: 31) (Underlines indicate recognition sites of restriction enzymes) for wild-type PBK/TOPK. The PCR products were inserted into the EocRI and XhoI sites of pCAGGS-nHA expression vector. Two-step mutagenesis PCR was performed to generate a kinase-dead mutant in which Lys64 and Lys65 were substituted to alanines (K64-65A), as described previously (Gaudet S, et al., Proc Natl Acad Sci USA 2000, 97:5167-72). The primer set used for mutant K64-65A were 5'-CATTCTCCTTGGGCTGTAG<u>CA</u>
<u>GC</u>GATTAATCCTATATGTAATG-3' (SEQ ID NO: 32) and
5'-CATTACATATAGGATTAATC<u>GCT</u>
<u>GC</u>TACAGCCCAAGGAGAATG-3' (SEQ ID NO: 33) (Underlines indicate nucleotides that were replaced from the wild type). All constructs were confirmed by DNA sequencing (ABI3700, PE Applied Biosystems, Foster, Calif.).

(8) Immunocytochemical Staining

To examine the sub-cellular localization of endogenous A7322 protein in breast cancer cells, SK-BR-3 cells were seeded at $1 \times 10^5$ cells per well (Lab-Tek II Chamber Slide System; Nalge Nunc International, Naperville, Ill.). After 24 hours of incubation, cells were fixed with PBS (−) containing 4% paraformaldehyde at 4° C. for 30 minutes and rendered permeable with PBS (−) containing 0.1% Triton X-100 at 4° C. for two minutes. Subsequently, the cells were covered with 3% BSA in PBS (−) for 1 hour to block non-specific hybridization followed by incubation with anti-A7322 polyclonal antibody diluted at 1:250 for another 1 hour. After washing with PBS (−), cells were stained by Alexa 488-conjugated anti-rabbit secondary antibody (Molecular Probe, Eugene, Oreg.) diluted at 1:1000 for 1 hour. Nuclei were counter-stained with 4',6'-diamidine-2'-phenylindole dihydrochloride (DAPI). Fluorescent images were obtained under TCS SP2 AOBS microscope (Leica, Tokyo, Japan).

To examine the sub-cellular localization of F3374, HBC5 cells were seeded at $5 \times 10^4$ cells per well. Then, cells were fixed with PBS containing 4% paraformaldehyde for 20 min, and rendered permeable with PBS containing 0.1% Triton X-100 for 2 min at room temperature. Subsequently the cells were covered with 3% BSA in PBS for 1 hour at room temperature to block non-specific hybridization. Subsequently, cells were incubated with a rabbit anti-F3374 antibody at 1:100 dilution. After washing with PBS, cells were stained by an Alexa488-conjugated anti-rabbit secondary antibody (Molecular Probe) at 1:1000 dilution. Nuclei were counter-stained with 4',6'-diamidine-2'-phenylindole dihydrochloride (DAPI). Fluorescent images were obtained under a TCS SP2 AOBS microscope (Leica, Tokyo, Japan). To examine the sub-cellular localization of endogenous F3374 and AURKB proteins, T47D cells were seeded at $1 \times 10^5$ cells per well. The cell fixation, blocking reaction, and staining procedures were performed under the described above condition except with anti-F3374 antibody at 1:100 dilutions or anti-AURKB antibody (Abcam, Cambridge, Mass.) at 1:500 dilutions.

To examine subcellular localization of endogenous PBK/TOPK protein in breast cancer cell-lines, T47D, BT-20 and HBC5, the cells were seeded at $2 \times 10^5$ cells per well (Lab-Tek II chamber slide, Nalgen Nunc International, Naperville, Ill.). 48 h after incubation, cells were fixed with PBS (−) containing 4% paraformaldehyde for 15 min, and rendered permeable with PBS (−) containing 0.1% Triton X-100 at 4° C. for 2.5 min. Subsequently, the cells were covered with 3% BSA in PBS (−) at 4° C. for 12 h to block non-specific hybridization followed by incubation with a mouse anti-PBK/TOPK monoclonal antibody (BD Biosciences) diluted at 1:100. After washing with PBS (−), the cells were stained with Alexa594-conjugated anti-mouse secondary antibody (Molecular Probe, Eugene, Oreg.) diluted at 1:1000. Nuclei were counter-stained with 4',6'-diamidine-2'-phenylindole dihydrochloride (DAPI). Fluorescent images were obtained under a TCS SP2 AOBS microscope (Leica, Tokyo, Japan). To examine histone H3 phosphorylated at Ser10, the protein was detected by phospho-histone H3 (Ser10)-specific rabbit polyclonal antibody (Cell Signaling Technologies, Berverly, Mass.).

(9) Western Blot Analysis

To detect the exogenous A7322 protein, pCAGGSnHsF-A7322 expression vector plasmid (20 μg) was transfected into BT-549 cells with FuGene 6 (Roche). After 24 hours, cells were lysed in lysis buffer (50 mM Tris-HCL, pH 8.0/150 mM NaCL/0.1% NP-40, 0.5% CHAPS) including 0.1% protease inhibitor cocktail 111 (Calbiochem, San Diego, Calif.). The amount of total protein was estimated by protein assay kit (Bio-Rad, Hercules, Calif.), and then proteins were mixed with SDS-sample buffer and boiled before loading at 6% SDS-PAGE gel. After electrophoresis, the proteins were blotted onto nitrocellulose membrane (GE Healthcare). Membranes including proteins were blocked by blocking solution and incubated with anti-Flag M2 monoclonal antibody for detection of exogenous A7322 protein. Finally the membrane was incubated with HRP conjugated secondary antibody and protein bands were visualized by ECL detection reagents (GE Healthcare).

To examine the expression of endogenous A7322 protein in SK-BR-3 cells, cells were lysed with lysis buffer (50 mM Tris-HCl, pH 8.0, 150 mM NaCl, 0.1% NP-40 and 0.5% CHAPS) including 0.1% protease inhibitor cocktail 111 (Calbiochem, San Diego, Calif.). After homogenization, cell lysates were incubated on ice for 30 minutes and centrifuged at 14,000 rpm for 5 minutes to separate only supernatant from cell debris. The amount of total protein was measured by protein assay kit (Bio-Rad), and then proteins were mixed with SDS-sample buffer and boiled for 5 minutes before loading at 7.5% SDS-PAGE gel. After electrophoresis, the proteins were blotted onto nitrocellulose membrane (GE Healthcare). Membranes including proteins were blocked by blocking solution for 1 hour, and incubated with purified anti-A7322 polyclonal antibody for another 1 hour to detect endogenous A7322 protein. Finally, the membrane was incubated with HRP conjugated secondary antibody for one hour and protein bands were visualized by ECL detection reagents (GE Healthcare).

To detect the endogenous F3374 and AURKB proteins in breast cancer cell lines (HBC4, BT-549, HBC5, HBL100, HCC1937, MCF-7, MDA-MB-231, MDA-MB-453, SKBR3, and T47D, and ZR75-1) and human mammary gland epithelial cell (HMEC), cells were lysed in lysis buffer (50 mM Tris-HCl, pH 8.0/150 mM NaCl/0.5% NP-40) including 0.1% protease inhibitor cocktail 111 (Calbiochem, San Diego, Calif.). The amount of total protein was estimated by protein assay kit (Bio-Rad, Hercules, Calif.), and then proteins were mixed with SDS-sample buffer and boiled before loading at 10% SDS-PAGE gel. After electrophoresis, the proteins were blotted onto nitrocellulose membrane (GE Healthcare). After blocking with blocking solution (4% BlockAce; Dainippon Pharmaceutical. Co., Ltd, Osaka, Japan), membranes blotting proteins were incubated with anti-F3374 polyclonal antibody at 1:100 dilutions or anti-AURKB rabbit polyclonal antibody (abcam, Cambridge, UK) at 1:100 dilutions for detection of endogenous F3374 or AURKB protein. Finally the membrane was incubated with HRP conjugated-secondary antibody and protein-bands were visualized by ECL detection reagents (GE Healthcare). Beta-actin was examined to serve as a loading control.

To detect endogenous PBK/TOPK protein in breast cancer cells (BT-20, HBC4, HBC5, HBL-100, MCF-7, MDA-MB-231, SKBR3, and T47D), cells were lysed in lysis buffer (50 mM Tris-HCl, pH 8.0/150 mM NaCl/0.5% NP-40) containing 0.1% protease inhibitor cocktail 111 (Calbiochem, San Diego, Calif.). After homogenization, the cell lysates were incubated on ice for 30 min and centrifuged at 14,000 rpm for 15 min to separate only the supernatant from the cell debris. The amount of total protein was estimated by protein assay kit (Bio-Rad, Hercules, Calif.), and then proteins were mixed with SDS-sample buffer and boiled before loading on 10% SDS-PAGE gel. After electrophoresis, the proteins were blotted onto nitrocellulose membrane (GE Healthcare). Membranes blotted with proteins were blocked using blocking solution and incubated with anti-PBK/TOPK monoclonal antibody (BD Biosciences) for detection of endogenous PBK/TOPK protein. Finally the membrane was incubated with HRP conjugated secondary antibody and protein bands were visualized with ECL detection reagents (GE Healthcare). Beta-actin was examined to serve as a loading control.

Wild-type and kinase-dead PBK/TOPK proteins were exogenously expressed by transfection into T47D cell using pCAGGS-nHA expression vector. Whole cell lysates were harvested 48 h after the transfection. The cells were lysed in the cell lysis buffer as described above. The following procedures are the same as described above except that anti-HA rat high-affinity antibody (Roche) was used for the antibody reaction. Furthermore, to endogenously detect activated PBK/TOPK protein, T47D cells were treated with 100 nM of okadaic acid (OA) (Calbiochem) or 0.3 ng/mL of nocodazole (Sigma-Aldrich) for 6 or 18 h before harvesting, respectively (see the text). The following procedures were also carried out as described above. Phosphorylated protein was confirmed by treatment with 1 U of lambda protein phosphatase (New England Biolabs, Ipswich, Mass.) at 30° C. for 2 h.

(10) Lambda Phosphatase Assay

To examine phosphorylation status of F3374 protein in breast cancer cells, the present inventors treated the cellular extracts from T47D cells with lambda-phosphatase (New England Biolabs, Beverly, Mass.). Cells were lysed by NP-40 lysis buffer (50 mM Tris-HCL(pH8.0), 150 mM NaCL, 0.5% NP-40) and the cell lysates were treated for two hours at 30° C. with 400 units of protein phosphatase (New England Biolabs) in phosphatase buffer containing 50 mM Tris-HCL (pH 7.5), 0.1 mM $Na_2$EDTA, 5 mM dithiothreitol, 2 mM $MgCL_2$, and 0.01% Brij-35. Furthermore, to define the phosphorylated site(s) of F7433 protein, HEK293T cells were seeded at $2\times10^6$ cells per 10 cm dish. After 24 hours, inventors transiently transfected with 8 µg of pCAGGS-F3374-Δ1-HA, Δ2 and Δ3 into HEK293T cells using FuGENE 6 transfection reagent (Roche) according to the manufacturer's instructions. Cells were lysed by NP-40 buffer (0.5% NP-40, 150 mM NaCl, 50 mM Tris-HCl(pH7.5)), phosphatase buffer containing 50 mM Tris-HCl, pH 7.5, 0.1 mM Na2EDTA, 5 mM dithiothreitol, 2 mM MgCl2, and 0.01% Brij-35. Forty-eight hours after the transfection, the cells were lysed by NP-40 lysis buffer. Lysed cells were then treated for 2 hr at 30° C. with 400 units of protein phosphatase (P0753 S New England Biolabs).

To examine phosphorylations of PBK/TOPK protein, 10 ng of the active PBK/TOPK protein and 15 ng and total mitotic cell lysates were incubated with 2 Units of λPPase and PP1α recombinant proteins according to the manufacturer's instructions. After 2-hour incubation at 30° C., the reactions were terminated by addition of SDS-sample buffer and boiling. Finally the protein samples were electrophoresed and immunoblotted as described above.

(11) Construction of A7322, F3374V1 or PBK/TOPK Specific-siRNA Expression Vectors Inventors established a vector-based RNAi (RNA interference) expression system using psiU6BX3.0 siRNA expression vector as described previously (Taniuchi K et al. Cancer Res., 65:105-112. 2005.). siRNA expression vectors against A7322 (psiU6BX3.0-A7322), F3374V1 (psiU6BX3.0-F3374V1), EGFP (psiU6BX3.0-EGFP), Scramble (psiU6BX3.0-SCR) and Mock (psiU6BX3.0-Mock) were prepared by cloning of double-stranded oligonucleotides into the BbsI site of the psiU6BX3.0 vector. The target sequences of synthetic oligonucleotides for siRNA were as follows;

si-#2; 5'-AAGAAAGCATCGCAGTCTCAG-3' (SEQ ID NO: 34),
si-#3; 5'-AAGATGCGTTCTCTGCCACAC-3' (SEQ ID NO: 35) and
si-#m3; 5'-AA<u>T</u>ATT<u>C</u>GA<u>T</u>CTCTGCCACAC-3' (SEQ ID NO: 36) (The underlines indicate mismatch sequence against si-#3) for A7322;
si-#1; 5'-GATCATGTCTCCGAGAAAA-3' (SEQ ID NO: 37),
si-#4; 5'-GGAAGCCATAGAATTGCTC-3' (SEQ ID NO: 38) for F3374;
si-#2; 5'-CTGGATGAATCATACCAGA-3' (SEQ ID NO: 39),
si-#3; 5'-GTGTGGCTTGCGTAAATAA-3' (SEQ ID NO: 40) for PBK/TOPK;
si-Scramble; 5'-GCGCGCTTTGTAGGATTCG-3' (SEQ ID NO: 41) and
si-EGFP; 5'-GAAGCAGCACGACTTCTTC-3' (SEQ ID NO: 42) for control.

All of constructs were also confirmed by DNA sequencing.

For effect of cell growth on siRNA against p97, T47D cells were seeded $1\times10^5$ cells in a 60 mm dish. Two days after incubation, the cells were transfected with 100 µmol each of the siRNA duplexes of si-EGFP and si-p97 (5'-AAGUAGGGUAUGAUGACAUUG-3': SEQ ID NO: 121; Wójcik C et al., J Cell Sci 117; 281-292 (2004)) using Lipofectamine RNAiMAX reagent according to the manufacturer's instructions. Two days after transfection with the siRNAs, cellular morphology was observed by a phase contrast microscopy. And then the cells were collected and equal amounts of total protein were immunoblotted with anti-TOPK monoclonal antibody (1:3,000) anti-β-actin monoclonal antibody (1:10,000).

TABLE 1

| | | | SEQ ID No. |
|---|---|---|---|
| A7322#2 | F | 5'-CACCAAGAAAGCATCGCAGTCTCAGTTC AAGAGACTGAGACTGCGATGCTTTCTT-3' | 43 |
| | R | 5'-AAAAAAGAAAGCATCGCAGTCTCAGTCT CTTGAACTGAGACTGCGATGCTTTCTT-3' | 44 |
| | hairpin | AAGAAAGCATCGCAGTCTCAGTTCAAGAGAC TGAGACTGCGATGCTTTCTT | 45 |
| | F | 5'-CACCAAGATGCGTTCTCTGCCACACTTC AAGAGAGTGTGGCAGAGAACGCATCTT-3' | 46 |
| #3 | R | 5'-AAAAAAGATGCGTTCTCTGCCACACTCT CTTGAAGTGTGGCAGAGAACGCATCTT-3' | 47 |
| | hairpin | AAGATGCGTTCTCTGCCACACTTCAAGAGAG TGTGGCAGAGAACGCATCTT | 48 |
| | F | 5'-CACCGATCATGTCTCCGAGAAAATTC AAGAGATTTTCTCGGAGACATGATC-3' | 49 |
| #1 | R | 5'-AAAAGATCATGTCTCCGAGAAAATCT CTTGAATTTTCTCGGAGACATGATC-3' | 50 |
| | hairpin | GATCATGTCTCCGAGAAAATTCAAGAGATTT TCTCGGAGACATGATC | 51 |
| F3374 | F | 5'-CACCGGAAGCCATAGAATTGCTCTTC AAGAGAGAGCAATTCTATGGCTTCC-3' | 52 |
| #4 | R | 5'-AAAAGGAAGCCATAGAATTGCTCTCT CTTGAAGAGCAATTCTATGGCTTCC-3'3' | 53 |

TABLE 1-continued

|  |  |  | SEQ ID No. |
|---|---|---|---|
|  | hairpin | GGAAGCCATAGAATTGCTCTTCAAGAGAGAG CAATTCTATGGCTTCC | 54 |
|  | F | 5'-CACCCTGGATGAATCATACCAGATTC AAGAGATCTGGTATGATTCATCCAG-3' | 55 |
| #2 | R | 5'-AAAACTGGATGAATCATACCAGATCTC TTGAATCTGGTATGATTCATCCAG-3' | 56 |
| PBK/T | hairpin | CTGGATGAATCATACCAGATTCAAGAGATCT GGTATGATTCATCCAG | 57 |
| OPK | F | 5'-CACCGTGTGGCTTGCGTAAATAATTCAA GAGATTATTTACGCAAGCCACAC-3' | 58 |
| #3 | R | 5'-AAAAGTGTGGCTTGCG-TAAATAATCTCTT GAATTATTTACGCAAGCCACAC-3' | 59 |
|  | hairpin | GTGTGGCTTGCGTAAATAATTCAAGAGATTA TTTACGCAAGCCACAC | 60 |

(12) Gene-Silencing Effect of A7322, F3374V1, AURKB or PBK/TOPK

Human breast cancer cells-lines, BT-549 and BT-474 (for A7322) and T47D and HBC4 (for F3374), were plated onto 10-cm dishes ($2\times10^6$ cells/dish) and transfected with 8 ng each of psiU6BX3.0-Mock (without insertion), psiU6BX3.0-A7322 (#2, #3 and a mismatch construct (m#3) including three-base substitutions in #3), psiU6BX3.0-F3374V1 (#1, and #4), psiU6BX3.0-EGFP, psiU6BX3.0-SCR using FuGENE6 reagent (Roche) as described above. Inventors selected the psiU6BX3.0-introduced BT-549, BT-474, T47D and HBC4, with medium containing 0.2 mg/ml or 1 mg/ml of neomycin (Geneticin, Gibco BRL, Carlsbad, Calif.), respectively. At 48 hours after treatment of geneticine, cells are re-seeded for colony formation assay ($2\times10^6$ cells/10 cm dish), RT-PCR ($2\times10^6$ cells/10 cm dish) and MTT assay ($2\times10^5$ cells/well). To evaluate an effect of siRNAs, total RNAs were extracted from the cells at 4-day incubation with neomycin, and then the knockdown effect of siRNAs was examined by a semi-quantitative RT-PCR using specific primer sets;

5'-AACTTAGAGGTGGGAGCAG-3' (SEQ ID NO: 1) and
5'-CACAACCATGCCTTACTTTATC-3' (SEQ ID NO: 2) for β2MG as an internal control, and
5'-GCCCTTGAAGCCAATATTCC-3' (SEQ ID NO: 61) and
5'-AGATGGTTTCAGTGGGCTTG-3' (SEQ ID NO: 62) for A7322;
5'-GCAATCTGCTATGTCAGCCAAC-3' (SEQ ID NO: 19) and
5'-CAGGATCAGCTCAAAGTCTGACA-3' (SEQ ID NO: 20) for F3374V1.

Transfectants expressing siRNA were grown for 4 weeks in selective media containing neomycin, then fixed with 4% paraformaldehyde for 15 min before staining with Giemsa's solution (Merck, Whitehouse Station, N.J.) to assess colony number. To quantify cell viability, MTT assays were performed with cell counting kit-8 4 days after transfection according to manufacturer's recommendation (Wako, Osaka, Japan). Absorbance at 570 nm wavelength was measured with a Microplate Reader 550 (Bio-Rad). These experiments were performed in triplicate.

Furthermore, the present inventors used siRNA oligonucleotides (Sigma Aldrich Japan KK, Tokyo, Japan) due to its high transfection efficiency to further verify the subcellular localization of PHB2/REA protein in cells which A7322 gene was knockdowned by siRNA. The sequences targeting A7322 or mock were as follows:

si-A7322; 5'-GAUGCGUUCUCUGCCACACUU-3' (SEQ ID NO: 63),
siEGFP (control); 5'-GCAGCACGACUUCUUCAAG-3' (SEQ ID NO: 64).

MCF-7 cells ($2.5\times10^5$ cells in 10 cm dish for FACS analysis) cells were transfected with those siRNAs using Lipofectamin RNAiMAX (Invitrogen, Carlsbad, Calif.) in Optimem (Invitrogen) medium according to the instructions of manufacture. Forty-eight hours after the transfection, cells were treated with 1 µM of E2 (β-estradiol; Sigma-Aldrich), and then did immunocytochmical staining and western blotting analyses using anti-PHB2/REA polyclonal antibody (abcam, Cambridge, UK) and anti-A7322 antibody and anti-ERα monoclonal antibody (LAB VISION, Fremount, Calif.) according to immunocytochemical staining analysis section. Fluorescent images were obtained under TCS SP2 AOBS microscope.

Furthermore, the present inventors used siRNA oligonucleotides (Sigma Aldrich Japan KK, Tokyo, Japan) due to its high transfection efficiency to further verify the knockdown effects of F3374 and AURKB on cell morphology. The sequences targeting each gene were as follows:

5'-ACUCCUACGUUCUCUAUUA-3' (SEQ ID NO: 65) for siF3374,
5'-AAGGUGAUGGAGAAUAGCAGU-3' (SEQ ID NO: 66) for siAURKB,
5'-GCAGCACGACUUCUUCAAG-3' (SEQ ID NO: 64) for siEGFP (control).

T47D or HBC4 cells ($2.5\times10^5$ cells in 10 cm dish for FACS analysis) cells were transfected with those siRNAs using Lipofectamin RNAiMAX (Invitrogen) in Optimem (Invitrogen) medium according to the instructions of manufacture. Forty-eight hours after transfection, morphological changes of the HBC4 cells were examined by microscopy and by immunocytochemical staining analysis using Alexa Fluor 594 Phalloidin (Molecular Probe).

|  |  | target sequence | SEQ ID No. |
|---|---|---|---|
| F3374 | siF3374 | ACTCCTACGTTCTCTATTA | 67 |
| AURKB | siAURKB | AAGGTGATGGAGAATAGCAGT | 68 |
| EGFP | siEGFP | GCAGCACGACTTCTTCAAG | 69 |

Human breast cancer cells-lines, T47D and BT-20, were plated onto 15-cm dishes ($4\times10^6$ cells/dish) and transfected with 16 mg each of psiU6BX3.0-Mock (without insertion) and psiU6BX3.0-PBK/TOPK (#2 and #3, Table 1) using FuGENE6 reagent (Roche) according to the manufacturer's instructions. 24 h after the transfection, the cells were re-seeded for colony formation assay ($2\times10^6$ cells/10 cm dish), RT-PCR ($2\times10^6$ cells/10 cm dish) and MTT assay ($1\times10^5$ cells/well). The psiU6BX3.0-introduced T47D or BT-20 cells were selected with medium containing 0.7 mg/ml or 0.6 mg/ml of neomycin (Geneticin, Invitrogen, Gibco BRL, Carlsbad, Calif.), respectively. The culture medium was changed twice a week. To evaluate the effect of siRNAs, total RNAs were extracted from the cells at 11-day incubation with neomycin, and then the knockdown effect of siRNAs was examined by semi-quantitative RT-PCR using specific primer sets;

5'-ATGGAAATCCCATCACCATCT-3' (SEQ ID NO: 70) and

5'-GGTTGAGCACAGGGTACTTTATT-3' (SEQ ID NO: 10) for GAPDH as an internal control, and 5'-GCCTTCATCATCCAAACATT-3' (SEQ ID NO: 71) and 5'-GGCAAATATGTCTGCCTTGT-3' (SEQ ID NO: 72) for the PBK/TOPK gene. Transfectants expressing siRNA were grown for 3 weeks in selective media containing neomycin, then fixed with 4% paraformaldehyde for 15 min before staining with Giemsa's solution (Merck, Whitehouse Station, N.J.) to assess colony number. To quantify cell viability, MTT assays were performed with cell counting kit-8 according to manufacturer's recommendation (Wako, Osaka, Japan). Absorbance at 570 nm wavelength was measured with a Microplate Reader 550 (Bio-Rad). These experiments were performed in triplicate.

(13) Construction of Truncated F3374V1 Protein Using pCAGGS-HA Vector

To determine the phosphorylation regions of F3374V1 protein, the deletion constructs was prepared using the following primer sets; dF3374V1-F703-NotI;

5'-AAGGAAAAAAGCGGCCGCGCTGTGGATGGGATAATCAAA-3' (SEQ ID NO: 73) and dF3374V1-R721-XhoI;

5'-CCGCTCGAGTTTGATTATCCCATCCACAGC-3' (SEQ ID NO: 74) for delta-1 construct (The first underline indicates NotI site, and second underline indicates XhoI site), dF3374V1-F1162-NotI;

5'-AAGGAAAAAAGCGGCCGCTGGCGCTTGAATAGAGGC-3' (SEQ ID NO: 75) and dF3374V1-R1203-XhoI;

5'-CCGCTCGAGATCACCTCCTGGTTTCTCCTC-3' (SEQ ID NO: 76) for delta-2 construct (The first underline indicates NotI site, and second underline indicates XhoI site), dF3374V1-F1729-NotI;

5'-AAGGAAAAAAGCGGCCGCCTTGATGGCCAAGTTGAAAAT-3' (SEQ ID NO: 77) and dF3374V1-R1770-XhoI;

5'-CCGCTCGAGGCAGCACAGATCCAAATGAAG-3' (SEQ ID NO: 78) for delta-3 construct (The first underline indicates NotI site, and second underline indicates XhoI site). The construct was confirmed by DNA sequencing (ABI3700, PE Applied Biosystems, Foster, Calif.).

(14) Immunohistochemical Staining

To examine the expression of A7322 protein in breast cancer and normal tissues, the present inventors prepared slides of paraffin-embedded breast cancer tissue sections (Sample No. 240, 241, 238, 242 and 290), normal mammary tissue sections (Sample No. 453) and other commercially-available normal human tissues (lung, heart, and liver) (BioChain). Specimens were deparaffinized by the treatment with xylene and ethanol, then processed for antigen retrieval by autoclave at 108° C. for 15 minutes in antigen retrieval solution, high pH (DAKO Cytomation, Glostrup, Denmark) and treated with peroxidase blocking reagent (DAKO Cytomation) for 1 hour. Tissue sections were incubated with anti-A7322 polyclonal antibody diluted at 1:150 for one hour and followed by horseradish peroxidase-conjugated secondary antibody (DAKO Cytomation) for 30 minutes. Specific immunostaining was visualized with peroxidase substrate (3,3'-diaminobenzidine tetrahydrochloride) (DAKO liquid DAB+ chromogen; DAKO Cytomation). Finally, tissue specimens were stained with hematoxylin to discriminate nucleus from cytoplasm.

Expression pattern of F3374V1 protein in breast cancer and normal human tissues were examined according to the procedures as described previously (Togashi A et al., Cancer Res 2005, 65:4817-26). Slides of paraffin-embedded specimens of breast cancer (10005T, 10317T, 10069T, 10571T, 10164T and 10185T), normal breast tissue (10441N) and normal human tissues (lung, heart, liver, kidney, colon, pancreas, skeletal muscle, small intestine and testis) were treated with xylene and ethanol to remove the paraffin. Antigen retrieval was carried out in Target Retrieval Solution High pH (DAKO, Carpinteria, Calif.) for 15 minutes at 121° C. with an autoclave. ENVISION+Kit/HRP (Dakocytomation, Kyoto, Japan) was used to detect F3374; after the endogenous peroxidase and protein-blocking reactions, affinity-purified rabbit anti-F3374 pAb was added as primary antibody at 1:50 dilution, and the mixture was treated with HRP-labeled anti-rabbit IgG. Finally, substrate-chromogen was added and the tissue specimens were counterstained with hematoxylin to discriminate nucleus from cytoplasm.

Expression patterns of PBK/TOPK protein in breast cancer and normal tissues were investigated as described previously (Togashi A et al., Cancer Res 2005, 65:4817-26) using anti-PBK/TOPK mouse monoclonal antibody (BD Biosciences). For investigation of normal organs, commercially-available tissue sections of heart, lung, liver, kidney and testis (Biochain) were purchased. Specifically, paraffin-embedded specimens were treated with xylene and ethanol, and were blocked by protein-blocking reagent (Dako Cytomation, Carpinteria, Calif.). The monoclonal antibody in antibody-diluted solution (1:50) was added and then stained with substrate-chromogen (DAKO liquid DAB chromogen, DakoCytomation). Finally, tissue specimens were stained with hematoxylin to discriminate the nucleus from the cytoplasm.

(15) Fluorescence-Activated Cell Sorting (FACS) Analysis.

BT-474 breast cancer cells, which were performed siRNA experiments as indicated above, were harvested after 2-day incubation in selective media containing 1.0 mg/ml of neomycin. Cells were collected and fixed with chilled 70% ethanol, and maintained at 4° C. before use. Cells were incubated with 10 mg/ml RNase I in PBS (−) at 37° C. for 30 minutes and stained with 50 μg of propidium iodide (PI) at room temperature for 30 minutes. Cell suspensions were analyzed for DNA content by flow cytometer (FACS calibur; Becton Dickinson, San Diego, Calif.). The data was analyzed by CELLQuest software (BD Biosciences). Assays were done in triplicate independently.

Cultured T47D breast cancer cells were synchronized their cell cycle by treatment with 2 ng/ml of aphidicolin (Sigma-Aldrich) for 24 hours. Subsequently, cells were washed five times with PBS (−), and added fresh culture media to release from the cell cycle arrest. After the release from the cell-cycle arrest, the cells were collected, and fixed with 70% ethanol, and then kept at 4° C. until their use. The cells were incubated with 10 mg/ml RNaseI in PBS (−) at 37° C. for 30 minutes and stained with 50 μg of propidium iodide (PI) at room temperature for 30 minutes. The cell suspensions at each time-point were analyzed with FACscan (Becton Dickinson, Franklin Lakes, N.J.). Additionally, to examine expression levels of endogenous F3374 protein, the present inventors performed western blot for cells harvested at every three hours, using anti-F3374 polyclonal antibody as described in western-blot analysis section.

For PBK/TOPK, the cell cycle of cultured T47D breast cancer cells were synchronized via the treatment with aphidicolin (Sigma-Aldrich) for 16 h, washing 5 times with PBS (−), and addition of fresh culture media to release from cell-cycle arrest. For 15 h (every 3 h) after releasing, cells were collected and fixed with 70% ethanol, and then kept at 4° C. before use. Cells were incubated with 10 mg/mL RNaseI in PBS (−) at 37° C. for 30 min and stained with 50 ng of propidium iodide at room temperature for 30 min. Cell suspensions at each time point were analyzed with FACscan (Becton Dickinson, Franklin Lakes, N.J.).

To collect the G2/M arrested cells, 0.3 ng/mL of nocodazole (Sigma-Aldrich) was treated to culture media for the last 16 hours before collection.

(16) Co-Immunoprecipitation and Immunoblotting Analyses.

To identify the interacting protein of A7322 protein, BT-549 human breast cancer cells were plated onto 15 cm dishes (1×10$^7$ cells/dish) and transfected with 20 ng of pCAGGSnH3F-Mock (without insertion) and pCAGGSnH3F-A7322 using FuGENE6 reagent (Roche) respectively according to the manufacturer's instructions. The present inventors transfected 6 dishes for each construct. After 48 hours, cells were lysed with 0.1% NP-40 lysis buffer as described in Western blot analysis section. Cell lysates were pre-cleaned with normal mouse IgG and rec-Protein G Sepharose 4B (Zymed, San Francisco, Calif.) at 4° C. for 1 hour. Subsequently, the lysates were incubated with anti-FLAG M2 agarose (Sigma-Aldrich) at 4° C. for overnight. After washing five times with lysis buffer, proteins on beads were eluted with SDS-sample buffer by boiling for 5 minutes. Eluted protein samples were separated by SDS-PAGE using NuPAGE 4-12% Bis-Tris gel (Invitrogen). Proteins in polyacrylamide gel were silver stained by SilverQuest Silver Staining Kit (Invitrogen) according to the manufacturer's instructions. Differential bands between mock and A7322 transfected lane were excised with a clean, sharp scalpel and PMF (Peptide Mass Fingerprint) analysis using MALDI TOF-MS were performed (Shimadzu Biotech, Tsukuba, Japan).

COS-7 cells were transiently transfected with pCAGGSn3FC-A7322, pCAGGSnHC-PHB2/REA individually or both together. 48 hours after transfection, cells were lysed with 0.1% NP-40 lysis buffer as described in Western blot analysis section. Cell lysates were pre-cleaned at 4° C. for 1 hour, subsequently incubated with anti-FLAG M2 agarose (Sigma-Aldrich) or monoclonal anti-HA agarose conjugate (Sigma-Aldrich) at 4° C. for overnight. Beads were washed and proteins were eluted as previously described. Finally, the present inventors performed Western blot analysis using anti-HA high affinity (3F10) rat monoclonal antibody (Roche) or anti-FLAG M2 monoclonal antibody (Sigma-Aldrich) to detect the exogenously-expressed PHB2/REA or A7322 protein, respectively.

HEK293T cells were plated onto five dishes (8×10$^6$ cells/15 cm-dish) and co-transfected with 8 μg of plasmids expressing F3374 (pCAGGSn-F3374-HA) and AURKB (pCAGGSn-AURKB-3F). The pCAGGSn-AURKB-3F plasmid was prepared previously (unpublished data; Daigo Y and Nakamura Y). 48 hours later of the transfection, cells were lysed by immunoprecipitation buffer (50 mM Tris-HCL (pH 7.5), 150 mM NaCL, 0.5% NP-40, 50 mM NaF, 1 mM NaVO$_3$ and 1 mM dithiothreitol) in the presence of protease inhibitor (Calbiochem). Cell lysate was precleared by incubation in 200 μl of protein G-agarose beads (Zymed Laboratories, South San Francisco, Calif.) with 3.75 μg of normal mouse IgG at 4° C. for three hours. After centrifugation at 14,000 rpm for one minute at 4° C., the supernatants were incubated at 4° C. with 30 μg of anti-Flag M2 or mouse normal IgG for one hour, and then added 100 μl of protein G-agarose beads. After the beads were collected from each sample by centrifugation at 14,000 rpm for one minute and washed five times with 1 ml of immunoprecipitation buffer, they were eluted by 30 μl Laemmli sample buffer and boiled for five minutes. The proteins were separated on 8% SDS-PAGE gels (Bio-Rad). After electrophoresis, the proteins were detected by western-blot analysis according to the method described in western-blot analysis section.

To examine interaction of endogenous F3374V1 and AURKB proteins, T47D cells were seeded at 6×10$^6$ cells/15 cm-dish. Two days later, cells were lysed in immunoprecipitation buffer (50 mM Tris-HCL (pH 7.5), 150 mM NaCL, 0.5% NP-40, 50 mM NaF, 1 mM NaVO3 and 1 mM DTT) in the presence of protease inhibitor (Calbiochem). Cell lysate was precleared by incubation in 750 μl of protein G-agarose beads with 7.5 μg of normal mouse IgG at 4° C. for three hours. The supernatants were incubated at 4° C. with 30 μg of anti-F3374V1 antibody or rabbit normal IgG for one hour, and then added 100 μl of protein G-agarose beads. After the beads were collected from each sample by centrifugation at 14,000 rpm for one minute and washed five times with 1 ml of immunoprecipitation buffer, they were eluted by 30 μl of Laemmli sample buffer and boiled for five minutes. The proteins were separated on 8% SDS-PAGE gels (Bio-Rad). After electrophoresis, the proteins were detected by western-blotting analysis according to the method described in western-blotting analysis section.

To detect expression of PBK/TOPK (WT, T9A, KD, T9A/KD), p47, p97 or PP1α proteins, immunoblottings were performed according to previous report (Park et al., 2006). Briefly, cells were lysed in lysis buffer (50 mM Tris-HCl, pH 8.0/150 mM NaCl/0.5% NP-40) followed by homogenization and incubation on ice for 30 minutes, only soluble fractions were separated from cell debris by centrifugation. After SDS-PAGE (sodium dodecyl sulfate polyacrylamide gel electrophoresis), the proteins were blotted onto nitrocellulose membrane (GE Healthcare, Buckinghamshire, United Kingdom), incubated with the corresponding antibodies, and visualized using an ECL detection kit (GE Healthcare). To collect the mitotic cells, the present inventors employed a "mitotic shake-off" method as described previously (Dechat T et al., EMBO J. 17: 4887-902 (1998)). A protein-protein interaction was examined by immunoprecipitation after co-transfection with above described constructs of interest to COS-7 cells using the FuGene6 reagent (Roche) as described previously (Shimo A et al., Cancer Sci 98: 174-81 (2007)) except using an anti-6×His antibody (Santa Cruz Biotechnology) to precipitated p97/VCP-myc-6×His protein. After washing 5 times with lysis buffer, immunocomplexes were loaded on a SDS-PAGE gel and immunoblotted as described above.

(17) In Vitro and In Vivo Kinase Assay.

To examine F3374V1 phosphorylation by AURKB, the present inventers performed in vitro kinase assay using the C-terminal recombinant protein of F3374 (437-730 amino acids) and full-length recombinant protein of AURKB (Upstate, Temecula, Calif.). The preparation of F3374 recombinant protein was performed according to the procedures described in generation of anti-F3374 polyclonal antibody section. Briefly, one microgram of AURKB was incubated in 20 μl kinase assay buffer (50 mM Tris-HCL (pH 7.5), 10 mM MgCL$_2$, 2 mM dithiothreitol, 1 mM EGTA, 0.01% Brij35, 500 μM ATP), and then supplemented with 5 μCi of [$^{32}$P-α] ATP (GE Healthcare). For the substrates, the present inventors added 1 μg of F3374 recombinant protein into the reaction solutions. After 10-minute incubation at 30° C., the reactions were terminated by addition of SDS sample buffer. After being boiled, the protein samples were electrophoresed on 10% SDS-gel, and then autoradiographed.

To evaluate the kinase activity of PBK/TOPK, in vitro kinase assay was performed using full-length recombinant PBK/TOPK protein (Invitrogen, Carlsbad, Calif.). Specifically, 1 μg of PBK/TOPK protein was incubated in 30 μl kinase assay buffer (50 mM Tris-HCl, pH 7.5/150 mM NaCl/ 10 mM MgCl$_2$/10 mM NaF/1 mM Na$_3$VO$_4$/1 mM EDTA/1 mM DTT/50 uM ATP) and then supplemented with 5 μCi of ($^{32}$P-γ)-ATP (GE Healthcare). As substrates, 5 μg of histone mixture or 2.5 μg of histone H3 (Roche) was added in the reaction solutions. After 30-min incubation at 30° C., the reactions were terminated by addition of SDS-sample buffer. After boiling, the protein samples were electrophoresed on 10-20% gradient gel (Bio-Rad), and then autoradiographed. To further examine whether histone H3 (Ser10) was phosphorylated by PBK/TOPK, the wild-type protein and kinase-dead mutant (K64-65A) were transfected into the T47D cells. After 48-h culture, the cells were treated with 100 nM of OA for 6 h to activate the PBK/TOPK protein. A total amount of H3 protein as well as the level of its phosphorylation were examined with anti-histone H3 (Abcam, Cambridge, UK) and anti-phospho-H3 (Ser10) antibodies (Cell Signaling Technologies), respectively.

For in vitro kinase assay, 0.5 μg of inactive recombinant PBK/TOPK protein which was generated by E. coli expression system was incubated with 0.5 unit of CDK1-cyclin B1 (New England Biolabs) in 30 μl reaction buffer (50 mM Tris-HCl, pH 7.5/10 mM MgCl2/2 mM Dithiothreitol/1 mM EGTA/0.01% Brij 35/50 μM of cold ATP) supplemented with 5 mCi of $^{32}$P-gamma-ATP (GE Healthcare). After 30 minutes incubation at 30° C., the reactions were terminated by addition of SDS-sample buffer. After boiling, the protein samples were electrophoresed and autoradiographed.

To examine p97 is a substrate for PBK/TOPK kinase, we performed in vitro kinase assay. Briefly, the precipitated p97 protein was reacted with 1 μg of recombinant TOPK protein according to the procedures described above.

(18) Cell Culture and Transfection Under Estrogen-Free Conditions

MCF-7 or SK-BR-3 cells were cultured with the following media; phenol red-free D-MEM/F-12 or RPMI-1640 (Invitrogen) respectively, supplemented with 10% FBS (Cansera International) and 1% antibiotic/antimycotic solution (Sigma-Aldrich) filtered with minisart-plus (Sartorius A G, Goettingen, Germany). Cells were maintained at 37° C. in atmosphere of humidified air with 5% CO$_2$. Transfection were performed using FuGENE6 transfection reagent (Roche), using phenol red-free Opti-MEM (Invitrogen), according to the manufacturer's instructions. Twenty-four hours after transfection, the media were exchanged with phenol red-free Opti-MEM containing 1 μM of E2 (β-estradiol; Sigma-Aldrich) and incubated for further 24 hours Immunocytochemical staining were performed using anti-HA high affinity (3F10) rat monoclonal antibody (Roche) and anti-FLAG rabbit polyclonal antibody (Sigma-Aldrich) diluted at 1:500 respectively, and Alexa 488-conjugated anti-rat mouse secondary antibody and Alexa 594-conjugated anti-rabbit or anti-rat secondary antibody (Molecular Probe, Eugene, Oreg.) diluted at 1:1000 respectively.

(19) Estrogen Responsive Element (ERE) Reporter Gene Assays

An ERE reporter gene construct plasmid and fluorescent SEAP assay kit were purchased from Clontech (Takara, Kyoto, Japan). MCF-7 (ER+) or SK-BR-3 (ER−) cells were co-transfected with the FLAG-tagged A7322 (FLAG-A7322) construct and estrogen responsive reporter gene (pERE-TA-SEAP) construct or a mock control and pERE-TA-SEAP reporter construct, respectively, using FUGENE transfection regent (Roche). Forty-eight hours after transfection, cells were treated with 1 μM of E2 (β-estradiol; Sigma-Aldrich) and incubated for further 48 and 72 hours for SEAP assay and western blotting analysis, respectively. The SEAP reporter assay was performed using SEAP assay kit (Clontech) according to the supplier's recommendations.

(20) Statistical Analysis

Statistical significance was calculated by Student's t test, using Statview 5.0 software (SAS Institute, Cary, N.C.). A difference of P<0.05 was considered to be statistically significant.

(21) Proteins, Constructs, Antibodies, and Reagents

An active recombinant PBK/TOPK protein was purchased from Invitrogen (Carlsbad, Calif.), and recombinant proteins of Histone H3 and Protein Phosohatase 1-alpha (PP1α were from Upstate Biotechnology (Lake Placidy, N.Y.). Cyclin-dependent kinase-1 (CDK1 kinase) (cdc2/cyclin B1) and lambda protein phosphatase (μPPase) were from New England Biolabs (Ipswich, Mass.). The glutathione S-transferase (GST)-tagged PBK/TOPK (GST-PBK/TOPK) protein was expressed in Escherichia coli and purified with Glutathione Sepharose 4B beads (GE Heath care, Buckinghamshire, United Kingdom) according to the previous report (Lin et al., 2007). The N-terminal HA-tagged PBK/TOPK (HA-PBK/TOPK), N-terminal GST-tagged PP1α (GST-PP1α, and C-terminal GST-tagged p47 (p47-GST) proteins were constructed using pCAGGSnHA, pCAGGS-nGST, and pCAGGS-cGST expression vectors, respectively according to the previous report (Park et al., 2006). The N-terminal HA-tagged alanine-substituted mutant at Thr9 (T9A), kinase-dead (KD), and double mutant (T9A/KD) proteins were constructed using pCAGGSnHA. The C-terminal myc-6×His-tagged p97/VCP-myc-6×His (p97/VCP-myc-His) was also constructed by using pcDNA3.1-myc-His vector (Invitrogen). The monoclonal antibodies to PBK/TOPK, beta-actin, and HA were purchased from BD Biosciences (San Jose, Calif.), Sigma-Aldrich (St. Louis, Mo.) and Roche (Basel, Switzerland), respectively. The polyclonal antibodies to total-PP1α, phospho-PP1α(T320) were purchased from Cell Signaling Technologies (Berverly, Mass.), and total-Rb, phospho-Rb (Ser807/811), and p97/VCP were from Santa Cruz Biotechnology (Santa. Cruz, Calif.). Okadaic acid (OA), CDK1 inhibitor (CGP74514A) and protease inhibitor cocktail III were purchased from Calbiochem (San Diego, Calif.).

(22) Immunocytochemical Staining of PBK/TOPK, CDK1-Cyclin B1, p47, p97 and PP1α

T47D cells were seeded at 5×10$^4$ cells in a 35 mm dish with a col-I coated glass (IWAKI). Two days after incubation, 0.3 μg/mL of nocodazole (Sigma-Aldrich) was treated for further 18 hours to investigate mitotic cells. After fixation and blocking, the cells were immunostained with anti-TOPK monoclonal antibody (BD Biosciences) diluted at 1:100 or anti-CDK1-monoclonal antibody (BD Biosciences) and Cyclin B1-monoclonal antibody (Santa Cruz) at 1:300. Finally, the cells were stained with Alexa594 (PBK/TOPK) or 488-conjugated (CDK1 and cyclin B1) anti-mouse secondary antibodies (Molecular Probe) diluted at 1:1000. Nuclei were counter-stained with 4',6'-diamidine-2'-phenylindole dihydrochloride (DAPI). Fluorescent images were obtained under a confocal microscopy (Leica).

To examine the subcellular localization of exogenously expressed-p47, p97 or PP1α proteins, we seeded T47D cells at 1×10$^5$ cells/well to a 6-well plate with a col-1 coated glass slide (Iwaki, Tokyo, Japan). Forty-eight hours after transfection, cells were fixed with PBS (−) containing 4% paraformaldehyde for 15 minutes, and rendered permeable with PBS (−) containing 0.1% Triton X-100 at 4° C. for 2.5 minutes.

Subsequently, the cells were covered with 3% BSA in PBS (−) at 4° C. for 12 hours to block non-specific hybridization followed by incubation with each the 1st and 2nd fluorescent-labeled antibodies diluted with 3% BSA in PBS (−) for 1 hour each (Park et al., 2006).

(23) Cell-Permeable Peptide Treatment and Inhibition of Phosphorylation of PBK/TOPK at Thr9

To inhibit the phosphorylation of PBK/TOPK at Thr9 by CDK1-cyclin B1, we designed permeable peptide (pp1-18) identical to the N-terminus (1-18 amino acids) of PBK/TOPK (RRRRRRRRRRR-G-MEGISNFKTPSKLSEKKK: SEQ ID NO: 99) was synthesized by Sigma-Aldrich. The efficacy of the peptide blocking the CDK1-cyclin B1-induced phosphorylation of PBK/TOPK was estimated by in vitro kinase assay according to in vitro kinase section. The recombinant proteins of inactive PBK/TOPK and CDK1-cyclin B1 were incubated as mentioned above, except the addition of the pp1-18 peptide at the various concentration of 0, 2.5, 5, 10 and 20 nM, respectively. The phosphorylation of PBK/TOPK and cyclin B1 proteins were observed by SDS-PAGE and autoradiography. For the cell proliferation assay, T47D and HMEC cells were seeded at $1.3 \times 10^4$ cells in a 12-well plate, respectively. At the following day, each concentration (0, 2.5, 5, and 10 nM) of pp1-18 peptide was treated everyday, and cell viability was measured by MTT assay at 5th day. A significance of the pp1-18 peptide to suppress T47D cell growth was statistically evaluated by the Student's t-test. To inhibit the phosphorylation of PBK/TOPK in mitotic cells by using pp1-18 peptide, T47D cells were seeded at $1 \times 10^5$ cells in a 60 mm dish. Two days after incubation, both nocodazole (0.3 ng/mL) and the permeable peptide (10 nM) were treated for further 18 or 24 hours before collection, and then phosphorylation of PBK/TOPK was investigated by western blotting using anti-PBK/TOPK monoclonal antibody and FACS analysis. Cellular morphology of T47D cells treated with 50 nM of the pp1-18 peptide was observed by a phase contrast microscopy at 5 days after treatment.

(24) GST Pull-Down Assay

The GST-tagged PP1α and p47 proteins were co-expressed with/without HA-tagged PBK/TOPK protein in COS-7 cells. Each cell lysate was prepared using the lysis buffer as described in the previous section. Total proteins were incubated with equilibrated Glutathione Sepharose 4B beads (GE Healthcare) at 4° C. for 1 hour. After washing five times with lysis buffer, the finally precipitated beads were kept at −20° C. before use for SDS-PAGE.

(25) Observation of Cell Structure Change

Cellular morphology was observed by a phase contrast microscopy (Olympus)$_2$ days after transfection with the siRNAs.

In the RNAi-rescue experiments, T47D cells were transfected with the pCAGGS-PBK/TOPK-HA construct at 24 hours prior to transfection with each siRNA as described previously (Zhu C et al., Proc Natl Acad Sci USA 103: 6196-201 (2006)). T47D cells were seeded at $1 \times 10^5$ cells in a 60 mm dish. Two days after incubation, the cells were transfected with 100 μmol of si-EGFP or siPBK/TOPK-#3 and the duration of cell mitosis was measured by a Time-lapse microscopy (Sanyo).

Example 2

A7322

(1) Identification of A7322 as an Up-Regulated Gene in Breast Cancer

To identify molecules that could be applicable as targets for novel therapeutic drugs, inventors previously established genome-wide gene-expression profiles of 81 breast cancer patients using cDNA microarray representing 27,648 cDNAs (Nishidate T et al. Int J Oncol 2004; 25:797-819.). Among the up-regulated genes, inventors focused on A7322 whose expressions were up-regulated in the majority of breast cancer specimens. Subsequent semi-quantitative RT-PCR and northern blot analyses confirmed that A7322 was significantly up-regulated in breast cancer specimens (FIG. 1A) as well as breast cancer cell lines (14 of 22), but not expressed in normal organs except brain (FIGS. 1B and D).

Since the assembled cDNA sequence of A7322 in the NCBI database was shorter than an approximately 15 kb transcript from northern blot analysis as shown in FIG. 1D, inventors performed exon-connection and 5' RACE experiments to obtain full-length of A7322 mRNA. The present inventors finally obtained a cDNA sequence of 14,763 nucleotides (Genbank Accession Number; AB252196) (SEQ ID NO: 23), containing open reading frame of 6534 nucleotides encoding 2,177 amino-acid protein (SEQ ID NO: 24). The simple modular architecture research tool (SMART) program revealed that the predicted A7322 protein contained a Sec7 domain that might be required for proper protein transport through the Golgi between codon 586 and 798 (Chardin P et al. Nature 1996; 384:481-4; Jackson C L et al. Trends Cell Biol 2000; 10:60-7; Shin H W et al. J Biochem (Tokyo) 2004; 136:761-7).

To examine the exogenous expression of A7322, the present inventors transfected A7322 expression vector into BT549 breast cancer cells and then performed western blotting analysis at 24 hours after transfection. FIG. 1G showed an approximately 250 kDa of A7322 were detected in BT549 at 24 hours after transfection.

(2) Immunocytochemical and Immunohistochemical Analysis of A7322

Figure 2:
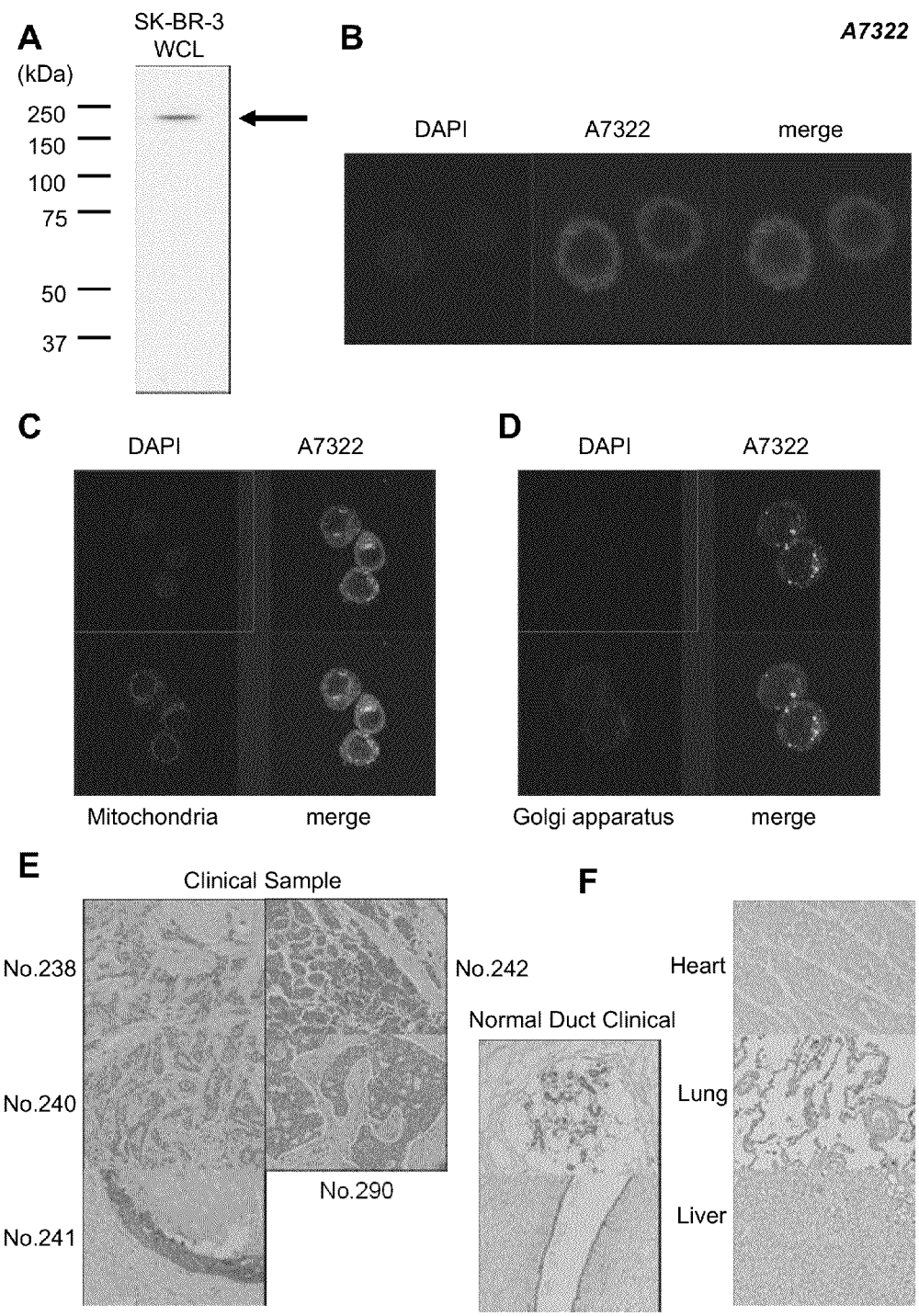
FIG. 2. Endogenous Expression of A7322 in Breast Cancer Cell Lines and Tissue Sections.
(A) Expression of endogenous A7322 protein in SK-BR-3 breast cancer cells by Western blot analysis using anti-A7322 polyclonal antibody.
(B) Sub-cellular localization of endogenous A7322 protein in SK-BR-3 breast cancer cells Immunocytochemical staining were performed using affinity-purified anti-A7322 polyclonal antibody (green) and DAPI (blue) to discriminate nucleus. Endogenous A7322 showed the localization in cytoplasm.
(C)-(E) Immunohistochemical staining analyses were performed using affinity-purified anti-A7322 polyclonal antibody. Cancer cells were strongly stained at cytoplasm in (C) papillotubular carcinoma (Sample nos. 240 and 241).
(D) solid-tubular carcinoma (Sample nos. 238, 242 and 290).
(E), and in normal breast tissue (Sample no. 453).
(F) Immunohistochemical staining of A7322 in normal human tissues (heart, lung, and liver). Expression of A7322 protein in heart, lung and liver were hardly detected.

To investigate the endogenous A7322 protein, the present inventors generated an anti-A7322 polyclonal antibody (see (6) Generation of anti-A7322 polyclonal antibody and anti-F3374 polyclonal antibody). The present inventors first confirmed that the purified A7322-polyclonal antibody could recognize the approximately 250-kDa endogenous A7322 protein in breast cancer cell line, SK-BR-3, without producing any non-specific bands (FIG. 2A). The present inventors carried out immunocytochemical staining analysis with anti-A7322 polyclonal antibody using SK-BR-3 breast cancer cells and found that this antibody could detect strong signals of endogenous A7322 protein in cytoplasm (FIG. 2B). Although the present inventors counter-stained mitochondria or Golgi apparatus using MitoTracker or anti-Golgi monoclonal antibody, A7322 was co-localized in neither of these organelles (FIGS. 2C and 2D).

Furthermore, the present inventors performed immunohistochemical staining experiments using breast cancer and normal tissue sections. The present inventors observed strong staining in the cytoplasm of two different histological subtypes of breast cancer, two papillotubular carcinomas and three solid-tubular carcinomas (FIG. 2E). However, no staining was observed in normal mammary duct (FIG. 2E) or in heart, lung, and liver (FIG. 2E).

(3) Growth-Inhibitory Effects of siRNA Against A7322

To assess the growth-promoting role of A7322, the present inventors knocked down the expression of endogenous A7322 in breast cancer lines BT-549 and BT-474 that have shown the overexpression of A7322, by means of the mammalian vector-based RNA interference (RNAi) technique (see (11) Construction of A7322, F3374V1 or PBK/TOPK specific-siRNA expression vectors and (12) Gene-silencing effect of A7322, F3374V1, AURKB or PBK/TOPK).

The present inventors examined expression level of A7322 by semi-quantitative RT-PCR analysis. A7322-specific siR-NAs (si-#2 and si-#3) significantly suppressed expression of each gene, compared with a control siRNA construct, psiU6BX-Mock (Mock) (FIGS. 5A, D and G). To confirm the cell growth inhibition with A7322-specific siRNAs, the present inventors performed colony-formation (FIGS. 5C and F) and MTT assays (FIGS. 5B, E and H), respectively. The present inventors also generated siRNA that contained 3-bp replacement in si-#3 (si-A7322-mismatch (m#3), see Materials and methods), and found that this had no suppressive effect on expression of A7322 or growth of BT-549 and BT-474 cells (FIGS. 5D, E, F, G and H), suggesting this si-#2 construct has specifically knock-down effect against A7322. Introduction of si-#2 and si-#3 constructs suppressed growth of BT-549 and BT-474 cells, consisting with the result of above reduced expression. Each result was verified by three independent experiments. These findings suggest that A7322 has a significant function in the cell growth of the breast cancer cell.

Furthermore, since the depletion of A7322 resulted in the significant decrease of the number of colonies and in the cell viability, the present inventors investigated the involvement of apoptosis. The present inventors performed fluorescence-activated cell sorting (FACS) analysis to measure the proportions of apoptotic cell population. The results showed the significant increase in the population of apoptotic (sub-G1) cells by si-#3, compared with mock (FIG. 5I), indicating the inhibition of A7322 expression induced apoptosis.

(4) Identification of PHB2/REA as an Interacting Protein of A7322

Since the biological functions of A7322 are totally unknown, the present inventors searched for a protein(s) interacting with A7322 by immunoprecipitation and mass spectrometry analyses (see (16) Co-immunoprecipitation and immunoblotting analyses.) to investigate biological functions of A7322 protein in breast cancer cells. Lysates of BT-549 cells transfected with pCAGGSnH3F-A7322 vector or pCAGGSnH3F-Mock (mock control) were extracted and immunoprecipitated with anti-FLAG M2 monoclonal antibody (see (16) Co-immunoprecipitation and immunoblotting analyses.). Protein complexes were silver stained on SDS-PAGE gels. An approximately 30-kDa protein, which was seen in immunoprecipitates of cell lysates transfected with the FLAG-tagged A7322 plasmid but not in those with mock control plasmid, was extracted and its peptide sequence was determined by mass-spectrometry analysis (FIG. 8A). This approach identified prohibitin 2/repressor of estrogen receptor activity (PHB2/REA) as a candidate for the interacting protein with A7322 (FIG. 8A). Subsequent semi-quantitative RT-PCR confirmed the expression of PHB2/REA in 9 of 10 breast cancer clinical samples and 16 of 22 breast cancer cell lines examined as similar to the expression of A7322 (FIG. 8B). To investigate an interaction between A7322 and PHB2/REA proteins, the present inventors constructed plasmids designed to express FLAG-tagged A7322 (A7322-FLAG) and HA-tagged PHB2/REA (PHB2/REA-HA) (see (5) Construction of expression vectors). These plasmids were co-transfected into COS-7 cells, and then the proteins were immunoprecipitated with anti-FLAG antibody. Immunoblotting of the precipitates using anti-HA antibody indicated that A7322-FLAG was co-precipitated with PHB2/REA-HA (FIG. 8C; left panel). Conversely, the present inventors performed immunoprecipitation using anti-HA antibody and then immunoblotting of the precipitates using anti-FLAG antibody. The results showed that PHB2/REA-HA was co-precipitated with A7322-FLAG (FIG. 8C; right panel). Moreover, to examine the localization of endogenous PHB2/REA and A7322 proteins in breast cancer cell line, SK-BR-3, the present inventors performed immunocytochemical staining analysis using anti-PHB2/REA polyclonal antibody (see (8) Immunocytochemical staining). the present inventors observed the localization of PHB2/REA as well as A7322 mainly in cytoplasm of most of the cells (FIG. 8D), but in a small number of cells, its expression was observed in both cytoplasm and the nucleus (FIG. 8D, arrows), suggesting those proteins might be partially co-localized at cytoplasm in breast cancer cells.

Since it has been reported that PHB2/REA, a protein recruited to the hormone-occupied estrogen receptor α (ERα) (Osborne C K. Breast Cancer Res Treat 1998; 51:227-38), selectively represses the transcriptional activity of ERα through its interaction in nucleus (Montano M M, et al. Proc Natl Acad Sci USA 1999; 96:6947-52; Delage-Mourroux R, et al. J Biol Chem 2000; 275:35848-56), the present inventors investigated the possibility that A7322 is also bound to ERα protein as well as PHB2/REA. To examine an interaction between A7322 and ERα proteins, the present inventors constructed plasmids designed to express FLAG-tagged ERα and HA-tagged A7322 (see (5) Construction of expression vectors). These plasmids were co-transfected into COS-7 cells, and then the proteins were immunoprecipitated using anti-FLAG antibody Immunoblotting of the precipitates using anti-HA antibody indicated that the two proteins were not co-immunoprecipitated (FIG. 9A; left panel). When the present inventors performed immunoprecipitation with anti-HA antibody and immunoblotting with anti-FLAG antibody, the present inventors also did not observe the interaction of these proteins (FIG. 9A; right panel). Furthermore, immunocytochemical analysis revealed that A7322 expression at cytoplasm and ERα at the nucleus in the presence or absence of estradiol (E2), supporting no interaction of these two proteins (FIG. 9B). In addition, similar results were observed when the present inventors used SK-BR-3 cells which show no ER expression (ER−) (FIG. 9C). Taken together, the present inventors conclude that A7322 binds directly with PHB2/REA, whereas it shows no direct binding with ERα protein regardless of the ER status of breast cancer cells.

(5) Inhibition of Nuclear Translocation of PHB2/REA by A7322

PHB2/REA was reported to be localized mainly at cytoplasm and translocates to the nucleus in the presence of E2 and ERα (Kasashima K, et al. J Biol Chem 2006; 281:36401-10). Since the present inventors observed that A7322 was localized at cytoplasm regardless to presence or absence of E2, the present inventors hypothesized that A7322 might interact with PHB2/REA in the cytoplasm and interfere the nuclear translocation of PHB2/REA. To examine this hypothesis, the present inventors investigated the sub-cellular distribution of PHB2/REA protein in a presence or an absence of the A7322 expression. The present inventors transfected constructs of HA-tagged PHB2/REA (HA-PHB2/REA), FLAG-tagged ERα (FLAG-ERα), and FLAG-tagged A7322 (FLAG-A7322) or a mock control into MCF-7 (ER+) cells, and then performed immunocytochemical staining (see (5) Construction of expression vectors and (8) Immunocytochemical staining).

The result showed that PHB2/REA translocated into nucleus as well as ERα in the absent of A7322 (FIG. 10A; left panel, arrow), while remained at cytoplasm in presence of A7322 under E2 treatment (FIG. 10A; right panel). The difference in the subcellular localization of PHB2/REA with or without A7322 was also observed in SK-BR-3 (ER−) cells (FIG. 10B). Furthermore, the present inventors investigated the subcellular localization of endogenous PHB2/REA in A7322-knockdowned MCF-7 cells. FIG. 10C showed confirmation of knockdown of A7322 expression in MCF-7 cells. As the present inventors expected, PHB2/REA was observed to be nucleus in A7322-knockdowned cells at 48 hours after E2 treatment, but was still observed to be cytoplasm in control siRNA (si-EGFP)-treated cells (FIG. 10D). Hence, these results implied that A7322 bound to PHB2/REA, inhibited the nuclear translocation of PHB2/REA, decreased ERα-PHB2/REA interaction and might result in enhancement of the ERα transcriptional activity.

(6) Enhancement of ER Transcriptional Activity by Inhibition of Nuclear Translocation of Endogenous PHB2/REA Since the present inventors observed as described above that A7322 interfered the nuclear translocation of PHB2/REA though interaction with PHB2/REA in the cytoplasm, the present inventors hypothesized that A7322 protein enhance ER transcriptional activity though inhibition of nuclear translocation PHB2/REA in breast cancer cells. To test this hypothesis, the present inventors co-transfected the FLAG-tagged A7322 (FLAG-A7322) construct and estrogen responsive reporter gene (pERE-TA-SEAP) construct or a mock control and pERE-TA-SEAP reporter construct into MCF-7 (ER+) or SK-BR-3 (ER−) cells, respectively, and then performed reporter assay using SEAP assay kit (see (19) Estrogen responsive element (ERE) reporter gene assays).

The present inventors confirmed expression of exogenous A7322 and endogenous PHB2/REA proteins in those cells by western blot analysis (FIG. 11A). Expectedly, introduction of A7322 protein drastically enhanced of ER transcriptional activity in MCF7 (ER+) cells at 48 hours after E2 treatment, while did not enhance ER transcriptional activity in SK-BR-3 (ER−) cells (FIG. 11B). These finding suggest that A7322 protein might enhance ER transcriptional activity though inhibition of nuclear translocation PHB2/REA in breast cancer cells.

Discussion

Identification and characterization of cancer-related genes and their products have contributed to the development of molecular-targeting drugs for cancer therapy in the last two decades. However, the proportion of patients showing good response to presently-available treatments is still limited (Taniuchi K, et al. Cancer Res 2005; 65:3092-9). Hence, it is urgent to develop new anticancer agents that will be highly specific to malignant cells, with minimal or no adverse reactions. In this report, through the precise expression profile analysis of breast cancer, the present inventors identified A7322 which was significantly overexpressed in the great majority of breast cancer cases and breast cancer cell lines. Furthermore, northern blot analysis showed that the expression of A7322 was hardly detectable in any normal human tissues examined except brain Immunohistochemical staining experiments using anti-A7322 polyclonal antibody clearly indicated up-regulation of A7322 expression in breast cancer cells, but no expression in surrounding normal cells or in vital organs.

The present inventors also characterized some biological function of the A7322 protein and indicated that it would be a good candidate as a molecular target for breast cancer therapy. The present inventors demonstrated by means of the siRNA technique that the knockdown of the endogenous A7322 expression resulted in remarkable growth suppression of breast cancer cells. Furthermore, the present inventors have found through our cDNA microarray analysis that A7322 was up-regulated commonly in almost all of cancers including bladder cancer, colon cancer, non-small cell lung cancer, prostate cancer as well as breast cancer. These results showed that this gene should serve as a valuable target for development of anti-cancer agents for many types of clinical cancers.

To find the clues to the biological significance of A7322 in breast cancer cells, the present inventors searched for the possible interacting proteins with A7322 by means of immunoprecipitation and mass spectrometry methods, and identified PHB2/REA as an A7322-interacting protein. The present inventors demonstrated in vivo interaction, and co-localization of A7322 and PHB2/REA at cytoplasm of breast cancer cells. PHB2/REA is known to be an estrogen receptor α (ERα)-selective coregulator and represses the transcriptional activity of the estradiol-liganded ERα (Kasashima K, J Biol Chem 2006; 281:36401-10). Hence, the present inventors hypothesized that A7322 activates the transcriptional activity of ERα through inhibition of the interaction of ERα and PHB2/REA (FIG. 11C), resulting in probably activation of ER-downstream genes.

In conclusion, our findings clearly suggested that A7322 was overexpressed in both breast cancer specimens and cancer cell lines, and its interaction with PHB2/REA is likely to play a significant role in the enhancement of breast cancer cell growth. Recent strategies for development of anti-cancer drugs have been focused on targeting molecules that are critically involved in the oncogenic pathways, such as imatinib mesylate and trastuzumab. The present inventors found that the down-regulation of A7322 by treatment with siRNA significantly suppressed the cell growth of breast cancer, indicating its crucial role in proliferation and tumorigenesis of breast cancer. Particularly, the present inventors suggested a possibility of A7322 function in breast carcinogenesis by reactivation of ERα through inhibition of nuclear-translocation of the PHB2/REA protein. These data should contribute to a better understanding of breast carcinogenesis, and suggests that A7322 is a promising molecular target for breast cancer treatment.

Example 3

F3374

(1) Identification of F3374 as an Up-Regulated Gene in Breast Cancer

To identify molecules that could be applicable as targets for novel therapeutic drugs, the present inventors previously established genome-wide gene-expression profiles of 81 breast cancer patients using cDNA microarray representing 27,648 cDNAs (Nishidate T et al. Int J Oncol 2004; 25:797-819.). Among the up-regulated genes, the present inventors focused on F3374 whose expressions were up-regulated in the majority of breast cancer specimens. Subsequent semi-quantitative RT-PCR and northern blot analyses confirmed that F3374 was significantly up-regulated in 10 of 12 breast cancer specimens (FIG. 1A) and all of breast cancer cell-lines (FIG. 1B), but not expressed in normal organs except testis and thymus, placenta, bone marrow (FIGS. 1C and D).

The full-length cDNA sequences of F3374V1 consist of 4,221 nucleotides, with an open reading frame of 2,193 nucleotides that encode 730-amino-acid peptides (FIG. 1E). Subsequently, to confirm the expression pattern of F3374V1 in breast cancer cell-lines and normal human tissues, the present inventors performed semi-quantitative RT-PCR using the primer sets recognized to F3374V1. The result by RT-PCR showed F3374V1 (1,296 bp) were dominantly overexpressed in breast cancer cells as compared with normal human tissues, whereas other variants not expressed in breast cancer cells. Therefore, the present inventors focused on F3374 V1 transcript for further analyses (FIG. 1F).

To examine expression pattern of endogenous F3374 protein, the present inventors initially developed a specific polyclonal antibody against F3374 protein. Subsequent western blotting analysis was performed using cell lysates from breast cancer cell-lines, HBC4, HBC5, HBL100, HCC1937, MCF-7, MDA-MB-231, SKBR3, T47D and YMB1 as well as HMEC (Human mammalian epithelial cell) cells. FIG. 1D showed strong bands were specifically detected in almost of cell-lines, but hardly detected in HMEC cells.

Figure 3:
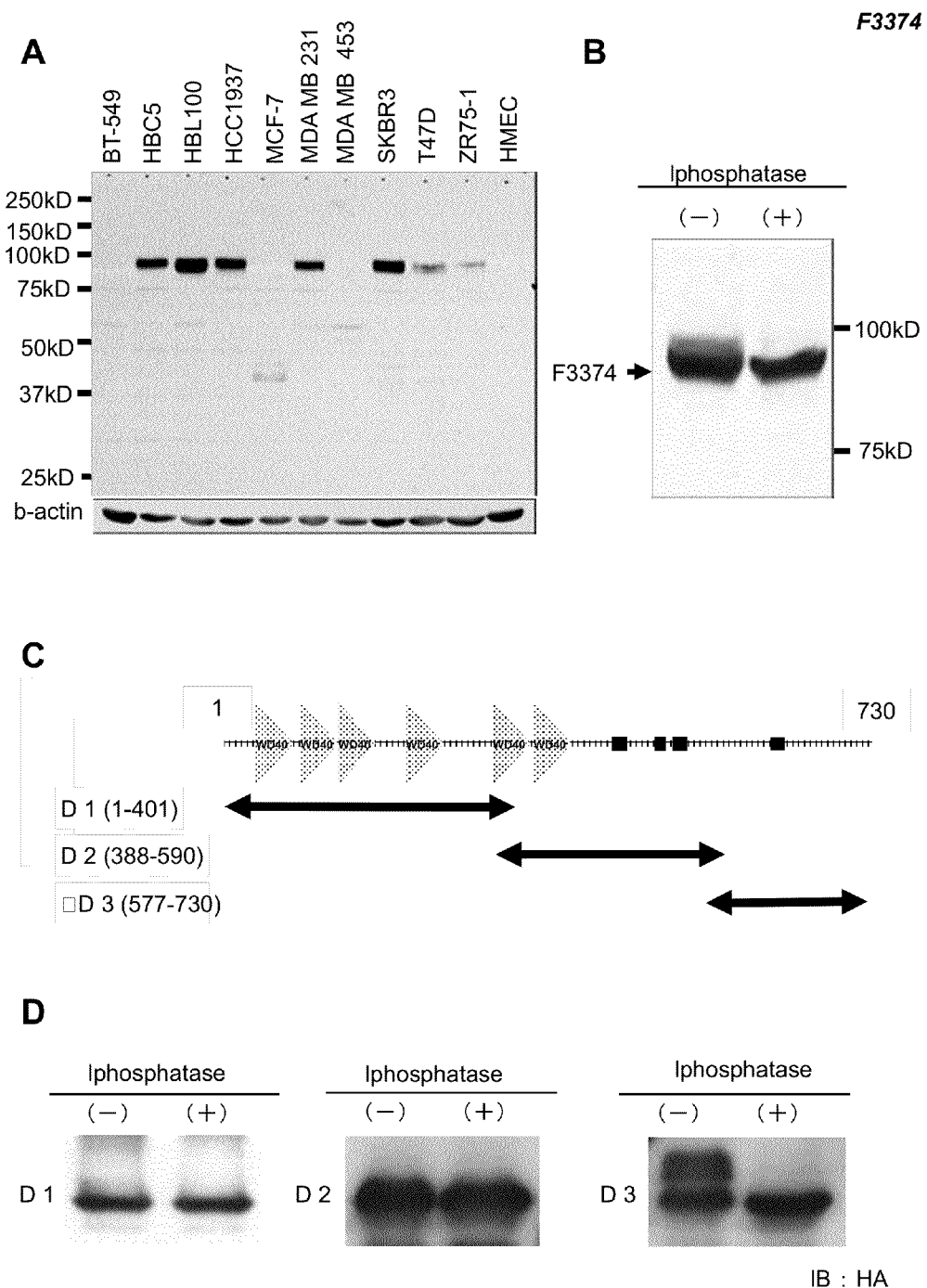
FIG. 3. Immunocytochemical and Immunohistochemical Analyses.
(A) Expression of endogenous F3374 protein in breast cancer cell lines and HMEC by western blot analysis using anti-F3374 antibody.
(B) Lambda phosphatase experiment when expressed exogenously with full-length F3374 proteins.
(C) Representative schema of F3374 deletion constructs for determination of phosphorylation regions.

Interestingly, BT-549, MCF-7 and MDA-MB231 showed no expression or shorten of F3374 proteins despite of overexpression of F3374 mRNA in these cell lines (FIG. 3A). This suggests that there might be some mutations, resulting in truncated protein due to alternative splicing in these cell-lines, although it will be necessary to perform sequencing analysis.

Furthermore, western blot results showed an additional band as well as a 79.5 kDa-band corresponding to the predicted size of F3374 protein (FIG. 3A). To test whether this additional band represented a form of F3374 protein modified by phosphorylation, the present inventors treated the cellular extracts from T47D cells with λ-phosphatase before immunoblotting. Since the extra band did not appear after treatment of λ-phosphatase, the present inventors judged that F3374 was phosphorylated in breast cancer cells (FIG. 3B). To determine the phosphorylated regions of F3374, the present inventors designed 3-fragments of F3374 (FIG. 3C). The results showed that the extra band disappeared after treatment of phosphatase when transiently expressed with delta-3 construct, but not changed when expressed with other constructs (FIG. 3D). These findings indicate that C-terminal region (591-730 amino-acid) was phosphorylated in cells.

(2) Immunocytochemical and Immunohistochemical Analysis of F3374V1

To examine sub-cellular localization of endogenous F3374V1 protein in breast cancer cell-line, HBC5 the present inventors performed immunocytochemical staining analysis using anti-F3374 polyclonal antibody. Interestingly, endogenous F3374V1 showed cell cycle-dependent localization (FIG. 3E). In interphase, it localized in nucleus, and then on the chromosomes in prophase. In anaphase, F3374V1 was concentrated as a series of narrow bars at the anaphase spindle midzone in cells (FIG. 3E). Finally, this protein was accumulated to midbody of telophase in all of breast cancer cells. F3374V1 underwent a remarkable redistribution when cells progressed through mitosis. These findings suggest F3374V1 might play an important role of during cell cycle especially, cytokinesis of breast cancer cells.

To further investigate F3374 expression in breast cancer and normal tissue sections, the present inventors performed immunohistochemical staining with anti-F3374 antibody. The present inventors identified highly expression in the nuclei and cytoplasm of three different histological subtypes of breast cancer, papillo-tubular carcinoma, solid tubular carcinoma, and scirrhous carcinoma, but its expression was hardly detectable in normal mammary duct cells (FIG. 3F, left panels). Furthermore the present inventors performed breast cancer tissue microarray analysis and verified positive staining of F3374V1 in 33 of 39 infiltrating ductal carcinomas, while no staining was observed in 5 normal mammary tissues including ductal cells (data not shown). Among nine normal tissues the present inventors examined, its expression was detected in testis, but hardly detectable in heart, liver, kidney, lung, colon, pancreas, skeletal muscle and small intestine in concordance with the result of northern-blot analysis (FIG. 3F, right panels). These results suggest F3374V1 protein is overexpressed in breast cancer cells in vivo.

(3) Cell-Cycle Dependent Expression of F3374.

To examine the expression of F3374 protein at various cell-cycle phases, the present inventors performed FACS analysis and western blot analyses using T47D cells after synchronization of the cell cycle by aphidicolin treatment. The expression of F3374 protein was high at a transition period from G1 to S phase (0-6 hours) and the highest at the point just after the release from the cell-cycle arrest (FIGS. 12A and B). On the other hand, its expression was strikingly reduced at the 9-12-hour points when most of the cells were at the G2/M phase. Interestingly, most of the F3374 protein was unphosphorylated during the G1/S phase, but its significant proportion was modified to the phosphorylated form during G2/M phase (9-12 hours) (FIG. 12B), suggesting that endogenous F3374 protein showed cell cycle-dependent localization and modification, and might play important roles in cell-cycle progression of breast cancer cells.

(4) Growth-Inhibitory Effects of siRNA Against F3374V1

To assess the growth-promoting role of F3374V1, the present inventors knocked down the expression of endogenous F3374V1 in breast cancer lines T47D and HBC4 that have shown the overexpression of F3374V1, by means of the mammalian vector-based RNA interference (RNAi) technique (see Materials and Methods). The present inventors examined expression level of F3374V1 by semi-quantitative RT-PCR analysis. Among the two siRNA constructs of each gene examined, F3374V1-specific siRNAs, si-#1 and si-#4 significantly and moderately suppressed expression of each gene, compared with control siRNA constructs, psiU6BX-EGFP (siEGFP) and psiU6BX-SCR (siSCR) (FIGS. 6A and D). To confirm the cell growth inhibition with F3374V1-specific siRNAs, the present inventors performed colony-formation (FIGS. 6B and E) and MTT assays and (FIGS. 6C and F), respectively. Introduction of F3374V1 (Si-#1 and Si-#4) constructs significantly suppressed growth of T47D and HBC4 cells, consisting with the result of above reduced expression. Each result was verified by three independent experiments. These findings suggest that F3374V1 has a significant function in the cell growth of the breast cancer cell.

Furthermore, the present inventors examined morphological alterations of the HBC4 cells transfected with an F3374-specific siRNA oligonucleotide (siF3374) (see (12) Gene-silencing effect of A7322, F3374V1, AURKB or PBK/TOPK), and confirmed the significant knockdown effect at the protein level (FIG. 6G). Interestingly, the present inventors observed that its knockdown led to appearance of the intercellular bridges between two separating-cells (FIG. 6H; the arrows in siF3374 panel), indicating dysfunction in the late stage of cytokinesis process. The present inventors also observed enlargement of the size of the cells transfected with siF3374 in comparison with those transfected with control siEGFP (FIG. 6H). Similar results were obtained in T47D cells (data not shown), indicating the dysfunction of cytokinesis process. These findings indicate that the absence of F3374 caused the failure of cytokinesis, resulted in arrest of G2/M phase cells and then induced cell death.

(5) F3374 Protein was Regulated by Aurora Kinase-B.

It was described above that F3374 was phosphorylated and concentrated at the contractile ring when cells were at telophase and cytokinesis stages in breast cancer cells. Since Aurora-B kinase (AURKB) is known to be a chromosome passenger protein that moves from centrosomes to midzone spindle in anaphase and to the midbody in telophase and cytokinesis in HeLa cells (Terada Y. Cell Struct Funct 2001; 26:653-7; Adams R R, et al. Trends Cell Biol 2001; 11:49-54; Carmena M, et al. Nat Rev Mol Cell Biol 2003; 4:842-54), the present inventors considered their similar subcellular-localization at some cell-cycle phases. In addition, as shown in FIG. 13A, the present inventors found three consensus phosphorylation sites for Aurora kinase-B ([R/K]X[T/S] and [R/K]X[T/S][I/L/V]; Cheeseman I M, et al. Cell 2002; 111: 163-72; Ohashi S, et al. Oncogene 2006; 25:7691-702) within the C-terminal region of F3374 (591-730 amino-acid) where phosphorylation was observed (FIG. 2D). Hence, it was examined a possible interaction of F3374 protein with AURKB in breast cancer cells.

The present inventors first compared the expression patterns of F3374 and AURKB by semi-quantitative RT-PCR analysis, and confirmed the up-regulation of both F3374 and AURKB in almost all of 10 breast cancer cell lines examined (FIG. 13B). To investigate an interaction between F3374 and AURKB proteins, the present inventors constructed plasmids designed to express HA-tagged F3374 (HA-F3374) and Flag-tagged AURKB (Flag-AURKB) (see (5) Construction of expression vectors). These plasmids were co-transfected into HEK293T cells, and then the proteins were immunoprecipitated with anti-Flag antibody. Immunoblotting of the precipitates using anti-HA antibody indicated that Flag-AURKB was co-precipitated with HA-F3374 (FIG. 13C). Moreover, immunocytochemical staining experiments confirmed both proteins accumulated to midbody in cytokinesis of T47D cells (FIG. 13F).

To further investigate weather F3374 is phosphorylated by AURKB, the present inventors performed in vitro kinase assay using a purified C-terminal F3374 (437-730 amino acids) recombinant protein and the full-length AURKB recombinant protein (see (17) In vitro and in vivo kinase assay.), and found phosphorylation of the F3374 protein by AURKB in vitro (FIG. 13D). To further investigate a possible role of the interaction between F3374 and AURBK proteins and its phosphorylation by AURKB, siRNA-AURKB (siAURKB) were transfected into T47D cells, and then performed western-blot analysis. It was observed the significant decrease of total F3374 protein as well as the phosphorylated F3374 protein in T47D cells transfected with siAURKB in comparison with those with a control siEGFP (FIG. 13E), implying a possibility that the phosphorylation of F3374 by AURKB could stabilize F3374 in a late phase of mitosis (FIG. 13F).

Discussion

Through identification and characterization of cancer-related genes and their products, molecular-targeting drugs for cancer therapy have been developed in the last two decades, but the proportion of patients who are able to have a benefit by presently-available treatments is still very limited (Navolanic P M, et al. Int J Oncol 2005; 27:1341-4; Bange J, et al. Nat Med 2001; 7:548-52). Therefore, it is urgent to develop new anticancer agents that will be highly specific to malignant cells and have the minimal risk of adverse reactions. In this study, through the detailed expression profile analysis of breast cancers, the present inventors identified F3374 that was significantly over-expressed in clinical breast cancer cases as well as in breast cancer cell lines, but was hardly detectable in any normal human tissues examined except a low level of expression in a few organs. Subsequent northern blot and immunohistochemical staining analyses clearly indicated up-regulation of F3374 expression in breast cancer cells at both transcriptional and protein level, but no expression in surrounding normal cells.

F3374 gene encodes a putative 730-amino acid protein that contains six highly-conserved WD40-repeat domains and a consensus nuclear-localization signal at N-terminus Our results also demonstrated that F3374 protein was mainly localized in the nucleus of interphase cells, accumulated as a series of narrow bars at spindle midzone in the anaphase cells, and was finally concentrated at the contractile ring in telophase and cytokinesis stages. These findings suggest the important role of this protein in cell-cycle progression.

The present inventors demonstrated by means of the siRNA technique that knocking down of the endogenous F3374 expression significantly suppressed the cell growth of breast cancer cell-lines, T47D and HBC4, due to abnormal cell division and subsequent cell death, probably due to the dysfunction in the cytokinetic process. The present inventors have also demonstrated that the proportion of cells with a larger size was increased in the siF3374-transfected cells although the present inventors did not find an increase of the multinucleated cells. Since it was reported that an inactivation of F3374 induced p53 stabilization in unstressed HeLa cells (Banks D, et al. Cell Cycle 2006; 5:1719-29), the accumulation of G2/M cells by knockdown of F3374 might be due to activation of the checkpoint system by p53 in breast cancer cell line HBC4.

Due to similarity of the subcellular-localization at some cell-cycle phases and its co-expression in breast cancer cells, the present inventors focused on the Aurora-B (AURKB) serine/threonine kinase as a candidate for the F3374 interacting protein. The present inventors demonstrated the in vivo interaction with AURKB, and its in vitro phosphorylation by AURKB as well as its possible stabilization by AURKB through the RNAi experiments. In addition, it was reported that knockdown of AURKB also suppressed growth of HeLa cells because of cytokinesis defects (Goto H, et al. J Biol Chem 2003; 278:8526-30; Severson A F, et al. Curr Biol 2000; 10:1162-71) as similar to depletion of F3374. Together, the present inventors demonstrated here for the first time that interaction of F3374 and AURKB might play an important role in cytokinesis. Furthermore, it was reported that F3374 was required in the initiation of a radiation-induced G2/M checkpoint as a component of the CUL4-DDB 1 ubiquitin E3 ligase complex (Sansam C L, et al. Genes Dev 2006; 20:3117-29; Higa L A, et al. Cell Cycle 2006; 5:1675-80; Higa L A, et al. Nat Cell Biol 2006; 8:1277-83), suggesting the multiple roles of F3374 in the cell-cycle progression.

Thus, since inhibition of their association may lead to cell death following the failure of cytokinesis in breast cancer cells, the inhibitor for their association would be a possible valuable target to develop agents against breast cancer.

In conclusion, our results have suggested that the interaction of F3374 and its phosphorylation with AURKB were likely to play a significant role in cytokinesis of breast cancer cells. The present inventors also found that down-regulation of F3374 with siRNA significantly suppressed the growth of breast cancer cells, indicating its crucial role in proliferation of breast cancer cells. Our data should contribute to a better understanding of mammary carcinogenesis, and imply that F3374 is likely to be a promising molecular target for breast cancer therapy. Furthermore, it is notable that our cDNA microarray data identified up-regulation of F3374 commonly in many types of clinical cancers including bladder cancer, cholangiocarcinoma, lung cancers and renal cell carcinoma as well as breast cancers (data not shown). These results showed that this gene should serve as a valuable target for development of anti-cancer agents for a wide range of human cancers.

Example 4

PBK/TOPK (1) Up-Regulation of PBK/TOPK in Breast Cancers

The present inventors previously performed genome-wide expression profile analysis of 81 breast cancer cases using cDNA microarray (Nishidate T et al., Int J Oncol 2004, 25: 797-819). Among genes up-regulated in breast cancers, genes that encode proteins containing a kinase domain, either on the basis of reported information or according to prediction by protein-motif program SMART (http://smart.embl-heidelberg.de) (Schultz J et al., Proc Natl Acad Sci USA 1998, 95: 5857-64; Letunic I et al., Nucleic Acids Res 2004, 32: D142-4) were searched. Among the searched genes the present inventors focused on the PBK/TOPK gene for which high level transactivation could be confirmed in great majority of breast cancer cells (FIG. 1A). Northern-blot analysis of 10 breast cancer cell-lines and 6 normal organs further confirmed that PBK/TOPK was specifically up-regulated in all of the breast cancer cell-lines examined, but its expression was hardly detectable in lung, heart, liver, kidney, bone marrow, and mammary gland (FIG. 1D).

To further examine the expression pattern of the PBK/TOPK gene in various normal tissues, Northern blot analysis was performed using mRNAs from 23 tissues to identify two transcripts exclusive in the testis and thymus (FIG. 1C). According to the NCBI database, two representative transcripts of 1,899 nucleotides (GenBank Accession No. NM_018492) and 1,548 nucleotides (#AF189722), that share the same open reading encoding a 322 amino-acid peptide, seemed to correspond to the two bands observed in the Northern analysis.

(2) Immunocytochemical and Immunohistochemical Analysis of PBK/TOPK

Endogenous PBK/TOPK protein expression was examined in cell lysates from breast cancer cell-lines, BT-20, HBC4, HBC5, HBL-100, MCF-7, MDA-MB-231, SKBR3, and T47D by Western-blot analysis (FIG. 4A), using HMEC (Human Mammalian Epithelial Cell) as a control of the experiments. All of the breast cancer cell-lines showed high levels of PBK/TOPK expression, whereas the normal breast epithelial cell-line, HMEC cells showed no expression. Subsequent immunocytochemical analysis of breast cancer cell-lines, T47D, BT-20 and HBC5, using anti-PBK/TOPK monoclonal antibody indicated endogenous PBK/TOPK localization mainly in the cytoplasm (FIG. 4B).

To further investigate PBK/TOPK expression in breast cancer and normal tissue sections, immunohistochemical staining was performed using anti-PBK/TOPK monoclonal antibody. Strong staining was detected in the cytoplasm of three different histological subtypes of breast cancers, intraductal carcinoma, papillo-tubular carcinoma, and scirrhous carcinoma (FIG. 4C (1)-(3)), but its expression was hardly detectable in normal breast tissues (FIG. 4C (4)). Furthermore, concordant with the results of Northern blot analysis, strong staining of PBK/TOPK protein was detected at the outer cell layer of seminiferous tubules of testis, while no expression was observed in heart, lung, liver, or kidney (FIG. 4D (1)-(4)).

(3) Knockdown Effects of Endogenous PBK/TOPK

To investigate the growth-promoting role of PBK/TOPK gene in breast cancer cells, the expression of endogenous PBK/TOPK was knocked down in two breast cancer cells, T47D and BT-20 (FIGS. 7A and B) by means of RNA interference (RNAi) technique. Semi-quantitative RT-PCR experiments detected significant knockdown effect of PBK/TOPK in the cells transfected with PBK/TOPK-si-#2 and si-#3, but not with control siRNA (Mock). In concordance with its revealed knockdown effect, colony-formation and MTT assays clearly revealed growth suppression of breast cancer cells by the two siRNAs, PBK/TOPK-si-#2 and si-#3, compared with two siRNAs showing no knockdown effect, which were used to exclude the possibility of off-target effect by PBK/TOPK-siRNA (si-#3) (FIGS. 7A and B). These results imply a critical role of PBK/TOPK in the growth of breast cancer cells.

In addition, phenotypic alterations were observed for the cells transfected with the siRNAs showing significant knockdown effect. Prolonged midbodies as well as incorrect cell divisions by abnormal cytokinesis were observed in T47D cells in which PBK/TOPK expression was suppressed (FIGS. 7C and D). Western blot and FACS analyses also identified an increase in the population of apoptotic (sub-G1) cells in the cells treated with PBK/TOPK siRNA, although no phenotypic alteration or increase of sub-G1 population was observed in those transfected with mock construct (FIGS. 7E and F), implying indispensable roles of PBK/TOPK on proliferation as well as on mitosis and/or cytokinesis for breast cancer cells.

(4) Cell-Cycle Dependent Expression of PBK/TOPK

Since PBK/TOPK was reported to be a possible mitotic kinase (Gaudet S et al., Proc Natl Acad Sci USA 2000, 97: 5167-72), the inventors investigated its relation to cell-cycle progression. The expression of PBK/TOPK protein was examined in T47D cells after synchronization of cell cycle by aphidicolin. FACS analysis showed that the proportion of cells at G2/M phase was significantly increased 6 h after the release from cell cycle arrest (FIG. 14A). Interestingly, Western-blot analysis detected an additional band of high molecular weight PBK/TOPK 9 to 12 h later when most of the cells were at the G2/M phase. The intensity of the high-molecular band decreased at the 15-h point (FIG. 14B). Immunochemical analysis also revealed subcellular localization of PBK/TOPK protein around the condensed chromosome in the cells at mitosis, especially at pro- and metaphase (FIG. 14C).

To further investigate the role of high-molecular PBK/TOPK in cell cycle progression, T47D breast cancer cells were treated with nocodazole to perform Western-blot and FACS analyses. As expected, the intensity of the additional high-molecular band of the endogenous PBK/TOPK in T47D cells elevated in a time-dependent manner (6 to 18 h) after the treatment with nocodazole (FIG. 14D, left panel), and the band disappeared via the treatment with lambda phosphatase (FIG. 14D, right panel). In addition, FACS analysis showed that the proportion of cells at the G2/M phase elevated from 6 to 18 h after the release from cell cycle arrest (FIG. 14E), indicating an important role of phosphorylated PBK/TOPK in mitosis.

(5) PBK/TOPK Phosphorylated Histone H3 (Ser10) In Vitro and In Vivo

Since PBK/TOPK protein was localized mainly around the chromosomal surfaces in mitotic cells, particularly at prophase and metaphase, the inventors focused on histone as a candidate substrate for PBK/TOPK protein. In vitro kinase assay was performed using purified recombinant PBK/TOPK and mixed histone proteins (H2a, H2b, H3, and H4) (FIG. 15A) to detected a phosphorylated protein of approximately 15 kDa (lane 2), indicating that PBK/TOPK protein might phosphorylate histone H3 protein on the basis of its molecular size (FIG. 15A, left panel). Further, in vitro kinase assay was performed using histone-H3 recombinant protein to confirm that PBK/TOPK protein phosphorylates histone H3 (FIG. 15A, right panel). In addition, an autophosphorylated PBK/TOPK of approximately 40 kDa was detected by in vitro kinase assay as shown in FIG. 15A (indicated by an asterisk).

Localization of PBK/TOPK around chromosome as well as its elevated phosphorylation in the early stage of mitosis suggested the physiological role of histone H3 phosphorylation by PBK/TOPK in breast cancer cells. Thus, first, wild-type or kinase-dead (K64-65A) PBK/TOPK were transfected into T47D cells and then the cells were stimulated by treating them with okadaic acid (OA), which treatment is known to induce premature mitosis (Gaudet S et al., Proc Natl Acad Sci USA 2000, 97: 5167-72). Both wild-type and kinase-dead PBK/TOPKs were detected by Western-blot analysis using anti-HA rat antibody to be phosphorylated at the same level via the OA treatment. However, the phosphorylation at Ser10 of histone H3 enhanced with wild-type protein as compared with kinase-dead mutant protein (FIG. 15B). Additionally, the phosphorylation of histone H3 at Ser10 was confirmed to be specifically reduced in PBK/TOPK-depleted T47D cells by siRNA (si-#3), as compared in Mock-siRNA transfected cells (FIG. 15C).

In addition, the localization of endogenous PBK/TOPK protein and phosphorylated histone H3 was examined Specifically, T47D and HBC5 cells were synchronized with aphidicolin, and then immunocytochemical staining was performed using anti-PBK/TOPK and anti-phospho-Ser10 H3 antibodies. As shown in FIG. 15D, partial overlapping of PBK/TOPK and phosphorylated histone H3 around condensed chromosome in prophase cells, overlapping of both proteins in metaphase cells (FIG. 15E), and disappearance of both at anaphase (FIG. 15F) were observed. Taking the results together, endogenous PBK/TOPK was determined to have the ability specifically phosphorylate histone H3 at Ser10 during mitosis, especially at the prophase to metaphase in breast cancer cells.

(6) Phosphorylation of Thr9 is Important for Cell Proliferation

It previously demonstrated that PBK/TOPK is upregulated in breast cancers and translocated from cytoplasm to nucleus during mitosis in breast cancer cells (Park J H et al., Cancer Res 66: 9186-95 (2006)). Furthermore, it has been reported that CDK1-cyclin B1 complex proteins also behave nuclear translocation in mitotic cells. Hence, the present inventors firstly did immunocytochemistry to confirm the subcellular localization of PBK/TOPK, CDK1 and cyclin B1 in breast cancer cells, respectively. The similar nuclear translocations of those proteins during mitosis of T47D breast cancer cells were observed and suggested a possible signal transduction between PBK/TOPK and CDK1-cyclin B1 complex in breast cancer cells (FIG. 16A). Although it has been reported that PBK/TOPK can be phosphorylated at Thr9 by CDK1-cyclin B1 though immunocomplex kinase assay using immunoprecipitates of CDK1, it is still unsolved whether its phosphorylation is direct or not (Matsumoto et al., Biochem Biophys Res Commun 325: 997-1004 (2004)). An inactive recombinant protein of wildtype and T9A mutant of PBK/TOPK were generated by *E. coli* expression system. It was demonstrated that a wildtype of PBK/TOPK recombinant protein was phosphorylated by CDK1-cyclin B1 recombinant protein complex, whereas an alanine-substituted mutant at Thr9 (T9A) of PBK/TOPK recombinant protein was not (FIG. 16B), suggesting direct phosphorylation of PBK/TOPK at Thr9 by CDK1-cyclin B1 complex in vitro.

To investigate the biological significance of phosphorylation at Thr9 of PBK/TOPK in breast carcinogenesis, it was attempted to inhibit its phosphorylation by use of the synthesized peptide. The inventors designed the N-terminus of PBK/TOPK peptide (pp1-18); SEQ ID NO: 98 that was conjugated with arginine (R)-repeat to facilitate cell permeability. FIG. 16C shows that the phosphorylation of recombinant PBK/TOPK protein by CDK1-cyclin B1 recombinant proteins was diminished in dose-dependent manner by addition of the pp1-18 peptide. Furthermore, it was examined whether this peptide could inhibit cancer cell growth, by treating cancers and normal human mammary epithelial cells (HMEC) with this peptide. Treatment of pp1-18 peptide clearly suppressed the growth of T47D breast cancer cells in dose dependent manner, but showed no effect on the growth of HMEC cells (5 µmol/mL, Student t-test; p=0.0096), excluding a possibility of the off-target effects of this peptide (FIG. 16D). Next, we further investigated whether this peptide inhibited the phosphorylation of PBK/TOPK in mitotic cells. T47D cells were treated with nocodazole and were subsequently added with pp1-18 peptide. FIG. 16E shows that the phosphorylation of PBK/TOPK in mitotic cells was drastically reduced with time-dependency by treatment of 10 µM pp1-18 peptide. Moreover, treatment of this peptide blocked shift to G2/M phase of cell cycle at 24 hours after treatment of nocodazole (FIG. 16E, down panels). Furthermore, it was observed prolonged midbodies by abnormal cytokinesis in pp1-18 treated (50 µM)-T47D cells (FIG. 16F) as well as in the PBK/TOPK-knockdowned T47D cells as described previously (Park J H et al., Cancer Res 66: 9186-95 (2006)). Taken together, these findings suggest that the phosphorylation of PBK/TOPK at Thr9 by CDK1-cyclin B1 might play a crucial role in cell growth of breast cancer, although this peptide may inhibit the possible interaction with other PBK/TOPK interacting partners though its N-terminal region.

(7) Autophosphorylation of PBK/TOPK in Mitotic Cells

To investigate phosphorylation of PBK/TOPK during mitosis, the present inventors isolated mitotic cells by the "mitotic shake-off" method (see Example 1-Materials and methods (16) Co-immunoprecipitation and immunoblotting analyses.) (FIG. 17A, upper panels), and performed immunoblotting analysis using the mitotic cell-lysates. Since the high molecular-weight band completely shifted after treatment with lambda phosphatase, this protein is hyperphosphorylated during cell mitosis in breast cancer cells (FIG. 17A). To further investigate whether this hyperphosphorylation of PBK/TOPK in mitotic cells exclusively occurred at its Thr9 by CDK1-cyclin B1 complex, T9A, kinase-dead (KD) and double (T9A/KD) mutant construct as well as wildtype of PBK/TOPK constructs were transfected into T47D breast cancer cells, respectively. Interestingly, the phosphorylated band of T9A protein was still preserved after treatment of nocodazole, whereas that of KD and double (T9A/KD) mutant was completely disappeared as well as that in cells treated with lambda phosphatase (FIG. 17B). These results strongly suggest that PBK/TOPK protein might be autophosphorylated by itself in mitotic cells.

(8) PP1α Regulates the Phosphorylation of PBK/TOPK

It was previously also demonstrated that the phosphorylation of PBK/TOPK protein was induced by treatment of Okadaic acid (OA), which is a potent inhibitor of Ser/Thr protein phosphatases, in T47D breast cancer cells as well as treatment of nocodazole (Park J H et al., Cancer Res 66: 9186-95 (2006)). However, how its phosphorylation is induced by treatment with OA in breast cancer cells remains unknown. Because it has been reported that protein phosphatase 1 alpha (PP1α) has relatively high IC50 value for OA and furthermore is inactivated during cell mitosis (Kwon Y G et al., Proc Natl Acad Sci USA 94: 2168-73 (1997); Ammosova T et al., Retrovirology 2:47 (2005)), it allowed the present inventors to focus on PP1α as a potential regulator for PBK/TOPK phosphorylation among human protein phosphatases. Firstly, the present inventors treated with high concentration (100 nM) or low concentration (less than 100 nM) of OA to T47D cells, and found that the phosphorylation of PBK/TOPK was induced by treatment with 100 nM of OA for 9 hours (FIG. 17C), but not by treatment with low concentrations (data not shown). Subsequently, to examine the interaction of PBK/TOPK with PP1α, GST-tagged PP1α (PP1α-GST) and HA-tagged PBK/TOPK (HA-PBK/TOPK) constructs were co-expressed into COS-7 cells followed by GST pull down assay. FIG. 17D shows that PP1α-GST was clearly pull-downed with HA-PBK/TOPK (upper panels), whereas conversely, HA-PBK/TOPK was co-immunoprecipitated with PP1α-GST (lower panels), indicating the interaction of both proteins. It was further examined whether PBK/TOPK protein was directly dephosphorylated by PP1α protein. The active recombinant PBK/TOPK protein was dephosphorylated after incubation with the recombinant PP1αprotein as well as the lambda phosphatase (FIG. 17E, upper panel). Moreover, the endogenous PBK/TOPK protein in mitotic cell-lysates from T47D cells was also dephosphorylated by treatment of PP1α protein (FIG. 17E, down panel). These findings implied that PP1α possibly regulates the autophosphorylation of PBK/TOPK during mitosis though their interaction.

(9) CDK1-Cyclin B1 Activates PBK/TOPK Though Inactivation of PP1α

It was described above indicated the phosphorylation of PBK/TOPK by CDK1-cyclin B1 kinase complex and regulation of its phosphorylation by PP1α in mitotic cells. Furthermore, PP1α is known to be inactivated in mitotic cells though its phosphorylation by CDK1-cyclin B1 complex (Kwon Y G et al., Proc Natl Acad Sci USA 94: 2168-73 (1997)). Therefore, it was further examined how PBK/TOPK was regulated by CDK1-cyclin B1 or PP1α during mitosis more in detail. T47D cells were synchronized at G2/M phase (61-70%) with treatment of nocodazole for 16 hours and subsequently incubated with a CDK1 inhibitor for up to 4 hours (FIGS. 17F and G). Subsequently, it was examined the phosphorylation levels of PBK/TOPK or PP1α by immunoblotting analysis. It was found that the phosphorylation of PBK/TOPK induced by G2/M arrest (0 hour) was diminished in time-dependent manner after treatment of a CDK1 inhibitor (0 to 4 hours) (FIG. 17H, first panel). Simultaneously, the present inventors found a reduced phosphorylation of PP1α at Thr320 where is known to be phosphorylated and inactivated by CDK1-cyclin B1 complex as well as the results in previous studies (FIG. 17H, third panel). It was verified the inactivation of CDK1 by the decreased phosphorylation level of the Rb protein at Ser807 and 811 (FIG. 17H, 4th panel). Taken together, these findings suggest that PBK/TOPK is activated in mitotic cells though its directly phosphorylation and inactivation of PP1α which suppresses its autophosphorylation, by CDK1-cyclin B1 to be remained in a steady level before the onset of mitosis.

(10) PBK/TOPK-Depletion by siRNA Resulted in Mitotic Failure and G1 Arrest

Since cytokinesis defects and delays induced by PBK/TOPK silencing were previously observed in breast cancer cells, the biological roles of PBK/TOPK in mitotic cells more in detail were examined by RNAi experiments. After treatment with a PBK/TOPK-specific siRNA or si-EGFP oligonucleotides as a control for 2 days, the knockdown of PBK/TOPK protein expression was confirmed in PBK/TOPK-specific siRNA-treated cells (FIG. 18A). As shown in FIG. 18B, the inventors observed the long intercellular bridges in the PBK/TOPK-siRNA treated-cells by microscopy and immunocytochemical staining with fluorescent phalloidin, but not in si-EGFP treated cells, indicating cytokinesis defect due to depletion of PBK/TOPK expression (white arrows in FIG. 18B). Furthermore, to examine the effect of knockdown of PBK/TOPK expression on the cell cycle, FACS analysis was performed to cells treated with PBK/TOPK-specific siRNA or si-EGFP oligonucleotides. The siEGFP treated cells showed a significant shift from G1 peak to G2/M peak. On the other hand the siPBK/TOPK treated cells showed no shift from G1 peak to G2/M peak after treatment of nocodazole to induce mitotic arrst (FIG. 18C), suggesting that knockdown of PBK/TOPK is likely to occur G1-arrest. To further classify cytokinesis defects in PBK/TOPK-depleted cells in detail, the present inventors examined real-time imaging of breast cancer T47D cells in the absence of PBK/TOPK by Time-lapse-microscopy. FIG. 18D showed that the cell division from anaphase to telophase was taken for 1 minute 30 seconds in EGFP-transfected cells (as indicated by white arrows). On the other hand, the cell division from analphase to telphase was taken for 4 minutes 30 seconds in PBK/TOPK-depleted cells, especially in cytokinesis step for 5 minutes, and then finally cleaved (as indicated by arrows in FIG. 18E).

Furthermore, to verify this result, the present invengtors did the RNAi-rescue experiments by introduction of wild-type PBK/TOPK and kinase-dead form, respectively. FIG. 18F showed that cytokinetic failure by depletion of PBK/TOPK was restored by the introduction of wild-type PBK/TOPK protein (shown by arrows), whereas not by kinase-dead did not (shown by arrows), supporting that the kinase activity of PBK/TOPK is indispensable for cytokinesis.

(11) PBK/TOPK Phosphorylates p97/VCP Protein Via p47 as an Adopter Protein In Vitro Because the kinase activity of PBK/TOPK is important for cytokinesis of breast cancer cells, the present inventors attempted to identify PBK/TOPK-specific substrates by in vitro protein pull-down assay using a GST fusion PBK/TOPK (GST-PBK/TOPK) recombinant protein and GST protein as a control. Comparison of silver staining of SDS-PAGE gels that contained the pull-downed proteins identified an approximately 47 kDa protein specifically in a lane corresponding to the proteins co-immunoprecipitated with the GST-PBK/TOPK protein, but not in that with the GST as a control (data not shown). MALDI-TOF analysis defined this 47-kDa protein to be p47 protein, an adaptor protein of p97/VCP (valosin-containing protein) which is belongs to AAA ATPase family involved in cell mitosis. The expression pattern of p47 at the transcriptional level in breast cancer cell-lines was examined by semi-quantitative RT-PCR, and found that p47 was expressed in all breast cancer cells examined (data not shown).

To validate an interaction between PBK/TOPK and P47 proteins, in vitro pull-down assay was performed. HA-tagged PBK/TOPK (HA-PBK/TOPK) construct was transfected into COS-7 cells, and then the cells were lysed with lysis buffer. Subsequently, cell lysates were mixed together with GST-tagged p47 (GST-p47) recombinant proteins, and then pull-downed with GST-beads Immunoblotting of the precipitates using anti-HA antibodies indicated that GST-p47 was co-precipitated with HA-PBK/TOPK (FIG. 19A). Furthermore, the present inventors did immunocytochemical staining, and observed co-localization of endogenous PBK/TOPK and exogenously expressed Flag-tagged p47 protein at cytoplasm in T47D cells. After treatment of nocodazole, the present inventors found their co-localization in nucleus of cells, suggesting PBK/TOPK protein interacts with p47, especially nucleus in mitotic cells (FIG. 19B). Since p47 is known to form a tight complex with p97 protein, the present inventors considered that PBK/TOPK may bind to p47/p97 protein complex. The expression of endogenous p97 protein in breast cancer cell-lines as well as HBL-100 and HMEC was first examined by western blot analysis using anti-p97 antibody and found the expression of endogenous p97 protein in all of breast cancer cell-lines examined as well as HBL-100 and HMEC (FIG. 19C). Subsequently, it was examined to interact PBK/TOPK and p97/p47 complex or not by co-IP experiments. HA-PBK/TOPK and myc-tagged p97 (myc-p97) constructs were co-transfected into COS7 cells, and then co-immunoprecipitated with HA-tag antibody. The results showed that HA-PBK/TOPK did not directly interact with myc-p97 (FIG. 19D). On the other hand, when myc-p97, GST-p47 and HA-PBK/TOPK constructs were co-transfected into COS-7 cells, and then immunoprecipitated with myc-tag antibody and western blotting with each tag antibody, respectively, it was detected HA-PBK-TOPK was co-immunoprecipitated with GST-p47/myc-97 complex (FIG. 19E). Taken together, these findings suggest that PBK-TOPK interact with p97 protein via p47 as an adaptor.

Furthermore, it was examined p97 was phosphorylated by PBK/TOPK by immunocomplex kinase assay using recombinant active PBK/TOPK protein. FIG. 19F showed PBK/TOPK recombinant protein phosphorylated the immunoprecipitated-p97 in breast cancer cells. To further examine the role of p97 on cytokinesis, the expression of p97 in T47D cells was knockdowned by using PBK-TOPK-siRNA (FIG. 19G). The result showed that depletion of p97 occurred to cytokinesis defects as well as the depletion of PBK/TOPK (FIG. 19H). It has been reported that p97/VCP (valosin-containing protein) is belongs to AAA ATPase family is, for instance regeneration of the Golgi apparatus that is once fragmented and reassembled at telophase (Uchiyama K et al., J Biochem (Tokyo) 137: 115-9 (2005)), and microtubule dynamics at the end of mitosis (Cao K et al., Cell 115: 355-67 (2003)). These findings indicate that p97/VCP might regulate cellular morphogenesis with potential roles in cytokinesis during M to G1 transition (Cao K et al., Cell Cycle 3: 422-4 (2004)). Hence, together, it was conclude that PBK/TOPK might regulate cytokinesis, especially exit of mitosis, in cancer cells though phosphorylation of p97/p47.

Discussion

The inventors previously reported that PBK/TOPK (PDZ-binding kinase/T-LAK cell-originated protein kinase was significantly up-regulated and phosphorylated during mitosis phase and was involved in the cell growth of breast cancers. However, the biological role of PBK/TOPK in cell mitosis and its pathophysiological roles in mammary carcinogenesis remain unknown. It was demonstrate that PBK/TOPK regulates mitotic progression, especially cytokinesis though phosphorylation of p97/VCP as its substrate and its regulation by CDK1/cyclin B1 complex.

INDUSTRIAL APPLICABILITY

The expression of novel human genes A7322 and F3374V1 is markedly elevated in breast cancer as compared to non-cancerous human tissues. Accordingly, these genes may serve as diagnostic markers of cancer and the proteins encoded thereby may be used in diagnostic assays of cancer.

Herein, the expression of novel proteins A7322 and F3374V1 were shown to promote cell growth whereas cell growth was suppressed by antisense oligonucleotides or small interfering RNAs corresponding to the A7322 and F3374V1 genes. These findings suggest that each of A7322 and F3374V1 proteins stimulate oncogenic activity. Thus, each of these novel oncoproteins is a useful target for the development of anti-cancer pharmaceuticals. For example, agents that block the expression of A7322 and F3374V1 or prevent its activity may find therapeutic utility as anti-cancer agents, particularly anti-cancer agents for the treatment of breast cancer. Examples of such agents include antisense oligonucleotides, small interfering RNAs, and antibodies that recognize A7322 and F3374V1.

All publications, databases, Genbank sequences, patents, and patent applications cited herein are hereby incorporated by reference.

While the invention has been described in detail and with reference to specific embodiments thereof, it will be apparent to one skilled in the art that various changes and modifications can be made therein without departing from the spirit and scope of the invention, the metes and bounds of which are set by the appended claims.

The present invention is based on the discovery of a novel mechanism of PBK/TOPK to phosphorylate histone H3 at Ser10 in vitro and in vivo. Since PBK/TOPK is a cancer/testis antigen and its kinase function is likely to be related to its oncogenic activity, the protein is suggested to be a promising molecular target for breast cancer therapy.

Due to the high possibility that the agents screened through the above mentioned methods induce apoptosis in breast cancer cells, the screened agents serve as candidates for treating or preventing breast cancer.

All patents, patent applications, and publications cited herein are incorporated by reference in their entirety.

Furthermore, while the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. A method of screening for a compound for treating or preventing breast cancer, said method comprising the steps of:
   (a) contacting an A7322 polypeptide with a PHB2/REA polypeptide in the presence of a test compound, wherein the A7322 polypeptide is a polypeptide comprising the amino acid sequence of SEQ ID NO: 80 (A7322);
   (b) detecting the binding between the polypeptides of step (a); and
   (c) selecting the test compound that inhibits the binding between the A7322 and PHB2/REA polypeptides.

* * * * *

SEQUENCE LISTING

```
<160> NUMBER OF SEQ ID NOS: 122

<210> SEQ ID NO 1
<211> LENGTH: 19
<212> TYPE: DNA
<213> ORGANISM: Artificial
<220> FEATURE:
<223> OTHER INFORMATION: An artificially synthesized primer for RT-PCR

<400> SEQUENCE: 1
aacttagagg tgggagcag                                                 19

<210> SEQ ID NO 2
<211> LENGTH: 22
<212> TYPE: DNA
<213> ORGANISM: Artificial
```

```
<220> FEATURE:
<223> OTHER INFORMATION: An artificially synthesized primer for RT-PCR

<400> SEQUENCE: 2
cacaaccatg ccttactttc tc                                              22

<210> SEQ ID NO 3
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 3
cttgacaagg cctttggagt                                                 20

<210> SEQ ID NO 4
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 4
caatatgctt ttcccgcttt                                                 20

<210> SEQ ID NO 5
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 5
aaccaagcac accatagcct ta                                              22

<210> SEQ ID NO 6
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 6
ggagatgggt agggatacaa ac                                              22

<210> SEQ ID NO 7
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 7
gggagagctg aagattgctg                                                 20

<210> SEQ ID NO 8
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 8
gacagattga agggcagagg                                                 20
```

```
<210> SEQ ID NO 9
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 9
cgaccacttt gtcaagctca                                              20

<210> SEQ ID NO 10
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 10
ggttgagcac agggtacttt att                                          23

<210> SEQ ID NO 11
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 11
agtgaaatgc aggtgagaag aac                                          23

<210> SEQ ID NO 12
<211> LENGTH: 25
<212> TYPE: DNA
<213> ORGANISM: Artificial
<220> FEATURE:
<223> OTHER INFORMATION: An artificially synthesized primer for RT-PCR

<400> SEQUENCE: 12
tcattctagc caggatcata ctaag                                        25

<210> SEQ ID NO 13
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 13
agaccctaaa gatcgtcctt ctg                                          23

<210> SEQ ID NO 14
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 14
gtgttttaag tcagcatgag cag                                          23

<210> SEQ ID NO 15
<211> LENGTH: 20
<212> TYPE: DNA
<213> ORGANISM: Artificial
<220> FEATURE:
<223> OTHER INFORMATION: An artificially synthesized primer for RT-PCR
```

```
<400> SEQUENCE: 15
gctgacaacc ttgtgctgaa                                                   20

<210> SEQ ID NO 16
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 16
tgagaaatca cgcactgtcc                                                   20

<210> SEQ ID NO 17
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 17
caagcttgct tacagagacc tg                                                22

<210> SEQ ID NO 18
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 18
gggccaaacc taccaaagtt                                                   20

<210> SEQ ID NO 19
<211> LENGTH: 22
<212> TYPE: DNA
<213> ORGANISM: Artificial
<220> FEATURE:
<223> OTHER INFORMATION: An artificially synthesized primer for PCR

<400> SEQUENCE: 19
gcaatctgct atgtcagcca ac                                                22

<210> SEQ ID NO 20
<211> LENGTH: 23
<212> TYPE: DNA
<213> ORGANISM: Artificial
<220> FEATURE:
<223> OTHER INFORMATION: An artificially synthesized primer for PCR

<400> SEQUENCE: 20
caggatcagc tcaaagtctg aca                                               23

<210> SEQ ID NO 21
<211> LENGTH: 28
<212> TYPE: DNA
<213> ORGANISM: Artificial
<220> FEATURE:
<223> OTHER INFORMATION: An artificially synthesis primer for 5' RACE

<400> SEQUENCE: 21
gcctccttct gcagcttcct caggattt                                          28

<210> SEQ ID NO 22
```

```
<211> LENGTH: 30
<212> TYPE: DNA
<213> ORGANISM: Artificial
<220> FEATURE:
<223> OTHER INFORMATION: An artificially synthesized primer for PCR

<400> SEQUENCE: 22
cggaattcat ggaagaaatc ctgaggaagc                                    30

<210> SEQ ID NO 23
<211> LENGTH: 37
<212> TYPE: DNA
<213> ORGANISM: Artificial
<220> FEATURE:
<223> OTHER INFORMATION: An artificially synthesized primer for PCR

<400> SEQUENCE: 23
atagtttagc ggccgcacaa tgatgtcata gacacgg                            37

<210> SEQ ID NO 24
<211> LENGTH: 41
<212> TYPE: DNA
<213> ORGANISM: Artificial
<220> FEATURE:
<223> OTHER INFORMATION: An artificially synthesized primer for PCR

<400> SEQUENCE: 24
cggaattcca gaccgtgcat catggcccag aacttgaagg a                       41

<210> SEQ ID NO 25
<211> LENGTH: 32
<212> TYPE: DNA
<213> ORGANISM: Artificial
<220> FEATURE:
<223> OTHER INFORMATION: An artificially synthesized primer for PCR

<400> SEQUENCE: 25
ccgctcgagt ttcttaccct tgatgaggct gt                                 32

<210> SEQ ID NO 26
<211> LENGTH: 38
<212> TYPE: DNA
<213> ORGANISM: Artificial
<220> FEATURE:
<223> OTHER INFORMATION: An artificially synthesized primer for PCR

<400> SEQUENCE: 26
cggaattcat gaccatgacc ctccacacca aagcatcc                           38

<210> SEQ ID NO 27
<211> LENGTH: 31
<212> TYPE: DNA
<213> ORGANISM: Artificial
<220> FEATURE:
<223> OTHER INFORMATION: An artificially synthesized primer for PCR

<400> SEQUENCE: 27
ccgctcgagg accgtggcag ggaaaccctc t                                  31

<210> SEQ ID NO 28
<211> LENGTH: 39
<212> TYPE: DNA
<213> ORGANISM: Artificial
<220> FEATURE:
<223> OTHER INFORMATION: An artificially synthesized primer for PCR

<400> SEQUENCE: 28
```

```
aaggaaaaaa gcggccgcga tgctcttcaa ttcggtgct                                    39

<210> SEQ ID NO 29
<211> LENGTH: 33
<212> TYPE: DNA
<213> ORGANISM: Artificial
<220> FEATURE:
<223> OTHER INFORMATION: An artificially synthesized primer for PCR

<400> SEQUENCE: 29
ccgctcgagt aattctgttg agtgttcagg acc                                          33

<210> SEQ ID NO 30
<211> LENGTH: 30
<212> TYPE: DNA
<213> ORGANISM: Artificial
<220> FEATURE:
<223> OTHER INFORMATION: An artificially synthesized primer for PCR

<400> SEQUENCE: 30
ccggaattca tggaagggat cagtaatttc                                              30

<210> SEQ ID NO 31
<211> LENGTH: 33
<212> TYPE: DNA
<213> ORGANISM: Artificial
<220> FEATURE:
<223> OTHER INFORMATION: An artificially synthesized primer for PCR

<400> SEQUENCE: 31
ccgctcgagt cagacatctg tttccagagc ttc                                          33

<210> SEQ ID NO 32
<211> LENGTH: 43
<212> TYPE: DNA
<213> ORGANISM: Artificial
<220> FEATURE:
<223> OTHER INFORMATION: An artificially synthesized primer for PCR

<400> SEQUENCE: 32
cattctcctt gggctgtagc agcgattaat cctatatgta atg                               43

<210> SEQ ID NO 33
<211> LENGTH: 43
<212> TYPE: DNA
<213> ORGANISM: Artificial
<220> FEATURE:
<223> OTHER INFORMATION: An artificially synthesized primer for PCR

<400> SEQUENCE: 33
cattacatat aggattaatc gctgctacag cccaaggaga atg                               43

<210> SEQ ID NO 34
<211> LENGTH: 21
<212> TYPE: DNA
<213> ORGANISM: Artificial
<220> FEATURE:
<223> OTHER INFORMATION: A target sequence for siRNA

<400> SEQUENCE: 34
aagaaagcat cgcagtctca g                                                       21

<210> SEQ ID NO 35
<211> LENGTH: 21
<212> TYPE: DNA
```

```
<213> ORGANISM: Artificial
<220> FEATURE:
<223> OTHER INFORMATION: A target sequence for siRNA

<400> SEQUENCE: 35
aagatgcgtt ctctgccaca c                                              21

<210> SEQ ID NO 36
<211> LENGTH: 21
<212> TYPE: DNA
<213> ORGANISM: Artificial
<220> FEATURE:
<223> OTHER INFORMATION: A target sequence for siRNA

<400> SEQUENCE: 36
aatattcgat ctctgccaca c                                              21

<210> SEQ ID NO 37
<211> LENGTH: 19
<212> TYPE: DNA
<213> ORGANISM: Artificial
<220> FEATURE:
<223> OTHER INFORMATION: A target sequence for siRNA

<400> SEQUENCE: 37
gatcatgtct ccgagaaaa                                                 19

<210> SEQ ID NO 38
<211> LENGTH: 19
<212> TYPE: DNA
<213> ORGANISM: Artificial
<220> FEATURE:
<223> OTHER INFORMATION: A target sequence for siRNA

<400> SEQUENCE: 38
ggaagccata gaattgctc                                                 19

<210> SEQ ID NO 39
<211> LENGTH: 19
<212> TYPE: DNA
<213> ORGANISM: Artificial
<220> FEATURE:
<223> OTHER INFORMATION: A target sequence for siRNA

<400> SEQUENCE: 39
ctggatgaat cataccaga                                                 19

<210> SEQ ID NO 40
<211> LENGTH: 19
<212> TYPE: DNA
<213> ORGANISM: Artificial
<220> FEATURE:
<223> OTHER INFORMATION: A target sequence for siRNA

<400> SEQUENCE: 40
gtgtggcttg cgtaaataa                                                 19

<210> SEQ ID NO 41
<211> LENGTH: 19
<212> TYPE: DNA
<213> ORGANISM: Artificial
<220> FEATURE:
<223> OTHER INFORMATION: A target sequence for siRNA

<400> SEQUENCE: 41
gcgcgctttg taggattcg                                                 19
```

```
<210> SEQ ID NO 42
<211> LENGTH: 19
<212> TYPE: DNA
<213> ORGANISM: Artificial
<220> FEATURE:
<223> OTHER INFORMATION: A target sequence for siRNA

<400> SEQUENCE: 42
gaagcagcac gacttcttc                                              19

<210> SEQ ID NO 43
<211> LENGTH: 55
<212> TYPE: DNA
<213> ORGANISM: Artificial
<220> FEATURE:
<223> OTHER INFORMATION: An artificially synthesized oligonucleotide for
      siRNA

<400> SEQUENCE: 43
caccaagaaa gcatcgcagt ctcagttcaa gagactgaga ctgcgatgct ttctt      55

<210> SEQ ID NO 44
<211> LENGTH: 55
<212> TYPE: DNA
<213> ORGANISM: Artificial
<220> FEATURE:
<223> OTHER INFORMATION: An artificially synthesized oligonucleotide for
      siRNA

<400> SEQUENCE: 44
aaaaaagaaa gcatcgcagt ctcagtctct tgaactgaga ctgcgatgct ttctt      55

<210> SEQ ID NO 45
<211> LENGTH: 51
<212> TYPE: DNA
<213> ORGANISM: Artificial
<220> FEATURE:
<223> OTHER INFORMATION: siRNA hairpin design

<400> SEQUENCE: 45
aagaaagcat cgcagtctca gttcaagaga ctgagactgc gatgctttct t          51

<210> SEQ ID NO 46
<211> LENGTH: 55
<212> TYPE: DNA
<213> ORGANISM: Artificial
<220> FEATURE:
<223> OTHER INFORMATION: An artificially synthesized oligonucleotide for
      siRNA

<400> SEQUENCE: 46
caccaagatg cgttctctgc cacacttcaa gagagtgtgg cagagaacgc atctt      55

<210> SEQ ID NO 47
<211> LENGTH: 55
<212> TYPE: DNA
<213> ORGANISM: Artificial
<220> FEATURE:
<223> OTHER INFORMATION: An artificially synthesized oligonucleotide for
      siRNA

<400> SEQUENCE: 47
aaaaaagatg cgttctctgc cacactctct tgaagtgtgg cagagaacgc atctt      55

<210> SEQ ID NO 48
```

```
<211> LENGTH: 51
<212> TYPE: DNA
<213> ORGANISM: Artificial
<220> FEATURE:
<223> OTHER INFORMATION: siRNA hairpin design

<400> SEQUENCE: 48
aagatgcgtt ctctgccaca cttcaagaga gtgtggcaga gaacgcatct t          51

<210> SEQ ID NO 49
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 49
caccgatcat gtctccgaga aaattcaaga gattttctcg gagacatgat c          51

<210> SEQ ID NO 50
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 50
aaaagatcat gtctccgaga aaatctcttg aattttctcg gagacatgat c          51

<210> SEQ ID NO 51
<211> LENGTH: 47
<212> TYPE: DNA
<213> ORGANISM: Artificial
<220> FEATURE:
<223> OTHER INFORMATION: siRNA hairpin design

<400> SEQUENCE: 51
gatcatgtct ccgagaaaat tcaagagatt ttctcggaga catgatc              47

<210> SEQ ID NO 52
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 52
caccggaagc catagaattg ctcttcaaga gagagcaatt ctatggcttc c          51

<210> SEQ ID NO 53
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 53
aaaaggaagc catagaattg ctctctcttg aagagcaatt ctatggcttc c          51

<210> SEQ ID NO 54
<211> LENGTH: 47
<212> TYPE: DNA
<213> ORGANISM: Artificial
```

```
<220> FEATURE:
<223> OTHER INFORMATION: siRNA hairpin design

<400> SEQUENCE: 54
ggaagccata gaattgctct tcaagagaga gcaattctat ggcttcc                47

<210> SEQ ID NO 55
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 55
caccctggat gaatcatacc agattcaaga gatctggtat gattcatcca g           51

<210> SEQ ID NO 56
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 56
aaaactggat gaatcatacc agatctcttg aatctggtat gattcatcca g           51

<210> SEQ ID NO 57
<211> LENGTH: 47
<212> TYPE: DNA
<213> ORGANISM: Artificial
<220> FEATURE:
<223> OTHER INFORMATION: siRNA hairpin design

<400> SEQUENCE: 57
ctggatgaat cataccagat tcaagagatc tggtatgatt catccag                47

<210> SEQ ID NO 58
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 58
caccgtgtgg cttgcgtaaa taattcaaga gattatttac gcaagccaca c           51

<210> SEQ ID NO 59
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 59
aaaagtgtgg cttgcgtaaa taatctcttg aattatttac gcaagccaca c           51

<210> SEQ ID NO 60
<211> LENGTH: 47
<212> TYPE: DNA
<213> ORGANISM: Artificial
<220> FEATURE:
<223> OTHER INFORMATION: siRNA hairpin design
```

-continued

<400> SEQUENCE: 60
gtgtggcttg cgtaaataat tcaagagatt atttacgcaa gccacac                47

<210> SEQ ID NO 61
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 61
gcccttgaag ccaatattcc                                              20

<210> SEQ ID NO 62
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 62
agatggtttc agtgggcttg                                              20

<210> SEQ ID NO 63
<211> LENGTH: 21
<212> TYPE: RNA
<213> ORGANISM: Artificial
<220> FEATURE:
<223> OTHER INFORMATION: An artificially synthesized oligonucleotide for
      siRNA

<400> SEQUENCE: 63
gaugcguucu cugccacacu u                                            21

<210> SEQ ID NO 64
<211> LENGTH: 19
<212> TYPE: RNA
<213> ORGANISM: Artificial
<220> FEATURE:
<223> OTHER INFORMATION: An artificially synthesized oligonucleotide for
      siRNA

<400> SEQUENCE: 64
gcagcacgac uucuucaag                                               19

<210> SEQ ID NO 65
<211> LENGTH: 19
<212> TYPE: RNA
<213> ORGANISM: Artificial
<220> FEATURE:
<223> OTHER INFORMATION: An artificially synthesized oligonucleotide for
      siRNA

<400> SEQUENCE: 65
acuccuacgu ucucuauua                                               19

<210> SEQ ID NO 66
<211> LENGTH: 21
<212> TYPE: RNA
<213> ORGANISM: Artificial
<220> FEATURE:
<223> OTHER INFORMATION: An artificially synthesized oligonucleotide for
      siRNA

<400> SEQUENCE: 66
aaggugaugg agaauagcag u                                            21

<210> SEQ ID NO 67
<211> LENGTH: 19
<212> TYPE: DNA
<213> ORGANISM: Artificial
<220> FEATURE:
<223> OTHER INFORMATION: A target sequence for siRNA

<400> SEQUENCE: 67
actcctacgt tctctatta                                                  19

<210> SEQ ID NO 68
<211> LENGTH: 21
<212> TYPE: DNA
<213> ORGANISM: Artificial
<220> FEATURE:
<223> OTHER INFORMATION: A target sequence for siRNA

<400> SEQUENCE: 68
aaggtgatgg agaatagcag t                                               21

<210> SEQ ID NO 69
<211> LENGTH: 19
<212> TYPE: DNA
<213> ORGANISM: Artificial
<220> FEATURE:
<223> OTHER INFORMATION: A target sequence for siRNA

<400> SEQUENCE: 69
gcagcacgac ttcttcaag                                                  19

<210> SEQ ID NO 70
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 70
atggaaatcc catcaccatc t                                               21

<210> SEQ ID NO 71
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 71
gccttcatca tccaaacatt                                                 20

<210> SEQ ID NO 72
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 72
ggcaaatatg tctgccttgt                                                 20

<210> SEQ ID NO 73
<211> LENGTH: 39
<212> TYPE: DNA
<213> ORGANISM: Artificial
<220> FEATURE:

<223> OTHER INFORMATION: An artificially synthesized primer for PCR

<400> SEQUENCE: 73
aaggaaaaaa gcggccgcgc tgtggatggg ataatcaaa        39

<210> SEQ ID NO 74
<211> LENGTH: 30
<212> TYPE: DNA
<213> ORGANISM: Artificial
<220> FEATURE:
<223> OTHER INFORMATION: An artificially synthesized primer for PCR

<400> SEQUENCE: 74
ccgctcgagt ttgattatcc catccacagc        30

<210> SEQ ID NO 75
<211> LENGTH: 36
<212> TYPE: DNA
<213> ORGANISM: Artificial
<220> FEATURE:
<223> OTHER INFORMATION: An artificially synthesized primer for PCR

<400> SEQUENCE: 75
aaggaaaaaa gcggccgctg gcgcttgaat agaggc        36

<210> SEQ ID NO 76
<211> LENGTH: 30
<212> TYPE: DNA
<213> ORGANISM: Artificial
<220> FEATURE:
<223> OTHER INFORMATION: An artificially synthesized primer for PCR

<400> SEQUENCE: 76
ccgctcgaga tcacctcctg gtttctcctc        30

<210> SEQ ID NO 77
<211> LENGTH: 39
<212> TYPE: DNA
<213> ORGANISM: Artificial
<220> FEATURE:
<223> OTHER INFORMATION: An artificially synthesized primer for PCR

<400> SEQUENCE: 77
aaggaaaaaa gcggccgcct tgatggccaa gttgaaaat        39

<210> SEQ ID NO 78
<211> LENGTH: 30
<212> TYPE: DNA
<213> ORGANISM: Artificial
<220> FEATURE:
<223> OTHER INFORMATION: An artificially synthesized primer for PCR

<400> SEQUENCE: 78
ccgctcgagg cagcacagat ccaaatgaag        30

<210> SEQ ID NO 79
<211> LENGTH: 14852
<212> TYPE: DNA
<213> ORGANISM: Homo sapiens

<400> SEQUENCE: 79
gtggcccgcg gcatggagcg ggcgtgattc atcagcatcc gcgccggggc ggcatggggg        60
cgcgcgcggc ggccgcctag gcgcccaggg ccaggcagcg gcggcttccc cggcccggct       120
cgcccgcgct tctctcccctg tgggcggcgg cccggcgcct ggaaggtcaa gatggaagaa       180

```
atcctgagga agctgcagaa ggaggcgtcc gggagcaagt acaaagccat caaggagagc    240
tgcacctggg ccctggaaac tctaggtggt ctggatacca ttgtcaagat ccctccacat    300
gtactgaggg agaaatgcct gctgcctctc cagttggctt tggaatccaa gaatgtgaag    360
ctggcccaac atgctttggc agggatgcag aagcttctgt cggaagagag gtttgtatcc    420
atggaaacag attctgatga gaagcagctg ctcaatcaga tactgaatgc cgtgaaagtg    480
acgccttcgc tcaacgagga cctgcaggtg gaagtgatga aggttttact atgcatcacc    540
tacacgccaa catttgatct gaatgggagt gccgtgctga agatcgcgga ggtgtgcatt    600
gagacgtaca taagcagctg tcaccagcgt agcataaaca ctgctgtgcg ggcaactctc    660
agtcaaatgc tgagtgactt gactttacag ttacgacaga ggcaggagaa tacgataatt    720
gaaaacccag atgtcccaca ggatttcggg aatcaagggt caacagtaga gtccctctgt    780
gatgatgttg tctctgtact caccgtcctg tgtgagaagc tgcaagccgc cataaatgac    840
agccagcagc tgcagcttct ctacctggag tgcatcctgt ctgtgctcag cagctcctcc    900
tcctccatgc acctgcacag gcgcttcacg gacctgatct ggaaaaacct ctgccctgct    960
ctcatcgtga tcttggggaa tccaattcat gacaaaacca tcacctctgc tcacaccagc    1020
agcaccagta ccagcctgga gtcggactct gcgtctccgg gagtgtctga ccacggccga    1080
ggatcaggct gctcctgcac tgcgccggcc ctgagcggac ctgtggctcg gactatctat    1140
tacatcgcag ccgagctggt ccggctggtg gggtctgtgg actccatgaa gcccgtgctc    1200
cagtccctct accaccgagt gctgctctac cccccacccc agcaccgggt ggaagccatc    1260
aaaataatga agagatact tgggagccca cagcgtctct gtgacttggc aggacccagc    1320
tccactgaat cagagtccag aaaaagatca atttcaaaaa gaaagtctca tctggatctc    1380
ctcaaactca tcatggatgg catgaccgaa gcatgcatca agggtggcat cgaagcttgc    1440
tatgcagccg tgtcctgtgt ctgcacctgg ctgggtgccc tggatgagct cagccagggg    1500
aagggcttga gcgaaggtca ggtgcaactg ctgcttctgc gccttgagga gctgaaggat    1560
ggggctgagt ggagccgaga ttccatggag atcaatgagg ctgacttccg ctggcagcgg    1620
cgagtgctgt cctcagaaca cacgccgtgg gagtcaggga acgagaggag ccttgacatc    1680
agcatcagtg tcaccacaga cacaggccag accactctcg agggagagtt gggtcagact    1740
acacccgagg accattcggg aaaccacaag aacagtctca gtcgccagc catcccagag     1800 ggtaaggaga cgctgagcaa agtattggaa acagaggcgg tagaccagcc agatgtcgtg    1860
cagagaagcc acacggtccc ttaccctgac ataactaact tcctgtcagt agactgcagg    1920
acaaggtcct atggatctag gtatagtgag agcaattttta gcgttgatga ccaagacctt    1980
tctaggacag agtttgattc ctgtgatcag tactctatgg cagcagaaaa ggactcgggc    2040
aggtccgacg tgtcagacat tgggtcggac aactgttcac tagccgatga agagcagaca    2100
ccccgggact gcctaggcca ccggtccctg cgaactgccg ccctgtctct aaaactgctg    2160
aagaaccagg aggcggatca gcacagcgcc aggctgttca tacagtccct ggaaggcctc    2220
ctccctcggc tcctgtctct ctccaatgta gaggaggtgg acaccgctct gcagaacttt    2280
gcctctactt tctgctcagg catgatgcac tctcctggct tgacgggaa tagcagcctc    2340 agcttccaga tgctgatgaa cgcagacagc ctctacacag ctgcacactg cgccctgctc    2400
ctcaacctga agctctccca cggtgactac tacaggaagc ggccgaccct ggcgccaggc    2460
gtgatgaagg acttcatgaa gcaggtgcag accagcggcg tgctgatggt cttctctcag    2520
```

| | |
|---|---|
| gcctggattg aggagctcta ccatcaggtg ctcgacagga acatgcttgg agaggctggc | 2580 |
| tattggggca gcccagaaga taacagcctt cccctcatca caatgctgac cgatattgac | 2640 |
| ggcttagaga gcagtgccat tggtggccag ctgatggcct cggctgctac agagtctcct | 2700 |
| ttcgcccaga gcaggagaat tgatgactcc acagtggcag gcgtggcatt tgctcgctat | 2760 |
| attctggtgg gctgctggaa gaacttgatc gatactttat caaccccact gactggtcga | 2820 |
| atggcgggga gctccaaagg ctggccttc attctgggag ctgaaggcat caaagagcag | 2880 |
| aaccagaagg agcgggacgc catctgcatg agcctcgacg ggctgcggaa agccgcacgg | 2940 |
| ctgagctgcg ctctaggcgt tgctgctaac tgcgcctcag cccttgccca gatggcagct | 3000 |
| gcctcctgtg tccaagaaga aaagaagag agggaggccc aagaacccag tgatgccatc | 3060 |
| acacaagtga aactaaaagt ggagcagaaa ctggagcaga ttgggaaggt gcaggggtg | 3120 |
| tggctgcaca ctgcccacgt cttgtgcatg gaggccatcc tcagcgtagg cctggagatg | 3180 |
| ggaagccaca cccggactg ctggccacac gtgttcaggg tgtgtgaata cgtgggcacc | 3240 |
| ctggagcaca accacttcag cgatggtgcc tcgcagcccc ctctgaccat cagccagccc | 3300 |
| cagaaggcca ctggaagcgc tggcctcctt ggggaccccg agtgtgaggg ctcgcccccc | 3360 |
| gagcacagcc cggagcaggg gcgctccctg agcacggccc ctgtcgtcca gcccctgtcc | 3420 |
| atccaggacc tcgtccggga aggcagccgg ggtcgggcct ccgacttccg cggcgggagc | 3480 |
| ctcatgagcg ggagcagcgc ggccaaggtg gtgctcaccc tctccacgca agccgacagg | 3540 |
| ctctttgaag atgctacgga taagttgaac ctcatggcct gggaggttt tctttaccag | 3600 |
| ctgaagaaag catcgcagtc tcagcttttc cattctgtta cagatacagt tgattactct | 3660 |
| ctggcaatgc caggagaagt taaatccact caagaccgaa aaagcgccct ccacctgttc | 3720 |
| cgcctgggga atgccatgct gaggattgtg cggagcaaag cacggcccct gctccacgtg | 3780 |
| atgcgctgct ggagccttgt ggccccacac ctggtggagg ctgcttgcca taaggaaaga | 3840 |
| catgtgtctc agaaggctgt ttccttcatc catgacatac tgacagaagt cctcactgac | 3900 |
| tggaatgagc cacctcattt tcacttcaat gaagcactct tccgaccttt cgagcgcatt | 3960 |
| atgcagctga aattgtgtga tgaggacgtc caagaccagg ttgtcacatc cattggtgag | 4020 |
| ctggttgaag tgtgttccac gcagatccag tcgggatgga gacccttgtt cagtgccctg | 4080 |
| gaaacagtgc atgcgcggaa caagtcagag atgaaggagt acctggttgg tgactactcc | 4140 |
| atgggaaaag gccaagctcc agtgtttgat gtatttgaag cttttctcaa tactgacaac | 4200 |
| atccaggtct ttgctaatgc agccactagc tacatcatgt gccttatgaa gtttgtcaaa | 4260 |
| ggactggggg aggtggactg taaagagatt ggagactgtg ccccagcacc cggagccccg | 4320 |
| tccacagacc tgtgcctccc ggccctggat tacctcaggc gctgctctca gttattggcc | 4380 |
| aaaatctaca aaatgccctt gaagccaata ttccttagtg ggagacttgc cggcttgcct | 4440 |
| cgaagacttc aggaacagtc agccagcagt gaggatggaa ttgaatcagt cctgtctgat | 4500 |
| tttgatgatg acaccggtct gatagaagtc tggataatcc tgctggagca gctgacagcg | 4560 |
| gctgtgtcca ttgtccacg gcagcaccaa ccaccaactc tggatttact ctttgagctg | 4620 |
| ttgagagatg tgacgaaaac accaggacca gggtttggta tctatgcagt ggttcacctc | 4680 |
| ctccttcctg tgatgtccgt ttggctccgc cggagccata agaccattc ctactgggat | 4740 |
| atggcctctg ccaatttcaa gcacgctatt ggtctgtcct gtgagctggt ggtggagcac | 4800 |
| attcaaagct ttctacattc agatatcagg tacgagagca tgatcaatac catgctgaag | 4860 |
| gacctctttg agttgctggt cgcctgtgtg gccaagccca ctgaaaccat ctccagagtg | 4920 |

```
ggctgctcct gtattagata cgtccttgtg acagcgggcc ctgtgttcac tgaggagatg   4980
tggaggcttg cctgctgtgc cctgcaagat gcgttctctg ccacactcaa gccagtgaag   5040
gacctgctgg gctgcttcca cagcggcacg gagagcttca gcggggaagg ctgccaggtg   5100
cgagtggcgg ccccgtcctc ctccccaagt gccgaggccg agtactggcg catccgagcc   5160
atggcccagc aggtgtttat gctggacacc cagtgctcac caaagacacc aaacaacttt   5220
gaccacgctc agtcctgcca gctcattatt gagctgcctc ctgatgaaaa accaaatgga   5280
cacaccaaga aaagcgtgtc tttcagggaa attgtggtga gcctgctgtc tcatcaggtg   5340
ttactccaga acttatatga catcttgtta aagagtttg tcaaaggccc ctctcctgga   5400
gaggaaaaga cgatacaagt gccagaagcc aagctggctg gcttcctcag atacatctct   5460
atgcagaact tggcagtcat attcgacctg ctgctggact cttataggac tgccagggag   5520
tttgacacca gccccgggct gaagtgcctg ctgaagaaag tgtctggcat cggggcgcc    5580 gccaacctct accgccagtc tgcgatgagc tttaacattt atttccacgc cctggtgtgt   5640
gctgttctca ccaatcaaga aaccatcacg gccgagcaag tgaagaaggt ccttttttgag  5700 gacgacgaga gaagcacgga ttcttcccag cagtgttcat ctgaggatga agacatcttt   5760
gaggaaaccg cccaggtcag cccccgaga ggcaaggaga agagacagtg gcgggcacgg    5820
atgcccttgc tcagcgtcca gcctgtcagc aacgcagatt gggtgtggct ggtcaagagg   5880
ctgcacaagc tgtgcatgga actgtgcaac aactacatcc agatgcactt ggacctggag   5940
aactgtatgg aggagcctcc catcttcaag ggcgacccgt tcttcatcct gccctccttc   6000
cagtccgagt catccacccc atccaccggg ggcttctctg ggaagaaaac cccttccgag   6060
gatgacagaa gccagtcccg ggagcacatg ggcgagtccc tgagcctgaa ggccggtggt   6120
ggggacctgc tgctgccccc cagccccaaa gtggagaaga aggatcccag ccggaagaag   6180
gagtggtggg agaatgcggg gaacaaaatc tacaccatgg cagccgacaa gaccatttca   6240
aagttgatga ccgaatacaa aaagaggaaa cagcagcaca acctgtccgc gttccccaaa   6300
gaggtcaaag tggagaagaa aggagagcca ctgggtccca ggggccagga ctccccgctg   6360
cttcagcgtc cccagcactt gatggaccaa ggcaaatgc ggcattcctt cagcgcaggc     6420
cccgagctgc tgcgacagga caagaggccc cgctcaggct ccaccgggag ctccctcagt   6480
gtctcggtga gagacgcaga agcacagatc caggcatgga ccaacatggt gctaacagtt   6540
ctcaatcaga ttcagattct cccagaccag accttcacgg ccctccagcc cgcagtgttc   6600
ccgtgcatca gtcagctgac ctgtcacgtg accgacatca gagttcgcca ggctgtgagg   6660
gagtggctgg gcagggtggg ccgtgtctat gacatcattg tgtagccgac tcctgttcta   6720
ctctcccacc aaataacagt agtgagggtt agagtcctgc caatacagct gttgcatttt   6780
ccccaccact agccccactt aaactactac tactgtctca gagaacagtg tttcctaatg   6840
taaaaagcct ttccaaccac tgatcagcat tgggccata ctaaggtttg tatctagatg      6900
acacaaacga tattctgatt ttgcacatta ttatagaaga atctataatc cttgatatgt   6960
ttctaactct tgaagtatat ttcccagtgc ttttgcttac agtgttgtcc ccaaatgggt   7020
cattttcaag gattactcat ttgaaaacac tatattgatc catttgatcc atcatttaaa   7080
aaataaatac aattcctaag gcaatatctg ctggtaagtc aagctgataa acactcagac   7140
atctagtacc agggattatt aattggagga agatttatgg ttatgggtct ggctgggaag   7200
aagacaacta taaatacata ttcttgggtg tcataatcaa gaaagaggtg acttctgttg   7260
```

```
taaaataatc cagaacactt caaaattatt cctaaatcat taagattttc aggtattcac    7320
caatttcccc atgtaaggta ctgtgttgta cctttatttc tgtatttcta aaagaagaaa    7380
gttctttcct agcagggttt gaagtctgtg cttatcagc ctgtgacaca gagtacccag     7440
tgaaagtggc tggtacgtag attgtcaaga gacataagac cgaccagcca ccctggctgt    7500
tcttgtggtg tttgtttcca tccccaaggc aaacaaggaa aggaaggaa agaagaaaag     7560
gtgccttagt cctttgttgc acttccattt ccatgcccca caattgtctg aacataaggt    7620
atagcatttg gttttaaga aaacaaaaca ttaagacgca actcatttta tatcaacacg     7680
cttggaggaa agggactcag ggaagggagc agggagtgtg gggtggggat ggattatgat    7740
gaaatcattt tcaatcttaa aatataatac aacaatcttg caaaattatg gtgtcagtta    7800
cacaagctct agtctcaaaa tgaaagtaat ggagaaagac actgaaattt agaaaatttt    7860
gtcgatttaa aatatttctc ctatctacca agtaaagtta cccatgtttt gatgtctttg    7920
cattcagacc aatatttcag gtggatattt ctaagtatta ctagaaaata cgtttgaaag    7980
ctttatctta ttatttacag tattttata tttcttacat tatcctaatg attgaaaact     8040
cctcaatcaa gcttacttac acacattcta cagagttatt taaggcatac attataatct    8100
cccagcccca ttcataatga ataagtcacc ctttaaatat aagacacaaa ttctacagta    8160
ttgaaataag gatttaaagg ggtatttgta aactttgccc tccttgagaa atatggaact    8220
acctagagg ttaagaggaa ggcagtgttc tgacttcttt aggtgatctg aaaaaaacac     8280
ccttatcatc cagtgtacca tctagagatc accacagaat ccattttttt cccagttcca    8340
caaaacactc tgtttgcctt cagtttttac tcactagaca ataattcaag tttagaaaca    8400
ggtaatcagc tatttgatct taaaaggcaa tgaattgttg ggatatcagt gaactatgtt    8460
gtatactttt gaatttttac attttataaa tggaattgaa agttggataa ctgcttttt     8520
taaattttcc aacagaagta acaccacagt tgctttgttt cttttatag cttacctgag     8580
gttcagttct tctttgtgaa cctgtgagta ctccacagtt tactggggga aaaggcttca    8640
gtaaagcaga ggctagaatt acagtattta tacatagcaa cttttcataa agtagaaaaa    8700
ttcaaaggaa gctgtctcaa tttgagaata ccagctgggc acggtggctc acgcctgtaa    8760
tcccagcact actttggga ggccaaggtg ggcagataac ctgcggtcag gagtttgaga     8820
ccaggctgga caacatggtg aaacctcgtc tctactaaaa atacaaaaat tagccaggtg    8880
tggtaggatg cacctgtaat cccagctact taggaggccg agacaggaga atcgctcgaa    8940
cccaggaggc ggacgttgca gtgagccaag attgcaccat tgcactccag actgggtgac    9000
aagagtgaaa ctccatctaa aaaaaaaaa aaaaaaagt gaatactgta tcccaaagta     9060
tgttagttgt ttgtttggaa atcagcattc tccccgatgc tctattatgg gatccaaaat    9120
tcttgaacat aagtttaccc tgtactgtgt ccaaacactg ttctagttct agcctgatta    9180
tgggtcccaa gaataaaagg atgagtaggt gtacagagct cttgacctac aatttttaa    9240
gagtgttttg gtaccttccc attgtcttct ctataactca gtcctaacat actctgcact    9300
cgagttacca gccatccaca ctgacatcag atttcaacca gaaccatcac tgagtgacag    9360
cagtacttct cagaggtatt tgcagcttga tgcaaagtag tctctaatga gtaggcattc    9420
aggtggttct tcccagcagg tggagaagaa agggaggaga tgaagaacac tgagagggga    9480
gtggcacctt cccaggctgc ccagctcagt ctcttgccct gttcctgtga ctcagctgcc    9540
cactccccca actttgtttc cctccctccc agtctctgaa agtgtcaggt gtttctctcc    9600
tcacagtctc ttttgcagca acagtaagac aaaattcaag gcagcctttt aaagttacga    9660
```

```
acagttatta gcatgtattt acagacctaa gcagaatgag agtttataca ttgtttttag    9720
ttgcctgtat ttatagccaa aagtatatta ccttaaagtt gagatctttc tcttcttttc    9780
ctaaattttg gtaaagtgtg cttcatgaaa caaacatctg gaaaactcca agtataagag    9840
accctggact gatgatggcc cagccaagta tatggaggga cagagttctc tctgtcatta    9900
atgaggacat cggttttcac aattgaacct catgcactgt ccacagcatc tcacctagct    9960
cctgtatctc ctgatctgct tttaaaaata gttagttagg ctgccttttt acaccacctt   10020
ctctctctcc ccttgtggta attttccagc cttccccata gatataaaac tagaacacct   10080
ttatgatttg gggtctatgt aatgactgac cgataagaac ccaggcagat gctaacatac   10140
ttaacagctc gcattaaaat actttaaatc aggcgtgatg gctcattcct gtaatctcaa   10200
gcactttggg aggctaaggt gggtggatct cttgaggtca ggagttcgag accaacctgg   10260
ccaacgtggt gaaaccccgt ctctactaaa aatacaaaat tagccgggca tggtggcagc   10320
tgcctgtaat cccagctact cgggaagctg aggcaggaga attgcttgaa cctgggaggt   10380
ggggattgca gtcagccaag attgttctgc agcatgggtg acaaagtgag acttcgtctc   10440
aagtaaataa aactaaaatt tttaaatcaa acatgacaaa aatgttaata taattcagaa   10500
gtaccttgaa attgaaacat atttgtgcaa tgatcattag gcttttttgtc cttgttgttt   10560
taaaatgagg cttatacaga gtgagttgag agtcaagtag ccttcgctgt gagacggtaa   10620
tgcagttata taatagatac ccttgacttt gccagattca tcacaatact gcttatacag   10680
gaaagttttc tcagaaagga aaatccatta gtatcagtcc catcaagcca acagaatga    10740
agacctttga tagtaatagc aagaggttac aaatagcagg gaggaggcga gtagtgaatg   10800
tcactgtgat tgcaaaccct tacctgtatt atcacacgta gtcctcacaa caaccttgtg   10860
agacaagtgt tgtgttcctc attttttcag aggggaacac agacccagag aggttaagaa   10920
atttgcccaa gataacaagt aaaaggcaaa gttggttgca aaagaggtgt ttctgaattc   10980
aagggccata ctctctctct gacaacatgc tctaagtcca tagagtaagc actctagtat   11040
gaaaaaagt ttcaaggaac gaggccatga aaatgagact atttgacatc tcagatctgt    11100
ctgggatgtt atggaggttt ttaaaaataa agttgaaaaa agaaaatgaa tcatgtttat   11160
acataaaaa atcacatgta acacatttca agtgtttgaa aataaaacca aaatctaaac    11220
tttagtcttc aagcagacat tcagtgttac tttagaaaac tcactgaatt aggtggaaat   11280
gatggaataa tactattcat ggccagctat taacacagaa gaacatggca gtgtgtgtct   11340
ggaacggcat gcacaatttg taaaccttttt tcaaatatca tttaatcaac tcagaataaa   11400
gtgccctgta gccaacagtg cctctttact tgcttctctg ggaaatacat ggtactaaat   11460
tagtagcaca aagtttggga atatgcaaaa taatggataa ccattttca aaatgtcat     11520
tctctgaaga ggaagcagct ggttggacag gatttcttga agagccaggt gctaagggca   11580
tcaggtcgac atccatagta accatgtgcc ataacatcta cacatttcca cttgtttac    11640
agacaaggta acaggcagaa ggaaaatcca gagtcttgca gtaagcagat gacaaaactt   11700
caatatgctt gggcaccact taggtgaccc cagggagatt tagtgtggcc ttaggaaagc   11760
aaaagagcac ttttttattgg aaatatgagc ttgtcactgg gaaagatttg taaaattgat   11820
caagaacttg atttataatt atgcctcaaa aaaaaagtt ctcatttagt agtggagcaa    11880
tctagaaaac atacctttt tgtttgtttg gaagatcctc tttccctggc tgtattgtag   11940
tgtttgctat ttgatgtgga aataactaat aacttaagat tttggaacag aacacccttt   12000
```

```
agatttccaa aacacaattc ttatttcagg gaagacagac caaaaatatc tcctgagatc  12060
attggtttct ttataaattg tggtaccact ccatcattga agagaaacca ctaccacacc  12120
actagcacca tacagaacct tttctctgta tctttgtaca atactacaaa ggggtaccag  12180
ggaggagaga gtggctgacc actttagtga caaaacagca ctccactgct ggtgaatccc  12240
atctaattat ggtccttcca cccttttcaa ccaccaacaa ctgttcgtac tgttaattcc  12300
tatcctgaag gtttaaccag tggttgtcta gtatcttctg tctttagaac agtggttctc  12360
aaactttagt acacatcagc atcacctgga gggccttttt ttaaaataag acacagattg  12420
ctgggctcat ggtcagagtt cccagttaag taaatcagga aatttgtatt tctaacaagt  12480
ttataggtga ggccaatact gctgttttgg gaactatgct ttgagaacca ctgccttgaa  12540
aaaatttcca acttctacct ttaagatcag cctgacttat caaacgctag agaaaaactg  12600
aatctaccct tgggcagatg acttgggatt ggattctata cagcagtctt gctcaatctt  12660
cccagtttcc agtttttatta taccaacaat tggtttttac aagctagaag acaatgaatg  12720
tataagttct atggaacagt gagataaatc taagcttctt gtctttgtat ttagaaacat  12780
tgattctatg gatgatcatt tgtatcatgt tgacccttg acttgtactg aaggtgattt  12840
taaatttaag tatgtagtgt ttgaatttct tccatccatg tcgttttaat gagatgtttc  12900
catgtcagct cctttacagc cttggctcct ggcttacaga ttttgaata gttgtttgct  12960 tgccagttgt tttacatctt tcattggcca ccaaaatatt agccatttga gatgagatga  13020
gactacttgt tgtaccttca tctttcattt aattttctgg cgtaaattaa catttaatt  13080 tcatatatat ctgtaaagag tctacccaaa ggcttcacgg aaatttgcaa aatgaactaa  13140
ttccctttta agcagcaggt gtgcctgttt ttgactttc agtaaatatg ttgtttgtgc  13200
acatatctac atggtggaga ccatattcat tatttcatct tccaaataat gggaaaaata  13260
taaaagtgaa tcagtgtgct ttgggaattc agtgaaatca tgttaactca tatagagggg  13320
gccttagttt atctcttctt tactgaatta attagttttg gaaattcttt taccattaaa  13380
aaaaattaag gaccatacag agaatgattt aagaaaaaac aagtcactta aaaatcatca  13440
cctatttata aactgtatta attacacata atgcttattg attcaatgag gtttctctaa  13500
agacttctgc ttaataaata tgctgacttc atttaaatta gtttagacta ttgtaggaat  13560
ggaaggaaat gattatattt actagaatta gtgagatcag aaagcatatc agaatgttga  13620
tgatatcaag gagacaatct acagagtttt tgcctctgtg gatggaaata agggtgtttt  13680
tttttggttt tttttttact ttagtttccc ataattttg gaaattatgt gtgcatttag  13740 ttctttagt aacactgatt ttaaaattaa atttcaaaag tcaatctcta agagtaattt  13800 attttgttt taccaaccag tgccaaaaag gagaggaggg aatccaaaag ccaatctttt  13860
gaaccaatgt gtaaaagatt atgttttttc ttaaagttag ggaggctcgg gccctgacac  13920
tgccagcccc agtgagcatc cctggctacc tcgggattat gtgcaagctg ctttgtccta  13980
catttctttc atctggttct tattgggagt gcttctctct aataaaaatt gatttcccac  14040
aaaataggca agctgaaca aagatgaatg cttttgataa gttgggtttc acttcagttg  14100
aaacaatgtg atagaatatc caggtgtggc atgatgggc aggaggaggt gcctagaggg  14160
aaaagttatt tttgtttctt agtgttgtgt tgtggggatg ggacagataa gaataagatg  14220
tttattgccc taatcatgct aagagactat tattcaatat gcttttcccg cttttctaag  14280
aggaataaac ttagacaaat tacattataa acagttcccc tactactatc tcccactcta  14340
gataaagcca gtgggtggta tgggtccttt tattccttat agtattatgc caaagaatca  14400
```

-continued

```
acttattttc attgaagatt ataaataaat gaagcttgtt atagccataa tgatttgagt    14460
cagtatacca ttttacctat aaaatgcaaa attcatcctt gcaacccat tcaccaggag     14520 ccttgaagca ttttgtttac tccaaaggcc ttgtcaagga agcataattt tttgttttgc    14580
cttcttattt agtcagtttg gtcatattta cttaaaaaaa caaactgaaa atcacactcc    14640
tttatatgtt gatataactg attttataga atctgtctgt tctttgttta acaggtctct    14700
gtaagcaagc ttgcaagtgt attttgtgta cattttatct gaggtggaaa tgaaaattct    14760
aaagagaaaa tattttaaaa gatattgtat ttatgttgct tgtgttgtag aataaagatt    14820
caaatgcatt aaaaatctgg tacatgaaac aa                                  14852
```

<210> SEQ ID NO 80
<211> LENGTH: 2177
<212> TYPE: PRT
<213> ORGANISM: Homo sapiens

<400> SEQUENCE: 80

```
Met Glu Glu Ile Leu Arg Lys Leu Gln Lys Glu Ala Ser Gly Ser Lys
1               5                   10                  15

Tyr Lys Ala Ile Lys Glu Ser Cys Thr Trp Ala Leu Glu Thr Leu Gly
                20                  25                  30

Gly Leu Asp Thr Ile Val Lys Ile Pro Pro His Val Leu Arg Glu Lys
            35                  40                  45

Cys Leu Leu Pro Leu Gln Leu Ala Leu Glu Ser Lys Asn Val Lys Leu
        50                  55                  60

Ala Gln His Ala Leu Ala Gly Met Gln Lys Leu Leu Ser Glu Glu Arg
65                  70                  75                  80

Phe Val Ser Met Glu Thr Asp Ser Asp Glu Lys Gln Leu Leu Asn Gln
                85                  90                  95

Ile Leu Asn Ala Val Lys Val Thr Pro Ser Leu Asn Glu Asp Leu Gln
            100                 105                 110

Val Glu Val Met Lys Val Leu Leu Cys Ile Thr Tyr Thr Pro Thr Phe
        115                 120                 125

Asp Leu Asn Gly Ser Ala Val Leu Lys Ile Ala Glu Val Cys Ile Glu
    130                 135                 140

Thr Tyr Ile Ser Ser Cys His Gln Arg Ser Ile Asn Thr Ala Val Arg
145                 150                 155                 160

Ala Thr Leu Ser Gln Met Leu Ser Asp Leu Thr Leu Gln Leu Arg Gln
                165                 170                 175

Arg Gln Glu Asn Thr Ile Ile Glu Asn Pro Asp Val Pro Gln Asp Phe
            180                 185                 190

Gly Asn Gln Gly Ser Thr Val Glu Ser Leu Cys Asp Val Val Ser
        195                 200                 205

Val Leu Thr Val Leu Cys Glu Lys Leu Gln Ala Ala Ile Asn Asp Ser
    210                 215                 220

Gln Gln Leu Gln Leu Leu Tyr Leu Glu Cys Ile Leu Ser Val Leu Ser
225                 230                 235                 240

Ser Ser Ser Ser Ser Met His Leu His Arg Arg Phe Thr Asp Leu Ile
                245                 250                 255

Trp Lys Asn Leu Cys Pro Ala Leu Ile Val Ile Leu Gly Asn Pro Ile
            260                 265                 270

His Asp Lys Thr Ile Thr Ser Ala His Thr Ser Ser Ser Thr Ser
        275                 280                 285
```

```
Leu Glu Ser Asp Ser Ala Ser Pro Gly Val Ser Asp His Gly Arg Gly
    290                 295                 300

Ser Gly Cys Ser Cys Thr Ala Pro Ala Leu Ser Gly Pro Val Ala Arg
305                 310                 315                 320

Thr Ile Tyr Tyr Ile Ala Ala Glu Leu Val Arg Leu Val Gly Ser Val
                325                 330                 335

Asp Ser Met Lys Pro Val Leu Gln Ser Leu Tyr His Arg Val Leu Leu
            340                 345                 350

Tyr Pro Pro Gln His Arg Val Glu Ala Ile Lys Ile Met Lys Glu
        355                 360                 365

Ile Leu Gly Ser Pro Gln Arg Leu Cys Asp Leu Ala Gly Pro Ser Ser
    370                 375                 380

Thr Glu Ser Glu Ser Arg Lys Arg Ser Ile Ser Lys Arg Lys Ser His
385                 390                 395                 400

Leu Asp Leu Leu Lys Leu Ile Met Asp Gly Met Thr Glu Ala Cys Ile
                405                 410                 415

Lys Gly Gly Ile Glu Ala Cys Tyr Ala Ala Val Ser Cys Val Cys Thr
            420                 425                 430

Leu Leu Gly Ala Leu Asp Glu Leu Ser Gln Gly Lys Gly Leu Ser Glu
        435                 440                 445

Gly Gln Val Gln Leu Leu Leu Arg Leu Glu Glu Leu Lys Asp Gly
    450                 455                 460

Ala Glu Trp Ser Arg Asp Ser Met Glu Ile Asn Glu Ala Asp Phe Arg
465                 470                 475                 480

Trp Gln Arg Arg Val Leu Ser Ser Glu His Thr Pro Trp Glu Ser Gly
                485                 490                 495

Asn Glu Arg Ser Leu Asp Ile Ser Ile Ser Val Thr Thr Asp Thr Gly
            500                 505                 510

Gln Thr Thr Leu Glu Gly Glu Leu Gly Gln Thr Thr Pro Glu Asp His
        515                 520                 525

Ser Gly Asn His Lys Asn Ser Leu Lys Ser Pro Ala Ile Pro Glu Gly
    530                 535                 540

Lys Glu Thr Leu Ser Lys Val Leu Glu Thr Glu Ala Val Asp Gln Pro
545                 550                 555                 560

Asp Val Val Gln Arg Ser His Thr Val Pro Tyr Pro Asp Ile Thr Asn
                565                 570                 575

Phe Leu Ser Val Asp Cys Arg Thr Arg Ser Tyr Gly Ser Arg Tyr Ser
            580                 585                 590

Glu Ser Asn Phe Ser Val Asp Asp Gln Asp Leu Ser Arg Thr Glu Phe
        595                 600                 605

Asp Ser Cys Asp Gln Tyr Ser Met Ala Ala Glu Lys Asp Ser Gly Arg
    610                 615                 620

Ser Asp Val Ser Asp Ile Gly Ser Asp Asn Cys Ser Leu Ala Asp Glu
625                 630                 635                 640

Glu Gln Thr Pro Arg Asp Cys Leu Gly His Arg Ser Leu Arg Thr Ala
                645                 650                 655

Ala Leu Ser Leu Lys Leu Leu Lys Asn Gln Glu Ala Asp Gln His Ser
            660                 665                 670

Ala Arg Leu Phe Ile Gln Ser Leu Glu Gly Leu Leu Pro Arg Leu Leu
        675                 680                 685

Ser Leu Ser Asn Val Glu Glu Val Asp Thr Ala Leu Gln Asn Phe Ala
    690                 695                 700

Ser Thr Phe Cys Ser Gly Met Met His Ser Pro Gly Phe Asp Gly Asn
```

```
                705                 710                 715                 720
        Ser Ser Leu Ser Phe Gln Met Leu Met Asn Ala Asp Ser Leu Tyr Thr
                        725                 730                 735

Ala Ala His Cys Ala Leu Leu Asn Leu Lys Leu Ser His Gly Asp
                        740                 745                 750

Tyr Tyr Arg Lys Arg Pro Thr Leu Ala Pro Gly Val Met Lys Asp Phe
                        755                 760                 765

Met Lys Gln Val Gln Thr Ser Gly Val Leu Met Val Phe Ser Gln Ala
                770                 775                 780

Trp Ile Glu Glu Leu Tyr His Gln Val Leu Asp Arg Asn Met Leu Gly
        785                 790                 795                 800

Glu Ala Gly Tyr Trp Gly Ser Pro Glu Asp Asn Ser Leu Pro Leu Ile
                        805                 810                 815

Thr Met Leu Thr Asp Ile Asp Gly Leu Glu Ser Ser Ala Ile Gly Gly
                        820                 825                 830

Gln Leu Met Ala Ser Ala Ala Thr Glu Ser Pro Phe Ala Gln Ser Arg
                        835                 840                 845

Arg Ile Asp Asp Ser Thr Val Ala Gly Val Ala Phe Ala Arg Tyr Ile
                        850                 855                 860

Leu Val Gly Cys Trp Lys Asn Leu Ile Asp Thr Leu Ser Thr Pro Leu
        865                 870                 875                 880

Thr Gly Arg Met Ala Gly Ser Ser Lys Gly Leu Ala Phe Ile Leu Gly
                        885                 890                 895

Ala Glu Gly Ile Lys Glu Gln Asn Gln Lys Glu Arg Asp Ala Ile Cys
                        900                 905                 910

Met Ser Leu Asp Gly Leu Arg Lys Ala Ala Arg Leu Ser Cys Ala Leu
                        915                 920                 925

Gly Val Ala Ala Asn Cys Ala Ser Ala Leu Ala Gln Met Ala Ala Ala
                        930                 935                 940

Ser Cys Val Gln Glu Glu Lys Glu Glu Arg Glu Ala Gln Glu Pro Ser
        945                 950                 955                 960

Asp Ala Ile Thr Gln Val Lys Leu Lys Val Glu Gln Lys Leu Glu Gln
                        965                 970                 975

Ile Gly Lys Val Gln Gly Val Trp Leu His Thr Ala His Val Leu Cys
                        980                 985                 990

Met Glu Ala Ile Leu Ser Val Gly Leu Glu Met Gly Ser His Asn Pro
                        995                 1000                1005

Asp Cys Trp Pro His Val Phe Arg Val Cys Glu Tyr Val Gly Thr
                1010                1015                1020

Leu Glu His Asn His Phe Ser Asp Gly Ala Ser Gln Pro Pro Leu
                1025                1030                1035

Thr Ile Ser Gln Pro Gln Lys Ala Thr Gly Ser Ala Gly Leu Leu
                1040                1045                1050

Gly Asp Pro Glu Cys Glu Gly Ser Pro Pro Glu His Ser Pro Glu
                1055                1060                1065

Gln Gly Arg Ser Leu Ser Thr Ala Pro Val Val Gln Pro Leu Ser
                1070                1075                1080

Ile Gln Asp Leu Val Arg Glu Gly Ser Arg Gly Arg Ala Ser Asp
                1085                1090                1095

Phe Arg Gly Gly Ser Leu Met Ser Gly Ser Ser Ala Ala Lys Val
                1100                1105                1110

Val Leu Thr Leu Ser Thr Gln Ala Asp Arg Leu Phe Glu Asp Ala
                1115                1120                1125
```

-continued

```
Thr Asp Lys Leu Asn Leu Met Ala Leu Gly Gly Phe Leu Tyr Gln
1130                1135                1140

Leu Lys Lys Ala Ser Gln Ser Gln Leu Phe His Ser Val Thr Asp
1145                1150                1155

Thr Val Asp Tyr Ser Leu Ala Met Pro Gly Glu Val Lys Ser Thr
1160                1165                1170

Gln Asp Arg Lys Ser Ala Leu His Leu Phe Arg Leu Gly Asn Ala
1175                1180                1185

Met Leu Arg Ile Val Arg Ser Lys Ala Arg Pro Leu Leu His Val
1190                1195                1200

Met Arg Cys Trp Ser Leu Val Ala Pro His Leu Val Glu Ala Ala
1205                1210                1215

Cys His Lys Glu Arg His Val Ser Gln Lys Ala Val Ser Phe Ile
1220                1225                1230

His Asp Ile Leu Thr Glu Val Leu Thr Asp Trp Asn Glu Pro Pro
1235                1240                1245

His Phe His Phe Asn Glu Ala Leu Phe Arg Pro Phe Glu Arg Ile
1250                1255                1260

Met Gln Leu Glu Leu Cys Asp Glu Asp Val Gln Asp Gln Val Val
1265                1270                1275

Thr Ser Ile Gly Glu Leu Val Glu Val Cys Ser Thr Gln Ile Gln
1280                1285                1290

Ser Gly Trp Arg Pro Leu Phe Ser Ala Leu Glu Thr Val His Gly
1295                1300                1305

Gly Asn Lys Ser Glu Met Lys Glu Tyr Leu Val Gly Asp Tyr Ser
1310                1315                1320

Met Gly Lys Gly Gln Ala Pro Val Phe Asp Val Phe Glu Ala Phe
1325                1330                1335

Leu Asn Thr Asp Asn Ile Gln Val Phe Ala Asn Ala Ala Thr Ser
1340                1345                1350

Tyr Ile Met Cys Leu Met Lys Phe Val Lys Gly Leu Gly Glu Val
1355                1360                1365

Asp Cys Lys Glu Ile Gly Asp Cys Ala Pro Ala Pro Gly Ala Pro
1370                1375                1380

Ser Thr Asp Leu Cys Leu Pro Ala Leu Asp Tyr Leu Arg Arg Cys
1385                1390                1395

Ser Gln Leu Leu Ala Lys Ile Tyr Lys Met Pro Leu Lys Pro Ile
1400                1405                1410

Phe Leu Ser Gly Arg Leu Ala Gly Leu Pro Arg Arg Leu Gln Glu
1415                1420                1425

Gln Ser Ala Ser Ser Glu Asp Gly Ile Glu Ser Val Leu Ser Asp
1430                1435                1440

Phe Asp Asp Asp Thr Gly Leu Ile Glu Val Trp Ile Ile Leu Leu
1445                1450                1455

Glu Gln Leu Thr Ala Ala Val Ser Asn Cys Pro Arg Gln His Gln
1460                1465                1470

Pro Pro Thr Leu Asp Leu Leu Phe Glu Leu Leu Arg Asp Val Thr
1475                1480                1485

Lys Thr Pro Gly Pro Gly Phe Gly Ile Tyr Ala Val Val His Leu
1490                1495                1500

Leu Leu Pro Val Met Ser Val Trp Leu Arg Arg Ser His Lys Asp
1505                1510                1515
```

```
His Ser Tyr Trp Asp Met Ala Ser Ala Asn Phe Lys His Ala Ile
1520                1525                1530

Gly Leu Ser Cys Glu Leu Val Val Glu His Ile Gln Ser Phe Leu
1535                1540                1545

His Ser Asp Ile Arg Tyr Glu Ser Met Ile Asn Thr Met Leu Lys
1550                1555                1560

Asp Leu Phe Glu Leu Leu Val Ala Cys Val Ala Lys Pro Thr Glu
1565                1570                1575

Thr Ile Ser Arg Val Gly Cys Ser Cys Ile Arg Tyr Val Leu Val
1580                1585                1590

Thr Ala Gly Pro Val Phe Thr Glu Glu Met Trp Arg Leu Ala Cys
1595                1600                1605

Cys Ala Leu Gln Asp Ala Phe Ser Ala Thr Leu Lys Pro Val Lys
1610                1615                1620

Asp Leu Leu Gly Cys Phe His Ser Gly Thr Glu Ser Phe Ser Gly
1625                1630                1635

Glu Gly Cys Gln Val Arg Val Ala Ala Pro Ser Ser Ser Pro Ser
1640                1645                1650

Ala Glu Ala Glu Tyr Trp Arg Ile Arg Ala Met Ala Gln Gln Val
1655                1660                1665

Phe Met Leu Asp Thr Gln Cys Ser Pro Lys Thr Pro Asn Asn Phe
1670                1675                1680

Asp His Ala Gln Ser Cys Gln Leu Ile Ile Glu Leu Pro Pro Asp
1685                1690                1695

Glu Lys Pro Asn Gly His Thr Lys Lys Ser Val Ser Phe Arg Glu
1700                1705                1710

Ile Val Val Ser Leu Leu Ser His Gln Val Leu Leu Gln Asn Leu
1715                1720                1725

Tyr Asp Ile Leu Leu Glu Glu Phe Val Lys Gly Pro Ser Pro Gly
1730                1735                1740

Glu Glu Lys Thr Ile Gln Val Pro Glu Ala Lys Leu Ala Gly Phe
1745                1750                1755

Leu Arg Tyr Ile Ser Met Gln Asn Leu Ala Val Ile Phe Asp Leu
1760                1765                1770

Leu Leu Asp Ser Tyr Arg Thr Ala Arg Glu Phe Asp Thr Ser Pro
1775                1780                1785

Gly Leu Lys Cys Leu Leu Lys Lys Val Ser Gly Ile Gly Gly Ala
1790                1795                1800

Ala Asn Leu Tyr Arg Gln Ser Ala Met Ser Phe Asn Ile Tyr Phe
1805                1810                1815

His Ala Leu Val Cys Ala Val Leu Thr Asn Gln Glu Thr Ile Thr
1820                1825                1830

Ala Glu Gln Val Lys Lys Val Leu Phe Glu Asp Asp Glu Arg Ser
1835                1840                1845

Thr Asp Ser Ser Gln Gln Cys Ser Ser Glu Asp Glu Asp Ile Phe
1850                1855                1860

Glu Glu Thr Ala Gln Val Ser Pro Pro Arg Gly Lys Glu Lys Arg
1865                1870                1875

Gln Trp Arg Ala Arg Met Pro Leu Leu Ser Val Gln Pro Val Ser
1880                1885                1890

Asn Ala Asp Trp Val Trp Leu Val Lys Arg Leu His Lys Leu Cys
1895                1900                1905

Met Glu Leu Cys Asn Asn Tyr Ile Gln Met His Leu Asp Leu Glu
```

|   |   |   |   |   |   |   |   |   |   |
|---|---|---|---|---|---|---|---|---|---|
| | 1910 | | | | 1915 | | | | 1920 |
| Asn | Cys | Met | Glu | Glu | Pro | Pro | Ile | Phe | Lys | Gly | Asp | Pro | Phe | Phe |
| | | 1925 | | | | 1930 | | | | 1935 |

Asn Cys Met Glu Glu Pro Pro Ile Phe Lys Gly Asp Pro Phe Phe
          1925                      1930                      1935

Ile Leu Pro Ser Phe Gln Ser Glu Ser Ser Thr Pro Ser Thr Gly
   1940                    1945                    1950

Gly Phe Ser Gly Lys Glu Thr Pro Ser Glu Asp Asp Arg Ser Gln
   1955                    1960                    1965

Ser Arg Glu His Met Gly Glu Ser Leu Ser Leu Lys Ala Gly Gly
   1970                    1975                    1980

Gly Asp Leu Leu Leu Pro Pro Ser Pro Lys Val Glu Lys Lys Asp
   1985                    1990                    1995

Pro Ser Arg Lys Lys Glu Trp Trp Glu Asn Ala Gly Asn Lys Ile
   2000                    2005                    2010

Tyr Thr Met Ala Ala Asp Lys Thr Ile Ser Lys Leu Met Thr Glu
   2015                    2020                    2025

Tyr Lys Lys Arg Lys Gln Gln His Asn Leu Ser Ala Phe Pro Lys
   2030                    2035                    2040

Glu Val Lys Val Glu Lys Lys Gly Glu Pro Leu Gly Pro Arg Gly
   2045                    2050                    2055

Gln Asp Ser Pro Leu Leu Gln Arg Pro Gln His Leu Met Asp Gln
   2060                    2065                    2070

Gly Gln Met Arg His Ser Phe Ser Ala Gly Pro Glu Leu Leu Arg
   2075                    2080                    2085

Gln Asp Lys Arg Pro Arg Ser Gly Ser Thr Gly Ser Ser Leu Ser
   2090                    2095                    2100

Val Ser Val Arg Asp Ala Glu Ala Gln Ile Gln Ala Trp Thr Asn
   2105                    2110                    2115

Met Val Leu Thr Val Leu Asn Gln Ile Gln Ile Leu Pro Asp Gln
   2120                    2125                    2130

Thr Phe Thr Ala Leu Gln Pro Ala Val Phe Pro Cys Ile Ser Gln
   2135                    2140                    2145

Leu Thr Cys His Val Thr Asp Ile Arg Val Arg Gln Ala Val Arg
   2150                    2155                    2160

Glu Trp Leu Gly Arg Val Gly Arg Val Tyr Asp Ile Ile Val
   2165                    2170                    2175

<210> SEQ ID NO 81
<211> LENGTH: 4221
<212> TYPE: DNA
<213> ORGANISM: Homo sapiens

<400> SEQUENCE: 81

| | | | | | |
|---|---|---|---|---|---|
| cgataacgat | ttgtgttgtg | agaggcgcaa | gctgcgattt | ctgctgaact | tggaggcatt | 60 |
| tctacgactt | ttctctcagc | tgaggctttt | cctccgaccc | tgatgctctt | caattcggtg | 120 |
| ctccgccagc | cccagcttgg | cgtcctgaga | aatggatggt | cttcacaata | ccctcttcaa | 180 |
| tcccttctga | ctggttatca | gtgcagtggt | aatgatgaac | acacttctta | tggagaaaca | 240 |
| ggagtcccag | ttcctccttt | tggatgtacc | ttctcttctg | ctcccaatat | ggaacatgta | 300 |
| ctagcagttg | ccaatgaaga | aggctttgtt | cgattgtata | acacagaatc | acaaagtttc | 360 |
| agaaagaagt | gcttcaaaga | atggatggct | cactggaatg | ccgtctttga | cctggcctgg | 420 |
| gttcctggtg | aacttaaact | tgttacagca | gcaggtgatc | aaacagccaa | attttgggac | 480 |
| gtaaaagctg | gtgagctgat | tggaacatgc | aaaggtcatc | aatgcagcct | caagtcagtt | 540 |

```
gccttttcta agtttgagaa agctgtattc tgtacgggtg aagagatgg caacattatg    600 gtctgggata ccaggtgcaa caaaaaagat gggttttata ggcaagtgaa tcaaatcagt    660
ggagctcaca atacctcaga caagcaaacc ccttcaaaac ccaagaagaa acagaattca    720
aaaggacttg ctccttctgt ggatttccag caaagtgtta ctgtggtcct ctttcaagac    780
gagaatacct tagtctcagc aggagctgtg gatgggataa tcaaagtatg ggatttacgt    840
aagaattata ctgcttatcg acaagaaccc atagcatcca agtctttcct gtacccaggt    900
agcagcactc gaaaacttgg atattcaagt ctgattttgg attccactgg ctctacttta    960
tttgctaatt gcacagacga taacatctac atgtttaata tgactgggtt gaagacttct    1020
ccagtggcta ttttcaatgg acaccagaac tctacctttt atgtaaaatc cagccttagt    1080
ccagatgacc agttttttagt cagtggctca agtgatgaag ctgcctacat atggaaggtc    1140
tccacaccct ggcaacctcc tactgtgctc ctgggtcatt ctcaagaggt cacgtctgtg    1200
tgctggtgtc catctgactt cacaaagatt gctacctgtt ctgatgacaa tacactaaaa    1260
atctggcgct tgaatagagg cttagaggag aaaccaggag gtgataaact ttccacggtg    1320
ggttgggcct ctcagaagaa aaagagtca agacctggcc tagtaacagt aacgagtagc    1380
cagagtactc ctgccaaagc ccccagggta aagtgcaatc catccaattc ttccccgtca    1440
tccgcagctt gtgccccaag ctgtgctgga gacctccctc ttccttcaaa tactcctacg    1500
ttctctatta aaacctctcc tgccaaggcc cggtctccca tcaacagaag aggctctgtc    1560
tcctccgtct ctcccaagcc accttcatct ttcaagatgt cgattagaaa ctgggtgacc    1620
cgaacacctt cctcatcacc acccatcact ccacctgctt cggagaccaa gatcatgtct    1680
ccgagaaaag ccottattcc tgtgagccag aagtcatccc aagcagaggc ttgctctgag    1740
tctagaaata gagtaaagag gaggctagac tcaagctgtc tggagagtgt gaaacaaaag    1800
tgtgtgaaga gttgtaactg tgtgactgag cttgatggcc aagttgaaaa tcttcatttg    1860
gatctgtgct gccttgctgg taaccaggaa gaccttagta aggactctct aggtcctacc    1920
aaatcaagca aaattgaagg agctggtacc agtatctcag agcctccgtc tcctatcagt    1980
ccgtatgctt cagaaagctg tggaacgcta cctcttcctt tgagaccttg tggagaaggg    2040
tctgaaatgg taggcaaaga gaatagttcc ccagagaata aaaactggtt gttggccatg    2100
gcagccaaac ggaaggctga gaatccatct ccacgaagtc cgtcatccca gacacccaat    2160
tccaggagac agagcggaaa gacattgcca agcccggtca ccatcacgcc cagctccatg    2220
aggaaaatct gcacatactt ccatagaaag tcccaggagg acttctgtgg tcctgaacac    2280
tcaacagaat tatagattct aatctgagtg agttactgag ctttggtcca ctaaaacaag    2340
ctgagctttg gtccactaaa acaagatgaa aaatacaaga gtgactctat aactctggtc    2400
tttaagaaag ctgcctttc attttttagac aaaatctttt caacgctgaa atgtacctaa    2460
tctggttcta ctaccataat gtatatgcag cttcccgagg atgaatgctg tgtttaaatt    2520
tcataaagta aatttgtcac tctagcattt tgaatgaata gtcttcactt tttaaattat    2580
tcatcttctc tataataatg catcccagt tcatggaggc aaaaaacaag tttcttgtta    2640
tcctgaaact ttctatgctc agtggaaagt atctgccagc cacagcatga ggcctgtgaa    2700
ggctgactga gaaatcctct gctgaagacc cctggttctg ttctgcctcc aacatgtata    2760
attttatttg aaatacataa tcttttcact atgcttttgt ggggtttttt ttaagtatgt    2820
gtaaaaatgt gatgctcaga taagtacatt tatatcagtt cagtgttaaa atgcagtctc    2880
ttgagttaaa gtcatcttta ttttaaatgc agtgataaat gtcaactctt cggagaaact    2940
```

```
aggagaacaa caacagaaag ctgtgtttgt cttttttctc tcaaatatat ctcccgtatg    3000
agatttcagg tccccatgtt ttcaccaagc aatctgctat gtcagccaac ccaacatcac    3060
tttctacagg aggttatgat ttttgccatt tactagagga agatgtttta tgaaatcaat    3120
ttggggtttg aattcaggtg cagtcatcag ttctttaggg gctgcaatgt tttaaaaaaa    3180
ataagtcatc agattttaag aaaaaagtga tgatttctta ttgatatttt tgtaacagaa    3240
tatagctctt aactgaaaat ccagaaccag aaacataaat cttgagtttc ttttcatgta    3300
cataaaaagc aatagccttt tagtatagat agccctgagc caaaaagtaa tagaattttc    3360
tctagatatt taatacagag agtgtataga ctgactctaa gttaataatg tgcaaaatat    3420
cttaaacatc cctcccctta ttcaacaatt atgtatcagt gatcttgaac cattgtttta    3480 tattttcac ctttgtaacc tcatggaaag aggcttaca tactttctat gtactattta    3540
cttagaaggg agccccttc cagtcatgaa acttcatttg ttttatccat atccctgagg    3600
actgtgtaga cttatgtca gttctgtgta gactttatgt cagttttgt cattatttga    3660 aaatctattc tgacaacttt ttaattcctt tgatcttata agttaaagct gtaacaactg    3720
aaattgcatg gatcaagtaa gcatagtttt atccagggag aaaataaaa ggaagccata    3780 gaattgctct ggtcaaaacc aagcacacca tagccttaac tgaatattta ggaaatctgc    3840
ctaatctgct tatatttggt gtttgttttt tgactgttgg gctttgggaa gatgttattt    3900
atgaccaata tctgccagta acgctgttta tctcacttgc tttgaaagcc aatggggaa    3960 aaaaatccat gaaaaaaaaa agattgataa agtagatgat tttgtttgta tccctaccca    4020
tctcctggca gccctactga gtgaaattgg gatacatttg gctgtcagaa attataccga    4080
gtctactggg tataacatgt ctcacttgga aagctagtac tttaaatgg gtgccaaagg    4140 tcaactgtaa tgagataatt atccctgcct gtgtccatgt cagactttga gctgatcctg    4200
aataataaag ccttttacct t                                              4221
```

<210> SEQ ID NO 82
<211> LENGTH: 730
<212> TYPE: PRT
<213> ORGANISM: Homo sapiens

<400> SEQUENCE: 82

```
Met Leu Phe Asn Ser Val Leu Arg Gln Pro Gln Leu Gly Val Leu Arg
1               5                   10                  15

Asn Gly Trp Ser Ser Gln Tyr Pro Leu Gln Ser Leu Leu Thr Gly Tyr
            20                  25                  30

Gln Cys Ser Gly Asn Asp Glu His Thr Ser Tyr Gly Glu Thr Gly Val
        35                  40                  45

Pro Val Pro Pro Phe Gly Cys Thr Phe Ser Ser Ala Pro Asn Met Glu
    50                  55                  60

His Val Leu Ala Val Ala Asn Glu Gly Phe Val Arg Leu Tyr Asn
65                  70                  75                  80

Thr Glu Ser Gln Ser Phe Arg Lys Lys Cys Phe Lys Glu Trp Met Ala
                85                  90                  95

His Trp Asn Ala Val Phe Asp Leu Ala Trp Val Pro Gly Glu Leu Lys
            100                 105                 110

Leu Val Thr Ala Ala Gly Asp Gln Thr Ala Lys Phe Trp Asp Val Lys
        115                 120                 125

Ala Gly Glu Leu Ile Gly Thr Cys Lys Gly His Gln Cys Ser Leu Lys
    130                 135                 140
```

-continued

```
Ser Val Ala Phe Ser Lys Phe Glu Lys Ala Val Phe Cys Thr Gly Gly
145                 150                 155                 160

Arg Asp Gly Asn Ile Met Val Trp Asp Thr Arg Cys Asn Lys Lys Asp
                165                 170                 175

Gly Phe Tyr Arg Gln Val Asn Gln Ile Ser Gly Ala His Asn Thr Ser
            180                 185                 190

Asp Lys Gln Thr Pro Ser Lys Pro Lys Lys Gln Asn Ser Lys Gly
        195                 200                 205

Leu Ala Pro Ser Val Asp Phe Gln Gln Ser Val Thr Val Val Leu Phe
210                 215                 220

Gln Asp Glu Asn Thr Leu Val Ser Ala Gly Ala Val Asp Gly Ile Ile
225                 230                 235                 240

Lys Val Trp Asp Leu Arg Lys Asn Tyr Thr Ala Tyr Arg Gln Glu Pro
                245                 250                 255

Ile Ala Ser Lys Ser Phe Leu Tyr Pro Gly Ser Ser Thr Arg Lys Leu
                260                 265                 270

Gly Tyr Ser Ser Leu Ile Leu Asp Ser Thr Gly Ser Thr Leu Phe Ala
            275                 280                 285

Asn Cys Thr Asp Asp Asn Ile Tyr Met Phe Asn Met Thr Gly Leu Lys
290                 295                 300

Thr Ser Pro Val Ala Ile Phe Asn Gly His Gln Asn Ser Thr Phe Tyr
305                 310                 315                 320

Val Lys Ser Ser Leu Ser Pro Asp Asp Gln Phe Leu Val Ser Gly Ser
                325                 330                 335

Ser Asp Glu Ala Ala Tyr Ile Trp Lys Val Ser Thr Pro Trp Gln Pro
            340                 345                 350

Pro Thr Val Leu Leu Gly His Ser Gln Glu Val Thr Ser Val Cys Trp
        355                 360                 365

Cys Pro Ser Asp Phe Thr Lys Ile Ala Thr Cys Ser Asp Asp Asn Thr
370                 375                 380

Leu Lys Ile Trp Arg Leu Asn Arg Gly Leu Glu Glu Lys Pro Gly Gly
385                 390                 395                 400

Asp Lys Leu Ser Thr Val Gly Trp Ala Ser Gln Lys Lys Lys Glu Ser
                405                 410                 415

Arg Pro Gly Leu Val Thr Val Thr Ser Ser Gln Ser Thr Pro Ala Lys
            420                 425                 430

Ala Pro Arg Val Lys Cys Asn Pro Ser Asn Ser Ser Pro Ser Ser Ala
        435                 440                 445

Ala Cys Ala Pro Ser Cys Ala Gly Asp Leu Pro Leu Pro Ser Asn Thr
450                 455                 460

Pro Thr Phe Ser Ile Lys Thr Ser Pro Ala Lys Ala Arg Ser Pro Ile
465                 470                 475                 480

Asn Arg Arg Gly Ser Val Ser Ser Val Ser Pro Lys Pro Pro Ser Ser
                485                 490                 495

Phe Lys Met Ser Ile Arg Asn Trp Val Thr Arg Thr Pro Ser Ser Ser
            500                 505                 510

Pro Pro Ile Thr Pro Pro Ala Ser Glu Thr Lys Ile Met Ser Pro Arg
        515                 520                 525

Lys Ala Leu Ile Pro Val Ser Gln Lys Ser Gln Ala Glu Ala Cys
530                 535                 540

Ser Glu Ser Arg Asn Arg Val Lys Arg Arg Leu Asp Ser Ser Cys Leu
545                 550                 555                 560
```

```
Glu Ser Val Lys Gln Lys Cys Val Lys Ser Cys Asn Cys Val Thr Glu
                565                 570                 575

Leu Asp Gly Gln Val Glu Asn Leu His Leu Asp Leu Cys Cys Leu Ala
            580                 585                 590

Gly Asn Gln Glu Asp Leu Ser Lys Asp Ser Leu Gly Pro Thr Lys Ser
        595                 600                 605

Ser Lys Ile Glu Gly Ala Gly Thr Ser Ile Ser Glu Pro Pro Ser Pro
    610                 615                 620

Ile Ser Pro Tyr Ala Ser Glu Ser Cys Gly Thr Leu Pro Leu Pro Leu
625                 630                 635                 640

Arg Pro Cys Gly Glu Gly Ser Glu Met Val Gly Lys Glu Asn Ser Ser
                645                 650                 655

Pro Glu Asn Lys Asn Trp Leu Leu Ala Met Ala Ala Lys Arg Lys Ala
            660                 665                 670

Glu Asn Pro Ser Pro Arg Ser Pro Ser Gln Thr Pro Asn Ser Arg
        675                 680                 685

Arg Gln Ser Gly Lys Thr Leu Pro Ser Pro Val Thr Ile Thr Pro Ser
    690                 695                 700

Ser Met Arg Lys Ile Cys Thr Tyr Phe His Arg Lys Ser Gln Glu Asp
705                 710                 715                 720

Phe Cys Gly Pro Glu His Ser Thr Glu Leu
                725                 730

<210> SEQ ID NO 83
<211> LENGTH: 1193
<212> TYPE: DNA
<213> ORGANISM: Homo sapiens

<400> SEQUENCE: 83
atgctcttca attcggtgct ccgccagccc cagcttggcg tcctgagaaa tggatggtct      60
tcacaatacc ctcttcaatc ccttctgact ggttatcagt gcagtggtaa tgatgaacac     120
acttcttatg gagaaacagg agtcccagtt cctccttttg atgtaccttc tcttctgct     180 cccaatatgg aacatgtact agcagttgcc aatgaagaag ctttgttcg attgtataac     240 acagaatcac aaagtttcag aaagaagtgc ttcaaagaat ggatggctca ctggaatgcc     300 gttttttgacc tggcctgggt tcctggtgaa cttaaacttg ttacagcagc aggtgatcaa     360
acagccaaat tttgggacgt aaaagctggt gagctgattg aacatgcaa aggtcatcaa     420 tgcagcctca gtcagttgc cttttctaag tttgagaaag ctgtattctg tacgggtgga     480
agagatggca acattatggt ctgggatacc aggtgcaaca aaaagatgg ttttataggg     540 caagtgaatc aaatcagtgg agctcacaat acctcagaca gcaaacccc ttcaaaaccc     600 aagaagaaac agaattcaaa aggacttgct ccttctgtgg atttccagca aagtgttact     660
gtggtcctct ttcaagacga gaataccta gtctcagcag gagctgtgga tgggataatc     720
aaagtatggg atttacgtaa gaattatact gcttatcgac aagaacccat agcatccaag     780
tctttcctgt acccaggtag cagcactcga aaacttggat attcaagtct gatttttgat     840
tccactggct ctactttatt tgctaattgc acagacgata acatctacat gtttaatatg     900 actggggttga agacttctcc agtggctatt tcaatggac accagaacgc tacctcttcc     960
tttgagacct tgtggagaat aaaaactggt tgttggccat ggcagccaaa cggaaggctg    1020
agaatccatc tccacgaagt ccgtcatccc agacacccaa ttccaggaga cagagcggaa    1080
agacattgcc aagcccggtc accatcacgc ccagctccat gaggaaaatc tgcacatact    1140
```
tccatagaaa gtcccaggag gacttctgtg gtcctgaaca ctcaacagaa tta         1193

<210> SEQ ID NO 84
<211> LENGTH: 373
<212> TYPE: PRT
<213> ORGANISM: Homo sapiens
<220> FEATURE:
<221> NAME/KEY: misc_feature
<222> LOCATION: (362)..(362)
<223> OTHER INFORMATION: Xaa can be any naturally occurring amino acid

<400> SEQUENCE: 84

Met Leu Phe Asn Ser Val Leu Arg Gln Pro Gln Leu Gly Val Leu Arg
1               5                   10                  15

Asn Gly Trp Ser Ser Gln Tyr Pro Leu Gln Ser Leu Leu Thr Gly Tyr
            20                  25                  30

Gln Cys Ser Gly Asn Asp Glu His Thr Ser Tyr Gly Glu Thr Gly Val
        35                  40                  45

Pro Val Pro Pro Phe Gly Cys Thr Phe Ser Ser Ala Pro Asn Met Glu
    50                  55                  60

His Val Leu Ala Val Ala Asn Glu Glu Gly Phe Val Arg Leu Tyr Asn
65                  70                  75                  80

Thr Glu Ser Gln Ser Phe Arg Lys Lys Cys Phe Lys Glu Trp Met Ala
                85                  90                  95

His Trp Asn Ala Val Phe Asp Leu Ala Trp Val Pro Gly Glu Leu Lys
            100                 105                 110

Leu Val Thr Ala Ala Gly Asp Gln Thr Ala Lys Phe Trp Asp Val Lys
        115                 120                 125

Ala Gly Glu Leu Ile Gly Thr Cys Lys Gly His Gln Cys Ser Leu Lys
    130                 135                 140

Ser Val Ala Phe Ser Lys Phe Glu Lys Ala Val Phe Cys Thr Gly Gly
145                 150                 155                 160

Arg Asp Gly Asn Ile Met Val Trp Asp Thr Arg Cys Asn Lys Lys Asp
                165                 170                 175

Gly Phe Tyr Arg Gln Val Asn Gln Ile Ser Gly Ala His Asn Thr Ser
            180                 185                 190

Asp Lys Gln Thr Pro Ser Lys Pro Lys Lys Gln Asn Ser Lys Gly
        195                 200                 205

Leu Ala Pro Ser Val Asp Phe Gln Gln Ser Val Thr Val Leu Phe
    210                 215                 220

Gln Asp Glu Asn Thr Leu Val Ser Ala Gly Ala Val Asp Gly Ile Ile
225                 230                 235                 240

Lys Val Trp Asp Leu Arg Lys Asn Tyr Thr Ala Tyr Arg Gln Glu Pro
                245                 250                 255

Ile Ala Ser Lys Ser Phe Leu Tyr Pro Gly Ser Ser Thr Arg Lys Leu
            260                 265                 270

Gly Tyr Ser Ser Leu Ile Leu Asp Ser Thr Gly Ser Thr Leu Phe Ala
        275                 280                 285

Asn Cys Thr Asp Asp Asn Ile Tyr Met Phe Asn Met Thr Gly Leu Lys
    290                 295                 300

Thr Ser Pro Val Ala Ile Phe Asn Gly His Gln Asn Ala Thr Ser Ser
305                 310                 315                 320

Phe Glu Thr Leu Trp Arg Ile Lys Thr Gly Cys Trp Pro Trp Gln Pro
                325                 330                 335

Asn Gly Arg Leu Arg Ile His Leu His Glu Val Arg His Pro Arg His
            340                 345                 350

Pro Ile Pro Gly Asp Arg Ala Glu Arg Xaa Cys Gln Ala Arg Ser Pro
        355                 360                 365

Ser Arg Pro Ala Pro
    370

<210> SEQ ID NO 85
<211> LENGTH: 1357
<212> TYPE: DNA
<213> ORGANISM: Homo sapiens

<400> SEQUENCE: 85

```
atgctcttca attcggtgct ccgccagccc cagcttggcg tcctgagaaa tggatggtct      60
tcacaatacc ctcttcaatc ccttctgact ggttatcagt gcagtggtaa tgatgaacac     120
acttcttatg gagaaacagg agtcccagtt cctccttttg gatgtacctt ctcttctgct     180
cccaatatgg aacatgtact agcagttgcc aatgaagaag ctttgttcg attgtataac     240
acagaatcac aaagtttcag aaagaagtgc ttcaaagaat ggatggctca ctggaatgcc    300
gtctttgacc tggcctgggt tcctggtgaa cttaaacttg ttacagcagc aggtgatcaa    360
acagccaaat tttgggacgt aaaagctggt gagctgattg aacatgcaa aggtcatcaa    420
tgcagcctca agtcagttgc ctttttctaag tttgagaaag ctgtattctg tacgggtgga   480
agagatggca acattatggt ctgggatacc aggtgcaaca aaaagatgg gtttatagg      540
caagtgaatc aaatcagtgg agctcacaat acctcagaca agcaaacccc ttcaaaaccc   600
aagaagaaac agaattcaaa aggacttgct ccttctgtgg atttccagca aagtgttact   660
gtggtcctct tcaagacga aataccctta gtctcagcag gagctgtgga tgggataatc    720
aaagtatggg atttacgtaa gaattatact gcttatcgac aagaacccat agcatccaag   780
tcttttcctgt acccaggtag cagcactcga aaacttggat attcaagtct gattttggat   840
tccactggct ctactttatt tgctaattgc acagacgata acatctacat gtttaatatg   900
actgggttga agacttctcc agtggctatt ttcaatggac accagaactc tacctttat   960
gtaaaatcca gccttagtcc agatgaccag tttttagtca gtggctcaag tgatgaagct   1020
gcctacatat ggaaggtctc cacaccctgg caacctccta ctgtgctcct gggtcattct   1080
caagaggtca cgtctgtgtg ctggtgtcca tctgacttca caaagattgc tacctgttct   1140
gatgacaata cactaaaaat ctggcgcttg aatagaggct tagaggagaa accaggaggt   1200
gataaacttt ccacggtggg ttgggcctct cagaagaaaa aagagtcaag acctggccta   1260
ggtcaccatc acgcccagct ccatgaggaa aatctgcaca tacttccata gaaagtccca   1320
ggaggacttc tgtggtcctg aacactcaac agaatta                              1357
```

<210> SEQ ID NO 86
<211> LENGTH: 436
<212> TYPE: PRT
<213> ORGANISM: Homo sapiens

<400> SEQUENCE: 86

Met Leu Phe Asn Ser Val Leu Arg Gln Pro Gln Leu Gly Val Leu Arg
1               5                   10                  15

Asn Gly Trp Ser Ser Gln Tyr Pro Leu Gln Ser Leu Leu Thr Gly Tyr
            20                  25                  30

Gln Cys Ser Gly Asn Asp Glu His Thr Ser Tyr Gly Glu Thr Gly Val
        35                  40                  45

Pro Val Pro Pro Phe Gly Cys Thr Phe Ser Ser Ala Pro Asn Met Glu

```
                50              55              60
His Val Leu Ala Val Ala Asn Glu Glu Gly Phe Val Arg Leu Tyr Asn
 65                      70                      75                      80

Thr Glu Ser Gln Ser Phe Arg Lys Lys Cys Phe Lys Glu Trp Met Ala
                         85                      90                      95

His Trp Asn Ala Val Phe Asp Leu Ala Trp Val Pro Gly Glu Leu Lys
                        100                     105                     110

Leu Val Thr Ala Ala Gly Asp Gln Thr Ala Lys Phe Trp Asp Val Lys
                115                     120                     125

Ala Gly Glu Leu Ile Gly Thr Cys Lys Gly His Gln Cys Ser Leu Lys
130                     135                     140

Ser Val Ala Phe Ser Lys Phe Glu Lys Ala Val Phe Cys Thr Gly Gly
145                     150                     155                     160

Arg Asp Gly Asn Ile Met Val Trp Asp Thr Arg Cys Asn Lys Lys Asp
                        165                     170                     175

Gly Phe Tyr Arg Gln Val Asn Gln Ile Ser Gly Ala His Asn Thr Ser
                180                     185                     190

Asp Lys Gln Thr Pro Ser Lys Pro Lys Lys Gln Asn Ser Lys Gly
                195                     200                     205

Leu Ala Pro Ser Val Asp Phe Gln Gln Ser Val Thr Val Leu Phe
210                     215                     220

Gln Asp Glu Asn Thr Leu Val Ser Ala Gly Ala Val Asp Gly Ile Ile
225                     230                     235                     240

Lys Val Trp Asp Leu Arg Lys Asn Tyr Thr Ala Tyr Arg Gln Glu Pro
                        245                     250                     255

Ile Ala Ser Lys Ser Phe Leu Tyr Pro Gly Ser Ser Thr Arg Lys Leu
                        260                     265                     270

Gly Tyr Ser Ser Leu Ile Leu Asp Ser Thr Gly Ser Thr Leu Phe Ala
                275                     280                     285

Asn Cys Thr Asp Asp Asn Ile Tyr Met Phe Asn Met Thr Gly Leu Lys
                        290                     295                     300

Thr Ser Pro Val Ala Ile Phe Asn Gly His Gln Asn Ser Thr Phe Tyr
305                     310                     315                     320

Val Lys Ser Ser Leu Ser Pro Asp Gln Phe Leu Val Ser Gly Ser
                        325                     330                     335

Ser Asp Glu Ala Ala Tyr Ile Trp Lys Val Ser Thr Pro Trp Gln Pro
                340                     345                     350

Pro Thr Val Leu Leu Gly His Ser Gln Glu Val Thr Ser Val Cys Trp
                355                     360                     365

Cys Pro Ser Asp Phe Thr Lys Ile Ala Thr Cys Ser Asp Asp Asn Thr
370                     375                     380

Leu Lys Ile Trp Arg Leu Asn Arg Gly Leu Glu Lys Pro Gly Gly
385                     390                     395                     400

Asp Lys Leu Ser Thr Val Gly Trp Ala Ser Gln Lys Lys Lys Glu Ser
                        405                     410                     415

Arg Pro Gly Leu Gly His His Ala Gln Leu His Glu Glu Asn Leu
                        420                     425                     430

His Ile Leu Pro
                435

<210> SEQ ID NO 87
<211> LENGTH: 1253
<212> TYPE: DNA
<213> ORGANISM: Homo sapiens
```

<400> SEQUENCE: 87

```
gggcggccgg gagagtagca gtgccttgga ccccagctct cctcccccctt tctctctaag    60
gatggcccag aaggagaact cctacccctg gccctacggc cgacagacgg ctccatctgg   120
cctgagcacc ctgccccagc gagtcctccg gaaagagcct gtcacccat ctgcacttgt    180
cctcatgagc cgctccaatg tccagcccac agctgcccct ggccagaagg tgatggagaa   240
tagcagtggg acacccgaca tcttaacgcg gcacttcaca attgatgact ttgagattgg   300
gcgtcctctg ggcaaaggca gtttggaaa cgtgtacttg gctcgggaga agaaaagcca    360
tttcatcgtg gcgctcaagg tcctcttcaa gtcccagata gagaaggagg gcgtggagca   420
tcagctgcgc agagagatcg aaatccaggc ccacctgcac catcccaaca tcctgcgtct   480
ctacaactat ttttatgacc ggaggaggat ctacttgatt ctagagtatg ccccccgcgg   540
ggagctctac aaggagctgc agaagagctg cacatttgac gagcagcgaa cagccacgat   600
catggaggag ttggcagatg ctctaatgta ctgccatggg aagaaggtga ttcacagaga   660
cataaagcca gaaaatctgc tcttagggct caagggagag ctgaagattg ctgacttcgg   720
ctggtctgtg catgcgccct ccctgaggag gaagacaatg tgtggcaccc tggactacct   780
gccccccagag atgattgagg ggcgcatgca caatgagaag gtggatctgt ggtgcattgg   840
agtgctttgc tatgagctgc tggtggggaa cccaccctt gagagtgcat acacaacga     900
gacctatcgc cgcatcgtca aggtggacct aaagttcccc gcttccgtgc ccatgggagc   960
ccaggacctc atctccaaac tgctcaggca taacccctcg gaacggctgc ccctggccca  1020
ggtctcagcc caccccttggg tccgggccaa ctctcggagg gtgctgcctc cctctgccct  1080
tcaatctgtc gcctgatggt ccctgtcatt cactcgggtg cgtgtgtttg tatgtctgtg  1140
tatgtatagg ggaaagaagg gatccctaac tgttcccttta tctgttttct acctcctcct  1200
ttgtttaata aaggctgaag cttttttgtac tcatgaaaaa aaaaaaaaaa aaa         1253
```

<210> SEQ ID NO 88
<211> LENGTH: 344
<212> TYPE: PRT
<213> ORGANISM: Homo sapiens

<400> SEQUENCE: 88

```
Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125

Gln Ala His Leu His His Pro Asn Ile Leu Arg Leu Tyr Asn Tyr Phe
    130                 135                 140
```

```
Tyr Asp Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
            165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
            195                 200                 205

Gly Leu Lys Gly Glu Leu Lys Ile Ala Asp Phe Gly Trp Ser Val His
    210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
            275                 280                 285

Asp Leu Lys Phe Pro Ala Ser Val Pro Met Gly Ala Gln Asp Leu Ile
290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
            325                 330                 335

Pro Ser Ala Leu Gln Ser Val Ala
            340

<210> SEQ ID NO 89
<211> LENGTH: 1416
<212> TYPE: DNA
<213> ORGANISM: Homo sapiens

<400> SEQUENCE: 89
aagttcgggt ccgtagtggg ctaaggggga gggtttcaaa gggagcgcac ttccgctgcc    60 cttctttcg ccagccttac gggcccgaac cctcgtgtga agggtgcagt acctaagccg   120
gagcggggta gaggcgggcc ggcaccccct tctgacctcc agtgccgccg gcctcaagat   180
cagacatggc ccagaacttg aaggacttgg cgggacggct gcccgccggg ccccggggca   240
tgggcacggc cctgaagctg ttgctggggg ccggcgccgt ggcctacggt gtgcgcgaat   300
ctgtgttcac cgtggaaggc gggcacagag ccatcttctt caatcggatc ggtggagtgc   360
agcaggacac tatcctggcc gagggccttc acttcaggat cccttggttc cagtacccca   420
ttatctatga cattcgggcc agacctcgaa aaatctcctc ccctacaggc tccaaagacc   480
tacagatggt gaatatctcc ctgcgagtgt tgtctcgacc caatgctcag gagcttccta   540
gcatgtacca gcgcctaggg ctggactacg aggaacgagt gttgccgtcc attgtcaacg   600
aggtgctcaa gagtgtggtg gccaagttca atgcctcaca gctgatcacc cagcgggccc   660
aggtatccct gttgatccgc cgggagctga cagagagggc caaggacttc agcctcatcc   720
tggatgatgt ggccatcaca gagctgagct ttagccgaga gtacacagct gctgtagaag   780
ccaaacaagt ggcccagcag gaggcccagc gggcccaatt cttggtagaa aaagcaaagc   840
aggaacagcg gcagaaaatt gtgcaggccg agggtgaggc cgaggctgcc aagatgcttg   900
gagaagcact gagcaagaac cctggctaca tcaaacttcg caagattcga gcagcccaga   960
```

```
atatctccaa gacgatcgcc acatcacaga atcgtatcta tctcacagct gacaaccttg    1020
tgctgaacct acaggatgaa agtttcacca ggggaagtga cagcctcatc aagggtaaga    1080
aatgagccta gtcaccaaga actccacccc cagaggaagt ggatctgctt ctccagtttt    1140
tgaggagcca gccaggggtc agcacagcc ctaccccgcc ccagtatcat gcgatggtcc     1200
cccacaccgg ttccctgaac ccctcttgga ttaaggaaga ctgaagacta gccccttttc    1260
tgggaaatta ctttcctcct ccctgtgtta actggggctg ttggggacag tgcgtgattt    1320
ctcagtgatt tcctacagtg ttgttccctc cctcaaggct gggaggagat aaacaccaac    1380
ccaggaattc tcaataaatt tttattactt aacctg                              1416
```

<210> SEQ ID NO 90
<211> LENGTH: 299
<212> TYPE: PRT
<213> ORGANISM: Homo sapiens

<400> SEQUENCE: 90

```
Met Ala Gln Asn Leu Lys Asp Leu Ala Gly Arg Leu Pro Ala Gly Pro
1               5                   10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
        195                 200                 205

Arg Ala Gln Phe Leu Val Glu Lys Ala Lys Gln Glu Gln Arg Gln Lys
    210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285
```

Arg Gly Ser Asp Ser Leu Ile Lys Gly Lys Lys
    290                 295

<210> SEQ ID NO 91
<211> LENGTH: 1899
<212> TYPE: DNA
<213> ORGANISM: Homo sapiens

<400> SEQUENCE: 91

```
agcgcgcgac tttttgaaag ccaggagggt tcgaattgca acggcagctg ccgggcgtat      60
gtgttggtgc tagaggcagc tgcagggtct cgctgggggc cgctcgggac caattttgaa     120
gaggtacttg gccacgactt attttcacct ccgacctttc cttccaggcg gtgagactct     180
ggactgagag tggctttcac aatggaaggg atcagtaatt tcaagacacc aagcaaatta     240
tcagaaaaaa agaaatctgt attatgttca actccaacta taaatatccc ggcctctccg     300
tttatgcaga agcttggctt tggtactggg gtaaatgtgt acctaatgaa agatctcca     360
agaggtttgt ctcattctcc ttgggctgta aaaagatta tcctatatg taatgatcat     420
tatcgaagtg tgtatcaaaa gagactaatg gatgaagcta agattttgaa aagccttcat     480
catccaaaca ttgttggtta tcgtgctttt actgaagcca atgatggcag tctgtgtctt     540
gctatggaat atggaggtga aaagtctcta aatgacttaa tagaagaacg atataaagcc     600
agccaagatc cttttccagc agccataatt ttaaaagttg ctttgaatat ggcaagaggg     660
ttaaagtatc tgcaccaaga aaagaaactg cttcatggag acataaagtc ttcaaatgtt     720
gtaattaaag gcgatttga acaattaaa atctgtgatg taggagtctc tctaccactg     780
gatgaaaata tgactgtgac tgaccctgag gcttgttaca ttggcacaga gccatggaaa     840
cccaaagaag ctgtggagga aatggtgtt attactgaca aggcagacat atttgccttt     900
ggccttactt tgtgggaaat gatgactta tcgattccac acattaatct ttcaaatgat     960
gatgatgatg aagataaaac ttttgatgaa agtgattttg atgatgaagc atactatgca    1020
gcgttgggaa ctaggccacc tattaatatg gaagaactgg atgaatcata ccagaaagta    1080
attgaactct ctctgtatg cactaatgaa gaccctaaag atcgtccttc tgctgcacac    1140
attgttgaag ctctggaaac agatgtctag tgatcatctc agctgaagtg tggcttgcgt    1200
aaataactgt ttattccaaa atatttacat agttactatc agtagttatt agactctaaa    1260
attggcatat ttgaggacca tagtttcttg ttaacatatg gataactatt tctaatatga    1320
aatatgctta tattggctat aagcacttgg aattgtactg ggttttctgt aaagttttag    1380
aaactagcta cataagtact ttgatactgc tcatgctgac ttaaaacact agcagtaaaa    1440
cgctgtaaac tgtaacatta aattgaatga ccattacttt tattaatgat ctttcttaaa    1500
tattctatat tttaatggat ctactgacat tagcactttg tacagtacaa aataaagtct    1560
acatttgttt aaaacactga accttttgct gatgtgttta tcaaatgata actggaagct    1620
gaggagaata tgcctcaaaa agagtagctc cttggatact tcagactctg gttacagatt    1680
gtcttgatct cttggatctc ctcagatctt tggttttgc tttaatttat taaatgtatt    1740
ttccatactg agtttaaaat ttattaattt gtaccttaag catttcccag ctgtgtaaaa    1800
acaataaaac tcaaatagga tgataaagaa taaggacac tttgggtacc agaaaaaaaa    1860
aaaaaaaaaa aaaaaaaaaa aaaaaaaaaa aaaaaaaa                            1899
```

<210> SEQ ID NO 92
<211> LENGTH: 322
<212> TYPE: PRT

<213> ORGANISM: Homo sapiens

<400> SEQUENCE: 92

Met Glu Gly Ile Ser Asn Phe Lys Thr Pro Ser Lys Leu Ser Glu Lys
1               5                   10                  15

Lys Lys Ser Val Leu Cys Ser Thr Pro Thr Ile Asn Ile Pro Ala Ser
            20                  25                  30

Pro Phe Met Gln Lys Leu Gly Phe Gly Thr Gly Val Asn Val Tyr Leu
        35                  40                  45

Met Lys Arg Ser Pro Arg Gly Leu Ser His Ser Pro Trp Ala Val Lys
    50                  55                  60

Lys Ile Asn Pro Ile Cys Asn Asp His Tyr Arg Ser Val Tyr Gln Lys
65                  70                  75                  80

Arg Leu Met Asp Glu Ala Lys Ile Leu Lys Ser Leu His His Pro Asn
                85                  90                  95

Ile Val Gly Tyr Arg Ala Phe Thr Glu Ala Asn Asp Gly Ser Leu Cys
            100                 105                 110

Leu Ala Met Glu Tyr Gly Gly Glu Lys Ser Leu Asn Asp Leu Ile Glu
        115                 120                 125

Glu Arg Tyr Lys Ala Ser Gln Asp Pro Phe Pro Ala Ala Ile Ile Leu
    130                 135                 140

Lys Val Ala Leu Asn Met Ala Arg Gly Leu Lys Tyr Leu His Gln Glu
145                 150                 155                 160

Lys Lys Leu Leu His Gly Asp Ile Lys Ser Ser Asn Val Val Ile Lys
                165                 170                 175

Gly Asp Phe Glu Thr Ile Lys Ile Cys Asp Val Gly Val Ser Leu Pro
            180                 185                 190

Leu Asp Glu Asn Met Thr Val Thr Asp Pro Glu Ala Cys Tyr Ile Gly
        195                 200                 205

Thr Glu Pro Trp Lys Pro Lys Glu Ala Val Glu Glu Asn Gly Val Ile
    210                 215                 220

Thr Asp Lys Ala Asp Ile Phe Ala Phe Gly Leu Thr Leu Trp Glu Met
225                 230                 235                 240

Met Thr Leu Ser Ile Pro His Ile Asn Leu Ser Asn Asp Asp Asp Asp
                245                 250                 255

Glu Asp Lys Thr Phe Asp Glu Ser Asp Phe Asp Asp Glu Ala Tyr Tyr
            260                 265                 270

Ala Ala Leu Gly Thr Arg Pro Pro Ile Asn Met Glu Glu Leu Asp Glu
        275                 280                 285

Ser Tyr Gln Lys Val Ile Glu Leu Phe Ser Val Cys Thr Asn Glu Asp
    290                 295                 300

Pro Lys Asp Arg Pro Ser Ala Ala His Ile Val Glu Ala Leu Glu Thr
305                 310                 315                 320

Asp Val

<210> SEQ ID NO 93
<211> LENGTH: 294
<212> TYPE: PRT
<213> ORGANISM: Homo sapiens

<400> SEQUENCE: 93

Lys Cys Asn Pro Ser Asn Ser Ser Pro Ser Ser Ala Ala Cys Ala Pro
1               5                   10                  15

Ser Cys Ala Gly Asp Leu Pro Leu Pro Ser Asn Thr Pro Thr Phe Ser
            20                  25                  30

```
Ile Lys Thr Ser Pro Ala Lys Ala Arg Ser Pro Ile Asn Arg Arg Gly
         35                  40                  45

Ser Val Ser Ser Val Ser Pro Lys Pro Pro Ser Ser Phe Lys Met Ser
 50                  55                  60

Ile Arg Asn Trp Val Thr Arg Thr Pro Ser Ser Pro Pro Ile Thr
 65              70                  75                  80

Pro Pro Ala Ser Glu Thr Lys Ile Met Ser Pro Arg Lys Ala Leu Ile
                 85                  90                  95

Pro Val Ser Gln Lys Ser Ser Gln Ala Glu Ala Cys Ser Glu Ser Arg
                100                 105                 110

Asn Arg Val Lys Arg Arg Leu Asp Ser Ser Cys Leu Glu Ser Val Lys
            115                 120                 125

Gln Lys Cys Val Lys Ser Cys Asn Cys Val Thr Glu Leu Asp Gly Gln
        130                 135                 140

Val Glu Asn Leu His Leu Asp Leu Cys Cys Leu Ala Gly Asn Gln Glu
145                 150                 155                 160

Asp Leu Ser Lys Asp Ser Leu Gly Pro Thr Lys Ser Ser Lys Ile Glu
                165                 170                 175

Gly Ala Gly Thr Ser Ile Ser Gly Pro Pro Ser Pro Ile Ser Pro Tyr
                180                 185                 190

Ala Ser Glu Ser Cys Gly Thr Leu Pro Leu Pro Leu Arg Pro Cys Gly
                195                 200                 205

Glu Gly Ser Glu Met Val Gly Lys Glu Asn Ser Ser Pro Glu Asn Lys
        210                 215                 220

Asn Trp Leu Leu Ala Met Ala Ala Lys Arg Lys Ala Glu Asn Pro Ser
225                 230                 235                 240

Pro Arg Ser Pro Ser Ser Gln Thr Pro Asn Ser Arg Arg Gln Ser Gly
                245                 250                 255

Lys Thr Leu Pro Ser Pro Val Thr Ile Thr Pro Ser Ser Met Arg Lys
                260                 265                 270

Ile Cys Thr Tyr Phe His Arg Lys Ser Gln Glu Asp Phe Cys Gly Pro
            275                 280                 285

Glu His Ser Thr Glu Leu
        290
```

<210> SEQ ID NO 94
<211> LENGTH: 1235
<212> TYPE: DNA
<213> ORGANISM: Homo sapiens

<400> SEQUENCE: 94

```
gggggggggg ggcacttggc ttcaaagctg gctcttggaa attgagcgga gagcgacgcg    60
gttgttgtag ctgccgctgc ggccgccgcg gaataataag ccgggatcta ccatacccat   120
tgactaacta tggaagatta taccaaaata gagaaattg gagaaggtac ctatggagtt    180
gtgtataagg gtagacacaa aactacaggt caagtggtag ccatgaaaaa aatcagacta    240
gaaagtgaag aggaagggt tcctagtact gcaattcggg aaatttctct attaaaggaa    300
cttcgtcatc caaatatagt cagtcttcag gatgtgctta tgcaggattc caggttatat    360
ctcatctttg agtttctttc catggatctg aagaaatact ggattctat ccctcctggt    420
cagtacatgg attcttcact tgttaagagt tatttatacc aaatcctaca ggggattgtg    480
ttttgtcact ctagaagagt tcttcacaga gacttaaaac ctcaaaatct cttgattgat    540
gacaaaggaa caattaaact ggctgatttt ggccttgcca gagcttttgg aatacctatc    600
```

```
agagtatata cacatgaggt agtaacactc tggtacagat ctccagaagt attgctgggg    660
tcagctcgtt actcaactcc agttgacatt tggagtatag gcaccatatt tgctgaacta    720
gcaactaaga aaccactttt ccatggggat tcagaaattg atcaactctt caggattttc    780
agagctttgg gcactcccaa taatgaagtg tggccagaag tggaatcttt acaggactat    840
aagaatacat ttcccaaatg gaaaccagga agcctagcat cccatgtcaa aaacttggat    900
gaaaatggct tggatttgct ctcgaaaatg ttaatctatg atccagccaa acgaatttct    960
ggcaaaatgg cactgaatca tccatatttt aatgatttgg acaatcagat taagaagatg   1020
tagctttctg acaaaaagtt tccatatgtt atgtcaacag atagttgtgt ttttattgtt   1080
aactcttgtc tattttgtc ttatatatat ttctttgtta tcaaacttca gctgtacttc    1140
gtcttctaat ttcaaaaata taacttaaaa atgtaaatat tctatatgaa tttaaatata   1200
attctgtaaa tgtgaaaaaa aaaaaaaaaa aaaaa                              1235
```

<210> SEQ ID NO 95
<211> LENGTH: 297
<212> TYPE: PRT
<213> ORGANISM: Homo sapiens

<400> SEQUENCE: 95

```
Met Glu Asp Tyr Thr Lys Ile Glu Lys Ile Gly Glu Gly Thr Tyr Gly
1               5                   10                  15

Val Val Tyr Lys Gly Arg His Lys Thr Thr Gly Gln Val Val Ala Met
            20                  25                  30

Lys Lys Ile Arg Leu Glu Ser Glu Glu Gly Val Pro Ser Thr Ala
        35                  40                  45

Ile Arg Glu Ile Ser Leu Leu Lys Glu Leu Arg His Pro Asn Ile Val
    50                  55                  60

Ser Leu Gln Asp Val Leu Met Gln Asp Ser Arg Leu Tyr Leu Ile Phe
65                  70                  75                  80

Glu Phe Leu Ser Met Asp Leu Lys Lys Tyr Leu Asp Ser Ile Pro Pro
                85                  90                  95

Gly Gln Tyr Met Asp Ser Ser Leu Val Lys Ser Tyr Leu Tyr Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
    130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
    210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255
```

Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
        275                 280                 285

Asp Leu Asp Asn Gln Ile Lys Lys Met
        290                 295

<210> SEQ ID NO 96
<211> LENGTH: 2101
<212> TYPE: DNA
<213> ORGANISM: Homo sapiens

<400> SEQUENCE: 96

| | | | |
|---|---|---|---|
| acgaacaggc caataaggag ggagcagtgc ggggtttaaa tctgaggcta ggctggctct | 60 |
| tctcggcgtg ctgcggcgga acggctgttg gtttctgctg ggtgtaggtc cttggctggt | 120 |
| cgggcctccg gtgttctgct tctccccgct gagctgctgc ctggtgaaga ggaagccatg | 180 |
| gcgctccgag tcaccaggaa ctcgaaaatt aatgctgaaa ataaggcgaa gatcaacatg | 240 |
| gcaggcgcaa agcgcgttcc tacggcccct gctgcaacct ccaagcccgg actgaggcca | 300 |
| agaacagctc ttggggacat tggtaacaaa gtcagtgaac aactgcaggc caaaatgcct | 360 |
| atgaagaagg aagcaaaacc ttcagctact ggaaaagtca ttgataaaaa actaccaaaa | 420 |
| cctcttgaaa aggtacctat gctggtgcca gtgccagtgt ctgagccagt gccagagcca | 480 |
| gaacctgagc cagaacctga gcctgttaaa gaagaaaaac tttcgcctga gcctattttg | 540 |
| gttgatactg cctctccaag cccaatggaa acatctggat gtgcccctgc agaagaagac | 600 |
| ctgtgtcagg cttttctctga tgtaattctt gcagtaaatg atgtggatgc agaagatgga | 660 |
| gctgatccaa acctttgtag tgaatatgtg aaagatattt atgcttatct gagacaactt | 720 |
| gaggaagagc aagcagtcag accaaaatac ctactgggtc gggaagtcac tggaaacatg | 780 |
| agagccatcc taattgactg gctagtacag gttcaaatga aattcaggtt gttgcaggag | 840 |
| accatgtaca tgactgtctc cattattgat cggttcatgc agaataattg tgtgcccaag | 900 |
| aagatgctgc agctggttgg tgtcactgcc atgtttattg caagcaaata tgaagaaatg | 960 |
| taccctccag aaattggtga ctttgctttt gtgactgaca cacttatac taagcaccaa | 1020 |
| atcagacaga tggaaatgaa gattctaaga gctttaaact ttggtctggg tcggcctcta | 1080 |
| cctttgcact tccttcggag agcatctaag attggagagg ttgatgtcga gcaacatact | 1140 |
| ttggccaaat acctgatgga actaactatg ttggactatg acatggtgca ctttcctcct | 1200 |
| tctcaaattg cagcaggagc ttttttgctta gcactgaaaa ttctggataa tggtgaatgg | 1260 |
| acaccaactc tacaacatta cctgtcatat actgaagaat ctcttcttcc agttatgcag | 1320 |
| cacctggcta agaatgtagt catggtaaat caaggactta caaagcacat gactgtcaag | 1380 |
| aacaagtatg ccacatcgaa gcatgctaag atcagcactc taccacagct gaattctgca | 1440 |
| ctagttcaag atttagccaa ggctgtggca aaggtgtaac ttgtaaactt gagttggagt | 1500 |
| actatattta caaataaaat tggcaccatg tgccatctgt acatattact gttgcattta | 1560 |
| cttttaataa agcttgtggc ccctttact tttttatagc ttaactaatt tgaatgtggt | 1620 |
| tacttcctac tgtagggtag cggaaaagtt gtcttaaaag gtatggtggg gatattttta | 1680 |
| aaaactcctt ttggtttacc tggggatcca attgatgtat atgtttatat actgggttct | 1740 |
| tgttttatat acctggcttt tactttatta atatgagtta ctgaaggtga tggaggtatt | 1800 |
| tgaaaatttt acttccatag gacatactgc atgtaagcca agtcatggag aatctgctgc | 1860 |

```
atagctctat tttaaagtaa aagtctacca ccgaatccct agtcccctg tttctgttt    1920 cttcttgtga ttgctgccat aattctaagt tatttacttt taccactatt taagttatca   1980
actttagcta gtatcttcaa actttcactt tgaaaatga gaattttata ttctaagcca    2040
gttttcattt tggttttgtg ttttggttaa taaacaata ctcaaataca aaaaaaaaa    2100 a                                                                  2101
```

<210> SEQ ID NO 97
<211> LENGTH: 433
<212> TYPE: PRT
<213> ORGANISM: Homo sapiens

<400> SEQUENCE: 97

```
Met Ala Leu Arg Val Thr Arg Asn Ser Lys Ile Asn Ala Glu Asn Lys
1               5                   10                  15

Ala Lys Ile Asn Met Ala Gly Ala Lys Arg Val Pro Thr Ala Pro Ala
            20                  25                  30

Ala Thr Ser Lys Pro Gly Leu Arg Pro Arg Thr Ala Leu Gly Asp Ile
        35                  40                  45

Gly Asn Lys Val Ser Glu Gln Leu Gln Ala Lys Met Pro Met Lys Lys
    50                  55                  60

Glu Ala Lys Pro Ser Ala Thr Gly Lys Val Ile Asp Lys Lys Leu Pro
65                  70                  75                  80

Lys Pro Leu Glu Lys Val Pro Met Leu Val Pro Val Pro Val Ser Glu
                85                  90                  95

Pro Val Pro Glu Pro Glu Pro Glu Pro Glu Pro Val Lys Glu
            100                 105                 110

Glu Lys Leu Ser Pro Glu Pro Ile Leu Val Asp Thr Ala Ser Pro Ser
        115                 120                 125

Pro Met Glu Thr Ser Gly Cys Ala Pro Ala Glu Glu Asp Leu Cys Gln
    130                 135                 140

Ala Phe Ser Asp Val Ile Leu Ala Val Asn Asp Val Asp Ala Glu Asp
145                 150                 155                 160

Gly Ala Asp Pro Asn Leu Cys Ser Glu Tyr Val Lys Asp Ile Tyr Ala
                165                 170                 175

Tyr Leu Arg Gln Leu Glu Glu Glu Gln Ala Val Arg Pro Lys Tyr Leu
            180                 185                 190

Leu Gly Arg Glu Val Thr Gly Asn Met Arg Ala Ile Leu Ile Asp Trp
        195                 200                 205

Leu Val Gln Val Gln Met Lys Phe Arg Leu Leu Gln Glu Thr Met Tyr
    210                 215                 220

Met Thr Val Ser Ile Ile Asp Arg Phe Met Gln Asn Asn Cys Val Pro
225                 230                 235                 240

Lys Lys Met Leu Gln Leu Val Gly Val Thr Ala Met Phe Ile Ala Ser
                245                 250                 255

Lys Tyr Glu Glu Met Tyr Pro Pro Glu Ile Gly Asp Phe Ala Phe Val
            260                 265                 270

Thr Asp Asn Thr Tyr Thr Lys His Gln Ile Arg Gln Met Glu Met Lys
        275                 280                 285

Ile Leu Arg Ala Leu Asn Phe Gly Leu Gly Arg Pro Leu Pro Leu His
    290                 295                 300

Phe Leu Arg Arg Ala Ser Lys Ile Gly Glu Val Asp Val Glu Gln His
305                 310                 315                 320

Thr Leu Ala Lys Tyr Leu Met Glu Leu Thr Met Leu Asp Tyr Asp Met
```

```
                    325                 330                 335
Val His Phe Pro Pro Ser Gln Ile Ala Ala Gly Ala Phe Cys Leu Ala
                340                 345                 350

Leu Lys Ile Leu Asp Asn Gly Glu Trp Thr Pro Thr Leu Gln His Tyr
            355                 360                 365

Leu Ser Tyr Thr Glu Glu Ser Leu Leu Pro Val Met Gln His Leu Ala
        370                 375                 380

Lys Asn Val Val Met Val Asn Gln Gly Leu Thr Lys His Met Thr Val
385                 390                 395                 400

Lys Asn Lys Tyr Ala Thr Ser Lys His Ala Lys Ile Ser Thr Leu Pro
                405                 410                 415

Gln Leu Asn Ser Ala Leu Val Gln Asp Leu Ala Lys Ala Val Ala Lys
            420                 425                 430

Val

<210> SEQ ID NO 98
<211> LENGTH: 18
<212> TYPE: PRT
<213> ORGANISM: Artificial
<220> FEATURE:
<223> OTHER INFORMATION: An artificialy designed dominant negative

<400> SEQUENCE: 98

Met Glu Gly Ile Ser Asn Phe Lys Thr Pro Ser Lys Leu Ser Glu Lys
1               5                   10                  15

Lys Lys

<210> SEQ ID NO 99
<211> LENGTH: 30
<212> TYPE: PRT
<213> ORGANISM: Artificial
<220> FEATURE:
<223> OTHER INFORMATION: An artificialy designed dominant negative

<400> SEQUENCE: 99

Arg Arg Arg Arg Arg Arg Arg Arg Arg Arg Gly Met Glu Gly Ile
1               5                   10                  15

Ser Asn Phe Lys Thr Pro Ser Lys Leu Ser Glu Lys Lys Lys
                20                  25                  30

<210> SEQ ID NO 100
<211> LENGTH: 9
<212> TYPE: PRT
<213> ORGANISM: Artificial
<220> FEATURE:
<223> OTHER INFORMATION: An artificially synthesised Tat sequence

<400> SEQUENCE: 100

Arg Lys Lys Arg Arg Gln Arg Arg Arg
1               5

<210> SEQ ID NO 101
<211> LENGTH: 16
<212> TYPE: PRT
<213> ORGANISM: Artificial
<220> FEATURE:
<223> OTHER INFORMATION: An artificially synthesised Penetratin sequence

<400> SEQUENCE: 101

Arg Gln Ile Lys Ile Trp Phe Gln Asn Arg Arg Met Lys Trp Lys Lys
1               5                   10                  15
```

```
<210> SEQ ID NO 102
<211> LENGTH: 21
<212> TYPE: PRT
<213> ORGANISM: Artificial
<220> FEATURE:
<223> OTHER INFORMATION: An artificially synthesised Buforin II sequence

<400> SEQUENCE: 102

Thr Arg Ser Ser Arg Ala Gly Leu Gln Phe Pro Val Gly Arg Val His
1               5                   10                  15

Arg Leu Leu Arg Lys
            20

<210> SEQ ID NO 103
<211> LENGTH: 27
<212> TYPE: PRT
<213> ORGANISM: Artificial
<220> FEATURE:
<223> OTHER INFORMATION: An artificially synthesised Transportan
      sequence

<400> SEQUENCE: 103

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 104
<211> LENGTH: 18
<212> TYPE: PRT
<213> ORGANISM: Artificial
<220> FEATURE:
<223> OTHER INFORMATION: An artificially synthesised MAP (model
      amphipathic peptide) sequence

<400> SEQUENCE: 104

Lys Leu Ala Leu Lys Leu Ala Leu Lys Ala Leu Lys Ala Ala Leu Lys
1               5                   10                  15

Leu Ala

<210> SEQ ID NO 105
<211> LENGTH: 16
<212> TYPE: PRT
<213> ORGANISM: Artificial
<220> FEATURE:
<223> OTHER INFORMATION: An artificially synthesised K-FGF sequence

<400> SEQUENCE: 105

Ala Ala Val Ala Leu Leu Pro Ala Val Leu Leu Ala Leu Leu Ala Pro
1               5                   10                  15

<210> SEQ ID NO 106
<211> LENGTH: 5
<212> TYPE: PRT
<213> ORGANISM: Artificial
<220> FEATURE:
<223> OTHER INFORMATION: An artificially synthesised Ku70 sequence

<400> SEQUENCE: 106

Val Pro Met Leu Lys
1               5

<210> SEQ ID NO 107
<211> LENGTH: 28
<212> TYPE: PRT
```

<213> ORGANISM: Artificial
<220> FEATURE:
<223> OTHER INFORMATION: An artificially synthesised Prion sequence

<400> SEQUENCE: 107

Met Ala Asn Leu Gly Tyr Trp Leu Leu Ala Leu Phe Val Thr Met Trp
1 5 10 15

Thr Asp Val Gly Leu Cys Lys Lys Arg Pro Lys Pro
20 25

<210> SEQ ID NO 108
<211> LENGTH: 18
<212> TYPE: PRT
<213> ORGANISM: Artificial
<220> FEATURE:
<223> OTHER INFORMATION: An artificially synthesised pVEC sequence

<400> SEQUENCE: 108

Leu Leu Ile Ile Leu Arg Arg Arg Ile Arg Lys Gln Ala His Ala His
1 5 10 15

Ser Lys

<210> SEQ ID NO 109
<211> LENGTH: 21
<212> TYPE: PRT
<213> ORGANISM: Artificial
<220> FEATURE:
<223> OTHER INFORMATION: An artificially synthesised Pep-1 sequence

<400> SEQUENCE: 109

Lys Glu Thr Trp Trp Glu Thr Trp Trp Thr Glu Trp Ser Gln Pro Lys
1 5 10 15

Lys Lys Arg Lys Val
20

<210> SEQ ID NO 110
<211> LENGTH: 18
<212> TYPE: PRT
<213> ORGANISM: Artificial
<220> FEATURE:
<223> OTHER INFORMATION: An artificially synthesised SynB1 sequence

<400> SEQUENCE: 110

Arg Gly Gly Arg Leu Ser Tyr Ser Arg Arg Arg Phe Ser Thr Ser Thr
1 5 10 15

Gly Arg

<210> SEQ ID NO 111
<211> LENGTH: 15
<212> TYPE: PRT
<213> ORGANISM: Artificial
<220> FEATURE:
<223> OTHER INFORMATION: An artificially synthesised Pep-7 sequence

<400> SEQUENCE: 111

Ser Asp Leu Trp Glu Met Met Met Val Ser Leu Ala Cys Gln Tyr
1 5 10 15

<210> SEQ ID NO 112
<211> LENGTH: 12
<212> TYPE: PRT
<213> ORGANISM: Artificial
<220> FEATURE:
<223> OTHER INFORMATION: An artificially synthesised HN-1 sequence

<400> SEQUENCE: 112

Thr Ser Pro Leu Asn Ile His Asn Gly Gln Lys Leu
1               5                   10

<210> SEQ ID NO 113
<211> LENGTH: 11
<212> TYPE: PRT
<213> ORGANISM: Artificial
<220> FEATURE:
<223> OTHER INFORMATION: An artificially synthesised poly-arginine
      sequence

<400> SEQUENCE: 113

Arg Arg Arg Arg Arg Arg Arg Arg Arg Arg
1               5                   10

<210> SEQ ID NO 114
<211> LENGTH: 5
<212> TYPE: PRT
<213> ORGANISM: Artificial
<220> FEATURE:
<223> OTHER INFORMATION: An artificially synthesised Ku70 sequence

<400> SEQUENCE: 114

Pro Met Leu Lys Glu
1               5

<210> SEQ ID NO 115
<211> LENGTH: 1488
<212> TYPE: DNA
<213> ORGANISM: Homo sapiens

<400> SEQUENCE: 115

```
gcggggccgc gggccggggg cggactgggg cgggcggaag gagagccagg ccggaaggag      60
gctgccggag ggcgggaggc aggagcgggc caggagctgc tgggctggag cggcggcgcc     120
gccatgtccg acagcgagaa gctcaacctg actcgatca tcgggcgcct gctgaagtg      180
cagggctcgc ggcctggcaa gaatgtacag ctgacagaga acgagatccg cggtctgtgc     240
ctgaaatccc gggagatttt tctgagccag cccattcttc tggagctgga ggcacccctc     300
aagatctgcg gtgacataca cggccagtac tacgaccttc tgcgactatt tgagtatggc     360
ggtttccctc ccgagagcaa ctacctcttt ctgggggact atgtggacag ggcaagcag      420
tccttggaga ccatctgcct gctgctggcc tataagatca agtaccccga gaacttcttc     480
ctgctccgtg ggaaccacga gtgtgccagc atcaaccgca tctatggttt ctacgatgag     540
tgcaagagac gctacaacat caaactgtgg aaaaccttca ctgactgctt caactgcctg     600
cccatcgcgg ccatagtgga cgaaaagatc ttctgctgcc acggaggcct gtccccggac     660
ctgcagtcta tggagcagat tcggcggatc atgcggccca cagatgtgcc tgaccagggc     720
ctgctgtgtg acctgctgtg gtctgaccct gacaaggacg tgcagggctg ggcgagaac      780
gaccgtggcg tctctttac ctttggagcc gaggtggtgg ccaagttcct ccacaagcac     840
gacttggacc tcatctgccg agcacaccag gtggtagaag acggctacga gttctttgcc     900
aagcggcagc tggtgacact tttctcagct cccaactact gtggcgagtt tgacaatgct     960
ggcgccatga tgagtgtgga cgagaccctc atgtgctctt tccagatcct caagcccgcc    1020
gacaagaaca aggggaagta cgggcagttc agtggcctga accctggagg ccgacccatc    1080
accccacccc gcaattccgc caaagccaag aaatagcccc cgcacaccac cctgtgcccc    1140
agatgatgga ttgattgtac agaaatcatg ctgccatgct gggggggggt caccccgacc    1200
```

-continued

```
cctcaggccc acctgtcacg gggaacatgg agccttggtg tattttttctt ttctttttttt    1260 aatgaatcaa tagcagcgtc cagtccccca gggctgcttc ctgcctgcac ctgcggtgac      1320
tgtgagcagg atcctggggc cgaggctgca gctcagggca acggcaggcc aggtcgtggg      1380
tctccagccg tgcttggcct cagggctggc agccggatcc tggggcaacc catctggtct     1440
cttgaataaa ggtcaaagct ggattctcgc aaaaaaaaaa aaaaaaaa                   1488
```

<210> SEQ ID NO 116
<211> LENGTH: 330
<212> TYPE: PRT
<213> ORGANISM: Homo sapiens

<400> SEQUENCE: 116

```
Met Ser Asp Ser Glu Lys Leu Asn Leu Asp Ser Ile Ile Gly Arg Leu
1               5                   10                  15

Leu Glu Val Gln Gly Ser Arg Pro Gly Lys Asn Val Gln Leu Thr Glu
            20                  25                  30

Asn Glu Ile Arg Gly Leu Cys Leu Lys Ser Arg Glu Ile Phe Leu Ser
        35                  40                  45

Gln Pro Ile Leu Leu Glu Leu Glu Ala Pro Leu Lys Ile Cys Gly Asp
    50                  55                  60

Ile His Gly Gln Tyr Tyr Asp Leu Leu Arg Leu Phe Glu Tyr Gly Gly
65                  70                  75                  80

Phe Pro Pro Glu Ser Asn Tyr Leu Phe Leu Gly Asp Tyr Val Asp Arg
                85                  90                  95

Gly Lys Gln Ser Leu Glu Thr Ile Cys Leu Leu Leu Ala Tyr Lys Ile
            100                 105                 110

Lys Tyr Pro Glu Asn Phe Phe Leu Leu Arg Gly Asn His Glu Cys Ala
        115                 120                 125

Ser Ile Asn Arg Ile Tyr Gly Phe Tyr Asp Glu Cys Lys Arg Arg Tyr
    130                 135                 140

Asn Ile Lys Leu Trp Lys Thr Phe Thr Asp Cys Phe Asn Cys Leu Pro
145                 150                 155                 160

Ile Ala Ala Ile Val Asp Glu Lys Ile Phe Cys Cys His Gly Gly Leu
                165                 170                 175

Ser Pro Asp Leu Gln Ser Met Glu Gln Ile Arg Arg Ile Met Arg Pro
            180                 185                 190

Thr Asp Val Pro Asp Gln Gly Leu Leu Cys Asp Leu Leu Trp Ser Asp
        195                 200                 205

Pro Asp Lys Asp Val Gln Gly Trp Gly Glu Asn Asp Arg Gly Val Ser
    210                 215                 220

Phe Thr Phe Gly Ala Glu Val Val Ala Lys Phe Leu His Lys His Asp
225                 230                 235                 240

Leu Asp Leu Ile Cys Arg Ala His Gln Val Val Glu Asp Gly Tyr Glu
                245                 250                 255

Phe Phe Ala Lys Arg Gln Leu Val Thr Leu Phe Ser Ala Pro Asn Tyr
            260                 265                 270

Cys Gly Glu Phe Asp Asn Ala Gly Ala Met Met Ser Val Asp Glu Thr
        275                 280                 285

Leu Met Cys Ser Phe Gln Ile Leu Lys Pro Ala Asp Lys Asn Lys Gly
    290                 295                 300

Lys Tyr Gly Gln Phe Ser Gly Leu Asn Pro Gly Gly Arg Pro Ile Thr
305                 310                 315                 320
```

Pro Pro Arg Asn Ser Ala Lys Ala Lys Lys
         325                 330

<210> SEQ ID NO 117
<211> LENGTH: 3644
<212> TYPE: DNA
<213> ORGANISM: Homo sapiens

<400> SEQUENCE: 117

| | | | | | | |
|---|---|---|---|---|---|---|
| aactagggt | aaggaggtac | aaagaacaag | gaagttaggc | tttgaaaata | gagaacaaag | 60 |
| aacaagtaag | ctgaacaagt | aagttcctct | ttggagaggc | aagagggcaa | agaagctgag | 120 |
| gacccagaag | acaggattgt | gcctaagaaa | gtggccttgg | agcagaggcc | caagaaagc | 180 |
| ggggagagcg | ccttgcccat | cggtaaggga | aaggtgctcc | aggcacagaa | gcagctaatg | 240 |
| caacggccct | gaggcaaatg | caagataact | ggcaagttcc | aggaacagca | aggagggcaa | 300 |
| ggcgcctgga | gcagaggaag | ctagcggatc | ccttgatgag | agggaggaac | tggcccatct | 360 |
| ctcatgggtc | ctgcaggcag | gccatgagac | tgtcttttat | gcgggcgag | ataacgaggc | 420 |
| atggacgtgt | tgtgagcgga | ggcctagcct | gttcaaggtc | tgaattttta | ccctagaat | 480 |
| gtaagaagca | tgggagcagg | gactttgttt | tgctccctgc | catatccaca | gccctagaaa | 540 |
| aacgtcgggc | cattgatagc | tctcagtaaa | tgcttgacaa | gtaagtgaat | gaacgaatgc | 600 |
| acaattaatg | aaatgagggc | tgcgtcaatg | aataactggg | aatctgactc | ctgcagggag | 660 |
| ccttcagccc | acaggtgtat | gtaagacccg | ccccgcctct | catccttcgg | gctcccaccc | 720 |
| ccgccgttag | gctgcggttc | gcgccgcggt | cgccagaggg | cgcggagcgg | cggggcttcc | 780 |
| cgcacggagg | gctttgcgtg | aggcaccgcg | tggggcgggg | ctgcgggcgg | gctcccagct | 840 |
| gctgggccct | catcggctgg | gcctcgtcga | ccggcaagcg | gaacgcggca | gcggggctgg | 900 |
| gcctgtgcgg | cggccgccgg | agcgctttgg | aaggcgcacg | gggcgaagat | ggcggcggag | 960 |
| cgacaggagg | cgctgaggga | gttcgtggcg | gtgacgggcg | ccgaggagga | ccgggccgc | 1020 |
| ttctttctcg | agtcggccgg | ctgggacttg | cagatcgcgc | tagcgagctt | ttatgaggac | 1080 |
| ggaggggatg | aagacattgt | gaccatttcg | caggcaaccc | ccagttcagt | gtccagaggc | 1140 |
| acagccccca | gtgataatag | agtgacatcc | ttcagagacc | tcattcatga | ccaagatgaa | 1200 |
| gatgaggagg | aagaggaagg | ccagaggttt | tatgctgggg | gctcagagag | aagtggacag | 1260 |
| cagattgttg | gccctcccag | gaagaaaagt | cccaacgagc | tggtgatga | tctctttaaa | 1320 |
| ggtgccaaag | agcatggagc | tgtagctgtg | gagcgagtga | ccaagagccc | tggagagacc | 1380 |
| agtaaaccga | gaccatttgc | aggaggtggc | taccgccttg | gggcagcacc | agaggaagag | 1440 |
| tctgcctatg | tggcaggaga | aaagaggcag | cattccagcc | aagatgttca | tgtagtattg | 1500 |
| aaactctgga | agagtggatt | cagcctggat | aatggagaac | tcagaagcta | ccaagaccca | 1560 |
| tccaatgccc | agtttctgga | gtctatccgc | agagggagg | tgccagcaga | gcttcggagg | 1620 |
| ctagctcacg | gtggacaggt | gaacttggat | atggaggacc | atcggacga | ggactttgtg | 1680 |
| aagcccaaag | gagccttcaa | agccttcact | ggcgagggtc | agaaactggg | cagcactgcc | 1740 |
| ccccaggtgt | tgagtaccag | ctctccagcc | caacaggcag | aaaatgaagc | caaagccagc | 1800 |
| tcttccatct | taatcgacga | atcagagcct | accacaaaca | tccaaattcg | gcttgcagac | 1860 |
| ggcgggaggc | tggtgcagaa | atttaaccac | agccacagga | tcagcgacat | ccgactcttc | 1920 |
| atcgtggatg | cccggccagc | catggctgcc | accagcttta | tcctcatgac | tactttcccg | 1980 |
| aacaaagagc | tggctgatga | gagccagacc | ctgaaggaag | ccaacctgct | caatgctgtc | 2040 |

```
atcgtgcagc ggttaacata accgcccagc cagctgcctg gcctccctcc tgtgtttccc    2100
atggccagtg ccatgcccc atggggatcg cccctcctgc ccccttgtgc acacccagca     2160
gtccagtgca acgtctcctc catagctctg ggttcttaga tcttggttgg acgtttgttt    2220
tctccttagt tgcatttcct gggttttttgt gatgatcaat ggactttaat gaaaaaaaaa   2280
ataaaaacaa ccaaaaaaat tgaaggaata tcaccagcat gttgtacgga aactctccca    2340
ctgaagcagg ctttaattgc tttaaaatta tatttatctt ggggcctgtg ggaggaaact    2400
tccttccatc ttctctgcat aaaaacttgt ggcacacaat gcttattcac tagtgtgtcc    2460
cacccgccag ccccacagat gactggagga aggaggggaa atgtgtagaa agaggcttcg    2520
ccaccacttg ttcccacgag aatatgtcac ttgcccagat aaaactgggc ggcagccaga    2580
gttccctgaa gtgggaagtc agagctccat gcacacagtg tcttcagaag gtgaaaataa    2640
atatttccct gtgctccttt tactcaaccc ctggggtatc taatcttgcc aggtcttggc    2700
cagttgagat tctgttccac ctgcctgcct ggccctttcc tccattacca tccagactgc    2760
tcgcctcctg gggattctca ggggctccat tatggcttga tttactccac gtgcagaagt    2820
cttgagtgga cctaggaggt aggtgggata ttttttttca ctaggataca gctcatgcca    2880
acccatccta agtgagttca gaatcagggt atcttgccct ataagataaa cagtcaaaat    2940
gccaccgagc tgttcactag tgatgtgtgg caaatcaaat caactgttga agaaggggtg    3000
agttttctgt gctacaagca cctgtcactg ttggtacttg caggaggctt ctgctgggta    3060
tgttttggaa gtgagtgtca ctacttggct ttgcttagca ggttctgctt cacacttgtt    3120
ctttgacctg ctgacttgtg acttgcagaa acataggcag tagtcctagc ctggtaaaga    3180
ccctccacca cccctataag tttgattgct atgcaggttt gggagaggag gcctattggg    3240
ctcttggatg gaacccttc ccgtattaaa caaaccagag acagaatcag tgctgactca     3300
ggatctcctg gtttggaatc gtaatgtgcc tcaatcctct ttccaagcag gcctcaccag    3360
tctctttctc tttcctgctt caccccctgca atgagccaag aaccaacact acatccacct    3420
agaactgcag aagggcttgt ggtttcaacc aagacccatc ctgagcaagg gacttggctt    3480
ggtgcttttg atcccaaagt tcccacaccg gcagtggcct gctggggcaa tggcatctgt    3540
cacggtgttt tctccagcag gtggagatta tggaacctac atatgggtct ggaaaaactg    3600
tacactgttg tcaccttgac cattaaaaac cagaatgagg acaa                    3644
```

<210> SEQ ID NO 118
<211> LENGTH: 370
<212> TYPE: PRT
<213> ORGANISM: Homo sapiens

<400> SEQUENCE: 118

```
Met Ala Ala Glu Arg Gln Glu Ala Leu Arg Glu Phe Val Ala Val Thr
1               5                   10                  15

Gly Ala Glu Glu Asp Arg Ala Arg Phe Phe Leu Glu Ser Ala Gly Trp
            20                  25                  30

Asp Leu Gln Ile Ala Leu Ala Ser Phe Tyr Glu Asp Gly Gly Asp Glu
        35                  40                  45

Asp Ile Val Thr Ile Ser Gln Ala Thr Pro Ser Val Ser Arg Gly
    50                  55                  60

Thr Ala Pro Ser Asp Asn Arg Val Thr Ser Phe Arg Asp Leu Ile His
65                  70                  75                  80

Asp Gln Asp Glu Asp Glu Glu Glu Glu Gly Gln Arg Phe Tyr Ala
            85                  90                  95
```

Gly Gly Ser Glu Arg Ser Gly Gln Gln Ile Val Gly Pro Pro Arg Lys
            100                 105                 110

Lys Ser Pro Asn Glu Leu Val Asp Asp Leu Phe Lys Gly Ala Lys Glu
            115                 120                 125

His Gly Ala Val Ala Val Glu Arg Val Thr Lys Ser Pro Gly Glu Thr
        130                 135                 140

Ser Lys Pro Arg Pro Phe Ala Gly Gly Tyr Arg Leu Gly Ala Ala
145                 150                 155                 160

Pro Glu Glu Glu Ser Ala Tyr Val Ala Gly Lys Arg Gln His Ser
                165                 170                 175

Ser Gln Asp Val His Val Val Leu Lys Leu Trp Lys Ser Gly Phe Ser
            180                 185                 190

Leu Asp Asn Gly Glu Leu Arg Ser Tyr Gln Asp Pro Ser Asn Ala Gln
            195                 200                 205

Phe Leu Glu Ser Ile Arg Arg Gly Glu Val Pro Ala Glu Leu Arg Arg
        210                 215                 220

Leu Ala His Gly Gly Gln Val Asn Leu Asp Met Glu Asp His Arg Asp
225                 230                 235                 240

Glu Asp Phe Val Lys Pro Lys Gly Ala Phe Lys Ala Phe Thr Gly Glu
                245                 250                 255

Gly Gln Lys Leu Gly Ser Thr Ala Pro Gln Val Leu Ser Thr Ser Ser
            260                 265                 270

Pro Ala Gln Gln Ala Glu Asn Glu Ala Lys Ala Ser Ser Ile Leu
            275                 280                 285

Ile Asp Glu Ser Glu Pro Thr Thr Asn Ile Gln Ile Arg Leu Ala Asp
290                 295                 300

Gly Gly Arg Leu Val Gln Lys Phe Asn His Ser His Arg Ile Ser Asp
305                 310                 315                 320

Ile Arg Leu Phe Ile Val Asp Ala Arg Pro Ala Met Ala Ala Thr Ser
                325                 330                 335

Phe Ile Leu Met Thr Thr Phe Pro Asn Lys Glu Leu Ala Asp Glu Ser
            340                 345                 350

Gln Thr Leu Lys Glu Ala Asn Leu Leu Asn Ala Val Ile Val Gln Arg
            355                 360                 365

Leu Thr
    370

<210> SEQ ID NO 119
<211> LENGTH: 3198
<212> TYPE: DNA
<213> ORGANISM: Homo sapiens

<400> SEQUENCE: 119
ctgccactgc cacctcgcgg atcaggagcc agcgttgttc gcccgacgcc tcgctgccgg      60
tgggaggaag cgagagggaa gccgcttggg ctcttgtcgc cgctgctcgc ccaccgcctg     120
gaagagccga gccccggcca gtcggtcgct tgccaccgct cgtagccgtt acccgcgggc     180
cgccacagcc gccggcggga gaggcgcgcg ccatggcttc tggagccgat tcaaaaggtg     240
atgacctatc aacagccatt ctcaaacaga gaaccgtcc caatcggtta attgttgatg     300
aagccatcaa tgaggacaac agtgtggtgt ccttgtccca gcccaagatg gatgaattgc     360
agttgttccg aggtgacaca gtgttgctga aggaaagaa gagacgagaa gctgttttgca    420 tcgtcctttc tgatgatact tgttctgatg agaagattcg gatgaataga gttgttcgga     480

```
ataaccttcg tgtacgccta ggggatgtca tcagcatcca gccatgccct gatgtgaagt      540
acggcaaacg tatccatgtg ctgcccattg atgacacagt ggaaggcatt actggtaatc      600
tcttcgaggt ataccttaag ccgtacttcc tggaagcgta tcgacccatc cggaaaggag      660
acattttcct tgtccgtggt gggatgcgtg ctgtggagtt caaagtggtg aaacagatc       720 ctagccctta ttgcattgtt gctccagaca cagtgatcca ctgcgaaggg agcctatca      780 aacgagagga tgaggaagag tccttgaatg aagtagggta tgatgacatt ggtggctgca      840
ggaagcagct agctcagatc aaagagatgg tggaactgcc cctgagacat cctgccctct      900
ttaaggcaat tggtgtgaag cctcctagag aatcctgct  ttacggacct cctggaacag      960
gaaagaccct gattgctcga gctgtagcaa atgagactgg agccttcttc ttcttgatca     1020
atggtcctga gatcatgagc aaattggctg gtgagtctga gagcaacctt cgtaaagcct     1080
tgagggaggc tgagaagaat gctcctgcca tcatcttcat tgatgagcta gatgccatcg     1140
ctcccaaaag agagaaaact catggcgagg tggagcggcg cattgtatca cagttgttga     1200
ccctcatgga tggcctaaag cagagggcac atgtgattgt tatggcagca accaacagac     1260
ccaacagcat tgacccagct ctacggcgat ttggtcgctt tgacagggag gtagatattg     1320
gaattcctga tgctacagga cgcttagaga ttcttcagat ccataccaag aacatgaagc     1380
tggcagatga tgtggacctg aacaggtag  ccaatgagac tcacgggcat gtgggtgctg     1440
acttagcagc cctgtgctca gaggctgctc tgcaagccat ccgcaagaag atggatctca     1500
ttgacctaga ggatgagacc attgatgccg aggtcatgaa ctctctagca gttactatgg     1560
atgacttccg gtgggccttg agccagagta acccatcagc actgcgggaa accgtggtag     1620
aggtgccaca ggtaacctgg aagacatcg  ggggcctaga ggatgtcaaa cgtgagctac     1680
aggagctggt ccagtatcct gtggagcacc cagacaaatt cctgaagttt ggcatgacac     1740
cttccaaggg agttctgttc tatggacctc ctggctgtgg aaaactttg  ttggccaaag     1800 ccattgctaa tgaatgccag gccaacttca tctccatcaa gggtcctgag ctgctcacca     1860
tgtggtttgg ggagtctgag gccaatgtca gagaaatctt tgacaaggcc cgccaagctg     1920
ccccctgtgt gctattcttt gatgagctgg attcgattgc caaggctcgt ggaggtaaca     1980
ttggagatgg tggtggggct gctgaccgag tcatcaacca gatcctgaca gaaatggatg     2040
gcatgtccac aaaaaaaaat gtgttcatca ttggcgctac caaccggcct gacatcattg     2100
atcctgccat cctcagacct ggccgtcttg atcagctcat ctacatccca cttcctgatg     2160
agaagtcccg tgttgccatc ctcaaggcta acctgcgcaa gtccccagtt gccaaggatg     2220
tggacttgga gttcctggct aaaatgacta atggcttctc tggagctgac ctgacagaga     2280
tttgccagcg tgcttgcaag ctggccatcc gtgaatccat cgagagtgag attaggcgag     2340
aacgagagag gcagacaaac ccatcagcca tggaggtaga agaggatgat ccagtgcctg     2400
agatccgtcg agatcacttt gaagaagcca tgcgctttgc gcgccgttct gtcagtgaca     2460
atgacattcg gaagtatgag atgtttgccc agacccttca gcagagtcgg ggctttggca     2520
gcttcagatt cccttcaggg aaccaggtg  gagctggccc cagtcagggc agtggaggcg     2580
gcacaggtgg cagtgtatac acagaagaca atgatgatga cctgtatggc taagtggtgg     2640
tggccagcgt gcagtgagct ggcctgcctg gaccttgttc cctgggggtg gggcgcttgc     2700
ccaggagagg gaccaggggt gcgcccacag cctgctccat tctccagtct gaacagttca     2760
gctacagtct gactctggac agggggtttc tgttgcaaaa atacaaaaca aaagcgataa     2820
aataaaagcg attttcattt ggtaggcgga gagtgaatta ccaacaggga attgggcctt     2880
```

-continued

```
gggcctatgc catttctgtt gtagtttggg gcagtgcagg ggacctgtgt ggggtgtgaa    2940
ccaaggcact actgccacct gccacagtaa agcatctgca cttgactcaa tgctgcccga    3000 gccctcccctt cccctatcc aacctgggta ggtgggtagg ggccacagtt gctggatgtt    3060
tatatagaga gtaggttgat ttatttaca tgcttttgag ttaatgttgg aaaactaatc    3120
acaagcagtt tctaaaccaa aaaatgacat gttgtaaaag gacaataaac gttgggtcaa    3180
aatggaaaaa aaaaaaaa                                                 3198
```

<210> SEQ ID NO 120
<211> LENGTH: 806
<212> TYPE: PRT
<213> ORGANISM: Homo sapiens

<400> SEQUENCE: 120

```
Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
                20                  25                  30

Asn Glu Asp Asn Ser Val Val Ser Leu Ser Gln Pro Lys Met Asp Glu
            35                  40                  45

Leu Gln Leu Phe Arg Gly Asp Thr Val Leu Leu Lys Gly Lys Lys Arg
        50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

Asp Glu Glu Glu Ser Leu Asn Glu Val Gly Tyr Asp Asp Ile Gly Gly
        195                 200                 205

Cys Arg Lys Gln Leu Ala Gln Ile Lys Glu Met Val Glu Leu Pro Leu
    210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Phe Leu Ile Asn Gly Pro
            260                 265                 270

Glu Ile Met Ser Lys Leu Ala Gly Glu Ser Glu Ser Asn Leu Arg Lys
        275                 280                 285

Ala Phe Glu Glu Ala Glu Lys Asn Ala Pro Ala Ile Ile Phe Ile Asp
    290                 295                 300

Glu Leu Asp Ala Ile Ala Pro Lys Arg Glu Lys Thr His Gly Glu Val
```

```
               305                 310                 315                 320
          Glu Arg Arg Ile Val Ser Gln Leu Leu Thr Leu Met Asp Gly Leu Lys
                          325                 330                 335
          Gln Arg Ala His Val Ile Val Met Ala Ala Thr Asn Arg Pro Asn Ser
                          340                 345                 350
          Ile Asp Pro Ala Leu Arg Arg Phe Gly Arg Phe Asp Arg Glu Val Asp
                          355                 360                 365
          Ile Gly Ile Pro Asp Ala Thr Gly Arg Leu Glu Ile Leu Gln Ile His
                          370                 375                 380
          Thr Lys Asn Met Lys Leu Ala Asp Asp Val Asp Leu Glu Gln Val Ala
          385                 390                 395                 400
          Asn Glu Thr His Gly His Val Gly Ala Asp Leu Ala Ala Leu Cys Ser
                          405                 410                 415
          Glu Ala Ala Leu Gln Ala Ile Arg Lys Lys Met Asp Leu Ile Asp Leu
                          420                 425                 430
          Glu Asp Glu Thr Ile Asp Ala Glu Val Met Asn Ser Leu Ala Val Thr
                          435                 440                 445
          Met Asp Asp Phe Arg Trp Ala Leu Ser Gln Ser Asn Pro Ser Ala Leu
          450                 455                 460
          Arg Glu Thr Val Val Glu Val Pro Gln Val Thr Trp Glu Asp Ile Gly
          465                 470                 475                 480
          Gly Leu Glu Asp Val Lys Arg Glu Leu Gln Glu Leu Val Gln Tyr Pro
                          485                 490                 495
          Val Glu His Pro Asp Lys Phe Leu Lys Phe Gly Met Thr Pro Ser Lys
                          500                 505                 510
          Gly Val Leu Phe Tyr Gly Pro Pro Gly Cys Gly Lys Thr Leu Leu Ala
                          515                 520                 525
          Lys Ala Ile Ala Asn Glu Cys Gln Ala Asn Phe Ile Ser Ile Lys Gly
                          530                 535                 540
          Pro Glu Leu Leu Thr Met Trp Phe Gly Glu Ser Glu Ala Asn Val Arg
          545                 550                 555                 560
          Glu Ile Phe Asp Lys Ala Arg Gln Ala Ala Pro Cys Val Leu Phe Phe
                          565                 570                 575
          Asp Glu Leu Asp Ser Ile Ala Lys Ala Arg Gly Gly Asn Ile Gly Asp
                          580                 585                 590
          Gly Gly Gly Ala Ala Asp Arg Val Ile Asn Gln Ile Leu Thr Glu Met
                          595                 600                 605
          Asp Gly Met Ser Thr Lys Lys Asn Val Phe Ile Ile Gly Ala Thr Asn
                          610                 615                 620
          Arg Pro Asp Ile Ile Asp Pro Ala Ile Leu Arg Pro Gly Arg Leu Asp
          625                 630                 635                 640
          Gln Leu Ile Tyr Ile Pro Leu Pro Asp Glu Lys Ser Arg Val Ala Ile
                          645                 650                 655
          Leu Lys Ala Asn Leu Arg Lys Ser Pro Val Ala Lys Asp Val Asp Leu
                          660                 665                 670
          Glu Phe Leu Ala Lys Met Thr Asn Gly Phe Ser Gly Ala Asp Leu Thr
                          675                 680                 685
          Glu Ile Cys Gln Arg Ala Cys Lys Leu Ala Ile Arg Glu Ser Ile Glu
                          690                 695                 700
          Ser Glu Ile Arg Arg Glu Arg Glu Arg Gln Thr Asn Pro Ser Ala Met
          705                 710                 715                 720
          Glu Val Glu Glu Asp Asp Pro Val Pro Glu Ile Arg Arg Asp His Phe
                          725                 730                 735
```

```
Glu Glu Ala Met Arg Phe Ala Arg Arg Ser Val Ser Asp Asn Asp Ile
            740                 745                 750

Arg Lys Tyr Glu Met Phe Ala Gln Thr Leu Gln Gln Ser Arg Gly Phe
        755                 760                 765

Gly Ser Phe Arg Phe Pro Ser Gly Asn Gln Gly Ala Gly Pro Ser
        770                 775                 780

Gln Gly Ser Gly Gly Thr Gly Gly Ser Val Tyr Thr Glu Asp Asn
785                 790                 795                 800

Asp Asp Asp Leu Tyr Gly
                805

<210> SEQ ID NO 121
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 121
aaguagggua ugaugacauu g                                            21

<210> SEQ ID NO 122
<211> LENGTH: 140
<212> TYPE: PRT
<213> ORGANISM: Homo sapiens

<400> SEQUENCE: 122

Leu Ala Gly Asn Gln Glu Asp Leu Ser Lys Asp Ser Leu Gly Pro Thr
1               5                   10                  15

Lys Ser Ser Lys Ile Glu Gly Ala Gly Thr Ser Ile Ser Glu Pro Pro
            20                  25                  30

Ser Pro Ile Ser Pro Tyr Ala Ser Glu Ser Cys Gly Thr Leu Pro Leu
        35                  40                  45

Pro Leu Arg Pro Cys Gly Glu Gly Ser Glu Met Val Gly Lys Glu Asn
    50                  55                  60

Ser Ser Pro Glu Asn Lys Asn Trp Leu Leu Ala Met Ala Ala Lys Arg
65                  70                  75                  80

Lys Ala Glu Asn Pro Ser Pro Arg Ser Pro Ser Ser Gln Thr Pro Asn
                85                  90                  95

Ser Arg Arg Gln Ser Gly Lys Thr Leu Pro Ser Pro Val Thr Ile Thr
            100                 105                 110

Pro Ser Ser Met Arg Lys Ile Cys Thr Tyr Phe His Arg Lys Ser Gln
        115                 120                 125

Glu Asp Phe Cys Gly Pro Glu His Ser Thr Glu Leu
    130                 135                 140
```